US007087598B2

(12) United States Patent
Clark

(10) Patent No.: US 7,087,598 B2
(45) Date of Patent: Aug. 8, 2006

(54) DIAMIDE INVERTEBRATE PEST CONTROL AGENTS CONTAINING A NON-AROMATIC HETEROCYCLIC RING

(75) Inventor: David Alan Clark, Landenberg, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 176 days.

(21) Appl. No.: 10/473,319

(22) PCT Filed: May 21, 2002

(86) PCT No.: PCT/US02/16117

§ 371 (c)(1),
(2), (4) Date: Sep. 24, 2003

(87) PCT Pub. No.: WO02/094791

PCT Pub. Date: Nov. 28, 2002

(65) Prior Publication Data

US 2004/0138450 A1 Jul. 15, 2004

Related U.S. Application Data

(60) Provisional application No. 60/292,427, filed on May 21, 2001.

(51) Int. Cl.
*A61K 31/44* (2006.01)
*A61K 31/505* (2006.01)
*A61K 35/5355* (2006.01)
*C07D 401/04* (2006.01)

(52) U.S. Cl. .................... 514/229.2; 514/256; 514/333; 514/341; 544/66; 544/294; 546/256; 546/272.1; 546/275.4; D22/120

(58) Field of Classification Search ............. 514/229.2, 514/256, 333, 341; 544/66, 294; 546/256, 546/272.1, 275.4; D22/120
See application file for complete search history.

(56) References Cited

U.S. PATENT DOCUMENTS

| | | |
|---|---|---|
| 5,091,405 A | 2/1992 | Stevenson |
| 5,708,170 A | 1/1998 | Annis et al. |

FOREIGN PATENT DOCUMENTS

| | | |
|---|---|---|
| NL | A 9202078 | 6/1994 |
| WO | WO 95/00208 | 1/1995 |
| WO | 9747589 | * 12/1997 |
| WO | WO 01/70671 | 9/2001 |
| WO | 2002048115 | * 6/2002 |

OTHER PUBLICATIONS

Gutschow, M., "One-Pot reactions of N-(mesyloxyl)phthallmides with secondary amines to 2-ureidobenzamides, 2-ureldobenzoic acids, ethyl 2-ureldibebzoates, or isatoic anhydrides", J. Org. Chem., vol. 64, No. 14, 1999, pp. 5109-5115, XP002210288 examples 4-7.

Database Crossfire Beilstein Online! Beilstein Institut zur Forderung der Chemischen Wissenchaften Frankfurt am Main, DE: Database accession No. BRN 297178 XP002210287 abstract & Kuehle et al.: Justus Liebigs Ann. Chem.., vol. 616, 1958, pp. 183-206.

Database Crossfire Beilstein Online! Beilstein Institut zur Forderung der Chemischen Wissenchaften, Frankfurt an Main, DE: Database accession No. BRN 4303754, 1156782, 1261028 XP002210288 abstract & Leistner et al.: Z. Chem., vol. 13, 1973, p. 135.

Database Crossfire Beilstein Online! Beilstein Institut zur Fordergun der Chemischen Wissenchaften, Frankfurt am Main, DE: Database accession No. BRN 1141992 , 1151281, 1154746, 1157107, 1166149 XP002210289 abstract & Rajappe et al.: Indian J. Chem. Sect. B, vol. 14, 1976, pp. 397-399.

(Continued)

*Primary Examiner*—Taofiq Solola

(57) ABSTRACT

This invention provides compounds of Formula I, their N-oxides and agriculturally suitable salts wherein A and B are independently O or S; J is an optionally substituted 5- or 6-memebered nonaromatic heterocyclic ring; K is taken together with the two contiguous linking carbon atoms to form a phenyl ring or a 5- or 6-membered heteroaromatic ring, each ring optionally substituted; and $R_1$, $R_2$, and $R_3$ are as defined in the disclosure. Also disclosed are methods for controlling an invertebrate pest comprising contacting the invertebrate pest or its environment with a biologically effective amount of a compound of Formula I, an N-oxide thereof or a suitable salt of the compound (e.g., as a composition described herein). This invention also pertains to a composition for controlling an invertebrate pest comprising a biologically effective amount of a compound of Formula I, an N-oxide thereof or a suitable salt of the compound and at least one additional component selected from the group consisting of surfactants, solid diluents and liquid diluents.

(I)

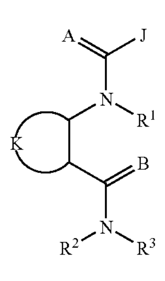

11 Claims, No Drawings

OTHER PUBLICATIONS

Patent Abstracts of Japan, vol. 1995, No. 5, Jun. 30, 1995 & JP 07 041459A (Sumitomo Pharmeceut Co. Ltd.), Feb. 10, 1995, abstract; example 32.

Soliman et al.: “Some reactions of pryazolinylbenzoxazones and -quinazolones.”, J. Chem. Soc. Pak., vol. 8, No. 2, 1986, pp. 97-106, XP001097456, examples (I)a-f, I.I.

McCann SF et al: “The Discovery of Indoxacarb: Oxadiazines As a New Class of Pyrazoline-type Insecticides” Pest Management Science, Elsevier, Barking, GB, vol. 57, No. 2, Feb. 1, 2001, pp. 153-164, XP001011693 ISSN: 1526-498X p. 154, paragraph headed “structural modifications” figure 2.

* cited by examiner

DIAMIDE INVERTEBRATE PEST CONTROL AGENTS CONTAINING A NON-AROMATIC HETEROCYCLIC RING

CROSS-REFERENCE TO RELATED APPLICATIONS

This application is a national stage application filed under 35 U.S.C. 371 of International Application No. PCT/US02/16117, filed May 21, 2002, which claims priority of U.S. Provisional Application No. 60/292,427, filed May 21, 2001.

BACKGROUND OF THE INVENTION

This invention relates to certain heterocyclic diamides, their N-oxides, suitable salts and compositions, and a method of their use for controlling invertebrate pests in both agronomic and nonagronomic environments.

The control of invertebrate pests is extremely important in achieving high crop efficiency. Damage by invertebrate pests to growing and stored agronomic crops can cause significant reduction in productivity and thereby result in increased costs to the consumer. The control of invertebrate pests in forestry, greenhouse crops, ornamentals, nursery crops, stored food and fiber products, livestock, household, and public and animal health is also important. Many products are commercially available for these purposes, but the need continues for new compounds that are more effective, less costly, less toxic, environmentally safer or have different modes of action.

NL 9202078 discloses N-acyl anthranilic acid derivatives of Formula i as insecticides i

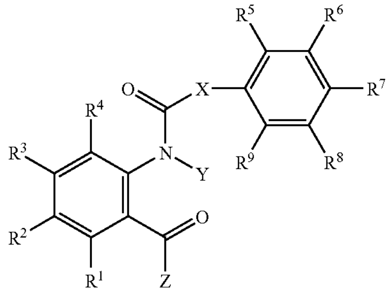

wherein, inter alia, X is a direct bond; Y is H or $C_1$–$C_6$ alkyl; Z is $NH_2$, $NH(C_1$–$C_3$ alkyl) or $N(C_1$–$C_3$ alkyl$)_2$; and $R^1$ through $R^9$ are independently H, halogen, $C_1$–$C_6$ alkyl, phenyl, hydroxy, $C_1$–$C_6$ alkoxy or $C_1$–$C_7$ acyloxy.

WO01/070671 discloses N-acyl anthranilic acid derivatives of Formula ii as arthropodicides ii

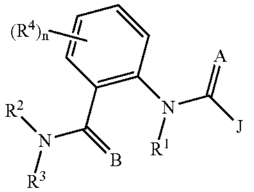

wherein, inter alia, A and B are independently O or S; J is an optionally substituted phenyl ring, 5- or 6-membered heteroaromatic ring, naphthyl ring system or an aromatic 8-, 9- or 10-membered fused heterobicyclic ring system; $R^1$ and $R^3$ are independently H or optionally substituted $C_1$–$C_6$ alkyl; $R^2$ is H or $C_1$–$C_6$ alkyl; each $R^4$ is independently H, $C_1$–$C_6$ alky, $C_1$–$C_6$ haloalkyl, halogen or CN; and n is 1 to 4.

SUMMARY OF THE INVENTION

This invention pertains to compounds of Formula I, and N-oxides or agriculturally suitable salts thereof

I

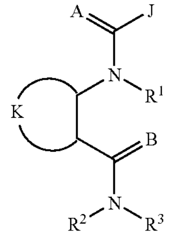

wherein

A and B are independently O or S;

J is an optionally substituted 5- or 6-membered nonaromatic heterocyclic ring;

K is taken together with the two contiguous linking carbon atoms to form a phenyl ring or a 5- or 6-membered heteroaromatic ring, each ring optionally substituted;

$R^1$ is H; $C_1$–$C_6$ alkyl, $C_2$–$C_6$ alkenyl, $C_2$–$C_6$ alkynyl or $C_3$–$C_6$ cycloalkyl, each optionally substituted; $C_2$–$C_6$ alkylcarbonyl; $C_2$–$C_6$ alkoxycarbonyl; $C_2$–$C_6$ alkylaminocarbonyl or $C_3$–$C_8$ dialkylaminocarbonyl;

$R^2$ is H, $C_1$–$C_6$ alkyl, $C_2$–$C_6$ alkenyl, $C_2$–$C_6$ alkynyl, $C_3$–$C_6$ cycloalkyl, $C_1$–$C_4$ alkoxy, $C_1$–$C_4$ alkylamino, $C_2$–$C_8$ dialkylamino, $C_3$–$C_6$ cycloalkylamino, $C_2$–$C_6$ alkoxycarbonyl or $C_2$–$C_6$ alkylcarbonyl;

$R^3$ is H; G; $C_1$–$C_6$ alkyl, $C_2$–$C_6$ alkenyl, $C_2$–$C_6$ alkynyl, $C_3$–$C_6$ cycloalkyl, each optionally substituted; or $R^2$ and $R^3$ can be taken together with the nitrogen to which they are attached to form a ring containing 2 to 6 atoms of carbon and optionally one additional atom of nitrogen, sulfur or oxygen, and said ring may be optionally substituted; and G is an optionally substituted 5- or 6-membered nonaromatic carbocyclic or heterocyclic ring, optionally including one or two ring members selected from the group consisting of C(═O), SO or $S(O)_2$.

This invention also pertains to a method for controlling an invertebrate pest comprising contacting the invertebrate pest or its environment with a biologically effective amount of a compound of Formula I, an N-oxide thereof or a suitable salt of the compound (e.g., as a composition described herein). This invention also relates to such a method wherein the invertebrate pest or its environment is contacted with a biologically effective amount of a compound of Formula I, an N-oxide thereof or a suitable salt thereof, or a composition comprising the compound, N-oxide thereof or a suitable salt thereof and a biologically effective amount of at least one additional compound or agent for controlling an invertebrate pest.

This invention also pertains to a composition for controlling an invertebrate pest comprising a biologically effective amount of a compound of Formula I, an N-oxide thereof or a suitable salt of the compound and at least one additional component selected from the group consisting of surfactants, solid diluents and liquid diluents. This invention also pertains to a composition comprising a biologically effective amount of a compound of Formula I, an N-oxide thereof or a suitable salt of the compound and an effective amount of at least one additional biologically active compound or agent.

DETAILS OF THE INVENTION

As noted above, J is an optionally substituted 5- or 6-membered nonaromatic heterocyclic ring. The term "optionally substituted" in connection with these J groups refers to J groups which are unsubstituted or have at least one non-hydrogen substituent that does not extinguish the biological activity. Examples of optionally substituted J groups wherein said rings are optionally substituted with from one to seven $R^5$ include the rings illustrated in Exhibit 1, wherein m is an integer from 1 to 7 and $R^5$ is as defined below. As with the carbon atoms in the ring, the nitrogen atoms that require substitution to fill their valence are substituted with hydrogen or with $R^5$. Although $(R^5)_m$ groups are shown in the structures J-1 to J-35, it is noted that $R^5$ does not need to be present since it is an optional substituent. It is also noted that when the $R^5$ substituent is H, that is equivalent to the atom to which the $R^5$ substituent is attached as being unsubstituted. Note that when the attachment point on the J group is illustrated as floating, the J group can be attached to the remainder of Formula I through any available carbon or nitrogen atom of the J group by replacement of a hydrogen atom. Note that J-3 and J-4 are subsets of J-19 in which the attachment point to the rest of Formula I is fixed. Note that in J-5, X is O or S, and that when X is O, J-5 is a subset of J-29 in which the attachment point to the rest of Formula I is fixed, and that when X is S, J-5 is a subset of J-30 in which the attachment point to the rest of Formula I is fixed. Preferred attachment points of J-17 and J-22 are at the positions indicated as 4 or 5 of the oxazoline J-17 and thiazoline J-22.

Exhibit 1

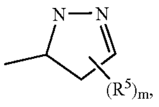
J-1

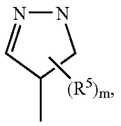
J-2

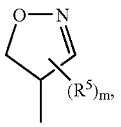
J-3

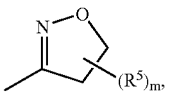
J-4

-continued

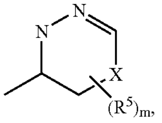
J-5

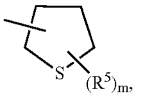
J-6

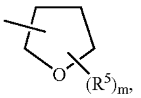
J-7

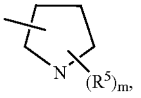
J-8

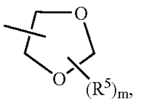
J-9

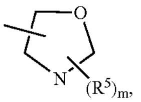
J-10

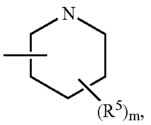
J-11

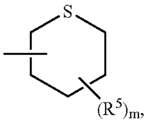
J-12

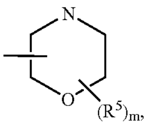
J-13

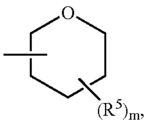
J-14

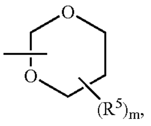
J-15

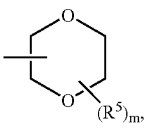
J-15

-continued

J-17

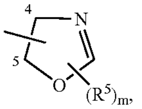

J-18

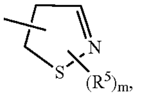

J-19

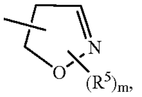

J-20

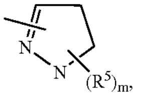

J-21

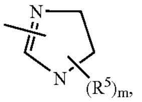

J-22

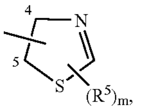

J-23

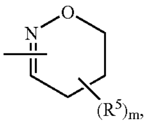

J-24

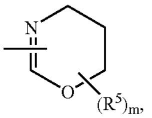

J-25

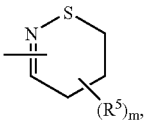

J-26

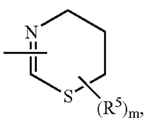

J-27

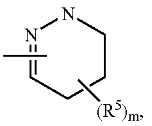

J-28

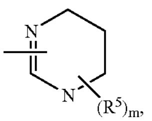

J-29

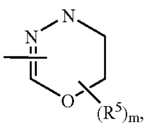

-continued

J-30

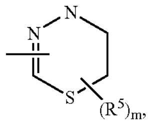

J-31

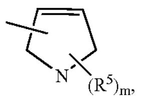

J-32

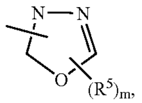

J-33

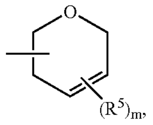

J-34

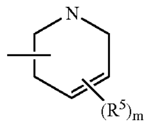

and

J-35

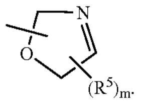

Examples of optional $R^5$ substituents when attached to J include those wherein each $R^5$ is independently H, $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $CO_2H$, $CONH_2$, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $C_1$–$C_4$ alkylamino, $C_2$–$C_8$ dialkylamino, $C_3$–$C_6$ cycloalkylamino, $C_2$–$C_6$ alkylcarbonyl, $C_2$–$C_6$ alkoxycarbonyl, $C_2$–$C_6$ alkylaminocarbonyl, $C_3$–$C_8$ dialkylaminocarbonyl, $C_3$–$C_6$ trialkylsilyl or W;

$(R^5)_2$ when attached to adjacent carbon atoms can be taken together as —$OCF_2O$—, —$CF_2CF_2O$—, or —$OCF_2CF_2O$—; and each W is independently a phenyl, benzyl, benzoyl, phenoxy, 5- or 6-membered heteroaromatic ring, a naphthyl ring system or an aromatic 8-, 9- or 10-membered fused heterobicyclic ring system, each ring or ring system optionally substituted with from one to three substituents independently selected from the group consisting of $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl.

As noted above, K is taken together with the two contiguous linking carbon atoms to form a phenyl ring or a 5- or 6-membered heteroaromatic ring, each ring optionally substituted. The term "optionally substituted" in connection with these K groups refers to K groups that are unsubstituted or have at least one non-hydrogen substituent that does not extinguish the biological activity. Examples of optionally substituted phenyl rings (K-38) and aromatic heterocyclic rings (K-1 to K-37) wherein said rings are optionally substituted with from 1 to 4 $R^4$ include the ring systems illustrated in Exhibit 2, wherein n is an integer from 1 to 4 and $R^4$ is as defined below. As with the carbon atoms in the ring, the nitrogen atoms that require substitution to fill their valence are substituted with hydrogen or with $R^4$. Although $(R^4)_n$ groups are shown in the structures K-1 to K-38, it is noted that $R^4$ does not need to be present since it is an optional substituent. Note that some K groups can only be substituted with less than 3 $R^4$ groups (e.g. K-7 through K-10, K-15, K-16, K-20, K-21, K-23, K-24, K-26 and K-27 can only be substituted with one $R^4$). In the exemplified K groups, the upper right bond is attached through the available linking carbon atom to the nitrogen atom of the $NR^1({=}A)J$ portion of Formula I and the lower right bond is attached through the available linking carbon atom to the carbon atom of the $C({=}B)NR^2R^3$ portion of Formula I. The wavy line indicates that the K ring is attached to the remainder of Formula I as illustrated below in Formula Ia.

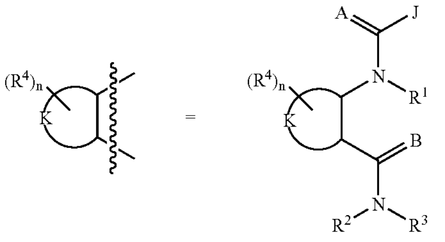

Ia

Exhibit 2

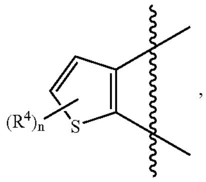
,

K-1

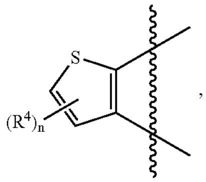
,

K-2

-continued

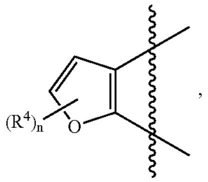
,

K-3

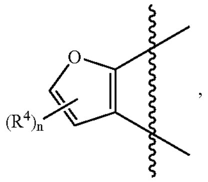
,

K-4

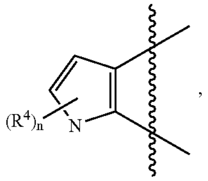
,

K-5

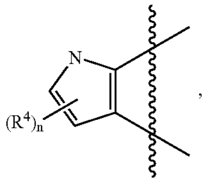
,

K-6

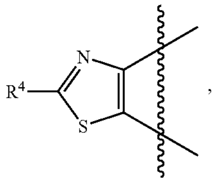
,

K-7

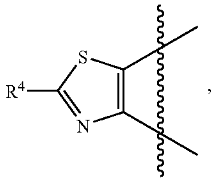
,

K-8

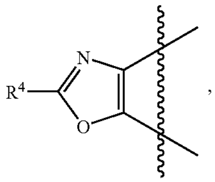
,

K-9

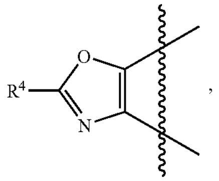
,

K-10

-continued
K-11
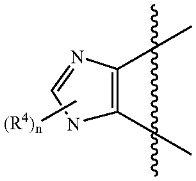
,
K-12
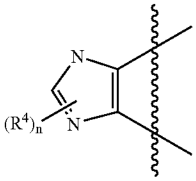
,
K-13
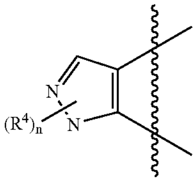
,
K-14
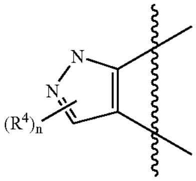
,
K-15
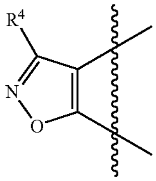
,
K-16
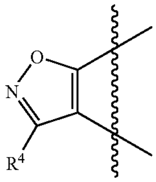
,
K-17
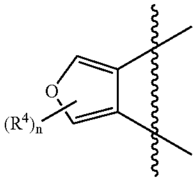
,
K-18
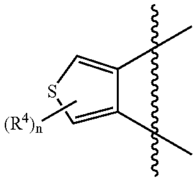
,
-continued
K-19
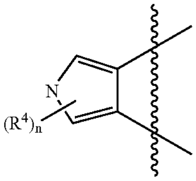
,
K-20
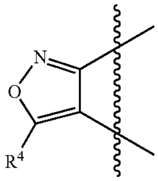
,
K-21
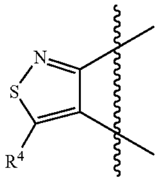
,
K-22
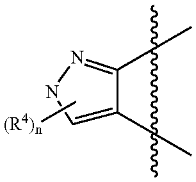
,
K-23
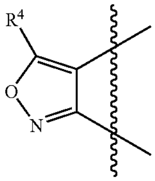
,
K-24
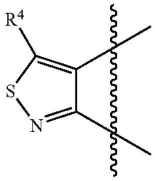
,
K-25
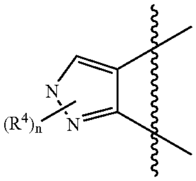
,
K-26
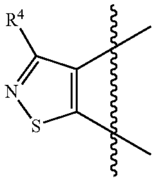
, -continued

K-27

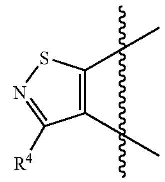

,

K-28

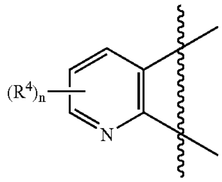

,

K-29

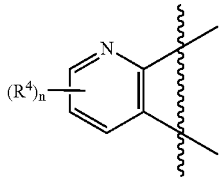

,

K-30

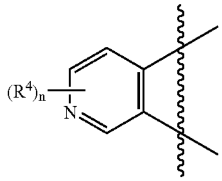

,

K-31

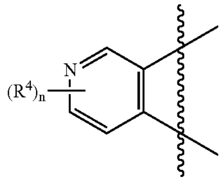

,

K-32

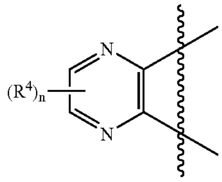

,

K-33

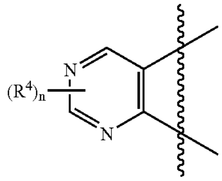

,

K-34

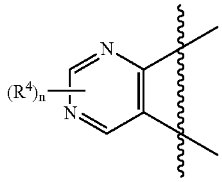

,

-continued

K-35

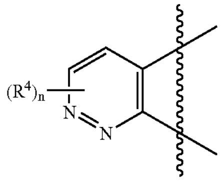

,

K-36

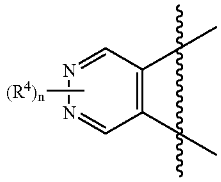

,

K-37

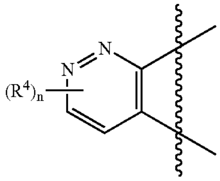

and

K-38

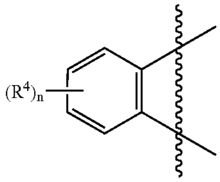

.

Preferred K rings include optionally substituted thiophene, isoxazole, isothiazole, pyrazole, pyridine, pyrimidine and phenyl rings. More preferred K rings include K-1, K-14, K-15, K-18, K-23, K-28, K-29, K-30, K-31, K33 and K-38. Most preferred K rings are K-28, K-31, K-33 and K-38.

Examples of optional $R^4$ substituents when attached to K include those wherein each $R^4$ is independently H, $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $NH_2$, $C_1$–$C_4$ alkylamino, $C_2$–$C_8$ dialkylamino, $C_3$–$C_6$ cycloalkylamino, or $C_3$–$C_6$ trialkylsilyl; or each $R^4$ is independently phenyl, benzyl or phenoxy, each optionally substituted with from one to three substituents selected from the group consisting of $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl and $C_3$–$C_6$ trialkylsilyl.

As noted above, $R^1$ is (among others) $C_1$–$C_6$ alkyl, $C_2$–$C_6$ alkenyl, $C_2$–$C_6$ alkynyl or $C_3$–$C_6$ cycloalkyl, each optionally substituted. The term "optionally substituted" in connection with these $R^1$ groups refers to $R^1$ groups that are unsubstituted or have at least one non-hydrogen substituent that does not extinguish the biological activity. Examples of optionally substituted $R^1$ groups include those optionally substituted with one or more substituents independently selected from the group consisting of halogen, CN, $NO_2$, hydroxy, $C_1$–$C_4$ alkoxy, $C_1$–$C_4$ alkylthio, $C_1$–$C_4$ alkylsulfinyl, $C_1$–$C_4$ alkylsulfonyl, $C_2$–$C_4$ alkoxycarbonyl, $C_1$–$C_4$ alkylamino, $C_2$–$C_8$ dialkylamino and $C_3$–$C_6$ cycloalkylamino. Of note are $R^1$ groups optionally substituted with from one to five substituents independently selected from the group above.

As noted above, $R^3$ is (among others) $C_1$–$C_6$ alkyl, $C_2$–$C_6$ alkenyl, $C_2$–$C_6$ alkynyl, $C_3$–$C_6$ cycloalkyl, each optionally substituted. The term "optionally substituted" in connection with these $R^3$ groups refers to $R^3$ groups that are unsubstituted or have at least one non-hydrogen substituent that does not extinguish the biological activity. Examples of optionally substituted $R^3$ groups include those optionally substituted with one or more substituents selected from the group consisting of halogen, G, CN, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_2$–$C_6$ alkoxycarbonyl, $C_2$–$C_6$ alkylcarbonyl, $C_3$–$C_6$ trialkylsilyl, or a phenyl, phenoxy or 5- or 6-membered heteroaromatic ring, each ring optionally substituted with from one to three substituents independently selected from $R^6$; $C_1$–$C_4$ alkylamino; $C_2$–$C_8$ dialkylamino; $C_3$–$C_6$ cycloalkylamino; $C_2$–$C_6$ alkoxycarbonyl or $C_2$–$C_6$ alkylcarbonyl. Of note are $R^3$ groups optionally substituted with from one to five substituents independently selected from the group above.

As noted above, $R^2$ and $R^3$ can be taken together with the nitrogen to which they are attached to form a ring containing 2 to 6 atoms of carbon and optionally one additional atom of nitrogen, sulfur or oxygen, and said ring may be optionally substituted. The term "optionally substituted" in connection with said rings refers to rings that are unsubstituted or have at least one non-hydrogen substituent that does not extinguish the biological activity. Examples of such optionally substituted rings include those optionally substituted with from 1 to 4 substituents independently selected from $R^7$ wherein each $R^7$ is independently $C_1$–$C_2$ alkyl, halogen, CN, $NO_2$ and $C_1$–$C_2$ alkoxy.

As noted above, G is a 5- or 6-membered nonaromatic carbocyclic or heterocyclic ring, optionally including one or two ring members selected from the group consisting of C(=O), SO or $S(O)_2$ and optionally substituted with 1 to 4 substituents selected from the group consisting of $C_1$–$C_2$ alkyl, halogen, CN, $NO_2$ and $C_1$–$C_2$ alkoxy. The term "optionally substituted" in connection with these G groups refers to groups which are unsubstituted or have at least one non-hydrogen substituent that does not extinguish the arthropodicidal activity possessed by the unsubstituted analog. Note that when the attachment point on the G group is illustrated as floating, the G group can be attached to the remainder of Formula I through any available carbon of the G group by replacement of a hydrogen atom. The optional substituents can be attached to any available carbon by replacing a hydrogen atom. Examples of 5- or 6-membered nonaromatic carbocyclic rings as G include the rings illustrated as G-1 through G-8 of Exhibit 3, wherein such rings are optionally substituted with 1 to 4 substituents selected from the group consisting of $C_1$–$C_2$ alkyl, halogen, CN, $NO_2$ and $C_1$–$C_2$ alkoxy. Examples of 5- or 6-membered nonaromatic heterocyclic rings as G include the rings illustrated as G-9 through G-38 of Exhibit 3, wherein such rings are optionally substituted with 1 to 4 substituents selected from the group consisting of $C_1$–$C_2$ alkyl, halogen, CN, $NO_2$ and $C_1$–$C_2$ alkoxy. Note that when G comprises a ring selected from G-31 through G-34, G-37 and G-38, $Q^1$ is selected from O, S or N. Note that when G is G-11, G13, G-14, G16, G-23, G-24, G-30 through G-34, G-37 and G-38 and $Q^1$ is N, the nitrogen atom can complete its valence by substitution with either H or $C_1$–$C_2$ alkyl.

Exhibit 3

G-1

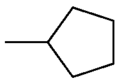,

G-2

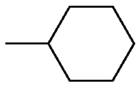,

G-3

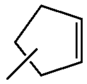,

G-4

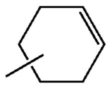,

G-5

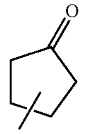,

G-6

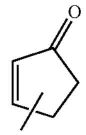,

G-7

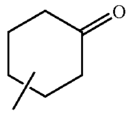,

G-8

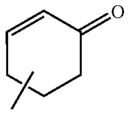,

G-9

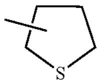,

G-10

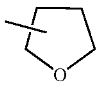,

G-11

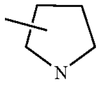,

G-12

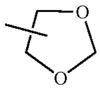,

G-13

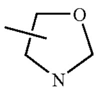,

-continued

G-14

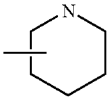 ,

G-15

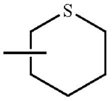 ,

G-16

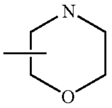 ,

G-17

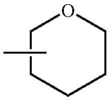 ,

G-18

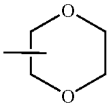 ,

G-19

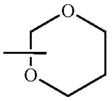 ,

G-20

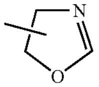 ,

G-21

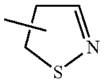 ,

G-22

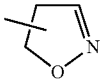 ,

G-23

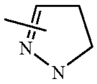 ,

G-24

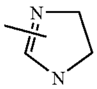 ,

G-25

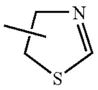 ,

G-26

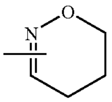 ,

G-27

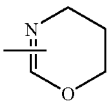 ,

-continued

G-28

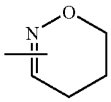 ,

G-29

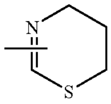 ,

G-30

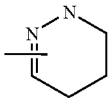 ,

G-31

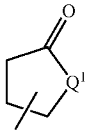 ,

G-32

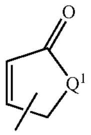 ,

G-33

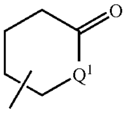 ,

G-34

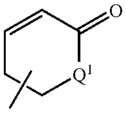 ,

G-35

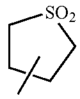 ,

G-36

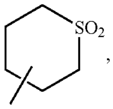 ,

G-37

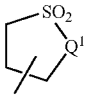 or

G-38

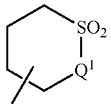 .

In the above recitations, “aromatic” indicates that each of the ring atoms is essentially in the same plane and has a p-orbital perpendicular to the ring plane, and in which $(4n+2)\pi$ electrons, when n is 0 or a positive integer, are associated with the ring to comply with Hückel’s rule. The term “aromatic ring system” denotes fully unsaturated carbocycles and heterocycles in which at least one ring of a polycyclic ring system is aromatic. Aromatic carbocyclic ring or ring systems includes fully aromatic carbocycles and carbocycles in which at least one ring of a polycyclic ring system is aromatic (e.g. phenyl and naphthyl). The term "nonaromatic carbocyclic ring" denotes filly saturated carbocycles as well as partially or fully unsaturated carbocycles where the Hückel rule is not satisfied by the ring. The term "hetero" in connection with rings or ring systems refers to a ring or ring system in which at least one ring atom is not carbon and which can contain 1 to 4 heteroatoms independently selected from the group consisting of nitrogen, oxygen and sulfur, provided that each ring contains no more than 4 nitrogens, no more than 2 oxygens and no more than 2 sulfurs. The terms "heteroaromatic ring or ring system" and "aromatic fused heterobicyclic ring system" includes fully aromatic heterocycles and heterocycles in which at least one ring of a polycyclic ring system is aromatic (where aromatic indicates that the Hückel rule is satisfied). The term "nonaromatic heterocyclic ring or ring system" denotes fully saturated heterocycles as well as partially or fully unsaturated heterocycles where the Hückel rule is not satisfied by any of the rings in the ring system. The heterocyclic ring or ring system can be attached through any available carbon or nitrogen by replacement of a hydrogen on said carbon or nitrogen.

The term "alkyl", used either alone or in compound words such as "alkylthio" or "haloalkyl" includes straight-chain or branched alkyl, such as methyl, ethyl, n-propyl, i-propyl, or the different butyl, pentyl or hexyl isomers. "Alkenyl" includes straight-chain or branched alkenes such as 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkylthio" includes branched or straight-chain alkylthio moieties such as methylthio, ethylthio, and the different propylthio and butylthio isomers. "Cycloalkyl" includes, for example, cyclopropyl, cyclobutyl, cyclopentyl and cyclohexyl.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. The terms "haloalkenyl", "haloalkynyl", "haloalkoxy", and the like, are defined analogously to the term "haloalkyl". Examples of "haloalkenyl" include $(Cl)_2C{=}CHCH_2$ and $CF_3CH_2CH{=}CHCH_2$. Examples of "haloalkynyl" include $HC{\equiv}CCHCl$, $CF_3C{\equiv}C$, $CCl_3C{\equiv}C$ and $FCH_2C{\equiv}CCH_2$. Examples of "haloalkoxy" include $CF_3O$, $CCl_3CH_2O$, $HCF_2CH_2CH_2O$ and $CF_3CH_2O$.

Examples of "alkylcarbonyl" include $C(O)CH_3$, $C(O)CH_2CH_2CH_3$ and $C(O)CH(CH_3)_2$. Examples of "alkoxycarbonyl" include $CH_3OC({=}O)$, $CH_3CH_2OC({=}O)$, $CH_3CH_2CH_2OC({=}O)$, $(CH_3)_2CHOC({=}O)$ and the different butoxy- or pentoxycarbonyl isomers. Examples of "alkylaminocarbonyl" include $CH_3NHC({=}O)$, $CH_3CH_2NHC({=}O)$, $CH_3CH_2CH_2NHC({=}O)$, $(CH_3)_2CHNHC({=}O)$ and the different butylamino- or pentylaminocarbonyl isomers. Examples of "dialkylaminocarbonyl" include $(CH_3)_2NC({=}O)$, $(CH_3CH_2)_2NC({=}O)$, $CH_3CH_2(CH_3)NC({=}O)$, $CH_3CH_2CH_2(CH_3)NC({=}O)$ and $(CH_3)_2CHN(CH3)C({=}O)$.

The total number of carbon atoms in a substituent group is indicated by the "$C_i$–$C_j$" prefix where i and j are numbers from 1 to 6. For example, $C_1$–$C_3$ alkylsulfonyl designates methylsulfonyl through propylsulfonyl; $C_2$ alkoxyalkyl designates $CH_3OCH_2$.

In the above recitations, when a compound of Formula I contains a heterocyclic ring, all substituents are attached to this ring through any available carbon or nitrogen by replacement of a hydrogen on said carbon or nitrogen.

When a group contains a substituent which can be hydrogen, for example $R^3$, then, when this substituent is taken as hydrogen, it is recognized that this is equivalent to said group being unsubstituted.

When a compound is substituted with a substituent bearing a subscript that indicates the number of said substituents can exceed 1, said substituents (when they exceed 1) are independently selected from the group of defined substituents. Further, when the subscript indicates a range, e.g. $(R)_{i-j}$, then the number of substituents maybe selected from the integers between i and j inclusive.

The term "optionally substituted with from one to three substituents" and the like indicates that from one to three of the available positions on the group may be substituted. When a group contains a substituent which can be hydrogen, for example $R^1$ or $R^5$, then, when this substituent is taken as hydrogen, it is recognized that this is equivalent to said group being unsubstituted.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the compounds of the invention may be present as a mixture of stereoisomers, individual stereoisomers, or as an optically active form.

The present invention comprises compounds selected from Formula I, N-oxides and agriculturally suitable salts thereof. One skilled in the art will appreciate that not all nitrogen containing heterocycles can form N-oxides since the nitrogen requires an available lone pair for oxidation to the oxide; one skilled in the art will recognize those nitrogen containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethydioxirane. These methods for the preparation of N-oxides have been extensively described and reviewed in the literature, see for example: T. L. Gilchrist in *Comprehensive Organic Synthesis*, vol. 7, pp 748–750, S. V. Ley, Ed., Pergamon Press; M. Tisler and B. Stanovnik in *Comprehensive Heterocyclic Chemistry*, vol. 3, pp 18–19, A. J. Boulton and A. McKillop, Eds., Pergamon Press; M. R. Grimmett and B. R. T. Keene in *Advances in Heterocyclic Chemistry*, vol. 43, pp 139–151, A. R. Katritzky, Ed., Academic Press; M. Tisler and B. Stanovnik in *Advances in Heterocyclic Chemistry*, vol. 9, pp 285–291, A. R. Katritzky and A. J. Boulton, Eds., Academic Press; and G. W. H. Cheeseman and E. S. G.

Werstiuk in *Advances in Heterocyclic Chemistry*, vol. 22, pp 390–392, A. R. Katritzky and A. J. Boulton, Eds., Academic Press.

The salts of the compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. The salts of the compounds of the invention also include those formed with organic bases (e.g., pyridine, ammonia, or triethylamine) or inorganic bases (e.g., hydrides, hydroxides, or carbonates of sodium, potassium, lithium, calcium, magnesium or barium) when the compound contains an acidic group such as a carboxylic acid or phenol.

Preferred compounds for reasons of cost, ease of synthesis and/or biological efficacy are:

Preferred 1. Compounds of Formula I illustrated as Formula Ia

Ia

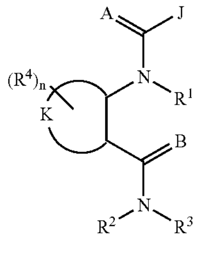

wherein

A and B are independently O or S;

J is

J-1

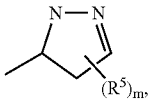

J-2

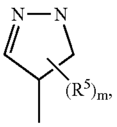

J-5

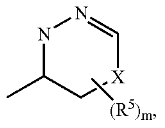

J-17

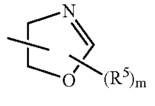

J-19

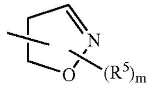

J-22

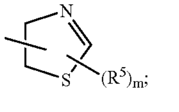

K is taken together with the two linking atoms to form a phenyl ring or a 5- or 6-membered heteroaromatic ring, each ring optionally substituted with from 1 to 4 $R^4$;

X is O or S;

$R^1$ is H; or $C_1$–$C_6$ alkyl, $C_2$–$C_6$ alkenyl, $C_2$–$C_6$ alkynyl or $C_3$–$C_6$ cycloalkyl each optionally substituted with one or more substituents independently selected from the group consisting of halogen, CN, $NO_2$, hydroxy, $C_1$–$C_4$ alkoxy, $C_1$–$C_4$ alkylthio, $C_1$–$C_4$ alkylsulfinyl, $C_1$–$C_4$ alkylsulfonyl, $C_2$–$C_4$ alkoxycarbonyl, $C_1$–$C_4$ alkylamino, $C_2$–$C_8$ dialkylamino and $C_3$–$C_6$ cycloalkylamino; or $R^1$ is $C_2$–$C_6$ alkylcarbonyl, $C_2$–$C_6$ alkoxycarbonyl, $C_2$–$C_6$ alkylaminocarbonyl or $C_3$–$C_8$ dialkylaminocarbonyl;

$R^2$ is H, $C_1$–$C_6$ alkyl, $C_2$–$C_6$ alkenyl, $C_2$–$C_6$ alkynyl, $C_3$–$C_6$ cycloalkyl, $C_1$–$C_4$ alkoxy, $C_1$–$C_4$ alkylamino, $C_2$–$C_8$ dialkylamino, $C_3$–$C_6$ cycloalkylamino, $C_2$–$C_6$ alkoxycarbonyl or $C_2$–$C_6$ alkylcarbonyl;

$R^3$ is H; G; $C_1$–$C_6$ alkyl, $C_2$–$C_6$ alkenyl, $C_2$–$C_6$ alkynyl, $C_3$–$C_6$ cycloalkyl, each optionally substituted with one or more substituents independently selected from the group consisting of halogen, G, CN, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_2$–$C_6$ alkoxycarbonyl, $C_2$–$C_6$ alkylcarbonyl, $C_3$–$C_6$ trialkylsilyl, or a phenyl, phenoxy or 5- or 6-membered heteroaromatic ring, each ring optionally substituted with from one to three substituents selected from $R^6$; $C_1$–$C_4$ alkylamino; $C_2$–$C_8$ dialkylamino; $C_3$–$C_6$ cycloalkylamino; $C_2$–$C_6$ alkoxycarbonyl or $C_2$–$C_6$ alkylcarbonyl; or $R^2$ and $R^3$ can be taken together with the nitrogen to which they are attached to form a ring containing 2 to 6 atoms of carbon and optionally one additional atom of nitrogen, sulfur or oxygen, said ring may be optionally substituted with from 1 to 4 substituents selected from $R^7$;

G is a 5- or 6-membered nonaromatic carbocyclic or heterocyclic ring, optionally including one or two ring members selected from the group consisting of C(=O), SO or $S(O)_2$ and optionally substituted with from 1 to 4 substituents selected from $R^7$;

each $R^4$ is independently H, $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $NH_2$, $C_1$–$C_4$ alkylamino, $C_2$–$C_8$ dialkylamino, $C_3$–$C_6$ cycloalkylamino, or $C_3$–$C_6$ trialkylsilyl; or each $R^4$ is independently phenyl, benzyl or phenoxy, each optionally substituted with from one to three substituents selected from $R^6$;

each $R^5$ is independently H, $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $CO_2H$, $CONH_2$, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $C_1$–$C_4$ alkylamino, $C_2$–$C_8$ dialkylamino, $C_3$–$C_6$ cycloalkylamino, $C_2$–$C_6$ alkylcarbonyl, $C_2$–$C_6$ alkoxycarbonyl, $C_2$–$C_6$ alkylaminocarbonyl, $C_3$–$C_8$ dialkylaminocarbonyl, $C_3$–$C_6$ trialkylsilyl or W;

$(R^5)_2$ when attached to adjacent carbon atoms can be taken together as $—OCF_2O—$, $—CF_2CF_2O—$, or $—OCF_2CF_2O—$;

each W is independently a phenyl, benzyl, benzoyl, phenoxy, 5- or 6-membered heteroaromatic ring or an aromatic 8-, 9- or 10-membered fused heterobicyclic ring system, each ring optionally substituted with from one to three substituents selected from $R^6$;

each $R^6$ is independently $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl;

each $R^7$ is independently $C_1$–$C_2$ alkyl, halogen, CN, $NO_2$ and $C_1$–$C_2$ alkoxy;

m is an integer from 1 to 7; and n is an integer from 1 to 3.

Preferred 2. Compounds of Preferred 1 wherein K is taken together with the two linking atoms to form a phenyl ring optionally substituted with from 1 to 3 $R^4$.

Preferred 3. Compounds of Preferred 1 wherein K is taken together with the two linking atoms to form a thiophene, pyrazole, isoxazole, pyridine or pyrimidine optionally substituted with from 1 to 3 $R^4$.

Preferred 4. Compounds of Preferred 2 or Preferred 3 wherein

A and B are both O;

n is 1 or 2;

$R^1$ is H, $C_1$–$C_4$ alkyl, $C_2$–$C_4$ alkenyl, $C_2$–$C_4$ alkynyl, $C_3$–$C_6$ cycloalkyl, $C_2$–$C_6$ alkylcarbonyl or $C_2$–$C_6$ alkoxycarbonyl;

$R^2$ is H, $C_1$–$C_4$ alkyl, $C_2$–$C_4$ alkenyl, $C_2$–$C_4$ alkynyl, $C_3$–$C_6$ cycloalkyl, $C_2$–$C_6$ alkylcarbonyl or $C_2$–$C_6$ alkoxycarbonyl;

$R^3$ is H; or $C_1$–$C_6$ alkyl, $C_2$–$C_6$ alkenyl, $C_2$–$C_6$ alkynyl or $C_3$–$C_6$ cycloalkyl each optionally substituted with one or more substituents selected from the group consisting of halogen, CN, $C_1$–$C_2$ alkoxy, $C_1$–$C_2$ alkylthio, $C_1$–$C_2$ alkylsulfinyl and $C_1$–$C_2$ alkylsulfonyl;

one of the $R^4$ groups is attached to the K ring at one of the two positions ortho to the two linking atoms, and said $R^4$ is $C_1$–$C_4$ alkyl, $C_1$–$C_4$ haloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl or $C_1$–$C_4$ haloalkylsulfonyl;

each $R^5$ is independently H, $C_1$–$C_4$ alkyl, $C_1$–$C_4$ haloalkyl, halogen, CN, $NO_2$, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl or $C_2$–$C_4$ alkoxycarbonyl; and one $R^5$ is optionally W; and W is a phenyl ring or a 5- or 6-membered heteroaromatic ring, each ring optionally substituted with one to three substituents independently selected from $R^6$.

More preferred W groups can be independently phenyl, pyrazole, imidazole, triazole, pyridine or pyrimidine, each ring optionally substituted with from one to three substituents independently selected from the group consisting of $C_1$–$C_4$ alkyl, $C_1$–$C_4$ haloalkyl, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, halogen or CN. Examples of such preferred W groups include the rings illustrated as rings W-1 through W-19 illustrated in Exhibit 4, wherein each $R^6$ is selected from the group consisting of $C_1$–$C_4$ alkyl, $C_1$–$C_4$ haloalkyl, $C_1$–$C_4$ alkoxy, $C_1$–$C_4$ haloalkoxy, $C_1$–$C_4$ allylthio, $C_1$–$C_4$ alkylsulfinyl, $C_1$–$C_4$ alkylsulfonyl, halogen and CN and q is an integer from 1 to 3. As with the carbon atoms in the ring, the nitrogen atoms that require substitution to fill their valence are substituted with hydrogen or with $R^6$. Although $(R^6)_q$ groups are shown in the structures W-1 through W-19, it is noted that $R^6$ does not need to be present since it is an optional substituent. Note that some W groups can only be substituted with less than 3 $R^6$ groups (e.g. W-5, W-6, W-10, W-12 and W-13 can be substituted with no more than two $R^6$). Note that an $R^6$ may be attached to any available carbon or nitrogen atom of the W group by replacement of a hydrogen atom. Particularly preferred W groups include W-1 and W-14.

Exhibit 4

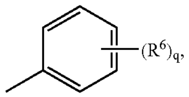

W-1

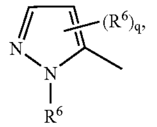

W-2

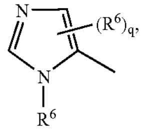

W-3

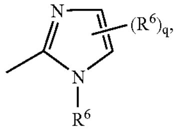

W-4

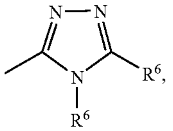

W-5

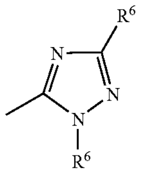

W-6

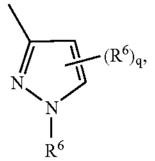

W-7

-continued

W-8

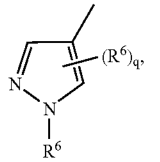

W-9

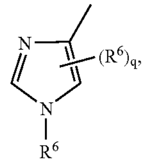

W-10

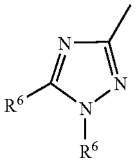

,

W-11

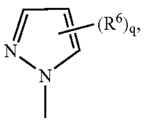

W-12

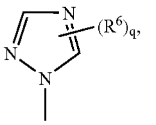

W-13

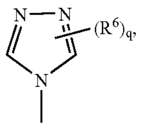

W-14

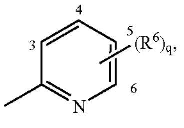

W-15

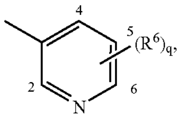

W-16

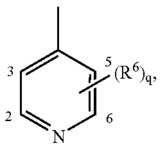

W-17

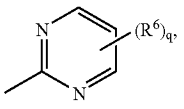

W-18

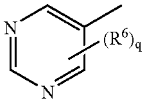

or

-continued

W-19

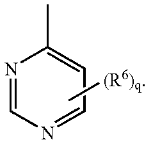

Preferred 5. Compounds of Preferred 4 wherein

J is J-36;

J-36

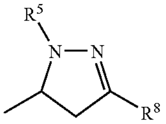

$R^1$ is H;

$R^2$ is H or $CH_3$;

$R^3$ is H; or $C_1$–$C_4$ alkyl, $C_1$–$C_4$ alkenyl or $C_1$–$C_4$ alkynyl, each optionally substituted with halogen, CN, $OCH_3$, $S(O)_pCH_3$;

each $R^4$ is independently $CH_3$, $CF_3$, CN or halogen, and one $R^4$ group is attached to the K ring at the atom adjacent to the $NR^1C({=}A)J$ moiety;

$R^5$ is H, $C_1$–$C_4$ alkyl, $C_1$–$C_4$ haloalkyl, or W;

W is

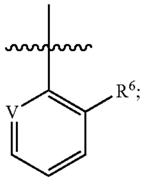

V is N, CH, CF, CCl, CBr or CI;

each $R^6$ and $R^8$ is independently H, $C_1$–$C_6$ alkyl, $C_3$–$C_6$ cycloalkyl, $C_1$–$C_6$ haloalkyl, halogen, CN, $C_1$–$C_4$ alkoxy, $C_1$–$C_4$ haloalkoxy or $C_1$–$C_4$ haloalkylthio;

m is 1 or 2; and p is 0, 1 or 2.

Note that J-36 is a subset of J-1 and $R^8$ is a subset of $R^5$.

Preferred 6. Compounds of Preferred 5 wherein V is N.

Preferred 7. Compounds of Preferred 5 wherein V is CH, CF, CCl or CBr.

Preferred 8. Compounds of Preferred 4 wherein

J is J-37;

J-37

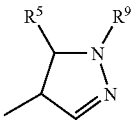

$R^1$ is H;

$R^2$ is H or $CH_3$;

$R^3$ is H; or $C_1$–$C_4$ alkyl, $C_1$–$C_4$ alkenyl or $C_1$–$C_4$ alkynyl, each optionally substituted with halogen, CN, $OCH_3$, $S(O)_pCH_3$;

each $R^4$ is independently $CH_3$, $CF_3$, CN or halogen, and one $R^4$ group is attached to the K ring at the atom adjacent to the $NR^1C(=A)J$ moiety;

$R^5$ is H, $C_1$–$C_4$ alkyl, $C_1$–$C_4$ haloalkyl, or W;

W is

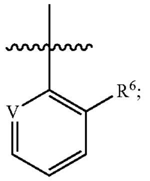

V is N, CH, CF, CCl, CBr or CI;

$R^6$ is independently H, $C_1$–$C_6$ alkyl, $C_3$–$C_6$ cycloalkyl, $C_1$–$C_6$ haloalkyl, halogen, CN, $C_1$–$C_4$ alkoxy, $C_1$–$C_4$ haloalkoxy or $C_1$–$C_4$ haloalkylthio;

$R^9$ is H, $C_1$–$C_6$ alkyl, $C_1$–$C_6$ haloalkyl, $C_3$–$C_6$ alkenyl, $C_3$–$C_6$ haloalkenyl, $C_3$–$C_6$ alkynyl or $C_3$–$C_6$ haloalkynyl;

m is 1 or 2; and p is 0, 1 or 2.

Note that J-37 is a subset of J-2 and $R^9$ is a subset of $R^5$.

Most preferred is the compound of Formula I selected from the group consisting of 1-(2-Chlorophenyl)-4,5-dihydro-N-[2-methyl-6-[[(1-methylethyl)amino]carbonyl]phenyl]-3-trifluoromethyl)-1H-pyrazole-5-carboxamide, Methyl 1-(2-chlorophenyl)-4,5-dihydro-5-[[[2-methyl-6-[[(1-methylethyl)amino]carbonyl]phenyl]amino]carbonyl]1H-pyrazole-3-carboxylate, Methyl 4,5-dihydro-5-[[[2-methyl-6-[[(1-methylethyl)amino]carbonyl]phenyl]amino]carbonyl]-1-(2-methylphenyl)-1H-pyrazole-3-carboxylate, 4,5-Dihydro-N-[2-methyl-6-[[(1-methylethyl)amino]carbonyl]phenyl]-1-(2-methylphenyl)-3-(trifluormethyl)-1H-pyrazole-5-carboxamide, 1-(2-Fluorophenyl)-4,5-dihydro-N-[2-methyl-6-[[(1-methylethyl)amino]carbonyl]phenyl]-3-(trifluoromethyl)-1H-pyrazole-5-carboxamide, N-[2-[[(1,1,-Dimethylethyl)amino]carbonyl]-6-methylphenyl]-4,5-dihydro-1-(2-methylphenyl)-3-(trifluoromethyl)-1H-pyrazole-5-carboxamide, and 1-(2,6-Difluorophenyl)-4,5-dihydro-N-[2-methyl-6-[[1-methylethyl)amino]carbonyl]phenyl]-3-(trifluoromethyl)-1H-pyrazole-5-carboxamide.

This invention also pertains to a composition for controlling an invertebrate pest comprising a biologically effective amount of a compound of Formula I, an N-oxide thereof or a suitable salt thereof and at least one additional component selected from the group consisting of surfactants, solid diluents and liquid diluents. This invention also pertains to a composition comprising a biologically effective amount of a compound of Formula I, an N-oxide thereof or a suitable salt thereof and an effective amount of at least one additional biologically active compound or agent. The preferred compositions of the present invention are those which comprise the above preferred compounds.

This invention also pertains to a method for controlling an invertebrate pest comprising contacting the invertebrate pest or its environment with a biologically effective amount of a compound of Formula I, an N-oxide thereof or a suitable salt thereof (e.g., as a composition described herein). This invention also relates to such a method wherein the invertebrate pest or its environment is contacted with a biologically effective amount of a compound of Formula I, an N-oxide thereof or a suitable salt thereof, or a composition comprising the compound, N-oxide thereof or a suitable salt thereof and a biologically effective amount of at least one additional compound or agent for controlling an invertebrate pest. The preferred methods of use are those involving the above preferred compounds.

Of note are compounds of Formula I, and N-oxides or agriculturally suitable salts thereof

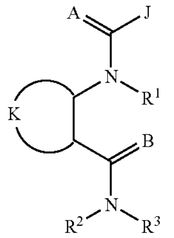

I wherein

A and B are independently O or S;

J is an optionally substituted 5- or 6-membered nonaromatic heterocyclic ring;

K is taken together with the two contiguous linking carbon atoms to form a phenyl ring or a 5- or 6-membered heteroaromatic ring, each ring optionally substituted;

$R^1$ is H; $C_1$–$C_6$ alkyl, $C_2$–$C_6$ alkenyl, $C_2$–$C_6$ alkynyl or $C_3$–$C_6$ cycloalkyl, each optionally substituted; $C_2$–$C_6$ alkylcarbonyl; $C_2$–$C_6$ alkoxycarbonyl; $C_2$–$C_6$ alkylaminocarbonyl or $C_3$–$C_8$ dialkylaminocarbonyl;

$R^2$ is H, $C_1$–$C_6$ alkyl, $C_2$–$C_6$ alkenyl, $C_2$–$C_6$ alkynyl, $C_3$–$C_6$ cycloalkyl, $C_1$–$C_4$ alkoxy, $C_1$–$C_4$ alkylamino, $C_2$–$C_8$ dialkylamino, $C_3$–$C_6$ cycloalkylamino, $C_2$–$C_6$ alkoxycarbonyl or $C_2$–$C_6$ alkylcarbonyl;

$R^3$ is H; G; $C_1$–$C_6$ alkyl, $C_2$–$C_6$ alkenyl, $C_2$–$C_6$ alkynyl, $C_3$–$C_6$ cycloalkyl, each optionally substituted; or $R^2$ and $R^3$ can be taken together with the nitrogen to which they are attached to form a ring containing 2 to 6 atoms of carbon and optionally one additional atom of nitrogen, sulfur or oxygen, and said ring may be optionally substituted; and G is an optionally substituted 5- or 6-membered nonaromatic carbocyclic or heterocyclic ring, optionally including one or two ring members selected from the group consisting of C(=O), SO or $S(O)_2$.

Also of note are compounds for reasons of cost, ease of synthesis and/or biological efficacy:

Selection A. Compounds of Formula I illustrated as Formula Ia

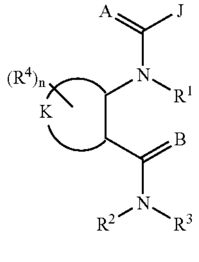

Ia wherein

A and B are independently O or S;

J is

J-1

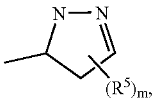

J-2

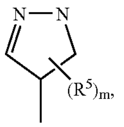

J-3

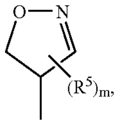

J-4

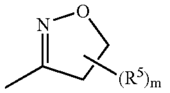

or

J-5

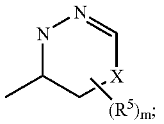

K is taken together with the two linking atoms to form a phenyl ring or a 5- or 6-membered heteroaromatic ring, each ring optionally substituted with from 1 to 4 $R^4$;

X is O or S;

$R^1$ is H; or $C_1$–$C_6$ alkyl, $C_2$–$C_6$ alkenyl, $C_2$–$C_6$ alkynyl or $C_3$–$C_6$ cycloalkyl each optionally substituted with one or more substituents selected from the group consisting of halogen, CN, $NO_2$, hydroxy, $C_1$–$C_4$ alkoxy, $C_1$–$C_4$ alkylthio, $C_1$–$C_4$ alkylsulfinyl, $C_1$–$C_4$ alkylsulfonyl, $C_2$–$C_4$ alkoxycarbonyl, $C_1$–$C_4$ alkylamino, $C_2$–$C_8$ dialkylamino and $C_3$–$C_6$ cycloalkylamino; or $R^1$ is $C_2$–$C_6$ alkylcarbonyl, $C_2$–$C_6$ alkoxycarbonyl, $C_2$–$C_6$ alkylaminocarbonyl or $C_3$–$C_8$ dialkylaminocarbonyl;

$R^2$ is H, $C_1$–$C_6$ alkyl, $C_2$–$C_6$ alkenyl, $C_2$–$C_6$ alkynyl, $C_3$–$C_6$ cycloalkyl, $C_1$–$C_4$ alkoxy, $C_1$–$C_4$ alkylamino, $C_2$–$C_8$ dialkylamino, $C_3$–$C_6$ cycloalkylamino, $C_2$–$C_6$ alkoxycarbonyl or $C_2$–$C_6$ alkylcarbonyl;

$R^3$ is H; G; $C_1$–$C_6$ alkyl, $C_2$–$C_6$ alkenyl, $C_2$–$C_6$ alkynyl, $C_3$–$C_6$ cycloalkyl, each optionally substituted with one or more substituents selected from the group consisting of halogen, G, CN, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_2$–$C_6$ alkoxycarbonyl, $C_2$–$C_6$ alkylcarbonyl, $C_3$–$C_6$ trialkylsilyl, or a phenyl, phenoxy or 5- or 6-membered heteroaromatic ring, each ring optionally substituted with one to three substituents independently selected from the group consisting of $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl; $C_1$–$C_4$ alkoxy; $C_1$–$C_4$ alkylamino; $C_2$–$C_8$ dialkylamino; $C_3$–$C_6$ cycloalkylamino; $C_2$–$C_6$ alkoxycarbonyl or $C_2$–$C_6$ alkylcarbonyl; or $R^2$ and $R^3$ can be taken together with the nitrogen to which they are attached to form a ring containing 2 to 6 atoms of carbon and optionally one additional atom of nitrogen, sulfur or oxygen, said ring may be optionally substituted with from 1 to 4 substituents selected from the group consisting of $C_1$–$C_2$ alkyl, halogen, CN, $NO_2$ and $C_1$–$C_2$ alkoxy;

G is a 5- or 6-membered nonaromatic carbocyclic or heterocyclic ring, optionally including one or two ring members selected from the group consisting of C(=O), SO or $S(O)_2$ and optionally substituted with from 1 to 4 substituents selected from the group consisting of $C_1$–$C_2$ alkyl, halogen, CN, $NO_2$ and $C_1$–$C_2$ alkoxy;

each $R^4$ is independently H, $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $C_1$–$C_4$ alkylamino, $C_2$–$C_8$ dialkylamino, $C_3$–$C_6$ cycloalkylamino, or $C_3$–$C_6$ trialkylsilyl; or each $R^4$ is independently phenyl, benzyl or phenoxy, each optionally substituted with from one to three substituents selected from the group consisting of $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl and $C_3$–$C_6$ trialkylsilyl;

each $R^5$ is independently H, $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $CO_2H$, $CONH_2$, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $C_1$–$C_4$ alkylamino, $C_2$–$C_8$ dialkylamino, $C_3$–$C_6$ cycloalkylamino, $C_2$–$C_6$ alkylcarbonyl, $C_2$–$C_6$ alkoxycarbonyl, $C_2$–$C_6$ alkylaminocarbonyl, $C_3$–$C_8$ dialkylaminocarbonyl, $C_3$–$C_6$ trialkylsilyl or W;

$(R^5)_2$ when attached to adjacent carbon atoms can be taken together as $—OCF_2O—$, $—CF_2CF_2O—$, or $—OCF_2CF_2O—$;

each W is independently a phenyl, benzyl, benzoyl, phenoxy, 5- or 6-membered heteroaromatic ring or an aromatic 8-, 9- or 10-membered fused heterobicyclic ring system, each ring optionally substituted with one to three substituents independently selected from the group consisting of $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl;

m is 1 to 7; and n is 1 to 3.

Selection B. Compounds of Selection A wherein K is taken together with the two linking atoms to form a phenyl ring optionally substituted with from 1 to 3 $R^4$.

Selection C. Compounds of Selection A wherein K is taken together with the two linking atoms to form a thiophene, pyrazole, isoxazole, pyridine or pyrimidine optionally substituted with from 1 to 3 $R^4$.

Selection D. Compounds of Selection B or Selection C wherein

A and B are both O;

n is 1 to 2;

$R^1$ is H, $C_1$–$C_4$ alkyl, $C_2$–$C_4$ alkenyl, $C_2$–$C_4$ alkynyl, $C_3$–$C_6$ cycloalkyl, $C_2$–$C_6$ alkylcarbonyl or $C_2$–$C_6$ alkoxycarbonyl;

$R^2$ is H, $C_1$–$C_4$ alkyl, $C_2$–$C_4$ alkenyl, $C_2$–$C_4$ alkynyl, $C_3$–$C_6$ cycloalkyl, $C_2$–$C_6$ alkylcarbonyl or $C_2$–$C_6$ alkoxycarbonyl;

$R^3$ is $C_1$–$C_6$ alkyl, $C_2$–$C_6$ alkenyl, $C_2$–$C_6$ alkynyl or $C_3$–$C_6$ cycloalkyl each optionally substituted with one or more substituents selected from the group consisting of halogen, CN, $C_1$–$C_2$ alkoxy, $C_1$–$C_2$ alkylthio, $C_1$–$C_2$ alkylsulfinyl and $C_1$–$C_2$ alkylsulfonyl;

one of the $R^4$ groups is attached to the K ring at one of the two positions ortho to the two linking atoms, and said $R^4$ is $C_1$–$C_4$ alkyl, $C_1$–$C_4$ haloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl or $C_1$–$C_4$ haloalkylsulfonyl;

each $R^5$ is independently H, $C_1$–$C_4$ alkyl, $C_1$–$C_4$ haloalkyl, halogen, CN, $NO_2$, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl or $C_2$–$C_4$ alkoxycarbonyl; and one $R^5$ is optionally W;

W is a phenyl ring or a 5- or 6-membered heteroaromatic ring, each ring optionally substituted with from one to three substituents independently selected from the group consisting of $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl.

Selection E. Compounds of Selection D wherein

J is J-1;

$R^1$ and $R^2$ are both H;

$R^3$ is $C_1$–$C_4$ alkyl, $C_2$–$C_4$ alkenyl or $C_2$–$C_4$ alkynyl, each optionally substituted with halogen, CN, $OCH_3$, $S(O)_pCH_3$;

each $R^4$ is independently $CH_3$, $CF_3$, $OCF_3$, $OCHF_2$, $S(O)_pCF_3$, $S(O)_pCHF_2$, CN or halogen;

each $R^5$ is independently H, halogen, $C_1$–$C_4$ alkyl, $CF_3$, $CHF_2$, $CH_2CF_3$, $S(O)_pCF_3$, $S(O)_pCHF_2$, $S(O)_pCH_2CF_3$, $S(O)_pCF_2CHF_2$ or CN; and one $R^5$ is optionally W;

W is a phenyl, pyrazole, imidazole, triazole, pyridine or pyrimidine ring, each ring optionally substituted with one to three substituents independently selected from the group consisting of $C_1$–$C_4$ alkyl, $C_1$–$C_4$ haloalkyl, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, halogen or CN;

m is 1 to 2; and p is 0, 1 or 2.

Selection F. Compounds of Selection E wherein W is a phenyl optionally substituted with $C_1$–$C_4$ alkyl, $C_1$–$C_4$ haloalkyl, halogen or CN.

Selection G. Compounds of Selection E wherein W is a pyrazole, imidazole, triazole, pyridine or pyrimidine, each ring optionally substituted with $C_1$–$C_4$ alkyl, $C_1$–$C_4$ haloalkyl, halogen or CN.

Selection H. Compounds of Selection D wherein

J is J-2;

$R^1$ and $R^2$ are both H;

$R^3$ is $C_1$–$C_4$ alkyl, $C_2$–$C_4$ alkenyl or $C_2$–$C_4$ alkynyl, each optionally substituted with halogen, CN, $OCH_3$, $S(O)_pCH_3$;

each $R^4$ is independently $CH_3$, $CF_3$, $OCF_3$, $OCHF_2$, $S(O)_pCF_3$, $S(O)_pCHF_2$, CN or halogen;

each $R^5$ is independently H, halogen, $C_1$–$C_4$ alkyl, $CF_3$, $S(O)_pCF_3$, $S(O)_pCHF_2$, $S(O)_pCH_2CF_3$, $S(O)_pCF_2CHF_2$ or CN; and one $R^5$ is optionally W;

W is a phenyl, pyrazole, imidazole, triazole, pyridine or pyrimidine ring, each ring optionally substituted with one to three substituents independently selected from the group consisting of $C_1$–$C_4$ alkyl, $C_1$–$C_4$ haloalkyl, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, halogen or CN;

m is 1 to 2; and p is 0, 1 or 2.

The compounds of Formula I can be prepared by one or more of the following methods and variations as described in Schemes 1–28. The definitions of A, B, J, K, V, W, X, $R^1$, $R^2$, $R^3$, $R^4$, $R^5$, m, n and q in the compounds of Formulae 1–59 below are as defined above. Compounds of Formulae Ib–Ie are various subsets of Formula I and compounds of Formula 1 are also subsets of Formula I. Compounds of Formulae 1a–c, 2a–g, 9a–b, 11a, 12a, 13a, 14a–c, 26a–c, 42a–c and 51a–d are various subsets of the compounds of Formula 1, 2, 9, 11, 12, 13, 14, 26, 42 and 51 respectively. In the Schemes, $R^{10}$ is $C_1$–$C_4$ alkyl, unless defined otherwise.

A typical procedure is illustrated in Scheme 1 and involves coupling of an ortho amino carboxylic acid amide of Formula 2 with an acid chloride of Formula 3 in the presence of an acid scavenger to provide the compound of Formula Ib. Typical acid scavengers include amine bases such as triethylamine, diisopropylethylamine and pyridine; other scavengers include hydroxides such as sodium and potassium hydroxide and carbonates such as sodium carbonate and potassium carbonate. In certain instances it is useful to use polymer-supported acid scavengers such as polymer-bound diisopropylethylamine and polymer-bound dimethylaminopyridine. In a subsequent step, amides of Formula Ib can be converted to thioamides of Formula Ic using a variety of standard thio transfer reagents including phosphorus pentasulfide and Lawesson's reagent.

Scheme 1

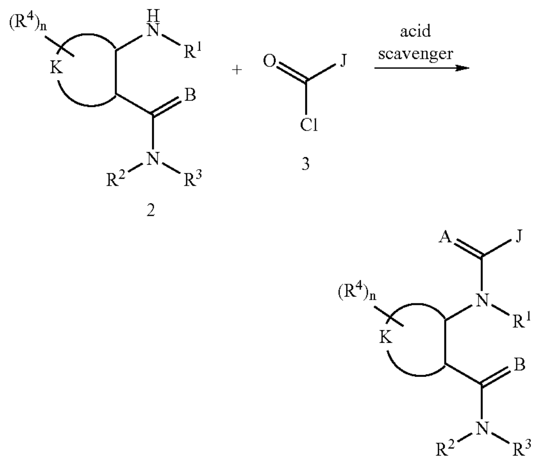

2 3

Ib (A is O)
Ic (A and B are both S)

An alternate procedure for the preparation of compounds of Formula Ib involves coupling of an amide of Formula 2 with an acid of Formula 4 in the presence of a dehydrative coupling agent such as dicyclohexylcarbodiimide (DCC) in Scheme 2. Polymer supported reagents such as polymer-bound cyclohexylcarbodiimide are useful here. Synthetic procedures of Schemes 1 and 2 are only representative examples of useful methods for the preparation of Formula I compounds by coupling an amine with an acid or acid equivalent, as the synthetic literature is extensive for this type of reaction.

Scheme 2

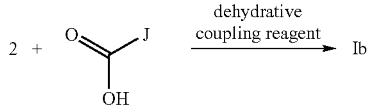

4

One skilled in the art will also realize that acid chlorides of Formula 3 may be prepared from acids of Formula 4 by numerous well-known methods.

A procedure for the preparation of compounds of Formula Id involves coupling of an ortho-amino carboxylic acid ester of Formula 5 (wherein $R^{10}$ is $C_1$–$C_4$ alkyl) with an acid chloride of Formula 3 by a method similar to that described in Scheme 1, followed by transformation of the ester group into an amide functionality. This transformation can be achieved by an amination with an amine of Formula 7. A Lewis acid, such as trimethylaluminum, as shown in Scheme 3 may promote this reaction.

Scheme 3

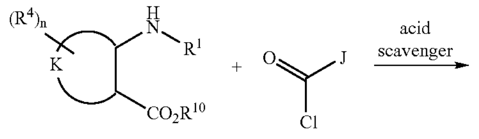

5 3

-continued

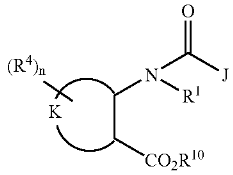

6

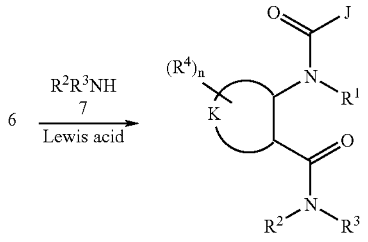

Id $R^{10}$ is $C_1$–$C_4$ alkyl

Alternatively the ester 6 can be transformed to an amide of Formula Id as shown in Scheme 4 by saponification with a base such as aqueous sodium hydroxide to provide the acid of Formula 8 followed by dehydrative coupling with an amine of Formula 7 by a procedure similar to that described in Scheme 2.

Scheme 4

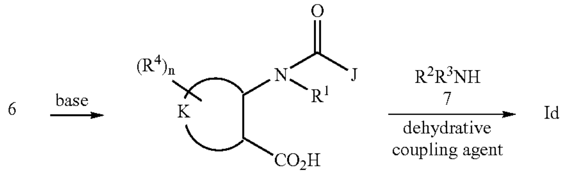

8

Of note are compounds of Formula I wherein K is an optionally substituted phenyl ring. A typical procedure is detailed in Scheme 5 and involves coupling of an anthranilic amide of Formula 2a with an acid chloride of Formula 3 in the presence of an acid scavenger to provide the compound of Formula Ie (a subset of Formula I). Typical acid scavengers include amine bases such as triethylamine, diisopropylethylamine and pyridine; other scavengers include hydroxides such as sodium and potassium hydroxide and carbonates such as sodium carbonate and potassium carbonate. In certain instances it is useful to use polymer-supported acid scavengers such as polymer-bound diisopropylethylamine and polymer-bound dimethylaminopyridine. In a subsequent step, amides of Formula Ie can be converted to thioamides of Formula If (a subset of Formula I) using a variety of standard thio transfer reagents including phosphorus pentasulfide and Lawesson's reagent.

Scheme 5

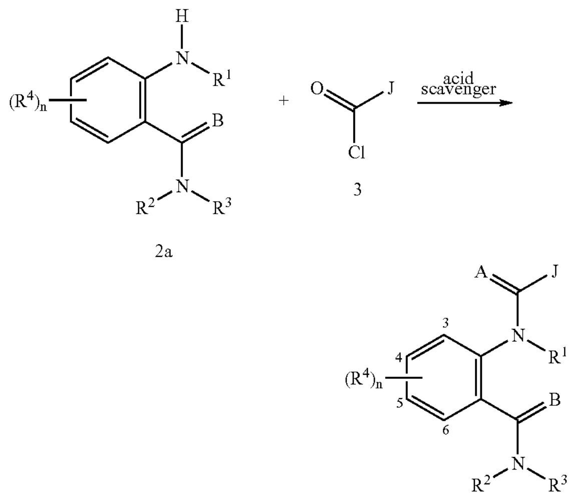

2a

3

Ie (A is O)
If (A and B are both S)

An alternate procedure for the preparation of compounds of Formula Ie involves coupling of an anthranilic amide of Formula 2a with an acid of Formula 4 in the presence of a dehydrative coupling agent such as dicyclohexylcarbodiimide (DCC) in Scheme 6. Polymer supported reagents such as polymer-bound cyclohexylcarbodiimide are again useful here. Synthetic procedures of Schemes 5 and 6 are only representative examples of useful methods for the preparation of Formula I compounds as the synthetic literature is extensive for this type of reaction.

Scheme 6

2a +

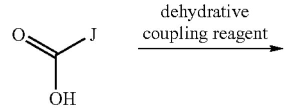

Ie

4

Anthranilic amides of Formula 2a are typically available from the corresponding 2-nitrobenzamides of Formula 9 via catalytic hydrogenation of the nitro group (Scheme 7). Typical procedures involve reduction with hydrogen in the presence of a metal catalyst such as palladium on carbon or platinum oxide and in hydroxylic solvents such as ethanol and isopropanol to provide compounds of Formula 2b (Compounds of Formula 2a wherein $R^1$ is H). These procedures are well documented in the chemical literature. $R^1$ substituents such as alkyl, substituted alkyl and the like can generally be introduced at this stage through known procedures including either direct alkylation or through the generally preferred method of reductive alkylation of the amine. A commonly employed procedure is to combine the aniline 2b with an aldehyde in the presence of a reducing agent such as sodium cyanoborohydride to produce the Formula 2c compounds (compounds of Formula 2a wherein $R^1$ is alkyl, alkenyl, alkynyl or substituted derivatives thereof).

Scheme 7

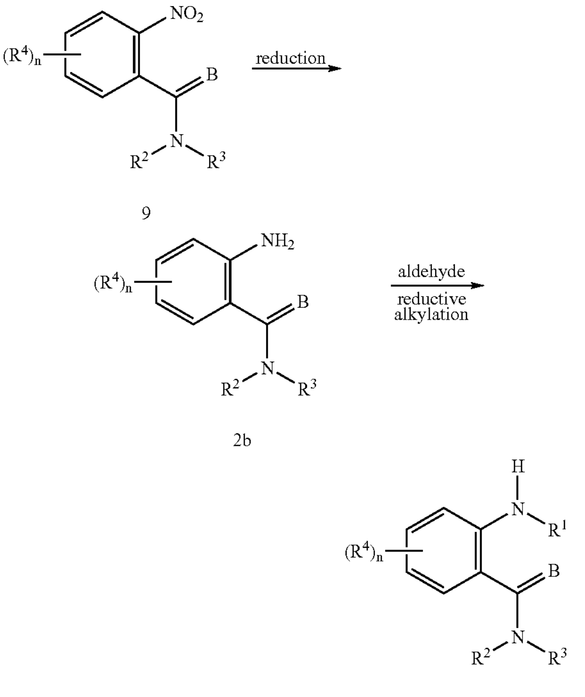

9

2b 2c ($R^1$ is other than H)

The intermediate amides of Formula 9a are readily prepared from commercially available 2-nitrobenzoic acids of Formula 10 (Scheme 8). Typical methods for amide formation can be applied here. These include direct dehydrative coupling of acids of Formula 10 with amines of Formula 7 using for example DCC, and conversion of the acids to an activated form such as the acid chlorides or anhydrides and subsequent coupling with amines to form amides of formula 9a. Ethyl chloroformate is an especially useful reagent for this type of reaction involving activation of the acid. The chemical literature is extensive on this type of reaction. Amides of Formula 9a are readily converted to thioamides of Formula 9b by using commercially available thio transfer reagents such as phosphorus pentasulfide and Lawesson's reagent.

Scheme 8

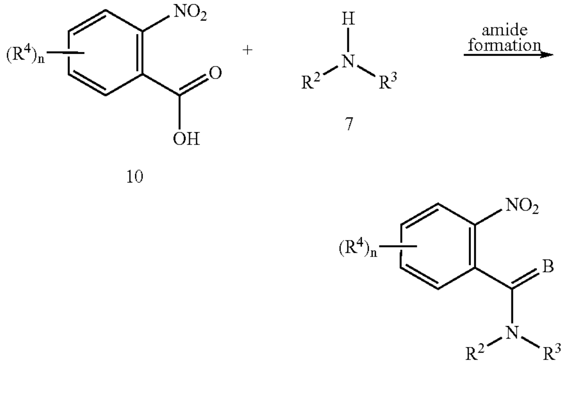

10

7

9a (B is O)
9b (B is S)

Intermediate ortho-amino carboxylic acid amides of Formulae 2d and 2e may also be prepared from anhydrides of Formulae 11 and 12 respectively (Scheme 9). Typical procedures involve combination of equimolar amounts of the amine 7 with the anhydride in polar aprotic solvents such as pyridine and dimethylformamide at temperatures ranging from room temperature to 100° C. $R^1$ substituents such as alkyl and substituted alkyl may be introduced by the base catalyzed alkylation of anhydride of Formula 11 with known alkylating reagents $R^1$-Lg (wherein Lg is a leaving group such as halogen, alkyl or aryl suphonates or alkyl sulfates) to provide the alkyl substituted intermediates of Formula 12. Anhydrides of Formula 11 may be made by methods described in Coppola, *Synthesis*, 1980, 505 and Fabis et al *Tetrahedron*, 1998, 10789.

Scheme 9

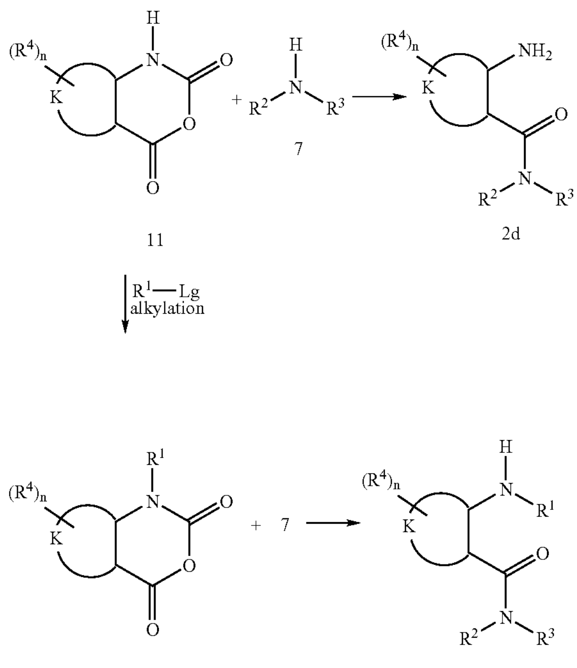

11 7 2d 12 2e ($R^1$ is other than H)

Intermediate anththranilic amides of Formula 2f and 2g may also be prepared from isatoic anhydrides of Formula 11a and 12a (Scheme 10). Typical procedures involve combination of equimolar amounts of the amine 7 with the isatoic anhydride in polar aprotic solvents such as pyridine or dimethylformamide at temperatures ranging from room temperature to 100° C. $R^1$ substituents such as alkyl and substituted alkyl may be introduced by the base catalyzed alkylation of isatoic anhydride 11a with known alkylating reagents $R^1$-Lg (wherein Lg is a leaving group such as halogen, alkyl or aryl suphonates or $OSO_2OR^1$) to provide the alkyl substituted intermediates 12a.

Scheme 10

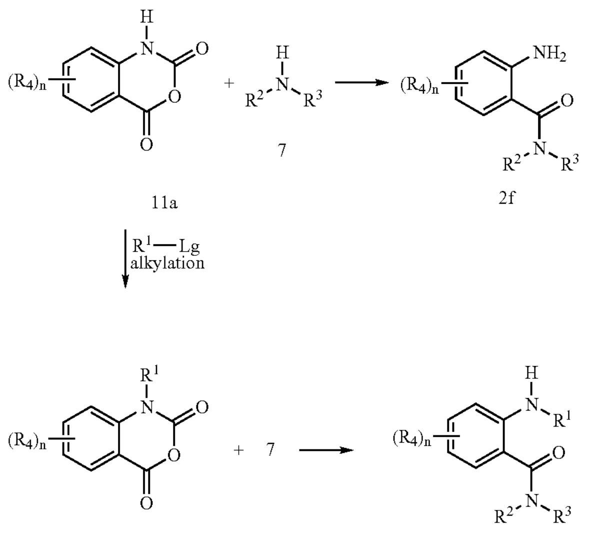

11a 7 2f 12a 2g ($R^1$ is other than H)

A procedure for the preparation of compounds of Formula Ig (compounds of Formula I wherein A is O, B is O and $R^1$ is H) involves reaction of an amine 7 with a heterocyclic fused oxazinone of Formula 13 (Scheme 11). Typical procedures involve combination of an amine 7 with a oxazinone in solvents such as tetrahydrofuran or pyridine at temperatures ranging from room temperature to the reflux temperature of the solvent. Oxazinones are well documented in the chemical literature and are available via known methods that involve the coupling of an ortho amino carboxylic acid with an acid chloride. For references to the synthesis and chemistry of heterocyclic fused oxazinones see Jakobsen et al, *Biorganic and Medicinal Chemistry*, 2000, 8, 2803–2812 and references cited therein.

Scheme 11

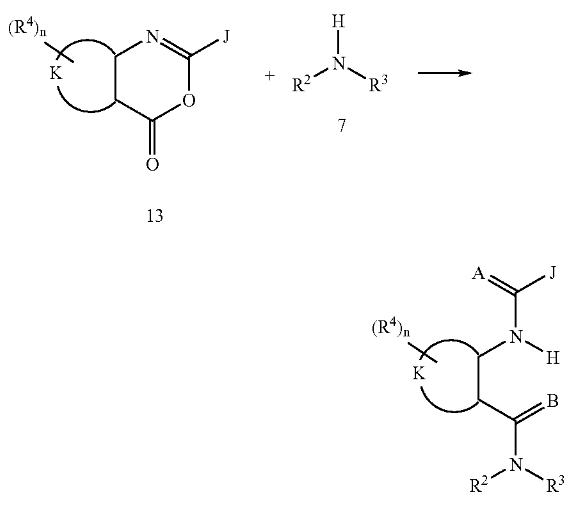

13 7

Ig
(A is O and B is O)

A procedure for the preparation of compounds of Formula Ih (compounds of Formula I wherein A is O, B is O and $R^1$ is H and K is optionally substituted phenyl) involves reaction of an amine 7 with a benzoxazinone of Formula 13a (Scheme 12). Typical procedures involve combination of the amine with the benzoxazinone in solvents such as tetrahydrofuran or pyridine at temperatures ranging from room temperature to the reflux temperature of the solvent. Benzoxazinones are well documented in the chemical literature and are available via known methods that involve the coupling of either an anthranilic acid or an isatoic anhydride with an acid chloride. For references to the synthesis and chemistry of Benzoxazinones see Jakobsen et al, *Biorganic and Medicinal Chemistry*, 2000, 8, 2095–2103 and references cited within. See also Coppola, *J. Heterocyclic Chemistry*, 1999, 36, 563–588.

Scheme 12

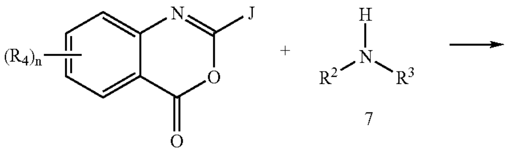

13a

7

-continued

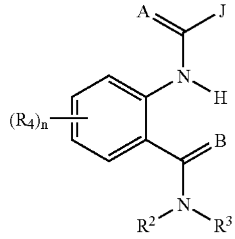

Ih
(A is O and B is O)

Methods of preparation of specific J-groups (and precursors thereof) are outlined in Schemes 13–28. In these schemes Z is any group attached to J that can be chemically transformed to provide compounds of Formula I. For example, Z may be $CO_2H$ (and Z-J corresponds to Formula 4), $CO_2(C_1–C_4$ alkyl), CN or $CH_2OH$. Compounds of Z-J wherein Z is $CO_2(C_1–C_4$ alkyl) or CN can be converted to compounds of Formula 4 by hydrolysis. The literature is extensive on the conversion of esters or nitriles to the corresponding carboxylic acids. Compounds of Z-J wherein Z is $CH_2OH$ can be converted to compounds of Formula 4 by oxidation. For the conversion of these compounds into compounds of Formula 4, numerous methods of oxidation are available and a selection may be found in *Comprehensive Organic Transformations*, Larock, R. C., VCH Publishers, Inc, 1989. Z may also be other groups corresponding to previously described intermediates summarized in Exhibit 5.

Exhibit 5

| Z | Z-J corresponds to | Z | Z-J corresponds to |
|---|---|---|---|
| 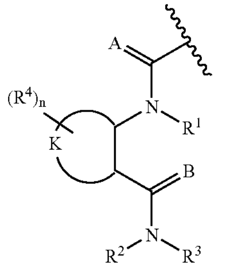 | Ib (A is O)<br>Ic (A is S, B is S)<br>Id (A is O, B is O)<br>Ig (A is O, B is O, $R^1$ is H) | 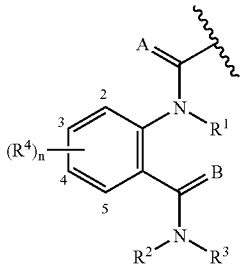 | Ie (A is O)<br>If (A is S)<br>Ih (A is O, B is O, $R^1$ is H) |
| 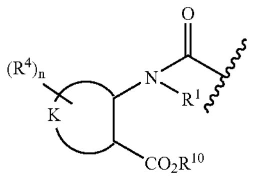<br>6 | | 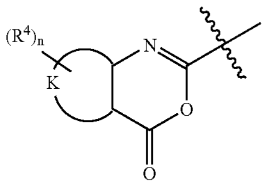<br>13 | |
| 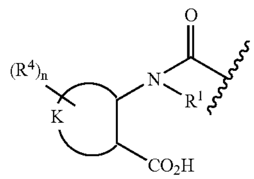<br>8 | | 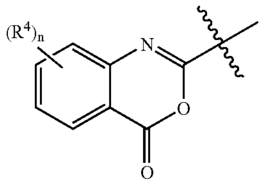<br>13a | |

Typical procedures for the preparation of some Z-J compounds are illustrated in Scheme 13 and involve cycloadditions of compounds of Formulae 15 or 16 with an alkene of Formula 14 to provide compounds of Formula 17.

Scheme 13

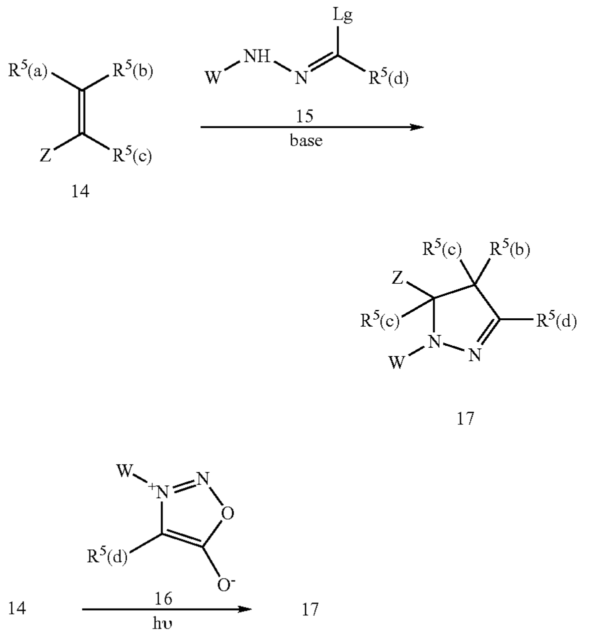

Cycloadditions of compounds of Formulae 18 or 19 provide compounds of Formulae 20 and 21 respectively (Scheme 14).

Scheme 14

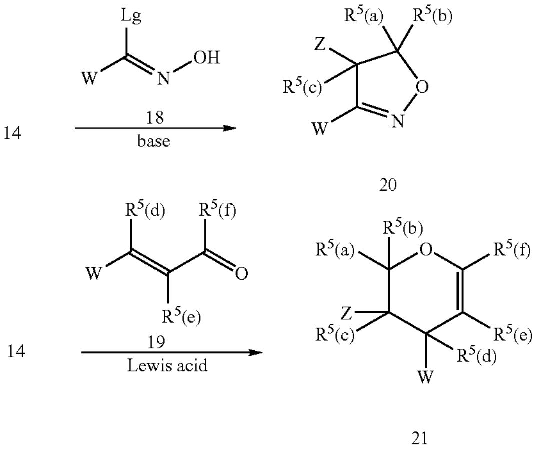

The cycloadditions can be 2+4 type such as a hetero-Diels Alder reaction (see for example Waldmann, H, *Synthesis*, 1994, 6, 535) or can be of the 2+3 type such as one of a number of 1,3-dipole cycloadditions (see *1,3-Dipolarcycloaddition Chemistry*, Padwa, A, Ed., J. Wiley & Sons, 1983).

Certain compounds of Formula 14a or 14b can be prepared by treating compounds of Formula 2 or 2a with acrylic acids of Formula 22 or acid chlorides of Formula 23 using methods analogous to those described above for Schemes 1, 2, 5 and 6 (Scheme 15). Compounds of Formula 14c can be prepared by treating compounds of Formula 5 with compounds of Formula 23 followed by further treatment with amines of Formula 7 using methods analogous to those described for Schemes 3 and 4.

Scheme 15

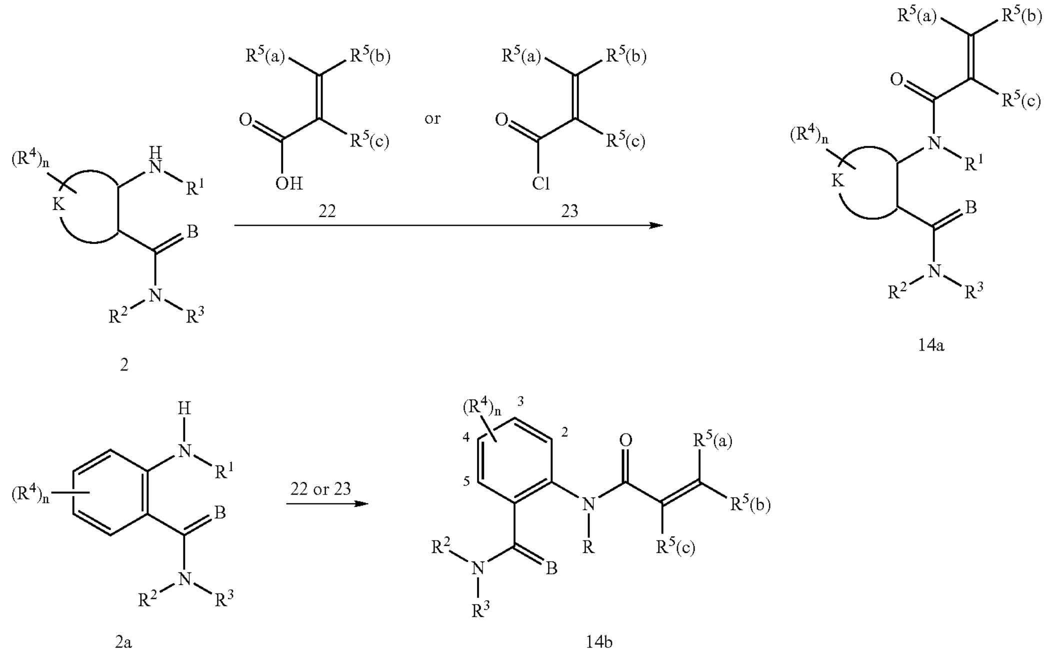

-continued

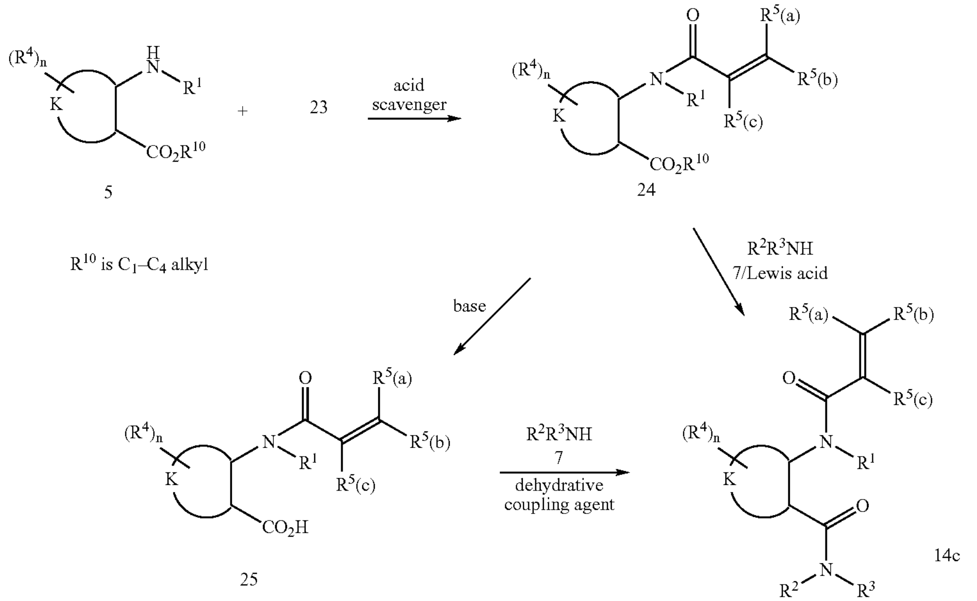

5, 24, 25, 14c $R^{10}$ is $C_1$–$C_4$ alkyl

Alternatively, some compounds of Formula Z-J can be prepared by a cycloaddition of compounds of Formula 27 or Formula 28, for example, with a glyoxyl or aldehydo derivative of Formula 26 to provide compounds of Formulae 29 and 30 respectively as shown in Scheme 16.

Scheme 16

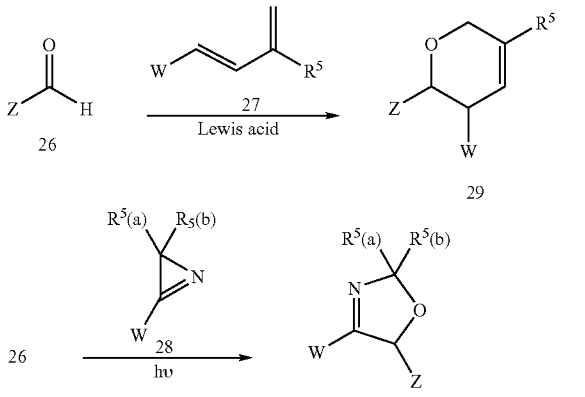

26, 27, 29, 26, 28, 30

Alternatively, compounds of Formula 33 (a subset of Z-J compounds) can be prepared by a cycloaddition of an alkene of Formula 32 with an oxime of Formula 31 (Scheme 17). Typically, the cycloaddition is accomplished by treatment of the oxime of Formula 31 with a halogenating agent such as N-chlorosuccinimide (NCS), followed by treatment with a suitable base such as triethylamine in the presence of the alkene of Formula 32.

Scheme 17

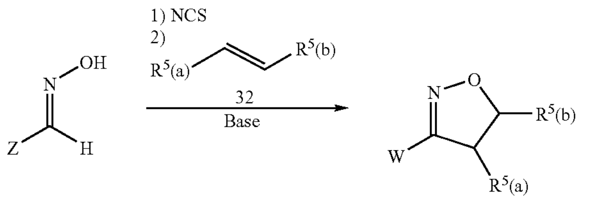

31, 32, 33

Certain compounds of Formula 26a or 26b can be prepared by treating compounds of Formula 2 or 2a with glyoxylic acid of Formula 34 or glyoxylic acid chloride of Formula 35 using methods analogous to those described above for Schemes 1, 2, 5 and 6 (Scheme 18). Compounds of Formula 26c can be prepared by treating compounds of Formula 5 with compounds of Formula 35 followed by further treatment with amines of Formula 7 using methods analogous to those described for Scheme 4.

Scheme 18

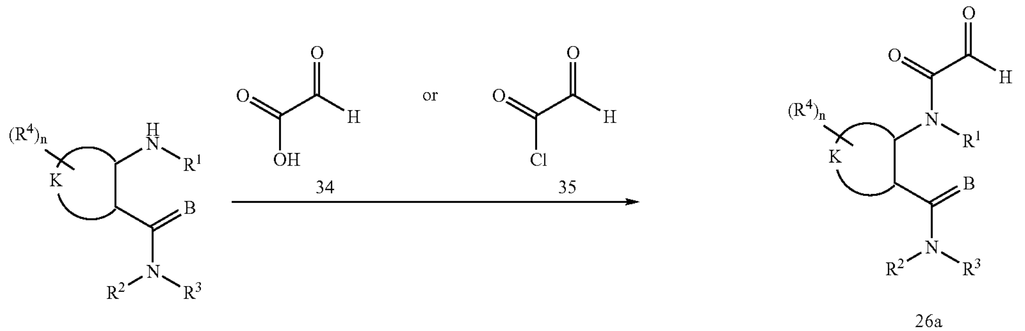

34 or 35

2, 26a

-continued

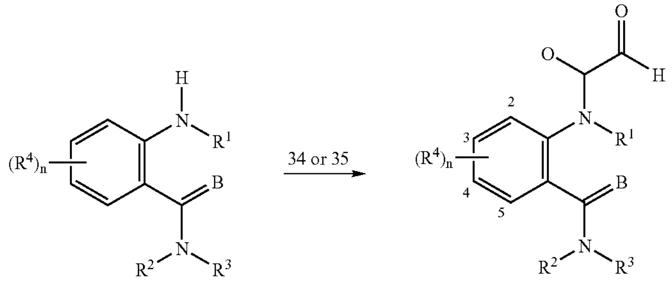

2a 26b

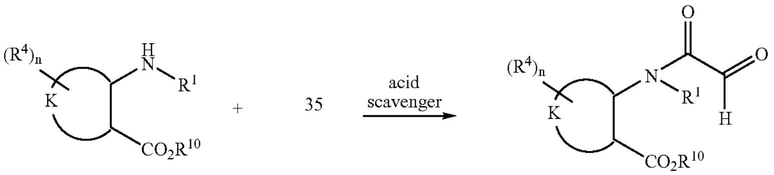

5 36

$R^{10}$ is $C_1$–$C_4$ alkyl

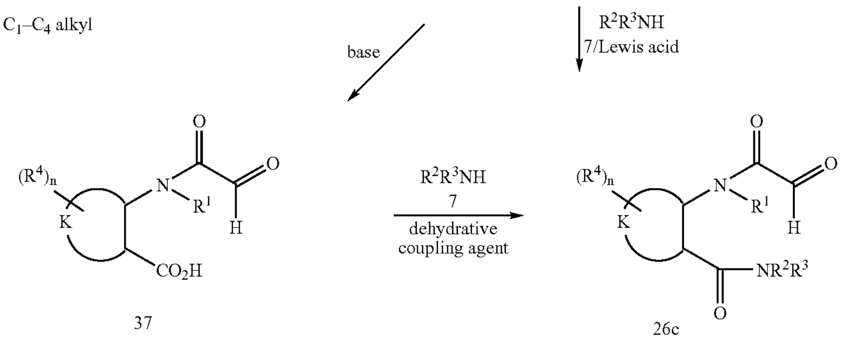

37 26c

Certain compounds of Formula Z-J (Formulae 40 and 42) can also be prepared by cyclization of a hydrazide of formula 38 or thiohydrazide of Formula 39 with a $C_1$ unit (Formula 26) or $C_2$ unit (Formula 41) respectively as illustrated in Scheme 19.

Scheme 19

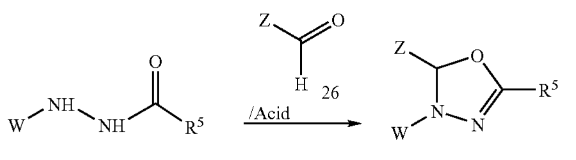

38 40

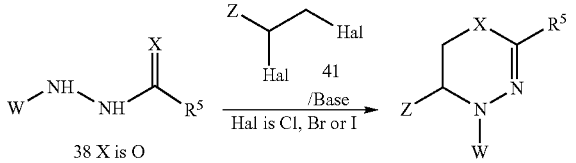

38 X is O
39 X is S

42 X is O or S

Certain compounds of Formula 42 can be prepared from compounds of Formula 38 or 39 by treatment with epihalohydrins of Formula 43 to provide compounds of Formula 42a (Scheme 20). Oxidation of compounds of Formula 42a provides compounds of Formula 42b, a subset of acids of Formula 4.

Scheme 20

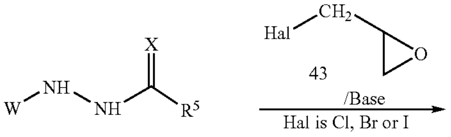

38 X is O
39 X is S

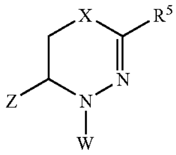

X is O or S
42a Z is $CH_2OH$
42b Z is COOH

Some compounds of Formula Z-J of Formula 45 can also be prepared by reduction of an aromatic heterocycle of Formula 44 (Scheme 21).

Scheme 21

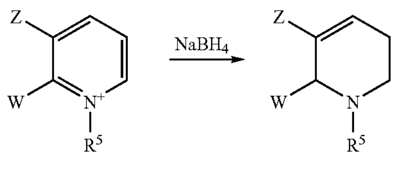

44 45

Oximes of Formula 31 can be obtained from compounds of Formula 26 by condensation with hydroxylamine under a number of conditions well known to those skilled in the art (Scheme 22).

Scheme 22

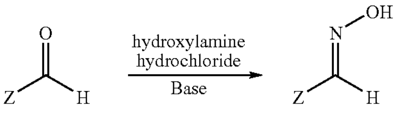

26 31

Some heterocyclic acids of Formula 47 (a subset of Formula 4) can be made via lithiation of a nonaromatic heterocycle of Formula 46 (e.g. using butyl lithium in the presence of tetramethylethylenediamine (TMEDA)) and treatment with carbon dioxide (Scheme 23).

Scheme 23

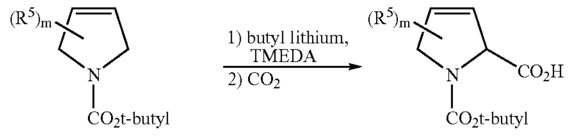

46 47

Some heterocyclic acids of Formula 51 can be prepared by the reaction sequence illustrated in Schemes 24–25.

As illustrated in Scheme 24, a compound of Formula 48 is treated with a compound of Formula 49 wherein $R^{10}$ is $C_1$–$C_4$ alkyl (a fumarate ester or maleate ester or a mixture thereof may be used) in the presence of a base and a solvent. The base is typically a metal alkoxide salt, such as sodium methoxide, potassium methoxide, sodium ethoxide, potassium ethoxide, potassium tert-butoxide, lithium tert-butoxide, and the like. Greater than 0.5 equivalents of base versus the compound of Formula 48 should be used, preferably between 0.9 and 1.3 equivalents. Greater than 1.0 equivalents of the compound of Formula 49 should be used, preferably between 1.0 to 1.3 equivalents. Polar protic and polar aprotic organic solvents can be used, such as alcohols, acetonitrile, tetrahydrofuran, N,N-dimethylformamide, dimethyl sulfoxide and the like. Preferred solvents are alcohols such as methanol and ethanol. It is especially preferred that the alcohol be the same as that making up the fumarate or maleate ester and the alkoxide base. The reaction is typically conducted by mixing the compound of Formula 48 and the base in the solvent. The mixture can be heated or cooled to a desired temperature and the compound of Formula 49 added over a period of time. Typically reaction temperatures are between 0° C. and the boiling point of the solvent used. The reaction may be conducted under greater than atmospheric pressure in order to increase the boiling point of the solvent. Temperatures between about 30 and 90° C. are generally preferred. The addition time can be as quick as heat transfer allows. Typical addition times are between 1 minute and 2 hours. Optimum reaction temperature and addition time vary depending upon the identities of the compounds of Formula 48 and Formula 49. After addition, the reaction mixture can be held for a time at the reaction temperature. Depending upon the reaction temperature, the required hold time may be from 0 to 2 hours. Typical hold times are 10 to 60 minutes. The reaction mass then can be acidified by adding an organic acid, such as acetic acid and the like, or an inorganic acid, such as hydrochloric acid, sulfuric acid and the like. Depending on the reaction conditions and the means of isolation, compounds of Formula 50 wherein $R^{11}$ is H or compounds of Formula 50 wherein $R^{11}$ is $C_1$–$C_4$ alkyl can be prepared. For example, a compound of Formula 50 wherein $R^{11}$ is $C_1$–$C_4$ alkyl can be hydrolyzed in situ to a compound of Formula 50 wherein $R^{11}$ is H when water is present in the reaction mixture. The desired product, a compound of Formula 50, can be isolated by methods known to those skilled in the art, such as crystallization, extraction or distillation.

Scheme 24

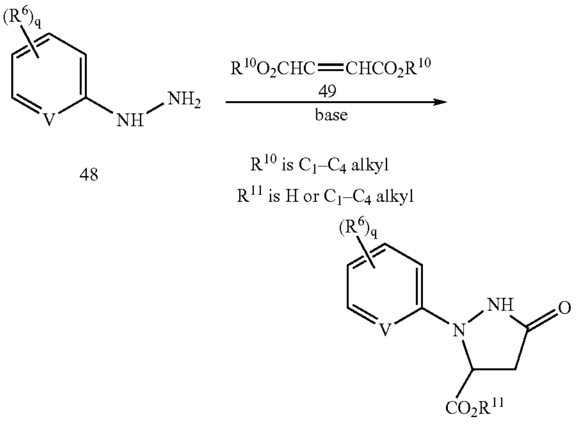

48

50

In the next step, illustrated as step 1 in Scheme 25, a compound of Formula 50 is treated with a halogenating reagent usually in the presence of a solvent. Halogenating reagents that can be used include phosphorus oxyhalides, phosphorus trihalides, phosphorus pentahalides, thionyl chloride, dihalotrialkylphophoranes, dihalodiphenylphosphoranes, oxalyl chloride and phosgene. Preferred are phosphorus oxyhalides and phosphorus pentahalides. To obtain complete conversion, at least 0.33 equivalents of phosphorus oxyhalide versus the compound of Formula 50 should be used, preferably between 0.33 and 1.2 equivalents. To obtain complete conversion, at least 0.20 equivalents of phosphorus pentahalide versus the compound of Formula 50 should be used, preferably between about 0.20 and 1.0 equivalents. Compounds of Formula 50 wherein $R^{11}$ is $C_1$–$C_4$ alkyl are preferred for this reaction.

Typical solvents for this halogenation include halogenated alkanes, such as dichloromethane, chloroform, chlorobutane and the like, aromatic solvents, such as benzene, xylene, chlorobenzene and the like, ethers, such as tetrahydrofaran, p-dioxane, diethyl ether, and the like, and polar aprotic solvents such as acetonitrile, N,N-dimethylformamide, and the like. Optionally, an organic base, such as triethylamine, pyridine, N,N-dimethylaniline or the like, can be added. Addition of a catalyst, such as N,N-dimethylformamide, is also an option. Preferred is the process in which the solvent is acetonitrile and a base is absent. Typically, neither a base nor a catalyst is required when acetonitrile solvent is used. The preferred process is conducted by mixing the compound of Formula 50 in acetonitrile. The halogenating reagent is then added over a convenient time and the mixture is then held at the desired temperature until the reaction is complete. The reaction temperature is typically between 20° C. and the boiling point of acetonitrile, and the reaction time is typically less than 2 hours. The reaction mass is then neutralized with an inorganic base, such as sodium bicarbonate, sodium hydroxide and the like, or an organic base, such as sodium acetate. The desired product, a compound of Formula 51, can be isolated by methods known to those skilled in the art, including crystallization, extraction and distillation.

Scheme 25

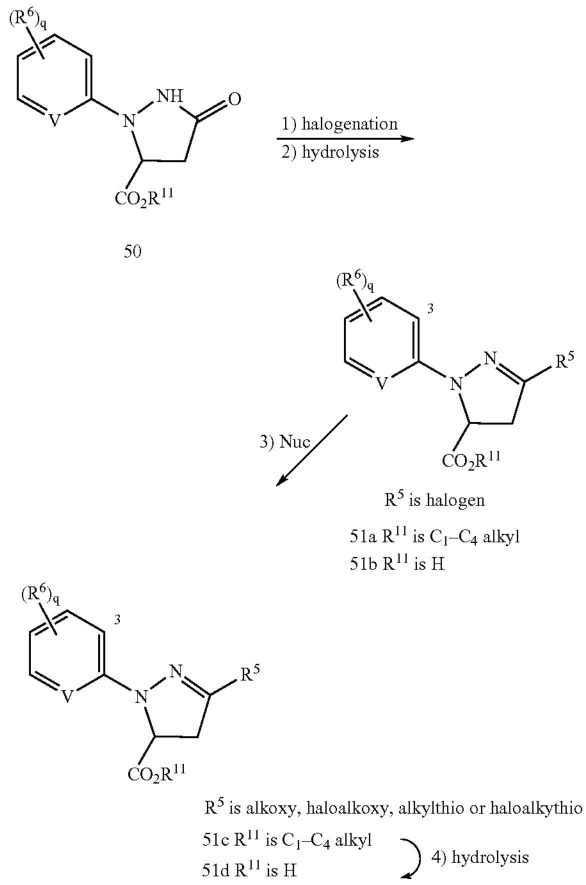

50

$R^5$ is halogen

51a $R^{11}$ is $C_1$–$C_4$ alkyl

51b $R^{11}$ is H $R^5$ is alkoxy, haloalkoxy, alkylthio or haloalkythio

51c $R^{11}$ is $C_1$–$C_4$ alkyl

51d $R^{11}$ is H

The halogen in compounds of Formula 51a may be displaced by a nucleophile (Nuc) such as the sodium or potassium salt of $C_1$–$C_4$ alkoxy, $C_1$–$C_4$ haloalkoxy, $C_1$–$C_4$ alkylthio or $C_1$–$C_4$ haloalkylthio (step 3 in Scheme 25). These displacements can be carried out in solvents such as ethers, such as tetrahydrofuran, p-dioxane, diethyl ether, and the like, and polar aprotic solvents such as acetonitrile, N,N-dimethylformamide, and the like. The reaction temperature is typically between 20° C. and the boiling point of the solvent.

The compounds of Formula 51a or Formula 51c wherein $R^{11}$ is $C_1$–$C_4$ alkyl, an ester, can be hydrolyzed to compounds of Formula 51b or Formula 51d, respectively, wherein $R^{11}$ is H, a carboxylic acid (step 2 or step 4 of Scheme 25). These hydrolyses can be catalyzed by acids, metal ions, and by enzymes. Iodotrimethylsilane is noted as an example of an acid which can be used to catalyze these hydrolyses (see *Advanced Organic Chemistry*, Third Ed., Jerry March, John Wiley & Sons, Inc. New York, 1985, pp. 334–338 for a review of methods). Base-catalyzed hydrolytic methods are not recommended for the hydrolysis of compounds of Formula 51 and can result in decomposition. The carboxylic acids can be isolated by methods known to those skilled in the art, including crystallization, extraction and distillation.

Some heterocyclic acids of Formula 55 can be prepared by the reaction sequence illustrated in Schemes 26–28.

As illustrated in Scheme 26, compounds of Formula 53 can be prepared from compounds of Formula 52 by treatment with a suitable base in a suitable organic solvent. Examples of suitable bases include (but are not limited to) sodium hydride, potassium t-butoxide, dimsyl sodium ($CH_3SOCH_2^-Na^+$), alkali metal (such as lithium, sodium or potassium) carbonates or hydroxides, tetraalkyl (such as methyl, ethyl or butyl)ammonium fluorides or hydroxides, or 2-tert-butylimino-2-diethylamino-1,3-dimethyl-perhydro-1,3,2-diazaphosphonine. Examples of suitable organic solvents include (but are not limited to) acetone, acetonitrile, tetrahydrofuran, dichloromethane, dimethylsulfoxide, or N,N-dimethylformamide. The cyclization reaction is usually conducted in a temperature range from about 0 to 120° C. The effects of solvent, base, temperature and addition time are all interdependent, and choice of reaction conditions is important to minimize the formation of byproducts. A preferred base is tetrabutylammonium fluoride. The intermediate formed in the reaction, Formula 53 wherein $M^+$ is a suitable counterion derived from the base, is then protonated by a suitable acid (for example, acetic acid) to give compounds of Formula 54a wherein $R^{12}$ is H. As one skilled in the art will know, intermediates such as 53 may be alkylated by the addition of a suitable alkylating agent to give compounds of Formula 54b wherein $R^{12}$ is $C_1$–$C_4$ alkyl. Alternatively, compounds of Formula 54b can be prepared from compounds of Formula 54a in a separate chemical step using a suitable base and alkylating agent. Suitable alkylating agents include $C_1$–$C_4$ alkyl halides (e.g. ethyl iodide), sulfates (e.g. dimethylsulfate) and sulfonates (e.g. methyl p-toluenesulfonate).

Cleavage of a compound of Formula 54b can provide a compound of 55. This conversion can be catalyzed by bases, nucleophiles, metal ions, and by enzymes. Some cleavage methods include treatment with lithium chloride or lithium iodide in solvents such as N,N-dimethylformamide or pyridine, treatment with magnesium iodide in toluene, and treatment with potassium-t-butoxide in dimethylsulfoxide or water. Methods of ester cleavage are reviewed in Greene, T. W.; Wuts, P. G. M. *Protective Groups in Organic Synthesis*, 2nd ed.; Wiley: New York, 1991. Acid-catalyzed hydrolytic methods are not recommended for the hydrolysis of compounds of Formula 54b and can result in decomposition. The carboxylic acid can be isolated by methods known to those skilled in the art, including crystallization, extraction and distillation.

Scheme 26

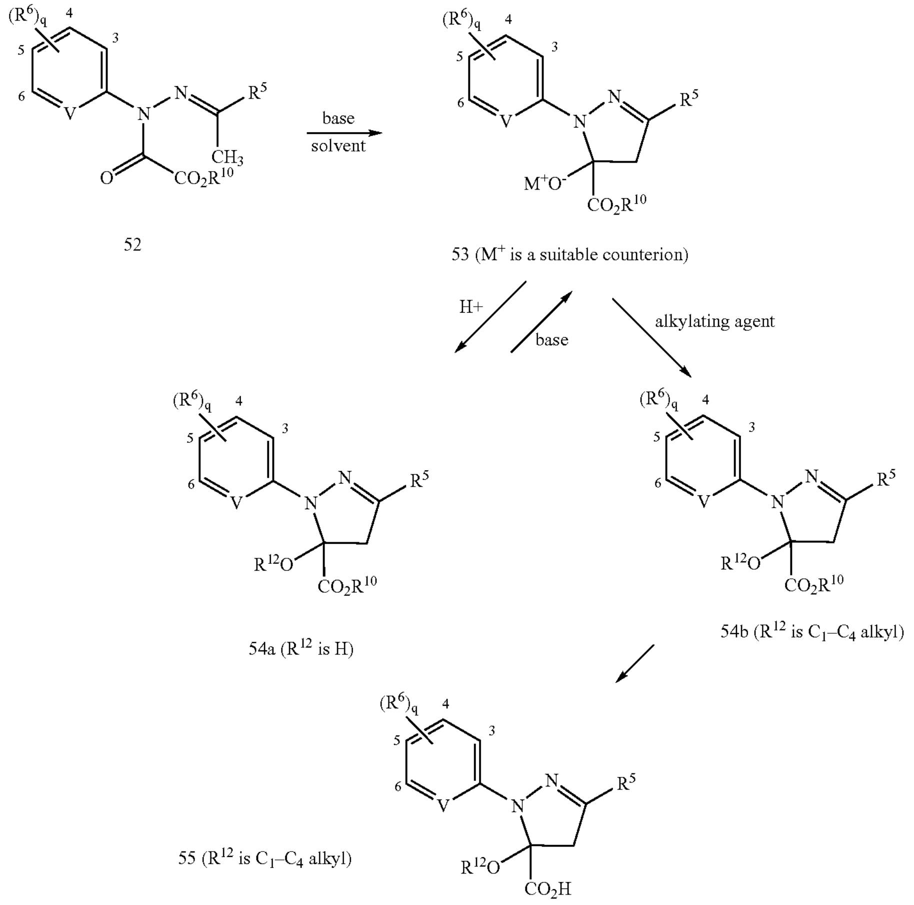

52

53 ($M^+$ is a suitable counterion)

54a ($R^{12}$ is H)

54b ($R^{12}$ is $C_1$–$C_4$ alkyl)

55 ($R^{12}$ is $C_1$–$C_4$ alkyl)

Compounds of Formula 52 can be prepared by treatment of compounds of Formula 56 with compounds of Formula 57 in a suitable organic solvent in the presence of an acid scavenger such as triethylamine. Examples of suitable organic solvents include (but are not limited to) dichioromethane and tetrahydrofuran. The reaction is usually conducted at a temperature between about 0 and 100° C. Scheme 27 illustrates this transformation.

Scheme 27

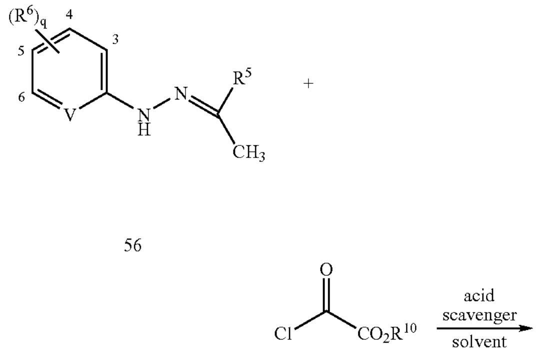

56

57

52

As illustrated by Scheme 28, the hydrazone compound of Formula 56 can be prepared from hydrazine compound of Formula 58 by treatment with a compound of Formula 59 in a solvent such as water, methanol or acetic acid. One skilled in the art will recognize that this reaction may require catalysis by an optional acid and may also require elevated temperatures depending on the molecular substitution pattern of the hydrazone of Formula 56.

Scheme 28

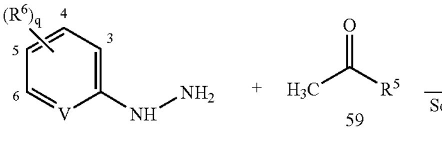

58

59

56

It is recognized that some reagents and reaction conditions described above for preparing compounds of Formula I may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula L. One skilled in the art will also recognize that it may be necessary to perform a combination of the steps illustrated in the above schemes in an order other than that implied by the particular sequence presented to prepare the compounds of Formula 1.

One skilled in the art will also recognize that compounds of Formula I and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except for chromatographic solvent mixtures or where otherwise indicated. Parts and percentages for chromatographic solvent mixtures are by volume unless otherwise indicated. $^1H$ NMR spectra are reported in ppm downfield from tetramethylsilane; s is singlet, d is doublet, t is triplet, q is quartet, m is multiplet, dd is doublet of doublets, dt is doublet of triplets, br s is broad singlet.

EXAMPLE 1

Preparation of 1-(2-Chlorophenyl)-4,5-dihydro-N-[2-methyl-6-[[(1-methylethyl)amino]carbonyl]phenyl]-3-trifluoromethyl)-1H-pyrazole-5-carboxamide Step A: Preparation of 3-methyl-N-(1-methylethyl-2-nitrobenzamide A solution of 3-methyl-2-nitrobenzoic acid (2.00 g, 11.0 mmol) and triethylamine (1.22 g, 12.1 mmol) in 25 mL of dichloromethane was cooled to 10° C. Ethyl chloroformate was carefully added and a solid precipitate formed. After the reaction mixture was stirred for 30 minutes, isopropylamine (0.94 g, 16.0 mmol) was added and a homogeneous solution resulted. The reaction mixture was stirred for an additional hour, poured into water and extracted with ethyl acetate. The organic extracts were washed with water, dried over magnesium sulfate and evaporated under reduced pressure to afford 1.96 g of the title compound as a white solid melting at 126–128° C.

$^1H$ NMR ($CDCl_3$) δ 1.24 (d,6H), 2.38 (s,3H), 4.22 (m,1H), 5.80 (br s,1H), 7.4 (m,3H).

Step B: Preparation of 2-amino-3-methyl-N-(1-methylethyl) benzamide

The 2-nitrobenzamide of Step A (1.70 g, 7.6 mmol) was hydrogenated over 5% Pd on carbon in 40 mL of ethanol at 345 kPa (50 psi). When the uptake of hydrogen ceased the reaction was filtered through Celite® and the Celite® was washed with ether. The filtrate was evaporated under reduced pressure to afford 1.41 g of the title compound as a solid melting at 149–151° C.

$^1H$ NMR ($CDCl_3$) δ 1.24 (dd,6H), 2.16 (s,3H), 4.25 (m,1H), 5.54 (br s,2H), 5.85 (br s,1H), 6.59 (t,1H), 7.13 (d,1H), 7.17 (d,1H).

Step) C: Preparation of 3-Methyl-N-(1-methylethyl)-2-[(1-oxo-2-propenyl)amino]benzamide To a solution of the title compound of Step B (0.93 g, 4.8 mmol) in dichloromethane (10 mL) was added triethylamine (0.876 mL, 6.2 mmol) and the mixture was cooled to 0° C. Acryloyl chloride (0.433 mL, 5.3 mmol) was then added and the mixture was warmed to ambient temperature and stirred overnight. Dimethylaminopyridine (1.0 g, 7.7 mmol) was then added followed by acryloyl chloride (0.475 mL, 5.8 mmol). The mixture was stirred at ambient temperature for 0.5 h before being diluted with 1N HCl and extracted twice with dichloromethane. The organic extracts were dried ($MgSO_4$) and concentrated to give the product of Step C (0.62 g) as a white solid.

$^1H$ NMR ($CDCl_3$) δ: 9.1 (bs, 1H); 7.4–7.1 (m, 3H), 6.5–6.3 (m, 2H), 6.1–6.0 (bd, 1H), 5.8–5.7 (m, 1H), 4.3–4.1 (m, 1H), 2.25 (s, 3H), 1.20 (d, 6H).

Step D: Preparation of N-(2-chlorophenyl)-2,2,2-trifluoroethanehydrazonic acid

To a solution of 2-chlorophenylhydrazine (1.65 g, 11.6 mmol) in tetrahydrofuran (40 mL) at 0° C. was added trifluoroacetic anhydride (1.8 mL, 12.8 mmol). The mixture was allowed to warm gradually to ambient temperature and stirred overnight. The mixture was concentrated, re-dissolved in ethyl ether and twice washed with a saturated solution of $NaHCO_3$. The mixture was dried ($MgSO_4$) and concentrated to give the title compound of Step D as a pale orange solid (2.77 g).

$^1H$ NMR ($CDCl_3$) δ: 7.32 (dd, 1H); 7.20 (s, 1H), 6.91 (td, 1H), 6.86 (dd, 1H), 6.49 (s, 1H).

Step E: Preparation of 4-Methylbenzenesulfonic acid anhydride with N-(2-chlorophenyl)-2,2,2-trifluoroethanehydrazonic acid To a solution of the title compound of Step D (2.77 g, 11.6 mmol) in ethyl acetate (20 mL) was added 4-Methyl morpholine (1.4 mL, 12.8 mmol) followed by p-toluenesulfonyl chloride (2.43 g, 12.8 mmol). The mixture was stirred overnight at ambient temperature and then diluted with ethyl ether, twice washed with 1N HCl, was dried ($MgSO_4$) and concentrated. The residue was triturated with hexane to yield the title compound of step E as a white solid.

$^1H$ NMR ($CDCl_3$) δ: 9.0–8.9 (bs, 1H), 8.0–7.9 (d, 2H), 7.6–7.5 (d, 1H); 7.5–7.4 (d, 2H), 7.4–7.2 (m, 2H), 7.0–6.9 (t, 1H), 2.50 (s, 3H).

Step F: Preparation of 1-(2-Chlorophenyl)-4,5-dihydro-N-[2-methyl-6-[[(1-methylethyl)amino]carbonyl]phenyl]-3-trifluoromethyl)-1H-pyrazole-5-carboxamide To a solution of the title compound of Step C (0.24 g, 0.98 mmol) in ethyl acetate (15 mL) was added 4-methyhmorpholine (0.267 mL, 2.45 mmol) and the compound of Step E (0.421 g, 1.08 mmol) and the mixture was heated at reflux for 24 hours. The mixture was cooled, diluted with dichloromethane, washed with water, dried ($MgSO_4$) and concentrated. The residue was purified by flash column chromatography (5% then 10% then 20% ethyl acetate in toluene) to give the title compound of Example 1, a compound of the invention, as a white solid (21 mg).

$^1H$ NMR ($CDCl_3$) δ: 9.4 (bs, 1H), 7.6–7.5 (d, 1H), 7.4–7.1 (m, 6H), 5.8 (bd, 1H), 5.4 (dd, 1H), 4.3–4.1 (m, 1H), 3.6–3.4 (m, 2H), 1.84 (s, 3H), 1.3–1.2 (m, 6H).

EXAMPLE 2

Preparation of Methyl 1-(2-chlorophenyl)-4,5-dihydro-5-[[[2-methyl-6-[[(1-methylethyl)amino]carbonyl]phenyl]amino]carbonyl]1H-pyrazole-3-carboxylate Step A: Preparation of Methyl (2E)-[(2-chlorophenyl)hydrazono]acetate To a solution of methyl glyoxylate (6.8 g, 77 mmol) in methanol (150 mL) was added 2-chlorophenylhydrazine hydrochloride (12.5 g, 77 mmol) and the mixture was heated at reflux overnight, cooled and concentrated. The residue was re-dissolved in toluene and concentrated to give the title compound of Step A.

$^1$H NMR ($CDCl_3$) δ: 12.6 (bs, 1H), 7.7–7.6 (d, 1H), 7.4–7.3 (d, 1H), 7.3–7.2 (m, 1H), 7.0–6.9 (m, 1H), 6.77 (s, 1H), 3.84 (s, 3H).

Step B: Preparation of Methyl (2Z)-bromo[(2-chlorophenyl)hydrazono]acetate

To a solution of the title compound of Step A (16.5 g, 77 mmol) in tetrahydrofuran (150 mL) was added N-bromosuccinimide (13.7 g, 77 mmol) and the mixture was stirred at ambient temperature for 2 hours. The mixture was concentrated and extracted with hexane and the hexane solution was concentrated to give the title compound of Step B (16 g) as an orange solid.

$^1$H NMR ($CDCl_3$) δ: 8.93 (bs, 1H), 7.63 (dd, 1H), 7.34 (dd, 1H), 7.28 (m, 1H), 6.98 (m, 1H), 3.95 (s, 3H).

Step C: Preparation of Methyl 1-(2-chlorophenyl)-4,5-dihydro-5-[[[2-methyl-6-[[(1-methylethyl)amino]carbonyl]phenyl]amino]carbonyl]1H-pyrazole-3-carboxylate To a solution of the product of Example 1, Step C (1.0 g, 4.1 mmol) and the product of Example 2, Step B (2.4 g, 8.2 mmol) in ethyl acetate (50 mL) was added 4-methyl-morpholine (1.1 mL, 12.3 mmol) and the mixture was heated at reflux for 2 hours. A further amount of 4-methylmorpholine was added (1.1 mL, 12.3 mmol) followed by the product of Step B (2.4 g, 8.2 mmol) and the reaction mixture was heated at reflux overnight. The mixture was stirred at ambient temperature for 2 days before being diluted with ethyl acetate, washed with 1N HCl, dried ($MgSO_4$) and concentrated. The residue was purified by flash column chromatography (10% then 20% then 30% ethyl acetate in toluene) to give compound the title compound of Example 2, a compound of the invention (22 mg) as an off white solid.

$^1$H NMR ($CDCl_3$) δ: 9.4–9.3 (bs, 1H), 7.6 (d, 1H), 7.4–7.3 (d, 1H), 7.3–7.0 (m, 5H), 5.8 (d, 1H), 5.5 (dd, 1H), 4.2–4.1 (m, 1H), 3.89 (s, 3H), 3.7–3.4 (m, 2H), 1.81 (s, 3H), 1.3–1.2 (m, 6H).

EXAMPLE 3

Preparation of 4-(2-Chlorophenyl)-5,6-dihydro-N-[2-methyl-6-[[(1-methylethyl)amino]carbonyl]phenyl]-2-(trifluoromethyl)-4H-1,3,4-oxadiazine-5-carboxamide Step A: Preparation of 4-(2-Chlorophenyl)-5,6-dihydro-2-(trifluoromethyl-4H-1,3,4-oxadiazine-5-methanol To a solution of the title compound of Example 1, step D (9.0 g, 37.7 mmol) in N,N-dimethylformamide (100 mL) was added potassium carbonate (7.8 g, 56.6 mmol) and epibromohydrin (5.6 mL, 45.3 mmol) and the mixture was heated at 90° C. for 1 hour. The mixture was then cooled, diluted with ethyl ether and twice washed with water. The solution was dried ($MgSO_4$), concentrated and purified by flash column chromatography (silica gel, 20% ethyl ether in petroleum ether) to give the title compound of step A contaminated with an equimolar amount of the regioisomer (2.4 g) as an orange oil.

$^1$H NMR ($CDCl_3$) δ 6 7.5–7.2 (m, 3H), 7.2–7.1 (m, 1H), 4.72 (dd, 1H), 4.60 (dd, 1H), 4.2–3.7 (2×m, 2H), 3.7 (m, 1H).

Step B: Preparation of 4-(2-Chlorophenyl)-5,6-dihydro-2-(trifluoromethyl)-4H-1,3,4-oxadiazine-5-carboxylic acid To a solution of the title compound of Step A (2.1 g, 7.1 mmol) in dichloromethane (30 mL) was added dried, powdered 4 Å molecular sieves (9 g) and pyridinium chlorochromate (1.54 g, 7.1 mmol) and the mixture was stirred at ambient temperature overnight. The mixture was then filtered through a pad of silica gel, washing with ethyl ether and concentrated. The residue was purified by flash column chromatography (silica gel, 20% then 40% ethyl ether in petroleum ether) to give 1.1 g of a colorless oil. This material was then dissolved in t-Butanol (35 mL) and water (35 mL). A solution of 2-methyl-2-butene (1.0M in tetrahydrofuran, 35 mL), sodium dihydrogen phosphate (3.16 g, 26.4 mmol) and sodium chlorate (2.9 g, 32.0 mmol) were then added and the mixture was stirred at ambient temperature overnight. The mixture was twice extracted with dichloromethane, dried ($MgSO_4$), concentrated and purified by flash column chromatography (silica gel, 40% ethyl ether in petroleum ether then ethyl ether then 10% methanol in dichloromethane) to give the title compound of step B (58 mg) as a colorless oil.

$^1$H NMR ($CDCl_3$) δ 7.6–7.5 (d, 1H), 7.4–7.2 (m, 2H), 7.1 (t, 1H), 5.6–5.0 (bs, 1H), 4.9 (s, 1H), 4.8 (d, 1H), 4.6 (m, 1H).

Step C: Preparation of 4-(2-Chlorophenyl)-5,6-dihydro-N-[2-methyl-6-[[(1-methylethyl)amino]carbonyl]phenyl]-2-(trifluoromethyl)-4H-1,3,4-oxadiazine-5-carboxamide To a solution of the title compound of Step B (58 mg, 0.19 mmol) in dichloromethane (10 mL) was added 2 drops of N,N-dimethylformamide followed by oxalyl chloride (20 μL, 0.23 mmol) and the mixture was stirred at ambient temperature for 45 minutes. The mixture was then concentrated and redissolved in dichloromethane (10 mL). The title compound of Example 1, Step B was then added (36 mg, 0.19 mmol) followed by N,N-dimethylamino-pyridine (2 mg, 0.02 mmol) and triethylamine (40 μL, 0.29 mmol) and the mixture was stirred at ambient temperature overnight. A saturated solution of sodium bicarbonate was then added and the mixture was filtered through a Celite® cartridge, concentrated and purified by flash column chromatography (silica gel, 20% then 40% the 60% ethyl ether in petroleum ether) to give the title compound of Example 3 (8 mg) as a white solid.

$^1$H NMR ($CDCl_3$) δ: 9.6 (s, 1H), 7.6–7.1 (m, 7H), 5.9–5.8 (d, 1H), 5.0–4.9 (dd, 1H), 4.8–4.7 (m, 1H), 4.3 (dd, 1H), 4.2–4.1 (m, 1H), 2.10 (s, 3H), 1.3–1.2 (m, 6H).

By the procedures described herein together with methods known in the art, the following compounds of Tables 1 to 13 can be prepared. The following abbreviations are used in the Tables: t means tertiary, s means secondary, i means iso, Me means methyl, Et means ethyl, Pr means propyl, i-Pr means isopropyl, t-Bu means tert butyl.

TABLE 1

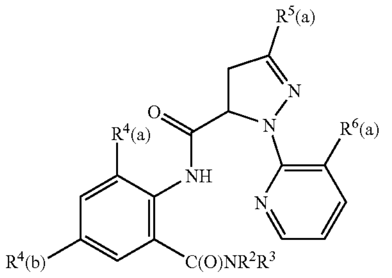

| $R^6$(a) | $R^5$(a) | $R^4$(a) | $R^4$(b) | $R^3$ | $R^2$ | $R^6$(a) | $R^5$(a) | $R^4$(a) | $R^4$(b) | $R^3$ | $R^2$ |
|---|---|---|---|---|---|---|---|---|---|---|---|
| Cl | $CF_3$ | $CH_3$ | H | Me | H | Cl | $CF_3$ | Cl | H | Me | H |
| Cl | $CF_3$ | $CH_3$ | H | Et | H | Cl | $CF_3$ | Cl | H | Et | H |
| Cl | $CF_3$ | $CH_3$ | H | i-Pr | H | Cl | $CF_3$ | Cl | H | i-Pr | H |
| Cl | $CF_3$ | $CH_3$ | H | t-Bu | H | Cl | $CF_3$ | Cl | H | t-Bu | H |
| Cl | $CF_3$ | $CH_3$ | H | Me | Me | Cl | $CF_3$ | Cl | H | Me | Me |
| Br | $CF_3$ | $CH_3$ | H | Me | H | Br | $CF_3$ | Cl | H | Me | H |
| Br | $CF_3$ | $CH_3$ | H | Et | H | Br | $CF_3$ | Cl | H | Et | H |
| Br | $CF_3$ | $CH_3$ | H | i-Pr | H | Br | $CF_3$ | Cl | H | i-Pr | H |
| Br | $CF_3$ | $CH_3$ | H | t-Bu | H | Br | $CF_3$ | Cl | H | t-Bu | H |
| Br | $CF_3$ | $CH_3$ | H | Me | Me | Br | $CF_3$ | Cl | H | Me | Me |
| Cl | Cl | $CH_3$ | H | Me | H | Cl | Cl | Cl | H | Me | H |
| Cl | Cl | $CH_3$ | H | Et | H | Cl | Cl | Cl | H | Et | H |
| Cl | Cl | $CH_3$ | H | i-Pr | H | Cl | Cl | Cl | H | i-Pr | H |
| Cl | Cl | $CH_3$ | H | t-Bu | H | Cl | Cl | Cl | H | t-Bu | H |
| Cl | Cl | $CH_3$ | H | Me | Me | Cl | Cl | Cl | H | Me | Me |
| Br | Cl | $CH_3$ | H | Me | H | Br | Cl | Cl | H | Me | H |
| Br | Cl | $CH_3$ | H | Et | H | Br | Cl | Cl | H | Et | H |
| Br | Cl | $CH_3$ | H | i-Pr | H | Br | Cl | Cl | H | i-Pr | H |
| Br | Cl | $CH_3$ | H | t-Bu | H | Br | Cl | Cl | H | t-Bu | H |
| Br | Cl | $CH_3$ | H | Me | Me | Br | Cl | Cl | H | Me | Me |
| Cl | Br | $CH_3$ | H | Me | H | Cl | Br | Cl | H | Me | H |
| Cl | Br | $CH_3$ | H | Et | H | Cl | Br | Cl | H | Et | H |
| Cl | Br | $CH_3$ | H | i-Pr | H | Cl | Br | Cl | H | i-Pr | H |
| Cl | Br | $CH_3$ | H | t-Bu | H | Cl | Br | Cl | H | t-Bu | H |
| Cl | Br | $CH_3$ | H | Me | Me | Cl | Br | Cl | H | Me | Me |
| Br | Br | $CH_3$ | H | Me | H | Br | Br | Cl | H | Me | H |
| Br | Br | $CH_3$ | H | Et | H | Br | Br | Cl | H | Et | H |
| Br | Br | $CH_3$ | H | i-Pr | H | Br | Br | Cl | H | i-Pr | H |
| Br | Br | $CH_3$ | H | t-Bu | H | Br | Br | Cl | H | t-Bu | H |
| Br | Br | $CH_3$ | H | Me | Me | Br | Br | Cl | H | Me | Me |
| Cl | $OCH_2CF_3$ | $CH_3$ | H | Me | H | Cl | $OCH_2CF_3$ | Cl | H | Me | H |
| Cl | $OCH_2CF_3$ | $CH_3$ | H | Et | H | Cl | $OCH_2CF_3$ | Cl | H | Et | H |
| Cl | $OCH_2CF_3$ | $CH_3$ | H | i-Pr | H | Cl | $OCH_2CF_3$ | Cl | H | i-Pr | H |
| Cl | $OCH_2CF_3$ | $CH_3$ | H | t-Bu | H | Cl | $OCH_2CF_3$ | Cl | H | t-Bu | H |
| Cl | $OCH_2CF_3$ | $CH_3$ | H | Me | Me | Cl | $OCH_2CF_3$ | Cl | H | Me | Me |
| Br | $OCH_2CF_3$ | $CH_3$ | H | Me | H | Br | $OCH_2CF_3$ | Cl | H | Me | H |
| Br | $OCH_2CF_3$ | $CH_3$ | H | Et | H | Br | $OCH_2CF_3$ | Cl | H | Et | H |
| Br | $OCH_2CF_3$ | $CH_3$ | H | i-Pr | H | Br | $OCH_2CF_3$ | Cl | H | i-Pr | H |
| Br | $OCH_2CF_3$ | $CH_3$ | H | t-Bu | H | Br | $OCH_2CF_3$ | Cl | H | t-Bu | H |
| Br | $OCH_2CF_3$ | $CH_3$ | H | Me | Me | Br | $OCH_2CF_3$ | Cl | H | Me | Me |
| Cl | $CF_3$ | $CH_3$ | F | Me | H | Cl | $CF_3$ | Cl | F | Me | H |
| Cl | $CF_3$ | $CH_3$ | F | Et | H | Cl | $CF_3$ | Cl | F | Et | H |
| Cl | $CF_3$ | $CH_3$ | F | i-Pr | H | Cl | $CF_3$ | Cl | F | i-Pr | H |
| Cl | $CF_3$ | $CH_3$ | F | t-Bu | H | Cl | $CF_3$ | Cl | F | t-Bu | H |
| Cl | $CF_3$ | $CH_3$ | F | Me | Me | Cl | $CF_3$ | Cl | F | Me | Me |
| Br | $CF_3$ | $CH_3$ | F | Me | H | Br | $CF_3$ | Cl | F | Me | H |
| Br | $CF_3$ | $CH_3$ | F | Et | H | Br | $CF_3$ | Cl | F | Et | H |
| Br | $CF_3$ | $CH_3$ | F | i-Pr | H | Br | $CF_3$ | Cl | F | i-Pr | H |
| Br | $CF_3$ | $CH_3$ | F | t-Bu | H | Br | $CF_3$ | Cl | F | t-Bu | H |
| Br | $CF_3$ | $CH_3$ | F | Me | Me | Br | $CF_3$ | Cl | F | Me | Me |
| Cl | Cl | $CH_3$ | F | Me | H | Cl | Cl | Cl | F | Me | H |
| Cl | Cl | $CH_3$ | F | Et | H | Cl | Cl | Cl | F | Et | H |
| Cl | Cl | $CH_3$ | F | i-Pr | H | Cl | Cl | Cl | F | i-Pr | H |
| Cl | Cl | $CH_3$ | F | t-Bu | H | Cl | Cl | Cl | F | t-Bu | H |
| Cl | Cl | $CH_3$ | F | Me | Me | Cl | Cl | Cl | F | Me | Me |
| Br | Cl | $CH_3$ | F | Me | H | Br | Cl | Cl | F | Me | H |
| Br | Cl | $CH_3$ | F | Et | H | Br | Cl | Cl | F | Et | H |
| Br | Cl | $CH_3$ | F | i-Pr | H | Br | Cl | Cl | F | i-Pr | H |
| Br | Cl | $CH_3$ | F | t-Bu | H | Br | Cl | Cl | F | t-Bu | H |
| Br | Cl | $CH_3$ | F | Me | Me | Br | Cl | Cl | F | Me | Me |

TABLE 1-continued

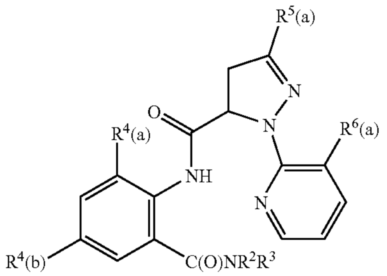

| $R^6(a)$ | $R^5(a)$ | $R^4(a)$ | $R^4(b)$ | $R^3$ | $R^2$ | $R^6(a)$ | $R^5(a)$ | $R^4(a)$ | $R^4(b)$ | $R^3$ | $R^2$ |
|---|---|---|---|---|---|---|---|---|---|---|---|
| Cl | Br | $CH_3$ | F | Me | H | Cl | Br | Cl | F | Me | H |
| Cl | Br | $CH_3$ | F | Et | H | Cl | Br | Cl | F | Et | H |
| Cl | Br | $CH_3$ | F | i-Pr | H | Cl | Br | Cl | F | i-Pr | H |
| Cl | Br | $CH_3$ | F | t-Bu | H | Cl | Br | Cl | F | t-Bu | H |
| Cl | Br | $CH_3$ | F | Me | Me | Cl | Br | Cl | F | Me | Me |
| Br | Br | $CH_3$ | F | Me | H | Br | Br | Cl | F | Me | H |
| Br | Br | $CH_3$ | F | Et | H | Br | Br | Cl | F | Et | H |
| Br | Br | $CH_3$ | F | i-Pr | H | Br | Br | Cl | F | i-Pr | H |
| Br | Br | $CH_3$ | F | t-Bu | H | Br | Br | Cl | F | t-Bu | H |
| Br | Br | $CH_3$ | F | Me | Me | Br | Br | Cl | F | Me | Me |
| Cl | $OCH_2CF_3$ | $CH_3$ | F | Me | H | Cl | $OCH_2CF_3$ | Cl | F | Me | H |
| Cl | $OCH_2CF_3$ | $CH_3$ | F | Et | H | Cl | $OCH_2CF_3$ | Cl | F | Et | H |
| Cl | $OCH_2CF_3$ | $CH_3$ | F | i-Pr | H | Cl | $OCH_2CF_3$ | Cl | F | i-Pr | H |
| Cl | $OCH_2CF_3$ | $CH_3$ | F | t-Bu | H | Cl | $OCH_2CF_3$ | Cl | F | t-Bu | H |
| Cl | $OCH_2CF_3$ | $CH_3$ | F | Me | Me | Cl | $OCH_2CF_3$ | Cl | F | Me | Me |
| Br | $OCH_2CF_3$ | $CH_3$ | F | Me | H | Br | $OCH_2CF_3$ | Cl | F | Me | H |
| Br | $OCH_2CF_3$ | $CH_3$ | F | Et | H | Br | $OCH_2CF_3$ | Cl | F | Et | H |
| Br | $OCH_2CF_3$ | $CH_3$ | F | i-Pr | H | Br | $OCH_2CF_3$ | Cl | F | i-Pr | H |
| Br | $OCH_2CF_3$ | $CH_3$ | F | t-Bu | H | Br | $OCH_2CF_3$ | Cl | F | t-Bu | H |
| Br | $OCH_2CF_3$ | $CH_3$ | F | Me | Me | Br | $OCH_2CF_3$ | Cl | F | Me | Me |
| Cl | $CF_3$ | $CH_3$ | Cl | Me | H | Cl | $CF_3$ | Cl | Cl | Me | H |
| Cl | $CF_3$ | $CH_3$ | Cl | Et | H | Cl | $CF_3$ | Cl | Cl | Et | H |
| Cl | $CF_3$ | $CH_3$ | Cl | i-Pr | H | Cl | $CF_3$ | Cl | Cl | i-Pr | H |
| Cl | $CF_3$ | $CH_3$ | Cl | t-Bu | H | Cl | $CF_3$ | Cl | Cl | t-Bu | H |
| Cl | $CF_3$ | $CH_3$ | Cl | Me | Me | Cl | $CF_3$ | Cl | Cl | Me | Me |
| Br | $CF_3$ | $CH_3$ | Cl | Me | H | Br | $CF_3$ | Cl | Cl | Me | H |
| Br | $CF_3$ | $CH_3$ | Cl | Et | H | Br | $CF_3$ | Cl | Cl | Et | H |
| Br | $CF_3$ | $CH_3$ | Cl | i-Pr | H | Br | $CF_3$ | Cl | Cl | i-Pr | H |
| Br | $CF_3$ | $CH_3$ | Cl | t-Bu | H | Br | $CF_3$ | Cl | Cl | t-Bu | H |
| Br | $CF_3$ | $CH_3$ | Cl | Me | Me | Br | $CF_3$ | Cl | Cl | Me | Me |
| Cl | Cl | $CH_3$ | Cl | Me | H | Cl | Cl | Cl | Cl | Me | H |
| Cl | Cl | $CH_3$ | Cl | Et | H | Cl | Cl | Cl | Cl | Et | H |
| Cl | Cl | $CH_3$ | Cl | i-Pr | H | Cl | Cl | Cl | Cl | i-Pr | H |
| Cl | Cl | $CH_3$ | Cl | t-Bu | H | Cl | Cl | Cl | Cl | t-Bu | H |
| Cl | Cl | $CH_3$ | Cl | Me | Me | Cl | Cl | Cl | Cl | Me | Me |
| Br | Cl | $CH_3$ | Cl | Me | H | Br | Cl | Cl | Cl | Me | H |
| Br | Cl | $CH_3$ | Cl | Et | H | Br | Cl | Cl | Cl | Et | H |
| Br | Cl | $CH_3$ | Cl | i-Pr | H | Br | Cl | Cl | Cl | i-Pr | H |
| Br | Cl | $CH_3$ | Cl | t-Bu | H | Br | Cl | Cl | Cl | t-Bu | H |
| Br | Cl | $CH_3$ | Cl | Me | Me | Br | Cl | Cl | Cl | Me | Me |
| Cl | Br | $CH_3$ | Cl | Me | H | Cl | Br | Cl | Cl | Me | H |
| Cl | Br | $CH_3$ | Cl | Et | H | Cl | Br | Cl | Cl | Et | H |
| Cl | Br | $CH_3$ | Cl | i-Pr | H | Cl | Br | Cl | Cl | i-Pr | H |
| Cl | Br | $CH_3$ | Cl | t-Bu | H | Cl | Br | Cl | Cl | t-Bu | H |
| Cl | Br | $CH_3$ | Cl | Me | Me | Cl | Br | Cl | Cl | Me | Me |
| Br | Br | $CH_3$ | Cl | Me | H | Br | Br | Cl | Cl | Me | H |
| Br | Br | $CH_3$ | Cl | Et | H | Br | Br | Cl | Cl | Et | H |
| Br | Br | $CH_3$ | Cl | i-Pr | H | Br | Br | Cl | Cl | i-Pr | H |
| Br | Br | $CH_3$ | Cl | t-Bu | H | Br | Br | Cl | Cl | t-Bu | H |
| Br | Br | $CH_3$ | Cl | Me | Me | Br | Br | Cl | Cl | Me | Me |
| Cl | $OCH_2CF_3$ | $CH_3$ | Cl | Me | H | Cl | $OCH_2CF_3$ | Cl | Cl | Me | H |
| Cl | $OCH_2CF_3$ | $CH_3$ | Cl | Et | H | Cl | $OCH_2CF_3$ | Cl | Cl | Et | H |
| Cl | $OCH_2CF_3$ | $CH_3$ | Cl | i-Pr | H | Cl | $OCH_2CF_3$ | Cl | Cl | i-Pr | H |
| Cl | $OCH_2CF_3$ | $CH_3$ | Cl | t-Bu | H | Cl | $OCH_2CF_3$ | Cl | Cl | t-Bu | H |
| Cl | $OCH_2CF_3$ | $CH_3$ | Cl | Me | Me | Cl | $OCH_2CF_3$ | Cl | Cl | Me | Me |
| Br | $OCH_2CF_3$ | $CH_3$ | Cl | Me | H | Br | $OCH_2CF_3$ | Cl | Cl | Me | H |
| Br | $OCH_2CF_3$ | $CH_3$ | Cl | Et | H | Br | $OCH_2CF_3$ | Cl | Cl | Et | H |
| Br | $OCH_2CF_3$ | $CH_3$ | Cl | i-Pr | H | Br | $OCH_2CF_3$ | Cl | Cl | i-Pr | H |
| Br | $OCH_2CF_3$ | $CH_3$ | Cl | t-Bu | H | Br | $OCH_2CF_3$ | Cl | Cl | t-Bu | H |
| Br | $OCH_2CF_3$ | $CH_3$ | Cl | Me | Me | Br | $OCH_2CF_3$ | Cl | Cl | Me | Me |

TABLE 1-continued

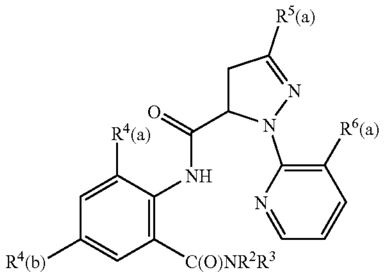

| $R^6$(a) | $R^5$(a) | $R^4$(a) | $R^4$(b) | $R^3$ | $R^2$ | $R^6$(a) | $R^5$(a) | $R^4$(a) | $R^4$(b) | $R^3$ | $R^2$ |
|---|---|---|---|---|---|---|---|---|---|---|---|
| Cl | $CF_3$ | $CH_3$ | Br | Me | H | Cl | $CF_3$ | Cl | Br | Me | H |
| Cl | $CF_3$ | $CH_3$ | Br | Et | H | Cl | $CF_3$ | Cl | Br | Et | H |
| Cl | $CF_3$ | $CH_3$ | Br | i-Pr | H | Cl | $CF_3$ | Cl | Br | i-Pr | H |
| Cl | $CF_3$ | $CH_3$ | Br | t-Bu | H | Cl | $CF_3$ | Cl | Br | t-Bu | H |
| Cl | $CF_3$ | $CH_3$ | Br | Me | Me | Cl | $CF_3$ | Cl | Br | Me | Me |
| Br | $CF_3$ | $CH_3$ | Br | Me | H | Br | $CF_3$ | Cl | Br | Me | H |
| Br | $CF_3$ | $CH_3$ | Br | Et | H | Br | $CF_3$ | Cl | Br | Et | H |
| Br | $CF_3$ | $CH_3$ | Br | i-Pr | H | Br | $CF_3$ | Cl | Br | i-Pr | H |
| Br | $CF_3$ | $CH_3$ | Br | t-Bu | H | Br | $CF_3$ | Cl | Br | t-Bu | H |
| Br | $CF_3$ | $CH_3$ | Br | Me | Me | Br | $CF_3$ | Cl | Br | Me | Me |
| Cl | Cl | $CH_3$ | Br | Me | H | Cl | Cl | Cl | Br | Me | H |
| Cl | Cl | $CH_3$ | Br | Et | H | Cl | Cl | Cl | Br | Et | H |
| Cl | Cl | $CH_3$ | Br | i-Pr | H | Cl | Cl | Cl | Br | i-Pr | H |
| Cl | Cl | $CH_3$ | Br | t-Bu | H | Cl | Cl | Cl | Br | t-Bu | H |
| Cl | Cl | $CH_3$ | Br | Me | Me | Cl | Cl | Cl | Br | Me | Me |
| Br | Cl | $CH_3$ | Br | Me | H | Br | Cl | Cl | Br | Me | H |
| Br | Cl | $CH_3$ | Br | Et | H | Br | Cl | Cl | Br | Et | H |
| Br | Cl | $CH_3$ | Br | i-Pr | H | Br | Cl | Cl | Br | i-Pr | H |
| Br | Cl | $CH_3$ | Br | t-Bu | H | Br | Cl | Cl | Br | t-Bu | H |
| Br | Cl | $CH_3$ | Br | Me | Me | Br | Cl | Cl | Br | Me | Me |
| Cl | Br | $CH_3$ | Br | Me | H | Cl | Br | Cl | Br | Me | H |
| Cl | Br | $CH_3$ | Br | Et | H | Cl | Br | Cl | Br | Et | H |
| Cl | Br | $CH_3$ | Br | i-Pr | H | Cl | Br | Cl | Br | i-Pr | H |
| Cl | Br | $CH_3$ | Br | t-Bu | H | Cl | Br | Cl | Br | t-Bu | H |
| Cl | Br | $CH_3$ | Br | Me | Me | Cl | Br | Cl | Br | Me | Me |
| Br | Br | $CH_3$ | Br | Me | H | Br | Br | Cl | Br | Me | H |
| Br | Br | $CH_3$ | Br | Et | H | Br | Br | Cl | Br | Et | H |
| Br | Br | $CH_3$ | Br | i-Pr | H | Br | Br | Cl | Br | i-Pr | H |
| Br | Br | $CH_3$ | Br | t-Bu | H | Br | Br | Cl | Br | t-Bu | H |
| Br | Br | $CH_3$ | Br | Me | Me | Br | Br | Cl | Br | Me | Me |
| Cl | $OCH_2CF_3$ | $CH_3$ | Br | Me | H | Cl | $OCH_2CF_3$ | Cl | Br | Me | H |
| Cl | $OCH_2CF_3$ | $CH_3$ | Br | Et | H | Cl | $OCH_2CF_3$ | Cl | Br | Et | H |
| Cl | $OCH_2CF_3$ | $CH_3$ | Br | i-Pr | H | Cl | $OCH_2CF_3$ | Cl | Br | i-Pr | H |
| Cl | $OCH_2CF_3$ | $CH_3$ | Br | t-Bu | H | Cl | $OCH_2CF_3$ | Cl | Br | t-Bu | H |
| Cl | $OCH_2CF_3$ | $CH_3$ | Br | Me | Me | Cl | $OCH_2CF_3$ | Cl | Br | Me | Me |
| Br | $OCH_2CF_3$ | $CH_3$ | Br | Me | H | Br | $OCH_2CF_3$ | Cl | Br | Me | H |
| Br | $OCH_2CF_3$ | $CH_3$ | Br | Et | H | Br | $OCH_2CF_3$ | Cl | Br | Et | H |
| Br | $OCH_2CF_3$ | $CH_3$ | Br | i-Pr | H | Br | $OCH_2CF_3$ | Cl | Br | i-Pr | H |
| Br | $OCH_2CF_3$ | $CH_3$ | Br | t-Bu | H | Br | $OCH_2CF_3$ | Cl | Br | t-Bu | H |
| Br | $OCH_2CF_3$ | $CH_3$ | Br | Me | Me | Br | $OCH_2CF_3$ | Cl | Br | Me | Me |
| Cl | $CF_3$ | $CH_3$ | I | Me | H | Cl | $CF_3$ | Cl | I | Me | H |
| Cl | $CF_3$ | $CH_3$ | I | Et | H | Cl | $CF_3$ | Cl | I | Et | H |
| Cl | $CF_3$ | $CH_3$ | I | i-Pr | H | Cl | $CF_3$ | Cl | I | i-Pr | H |
| Cl | $CF_3$ | $CH_3$ | I | t-Bu | H | Cl | $CF_3$ | Cl | I | t-Bu | H |
| Cl | $CF_3$ | $CH_3$ | I | Me | Me | Cl | $CF_3$ | Cl | I | Me | Me |
| Br | $CF_3$ | $CH_3$ | I | Me | H | Br | $CF_3$ | Cl | I | Me | H |
| Br | $CF_3$ | $CH_3$ | I | Et | H | Br | $CF_3$ | Cl | I | Et | H |
| Br | $CF_3$ | $CH_3$ | 1 | i-Pr | H | Br | $CF_3$ | Cl | I | i-Pr | H |
| Br | $CF_3$ | $CH_3$ | I | t-Bu | H | Br | $CF_3$ | Cl | I | t-Bu | H |
| Br | $CF_3$ | $CH_3$ | I | Me | Me | Br | $CF_3$ | Cl | I | Me | Me |
| Cl | Cl | $CH_3$ | I | Me | H | Cl | Cl | Cl | I | Me | H |
| Cl | Cl | $CH_3$ | I | Et | H | Cl | Cl | Cl | I | Et | H |
| Cl | Cl | $CH_3$ | I | i-Pr | H | Cl | Cl | Cl | I | i-Pr | H |
| Cl | Cl | $CH_3$ | I | t-Bu | H | Cl | Cl | Cl | I | t-Bu | H |
| Cl | Cl | $CH_3$ | I | Me | Me | Cl | Cl | Cl | I | Me | Me |
| Br | Cl | $CH_3$ | I | Me | H | Br | Cl | Cl | I | Me | H |
| Br | Cl | $CH_3$ | I | Et | H | Br | Cl | Cl | I | Et | H |
| Br | Cl | $CH_3$ | I | i-Pr | H | Br | Cl | Cl | I | i-Pr | H |
| Br | Cl | $CH_3$ | I | t-Bu | H | Br | Cl | Cl | I | t-Bu | H |
| Br | Cl | $CH_3$ | I | Me | Me | Br | Cl | Cl | I | Me | Me |

TABLE 1-continued

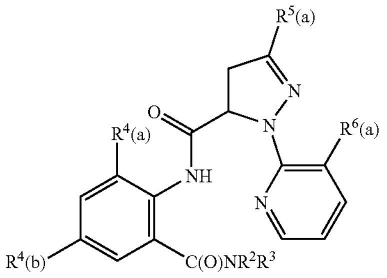

| $R^6$(a) | $R^5$(a) | $R^4$(a) | $R^4$(b) | $R^3$ | $R^2$ | $R^6$(a) | $R^5$(a) | $R^4$(a) | $R^4$(b) | $R^3$ | $R^2$ |
|---|---|---|---|---|---|---|---|---|---|---|---|
| Cl | Br | $CH_3$ | I | Me | H | Cl | Br | Cl | I | Me | H |
| Cl | Br | $CH_3$ | I | Et | H | Cl | Br | Cl | I | Et | H |
| Cl | Br | $CH_3$ | I | i-Pr | H | Cl | Br | Cl | I | i-Pr | H |
| Cl | Br | $CH_3$ | I | t-Bu | H | Cl | Br | Cl | I | t-Bu | H |
| Cl | Br | $CH_3$ | I | Me | Me | Cl | Br | Cl | I | Me | Me |
| Br | Br | $CH_3$ | I | Me | H | Br | Br | Cl | I | Me | H |
| Br | Br | $CH_3$ | I | Et | H | Br | Br | Cl | I | Et | H |
| Br | Br | $CH_3$ | I | i-Pr | H | Br | Br | Cl | I | i-Pr | H |
| Br | Br | $CH_3$ | I | t-Bu | H | Br | Br | Cl | I | t-Bu | H |
| Br | Br | $CH_3$ | I | Me | Me | Br | Br | Cl | I | Me | Me |
| Cl | $OCH_2CF_3$ | $CH_3$ | I | Me | H | Cl | $OCH_2CF_3$ | Cl | I | Me | H |
| Cl | $OCH_2CF_3$ | $CH_3$ | I | Et | H | Cl | $OCH_2CF_3$ | Cl | I | Et | H |
| Cl | $OCH_2CF_3$ | $CH_3$ | I | i-Pr | H | Cl | $OCH_2CF_3$ | Cl | I | i-Pr | H |
| Cl | $OCH_2CF_3$ | $CH_3$ | I | t-Bu | H | Cl | $OCH_2CF_3$ | Cl | I | t-Bu | H |
| Cl | $OCH_2CF_3$ | $CH_3$ | I | Me | Me | Cl | $OCH_2CF_3$ | Cl | I | Me | Me |
| Br | $OCH_2CF_3$ | $CH_3$ | I | Me | U | Br | $OCH_2CF_3$ | Cl | I | Me | H |
| Br | $OCH_2CF_3$ | $CH_3$ | I | Et | U | Br | $OCH_2CF_3$ | Cl | I | Et | H |
| Br | $OCH_2CF_3$ | $CH_3$ | I | i-Pr | H | Br | $OCH_2CF_3$ | Cl | I | i-Pr | H |
| Br | $OCH_2CF_3$ | $CH_3$ | I | t-Bu | H | Br | $OCH_2CF_3$ | Cl | I | t-Bu | H |
| Br | $OCH_2CF_3$ | $CH_3$ | I | Me | Me | Br | $OCH_2CF_3$ | Cl | I | Me | Me |
| Cl | $CF_3$ | $CH_3$ | $CF_3$ | Me | H | Cl | $CF_3$ | Cl | $CF_3$ | Me | H |
| Cl | $CF_3$ | $CH_3$ | $CF_3$ | Et | H | Cl | $CF_3$ | Cl | $CF_3$ | Et | H |
| Cl | $CF_3$ | $CH_3$ | $CF_3$ | i-Pr | H | Cl | $CF_3$ | Cl | $CF_3$ | i-Pr | H |
| Cl | $CF_3$ | $CH_3$ | $CF_3$ | t-Bu | H | Cl | $CF_3$ | Cl | $CF_3$ | t-Bu | H |
| Cl | $CF_3$ | $CH_3$ | $CF_3$ | Me | Me | Cl | $CF_3$ | Cl | $CF_3$ | Me | Me |
| Br | $CF_3$ | $CH_3$ | $CF_3$ | Me | H | Br | $CF_3$ | Cl | $CF_3$ | Me | H |
| Br | $CF_3$ | $CH_3$ | $CF_3$ | Et | H | Br | $CF_3$ | Cl | $CF_3$ | Et | H |
| Br | $CF_3$ | $CH_3$ | $CF_3$ | i-Pr | H | Br | $CF_3$ | Cl | $CF_3$ | i-Pr | H |
| Br | $CF_3$ | $CH_3$ | $CF_3$ | t-Bu | H | Br | $CF_3$ | Cl | $CF_3$ | t-Bu | H |
| Br | $CF_3$ | $CH_3$ | $CF_3$ | Me | Me | Br | $CF_3$ | Cl | $CF_3$ | Me | Me |
| Cl | Cl | $CH_3$ | $CF_3$ | Me | H | Cl | Cl | Cl | $CF_3$ | Me | H |
| Cl | Cl | $CH_3$ | $CF_3$ | Et | H | Cl | Cl | Cl | $CF_3$ | Et | H |
| Cl | Cl | $CH_3$ | $CF_3$ | i-Pr | H | Cl | Cl | Cl | $CF_3$ | i-Pr | H |
| Cl | Cl | $CH_3$ | $CF_3$ | t-Bu | H | Cl | Cl | Cl | $CF_3$ | t-Bu | H |
| Cl | Cl | $CH_3$ | $CF_3$ | Me | Me | Cl | Cl | Cl | $CF_3$ | Me | Me |
| Br | Cl | $CH_3$ | $CF_3$ | Me | H | Br | Cl | Cl | $CF_3$ | Me | H |
| Br | Cl | $CH_3$ | $CF_3$ | Et | H | Br | Cl | Cl | $CF_3$ | Et | H |
| Br | Cl | $CH_3$ | $CF_3$ | i-Pr | H | Br | Cl | Cl | $CF_3$ | i-Pr | H |
| Br | Cl | $CH_3$ | $CF_3$ | t-Bu | H | Br | Cl | Cl | $CF_3$ | t-Bu | H |
| Br | Cl | $CH_3$ | $CF_3$ | Me | Me | Br | Cl | Cl | $CF_3$ | Me | Me |
| Cl | Br | $CH_3$ | $CF_3$ | Me | H | Cl | Br | Cl | $CF_3$ | Me | H |
| Cl | Br | $CH_3$ | $CF_3$ | Et | H | Cl | Br | Cl | $CF_3$ | Et | H |
| Cl | Br | $CH_3$ | $CF_3$ | i-Pr | H | Cl | Br | Cl | $CF_3$ | i-Pr | H |
| Cl | Br | $CH_3$ | $CF_3$ | t-Bu | H | Cl | Br | Cl | $CF_3$ | t-Bu | H |
| Cl | Br | $CH_3$ | $CF_3$ | Me | Me | Cl | Br | Cl | $CF_3$ | Me | Me |
| Br | Br | $CH_3$ | $CF_3$ | Me | H | Br | Br | Cl | $CF_3$ | Me | H |
| Br | Br | $CH_3$ | $CF_3$ | Et | H | Br | Br | Cl | $CF_3$ | Et | H |
| Br | Br | $CH_3$ | $CF_3$ | i-Pr | H | Br | Br | Cl | $CF_3$ | i-Pr | H |
| Br | Br | $CH_3$ | $CF_3$ | t-Bu | H | Br | Br | Cl | $CF_3$ | t-Bu | H |
| Br | Br | $CH_3$ | $CF_3$ | Me | Me | Br | Br | Cl | $CF_3$ | Me | Me |
| Cl | $OCH_2CF_3$ | $CH_3$ | $CF_3$ | Me | H | Cl | $OCH_2CF_3$ | Cl | $CF_3$ | Me | H |
| Cl | $OCH_2CF_3$ | $CH_3$ | $CF_3$ | Et | H | Cl | $OCH_2CF_3$ | Cl | $CF_3$ | Et | H |
| Cl | $OCH_2CF_3$ | $CH_3$ | $CF_3$ | i-Pr | H | Cl | $OCH_2CF_3$ | Cl | $CF_3$ | i-Pr | H |
| Cl | $OCH_2CF_3$ | $CH_3$ | $CF_3$ | t-Bu | H | Cl | $OCH_2CF_3$ | Cl | $CF_3$ | t-Bu | H |
| Cl | $OCH_2CF_3$ | $CH_3$ | $CF_3$ | Me | Me | Cl | $OCH_2CF_3$ | Cl | $CF_3$ | Me | Me |
| Br | $OCH_2CF_3$ | $CH_3$ | $CF_3$ | Me | H | Br | $OCH_2CF_3$ | Cl | $CF_3$ | Me | H |
| Br | $OCH_2CF_3$ | $CH_3$ | $CF_3$ | Et | H | Br | $OCH_2CF_3$ | Cl | $CF_3$ | Et | H |
| Br | $OCH_2CF_3$ | $CH_3$ | $CF_3$ | i-Pr | H | Br | $OCH_2CF_3$ | Cl | $CF_3$ | i-Pr | H |
| Br | $OCH_2CF_3$ | $CH_3$ | $CF_3$ | t-Bu | H | Br | $OCH_2CF_3$ | Cl | $CF_3$ | t-Bu | H |
| Br | $OCH_2CF_3$ | $CH_3$ | $CF_3$ | Me | Me | Br | $OCH_2CF_3$ | Cl | $CF_3$ | Me | Me |

TABLE 1-continued

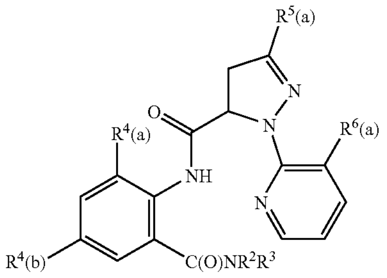

| $R^6$(a) | $R^5$(a) | $R^4$(a) | $R^4$(b) | $R^3$ | $R^2$ | $R^6$(a) | $R^5$(a) | $R^4$(a) | $R^4$(b) | $R^3$ | $R^2$ |
|---|---|---|---|---|---|---|---|---|---|---|---|
| Cl | Cl | $CH_3$ | Cl | n-Pr | H | Cl | Cl | Cl | Cl | n-Pr | H |
| Cl | Cl | $CH_3$ | Cl | n-Bu | H | Cl | Cl | Cl | Cl | n-Bu | H |
| Cl | Cl | $CH_3$ | Cl | s-Bu | H | Cl | Cl | Cl | Cl | s-Bu | H |
| Cl | Cl | $CH_3$ | Cl | i-Bu | H | Cl | Cl | Cl | Cl | i-Bu | H |
| Cl | Cl | $CH_3$ | Cl | Et | Me | Cl | Cl | Cl | Cl | Et | Et |
| Cl | $CF_3$ | F | H | Me | H | Cl | $CF_3$ | Br | H | Me | H |
| Cl | $CF_3$ | F | H | Et | H | Cl | $CF_3$ | Br | H | Et | H |
| Cl | $CF_3$ | F | H | i-Pr | H | Cl | $CF_3$ | Br | H | i-Pr | H |
| Cl | $CF_3$ | F | H | t-Bu | H | Cl | $CF_3$ | Br | H | t-Bu | H |
| Cl | $CF_3$ | F | H | Me | Me | Cl | $CF_3$ | Br | H | Me | Me |
| Br | $CF_3$ | F | H | Me | H | Br | $CF_3$ | Br | H | Me | H |
| Br | $CF_3$ | F | H | Et | H | Br | $CF_3$ | Br | H | Et | H |
| Br | $CF_3$ | F | H | i-Pr | H | Br | $CF_3$ | Br | H | i-Pr | H |
| Br | $CF_3$ | F | H | t-Bu | H | Br | $CF_3$ | Br | H | t-Bu | H |
| Br | $CF_3$ | F | H | Me | Me | Br | $CF_3$ | Br | H | Me | Me |
| Cl | Cl | F | H | Me | H | Cl | Cl | Br | H | Me | H |
| Cl | Cl | F | H | Et | H | Cl | Cl | Br | H | Et | H |
| Cl | Cl | F | H | i-Pr | H | Cl | Cl | Br | H | i-Pr | H |
| Cl | Cl | F | H | t-Bu | H | Cl | Cl | Br | H | t-Bu | H |
| Cl | Cl | F | H | Me | Me | Cl | Cl | Br | H | Me | Me |
| Br | Cl | F | H | Me | H | Br | Cl | Br | H | Me | H |
| Br | Cl | F | H | Et | H | Br | Cl | Br | H | Et | H |
| Br | Cl | F | H | i-Pr | H | Br | Cl | Br | H | i-Pr | H |
| Br | Cl | F | H | t-Bu | H | Br | Cl | Br | H | t-Bu | H |
| Br | Cl | F | H | Me | Me | Br | Cl | Br | H | Me | Me |
| Cl | Br | F | H | Me | H | Cl | Br | Br | H | Me | H |
| Cl | Br | F | H | Et | H | Cl | Br | Br | H | Et | H |
| Cl | Br | F | H | i-Pr | H | Cl | Br | Br | H | i-Pr | H |
| Cl | Br | F | H | t-Bu | H | Cl | Br | Br | H | t-Bu | H |
| Cl | Br | F | H | Me | Me | Cl | Br | Br | H | Me | Me |
| Br | Br | F | H | Me | H | Br | Br | Br | H | Me | H |
| Br | Br | F | H | Et | H | Br | Br | Br | H | Et | H |
| Br | Br | F | H | i-Pr | H | Br | Br | Br | H | i-Pr | H |
| Br | Br | F | H | t-Bu | H | Br | Br | Br | H | t-Bu | H |
| Br | Br | F | H | Me | Me | Br | Br | Br | H | Me | Me |
| Cl | $OCH_2CF_3$ | F | H | Me | H | Cl | $OCH_2CF_3$ | Br | H | Me | H |
| Cl | $OCH_2CF_3$ | F | H | Et | H | Cl | $OCH_2CF_3$ | Br | H | Et | H |
| Cl | $OCH_2CF_3$ | F | H | i-Pr | H | Cl | $OCH_2CF_3$ | Br | H | i-Pr | H |
| Cl | $OCH_2CF_3$ | F | H | t-Bu | H | Cl | $OCH_2CF_3$ | Br | H | t-Bu | H |
| Cl | $OCH_2CF_3$ | F | H | Me | Me | Cl | $OCH_2CF_3$ | Br | H | Me | Me |
| Br | $OCH_2CF_3$ | F | H | Me | H | Br | $OCH_2CF_3$ | Br | H | Me | H |
| Br | $OCH_2CF_3$ | F | H | Et | H | Br | $OCH_2CF_3$ | Br | H | Et | H |
| Br | $OCH_2CF_3$ | F | H | i-Pr | H | Br | $OCH_2CF_3$ | Br | H | i-Pr | H |
| Br | $OCH_2CF_3$ | F | H | t-Bu | H | Br | $OCH_2CF_3$ | Br | H | t-Bu | H |
| Br | $OCH_2CF_3$ | F | H | Me | Me | Br | $OCH_2CF_3$ | Br | H | Me | Me |
| Cl | $CF_3$ | F | F | Me | H | Cl | $CF_3$ | Br | F | Me | H |
| Cl | $CF_3$ | F | F | Et | H | Cl | $CF_3$ | Br | F | Et | H |
| Cl | $CF_3$ | F | F | I-Pr | H | Cl | $CF_3$ | Br | F | i-Pr | H |
| Cl | $CF_3$ | F | F | t-Bu | H | Cl | $CF_3$ | Br | F | t-Bu | H |
| Cl | $CF_3$ | F | F | Me | Me | Cl | $CF_3$ | Br | F | Me | Me |
| Br | $CF_3$ | F | F | Me | H | Br | $CF_3$ | Br | F | Me | H |
| Br | $CF_3$ | F | F | Et | H | Br | $CF_3$ | Br | F | Et | H |
| Br | $CF_3$ | F | F | i-Pr | H | Br | $CF_3$ | Br | F | i-Pr | H |
| Br | $CF_3$ | F | F | t-Bu | H | Br | $CF_3$ | Br | F | t-Bu | H |
| Br | $CF_3$ | F | F | Me | Me | Br | $CF_3$ | Br | F | Me | Me |
| Cl | Cl | F | F | Me | H | Cl | Cl | Br | F | Me | H |
| Cl | Cl | F | F | Et | H | Cl | Cl | Br | F | Et | H |
| Cl | Cl | F | F | i-Pr | H | Cl | Cl | Br | F | i-Pr | H |
| Cl | Cl | F | F | t-Bu | H | Cl | Cl | Br | F | t-Bu | H |
| Cl | Cl | F | F | Me | Me | Cl | Cl | Br | F | Me | Me |

TABLE 1-continued

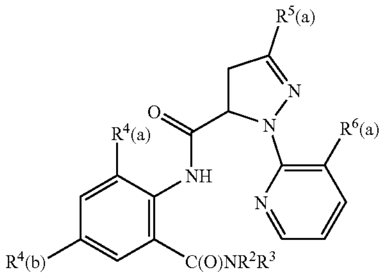

| $R^6$(a) | $R^5$(a) | $R^4$(a) | $R^4$(b) | $R^3$ | $R^2$ | $R^6$(a) | $R^5$(a) | $R^4$(a) | $R^4$(b) | $R^3$ | $R^2$ |
|---|---|---|---|---|---|---|---|---|---|---|---|
| Br | Cl | F | F | Me | H | Br | Cl | Br | F | Me | H |
| Br | Cl | F | F | Et | H | Br | Cl | Br | F | Et | H |
| Br | Cl | F | F | i-Pr | H | Br | Cl | Br | F | i-Pr | H |
| Br | Cl | F | F | t-Bu | H | Br | Cl | Br | F | t-Bu | H |
| Br | Cl | F | F | Me | Me | Br | Cl | Br | F | Me | Me |
| Cl | Br | F | F | Me | H | Cl | Br | Br | F | Me | H |
| Cl | Br | F | F | Et | H | Cl | Br | Br | F | Et | H |
| Cl | Br | F | F | i-Pr | H | Cl | Br | Br | F | i-Pr | H |
| Cl | Br | F | F | t-Bu | H | Cl | Br | Br | F | t-Bu | H |
| Cl | Br | F | F | Me | Me | Cl | Br | Br | F | Me | Me |
| Br | Br | F | F | Me | H | Br | Br | Br | F | Me | H |
| Br | Br | F | F | Et | H | Br | Br | Br | F | Et | H |
| Br | Br | F | F | i-Pr | H | Br | Br | Br | F | i-Pr | H |
| Br | Br | F | F | t-Bu | H | Br | Br | Br | F | t-Bu | H |
| Br | Br | F | F | Me | Me | Br | Br | Br | F | Me | Me |
| Cl | $OCH_2CF_3$ | F | F | Me | H | Cl | $OCH_2CF_3$ | Br | F | Me | H |
| Cl | $OCH_2CF_3$ | F | F | Et | H | Cl | $OCH_2CF_3$ | Br | F | Et | H |
| Cl | $OCH_2CF_3$ | F | F | i-Pr | H | Cl | $OCH_2CF_3$ | Br | F | i-Pr | H |
| Cl | $OCH_2CF_3$ | F | F | t-Bu | H | Cl | $OCH_2CF_3$ | Br | F | t-Bu | H |
| Cl | $OCH_2CF_3$ | F | F | Me | Me | Cl | $OCH_2CF_3$ | Br | F | Me | Me |
| Br | $OCH_2CF_3$ | F | F | Me | H | Br | $OCH_2CF_3$ | Br | F | Me | H |
| Br | $OCH_2CF_3$ | F | F | Et | H | Br | $OCH_2CF_3$ | Br | F | Et | H |
| Br | $OCH_2CF_3$ | F | F | i-Pr | H | Br | $OCH_2CF_3$ | Br | F | i-Pr | H |
| Br | $OCH_2CF_3$ | F | F | t-Bu | H | Br | $OCH_2CF_3$ | Br | F | t-Bu | H |
| Br | $OCH_2CF_3$ | F | F | Me | Me | Br | $OCH_2CF_3$ | Br | F | Me | Me |
| Cl | $CF_3$ | F | Cl | Me | H | Cl | $CF_3$ | Br | Cl | Me | H |
| Cl | $CF_3$ | F | Cl | Et | H | Cl | $CF_3$ | Br | Cl | Et | H |
| Cl | $CF_3$ | F | Cl | i-Pr | H | Cl | $CF_3$ | Br | Cl | i-Pr | H |
| Cl | $CF_3$ | F | Cl | t-Bu | H | Cl | $CF_3$ | Br | Cl | t-Bu | H |
| Cl | $CF_3$ | F | Cl | Me | Me | Cl | $CF_3$ | Br | Cl | Me | Me |
| Br | $CF_3$ | F | Cl | Me | H | Br | $CF_3$ | Br | Cl | Me | H |
| Br | $CF_3$ | F | Cl | Et | H | Br | $CF_3$ | Br | Cl | Et | H |
| Br | $CF_3$ | F | Cl | i-Pr | H | Br | $CF_3$ | Br | Cl | i-Pr | H |
| Br | $CF_3$ | F | Cl | t-Bu | H | Br | $CF_3$ | Br | Cl | t-Bu | H |
| Br | $CF_3$ | F | Cl | Me | Me | Br | $CF_3$ | Br | Cl | Me | Me |
| Cl | Cl | F | Cl | Me | H | Cl | Cl | Br | Cl | Me | H |
| Cl | Cl | F | Cl | Et | H | Cl | Cl | Br | Cl | Et | H |
| Cl | Cl | F | Cl | i-Pr | H | Cl | Cl | Br | Cl | i-Pr | H |
| Cl | Cl | F | Cl | t-Bu | H | Cl | Cl | Br | Cl | t-Bu | H |
| Cl | Cl | F | Cl | Me | Me | Cl | Cl | Br | Cl | Me | Me |
| Br | Cl | F | Cl | Me | H | Br | Cl | Br | Cl | Me | H |
| Br | Cl | F | Cl | Et | H | Br | Cl | Br | Cl | Et | H |
| Br | Cl | F | Cl | i-Pr | H | Br | Cl | Br | Cl | i-Pr | H |
| Br | Cl | F | Cl | t-Bu | H | Br | Cl | Br | Cl | t-Bu | H |
| Br | Cl | F | Cl | Me | Me | Br | Cl | Br | Cl | Me | Me |
| Cl | Br | F | Cl | Me | H | Cl | Br | Br | Cl | Me | H |
| Cl | Br | F | Cl | Et | H | Cl | Br | Br | Cl | Et | H |
| Cl | Br | F | Cl | i-Pr | H | Cl | Br | Br | Cl | i-Pr | H |
| Cl | Br | F | Cl | t-Bu | H | Cl | Br | Br | Cl | t-Bu | H |
| Cl | Br | F | Cl | Me | Me | Cl | Br | Br | Cl | Me | Me |
| Br | Br | F | Cl | Me | H | Br | Br | Br | Cl | Me | H |
| Br | Br | F | Cl | Et | H | Br | Br | Br | Cl | Et | H |
| Br | Br | F | Cl | i-Pr | H | Br | Br | Br | Cl | i-Pr | H |
| Br | Br | F | Cl | t-Bu | H | Br | Br | Br | Cl | t-Bu | H |
| Br | Br | F | Cl | Me | Me | Br | Br | Br | Cl | Me | Me |
| Cl | $OCH_2CF_3$ | F | Cl | Me | H | Cl | $OCH_2CF_3$ | Br | Cl | Me | H |
| Cl | $OCH_2CF_3$ | F | Cl | Et | H | Cl | $OCH_2CF_3$ | Br | Cl | Et | H |
| Cl | $OCH_2CF_3$ | F | Cl | i-Pr | H | Cl | $OCH_2CF_3$ | Br | Cl | i-Pr | H |
| Cl | $OCH_2CF_3$ | F | Cl | t-Bu | H | Cl | $OCH_2CF_3$ | Br | Cl | t-Bu | H |
| Cl | $OCH_2CF_3$ | F | Cl | Me | Me | Cl | $OCH_2CF_3$ | Br | Cl | Me | Me |
| Br | $OCH_2CF_3$ | F | Cl | Me | H | Br | $OCH_2CF_3$ | Br | Cl | Me | H |
| Br | $OCH_2CF_3$ | F | Cl | Et | H | Br | $OCH_2CF_3$ | Br | Cl | Et | H |
| Br | $OCH_2CF_3$ | F | Cl | i-Pr | H | Br | $OCH_2CF_3$ | Br | Cl | i-Pr | H |

TABLE 1-continued

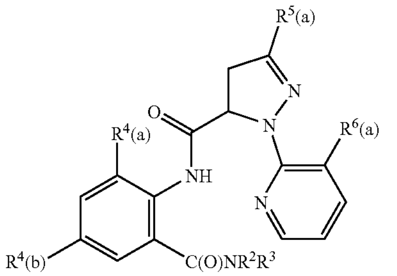

| $R^6$(a) | $R^5$(a) | $R^4$(a) | $R^4$(b) | $R^3$ | $R^2$ | $R^6$(a) | $R^5$(a) | $R^4$(a) | $R^4$(b) | $R^3$ | $R^2$ |
|---|---|---|---|---|---|---|---|---|---|---|---|
| Br | $OCH_2CF_3$ | F | Cl | t-Bu | H | Br | $OCH_2CF_3$ | Br | Cl | t-Bu | H |
| Br | $OCH_2CF_3$ | F | Cl | Me | Me | Br | $OCH_2CF_3$ | Br | Cl | Me | Me |
| Cl | $CF_3$ | F | Br | Me | H | Cl | $CF_3$ | Br | Br | Me | H |
| Cl | $CF_3$ | F | Br | Et | H | Cl | $CF_3$ | Br | Br | Et | H |
| Cl | $CF_3$ | F | Br | i-Pr | H | Cl | $CF_3$ | Br | Br | i-Pr | H |
| Cl | $CF_3$ | F | Br | t-Bu | H | Cl | $CF_3$ | Br | Br | t-Bu | H |
| Cl | $CF_3$ | F | Br | Me | Me | Cl | $CF_3$ | Br | Br | Me | Me |
| Br | $CF_3$ | F | Br | Me | H | Br | $CF_3$ | Br | Br | Me | H |
| Br | $CF_3$ | F | Br | Et | H | Br | $CF_3$ | Br | Br | Et | H |
| Br | $CF_3$ | F | Br | i-Pr | H | Br | $CF_3$ | Br | Br | i-Pr | H |
| Br | $CF_3$ | F | Br | t-Bu | H | Br | $CF_3$ | Br | Br | t-Bu | H |
| Br | $CF_3$ | F | Br | Me | Me | Br | $CF_3$ | Br | Br | Me | Me |
| Cl | Cl | F | Br | Me | H | Cl | Cl | Br | Br | Me | H |
| Cl | Cl | F | Br | Et | H | Cl | Cl | Br | Br | Et | H |
| Cl | Cl | F | Br | i-Pr | H | Cl | Cl | Br | Br | i-Pr | H |
| Cl | Cl | F | Br | t-Bu | H | Cl | Cl | Br | Br | t-Bu | H |
| Cl | Cl | F | Br | Me | Me | Cl | Cl | Br | Br | Me | Me |
| Br | Cl | F | Br | Me | H | Br | Cl | Br | Br | Me | H |
| Br | Cl | F | Br | Et | H | Br | Cl | Br | Br | Et | H |
| Br | Cl | F | Br | i-Pr | H | Br | Cl | Br | Br | i-Pr | H |
| Br | Cl | F | Br | t-Bu | H | Br | Cl | Br | Br | t-Bu | H |
| Br | Cl | F | Br | Me | Me | Br | Cl | Br | Br | Me | Me |
| Cl | Br | F | Br | Me | H | Cl | Br | Br | Br | Me | H |
| Cl | Br | F | Br | Et | H | Cl | Br | Br | Br | Et | H |
| Cl | Br | F | Br | i-Pr | H | Cl | Br | Br | Br | i-Pr | H |
| Cl | Br | F | Br | t-Bu | H | Cl | Br | Br | Br | t-Bu | H |
| Cl | Br | F | Br | Me | Me | Cl | Br | Br | Br | Me | Me |
| Br | Br | F | Br | Me | H | Br | Br | Br | Br | Me | H |
| Br | Br | F | Br | Et | H | Br | Br | Br | Br | Et | H |
| Br | Br | F | Br | i-Pr | H | Br | Br | Br | Br | i-Pr | H |
| Br | Br | F | Br | t-Bu | H | Br | Br | Br | Br | t-Bu | H |
| Br | Br | F | Br | Me | Me | Br | Br | Br | Br | Me | Me |
| Cl | $OCH_2CF_3$ | F | Br | Me | H | Cl | $OCH_2CF_3$ | Br | Br | Me | H |
| Cl | $OCH_2CF_3$ | F | Br | Et | H | Cl | $OCH_2CF_3$ | Br | Br | Et | H |
| Cl | $OCH_2CF_3$ | F | Br | i-Pr | H | Cl | $OCH_2CF_3$ | Br | Br | i-Pr | H |
| Cl | $OCH_2CF_3$ | F | Br | t-Bu | H | Cl | $OCH_2CF_3$ | Br | Br | t-Bu | H |
| Cl | $OCH_2CF_3$ | F | Br | Me | Me | Cl | $OCH_2CF_3$ | Br | Br | Me | Me |
| Br | $OCH_2CF_3$ | F | Br | Me | H | Br | $OCH_2CF_3$ | Br | Br | Me | H |
| Br | $OCH_2CF_3$ | F | Br | Et | H | Br | $OCH_2CF_3$ | Br | Br | Et | H |
| Br | $OCH_2CF_3$ | F | Br | i-Pr | H | Br | $OCH_2CF_3$ | Br | Br | i-Pr | H |
| Br | $OCH_2CF_3$ | F | Br | t-Bu | H | Br | $OCH_2CF_3$ | Br | Br | t-Bu | H |
| Br | $OCH_2CF_3$ | F | Br | Me | Me | Br | $OCH_2CF_3$ | Br | Br | Me | Me |
| Cl | $CF_3$ | F | I | Me | H | Cl | $CF_3$ | Br | I | Me | H |
| Cl | $CF_3$ | F | I | Et | H | Cl | $CF_3$ | Br | I | Et | H |
| Cl | $CF_3$ | F | I | i-Pr | H | Cl | $CF_3$ | Br | I i-Pr | H | |
| Cl | $CF_3$ | F | I | t-Bu | H | Cl | $CF_3$ | Br | I t-Bu | H | |
| Cl | $CF_3$ | F | I | Me | Me | Cl | $CF_3$ | Br | I | Me | Me |
| Br | $CF_3$ | F | I | Me | H | Br | $CF_3$ | Br | I | Me | H |
| Br | $CF_3$ | F | I | Et | H | Br | $CF_3$ | Br | I | Et | H |
| Br | $CF_3$ | F | I | i-Pr | H | Br | $CF_3$ | Br | I i-Pr | H | |
| Br | $CF_3$ | F | I | t-Bu | H | Br | $CF_3$ | Br | I t-Bu | H | |
| Br | $CF_3$ | F | I | Me | Me | Br | $CF_3$ | Br | I | Me | Me |
| Cl | Cl | F | I | Me | H | Cl | Cl | Br | I | Me | H |
| Cl | Cl | F | I | Et | H | Cl | Cl | Br | I | Et | H |
| Cl | Cl | F | I | i-Pr | H | Cl | Cl | Br | I | i-Pr | H |
| Cl | Cl | F | I | t-Bu | H | Cl | Cl | Br | I | t-Bu | H |
| Cl | Cl | F | I | Me | Me | Cl | Cl | Br | I | Me | Me |
| Br | Cl | F | I | Me | H | Br | Cl | Br | I | Me | H |
| Br | Cl | F | I | Et | H | Br | Cl | Br | I | Et | H |
| Br | Cl | F | I | i-Pr | H | Br | Cl | Br | I | i-Pr | H |
| Br | Cl | F | I | t-Bu | H | Br | Cl | Br | I | t-Bu | H |
| Br | Cl | F | I | Me | Me | Br | Cl | Br | I | Me | Me |
| Cl | Br | F | I | Me | H | Cl | Br | Br | I | Me | H |

TABLE 1-continued

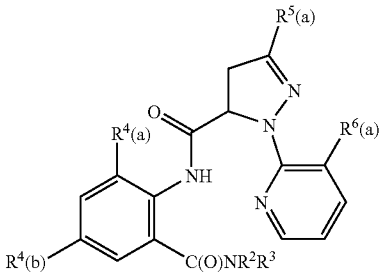

| $R^6(a)$ | $R^5(a)$ | $R^4(a)$ | $R^4(b)$ | $R^3$ | $R^2$ | $R^6(a)$ | $R^5(a)$ | $R^4(a)$ | $R^4(b)$ | $R^3$ | $R^2$ |
|---|---|---|---|---|---|---|---|---|---|---|---|
| Cl | Br | F | I | Et | H | Cl | Br | Br | I | Et | H |
| Cl | Br | F | I | i-Pr | H | Cl | Br | Br | I | i-Pr | H |
| Cl | Br | F | I | t-Bu | H | Cl | Br | Br | I | t-Bu | H |
| Cl | Br | F | I | Me | Me | Cl | Br | Br | I | Me | Me |
| Br | Br | F | I | Me | H | Br | Br | Br | I | Me | H |
| Br | Br | F | I | Et | H | Br | Br | Br | I | Et | H |
| Br | Br | F | I | i-Pr | H | Br | Br | Br | I | i-Pr | H |
| Br | Br | F | I | t-Bu | H | Br | Br | Br | I | t-Bu | H |
| Br | Br | F | I | Me | Me | Br | Br | Br | I | Me | Me |
| Cl | $OCH_2CF_3$ | F | I | Me | H | Cl | $OCH_2CF_3$ | Br | I | Me | H |
| Cl | $OCH_2CF_3$ | F | I | Et | H | Cl | $OCH_2CF_3$ | Br | I | Et | H |
| Cl | $OCH_2CF_3$ | F | I | i-Pr | H | Cl | $OCH_2CF_3$ | Br | I | i-Pr | H |
| Cl | $OCH_2CF_3$ | F | I | t-Bu | H | Cl | $OCH_2CF_3$ | Br | I | t-Bu | H |
| Cl | $OCH_2CF_3$ | F | I | Me | Me | Cl | $OCH_2CF_3$ | Br | I | Me | Me |
| Br | $OCH_2CF_3$ | F | I | Me | H | Br | $OCH_2CF_3$ | Br | I | Me | H |
| Br | $OCH_2CF_3$ | F | I | Et | H | Br | $OCH_2CF_3$ | Br | I | Et | H |
| Br | $OCH_2CF_3$ | F | I | i-Pr | H | Br | $OCH_2CF_3$ | Br | I | i-Pr | H |
| Br | $OCH_2CF_3$ | F | I | t-Bu | H | Br | $OCH_2CF_3$ | Br | I | t-Bu | H |
| Br | $OCH_2CF_3$ | F | I | Me | Me | Br | $OCH_2CF_3$ | Br | I | Me | Me |
| Cl | $CF_3$ | F | $CF_3$ | Me | H | Cl | $CF_3$ | Br | $CF_3$ | Me | H |
| Cl | $CF_3$ | F | $CF_3$ | Et | H | Cl | $CF_3$ | Br | $CF_3$ | Et | H |
| Cl | $CF_3$ | F | $CF_3$ | i-Pr | H | Cl | $CF_3$ | Br | $CF_3$ | i-Pr | H |
| Cl | $CF_3$ | F | $CF_3$ | t-Bu | H | Cl | $CF_3$ | Br | $CF_3$ | t-Bu | H |
| Cl | $CF_3$ | F | $CF_3$ | Me | Me | Cl | $CF_3$ | Br | $CF_3$ | Me | Me |
| Br | $CF_3$ | F | $CF_3$ | Me | H | Br | $CF_3$ | Br | $CF_3$ | Me | H |
| Br | $CF_3$ | F | $CF_3$ | Et | H | Br | $CF_3$ | Br | $CF_3$ | Et | H |
| Br | $CF_3$ | F | $CF_3$ | i-Pr | H | Br | $CF_3$ | Br | $CF_3$ | i-Pr | H |
| Br | $CF_3$ | F | $CF_3$ | t-Bu | H | Br | $CF_3$ | Br | $CF_3$ | t-Bu | H |
| Br | $CF_3$ | F | $CF_3$ | Me | Me | Br | $CF_3$ | Br | $CF_3$ | Me | Me |
| Cl | Cl | F | $CF_3$ | Me | H | Cl | Cl | Br | $CF_3$ | Me | H |
| Cl | Cl | F | $CF_3$ | Et | H | Cl | Cl | Br | $CF_3$ | Et | H |
| Cl | Cl | F | $CF_3$ | i-Pr | H | Cl | Cl | Br | $CF_3$ | i-Pr | H |
| Cl | Cl | F | $CF_3$ | t-Bu | H | Cl | Cl | Br | $CF_3$ | t-Bu | H |
| Cl | Cl | F | $CF_3$ | Me | Me | Cl | Cl | Br | $CF_3$ | Me | Me |
| Br | Cl | F | $CF_3$ | Me | H | Br | Cl | Br | $CF_3$ | Me | H |
| Br | Cl | F | $CF_3$ | Et | H | Br | Cl | Br | $CF_3$ | Et | H |
| Br | Cl | F | $CF_3$ | i-Pr | H | Br | Cl | Br | $CF_3$ | i-Pr | H |
| Br | Cl | F | $CF_3$ | t-Bu | H | Br | Cl | Br | $CF_3$ | t-Bu | H |
| Br | Cl | F | $CF_3$ | Me | Me | Br | Cl | Br | $CF_3$ | Me | Me |
| Cl | Br | F | $CF_3$ | Me | H | Cl | Br | Br | $CF_3$ | Me | H |
| Cl | Br | F | $CF_3$ | Et | H | Cl | Br | Br | $CF_3$ | Et | H |
| Cl | Br | F | $CF_3$ | i-Pr | H | Cl | Br | Br | $CF_3$ | i-Pr | H |
| Cl | Br | F | $CF_3$ | t-Bu | H | Cl | Br | Br | $CF_3$ | t-Bu | H |
| Cl | Br | F | $CF_3$ | Me | Me | Cl | Br | Br | $CF_3$ | Me | Me |
| Br | Br | F | $CF_3$ | Me | H | Br | Br | Br | $CF_3$ | Me | H |
| Br | Br | F | $CF_3$ | Et | H | Br | Br | Br | $CF_3$ | Et | H |
| Br | Br | F | $CF_3$ | i-Pr | H | Br | Br | Br | $CF_3$ | i-Pr | H |
| Br | Br | F | $CF_3$ | t-Bu | H | Br | Br | Br | $CF_3$ | t-Bu | H |
| Br | Br | F | $CF_3$ | Me | Me | Br | Br | Br | $CF_3$ | Me | Me |
| Cl | $OCH_2CF_3$ | F | $CF_3$ | Me | H | Cl | $OCH_2CF_3$ | Br | $CF_3$ | Me | H |
| Cl | $OCH_2CF_3$ | F | $CF_3$ | Et | H | Cl | $OCH_2CF_3$ | Br | $CF_3$ | Et | H |
| Cl | $OCH_2CF_3$ | F | $CF_3$ | i-Pr | H | Cl | $OCH_2CF_3$ | Br | $CF_3$ | i-Pr | H |
| Cl | $OCH_2CF_3$ | F | $CF_3$ | t-Bu | H | Cl | $OCH_2CF_3$ | Br | $CF_3$ | t-Bu | H |
| Cl | $OCH_2CF_3$ | F | $CF_3$ | Me | Me | Cl | $OCH_2CF_3$ | Br | $CF_3$ | Me | Me |
| Br | $OCH_2CF_3$ | F | $CF_3$ | Me | H | Br | $OCH_2CF_3$ | Br | $CF_3$ | Me | H |
| Br | $OCH_2CF_3$ | F | $CF_3$ | Et | H | Br | $OCH_2CF_3$ | Br | $CF_3$ | Et | H |
| Br | $OCH_2CF_3$ | F | $CF_3$ | i-Pr | H | Br | $OCH_2CF_3$ | Br | $CF_3$ | i-Pr | H |
| Br | $OCH_2CF_3$ | F | $CF_3$ | t-Bu | H | Br | $OCH_2CF_3$ | Br | $CF_3$ | t-Bu | H |
| Br | $OCH_2CF_3$ | F | $CF_3$ | Me | Me | Br | $OCH_2CF_3$ | Br | $CF_3$ | Me | Me |

TABLE 2

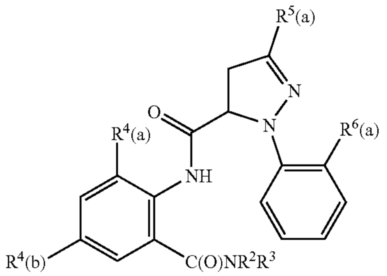

| $R^6$(a) | $R^5$(a) | $R^4$(a) | $R^4$(b) | $R^3$ | $R^2$ | $R^6$(a) | $R^5$(a) | $R^4$(a) | $R^4$(b) | $R^3$ | $R^2$ |
|---|---|---|---|---|---|---|---|---|---|---|---|
| Cl | $CF_3$ | $CH_3$ | H | Me | H | Cl | $CF_3$ | Cl | H | Me | H |
| Cl | $CF_3$ | $CH_3$ | H | Et | H | Cl | $CF_3$ | Cl | H | Et | H |
| Cl | $CF_3$ | $CH_3$ | H | i-Pr | H | Cl | $CF_3$ | Cl | H | i-Pr | H |
| Cl | $CF_3$ | $CH_3$ | H | t-Bu | H | Cl | $CF_3$ | Cl | H | t-Bu | H |
| Cl | $CF_3$ | $CH_3$ | H | Me | Me | Cl | $CF_3$ | Cl | H | Me | Me |
| Br | $CF_3$ | $CH_3$ | H | Me | H | Br | $CF_3$ | Cl | H | Me | H |
| Br | $CF_3$ | $CH_3$ | H | Et | H | Br | $CF_3$ | Cl | H | Et | H |
| Br | $CF_3$ | $CH_3$ | H | i-Pr | H | Br | $CF_3$ | Cl | H | i-Pr | H |
| Br | $CF_3$ | $CH_3$ | H | t-Bu | H | Br | $CF_3$ | Cl | H | t-Bu | H |
| Br | $CF_3$ | $CH_3$ | H | Me | Me | Br | $CF_3$ | Cl | H | Me | Me |
| Cl | Cl | $CH_3$ | H | Me | H | Cl | Cl | Cl | H | Me | H |
| Cl | Cl | $CH_3$ | H | Et | H | Cl | Cl | Cl | H | Et | H |
| Cl | Cl | $CH_3$ | H | i-Pr | H | Cl | Cl | Cl | H | i-Pr | H |
| Cl | Cl | $CH_3$ | H | t-Bu | H | Cl | Cl | Cl | H | t-Bu | H |
| Cl | Cl | $CH_3$ | H | Me | Me | Cl | Cl | Cl | H | Me | Me |
| Br | Cl | $CH_3$ | H | Me | H | Br | Cl | Cl | H | Me | H |
| Br | Cl | $CH_3$ | H | Et | H | Br | Cl | Cl | H | Et | H |
| Br | Cl | $CH_3$ | H | i-Pr | H | Br | Cl | Cl | H | i-Pr | H |
| Br | Cl | $CH_3$ | H | t-Bu | H | Br | Cl | Cl | H | t-Bu | H |
| Br | Cl | $CH_3$ | H | Me | Me | Br | Cl | Cl | H | Me | Me |
| Cl | Br | $CH_3$ | H | Me | H | Cl | Br | Cl | H | Me | H |
| Cl | Br | $CH_3$ | H | Et | H | Cl | Br | Cl | H | Et | H |
| Cl | Br | $CH_3$ | H | i-Pr | H | Cl | Br | Cl | H | i-Pr | H |
| Cl | Br | $CH_3$ | H | t-Bu | H | Cl | Br | Cl | H | t-Bu | H |
| Cl | Br | $CH_3$ | H | Me | Me | Cl | Br | Cl | H | Me | Me |
| Br | Br | $CH_3$ | H | Me | H | Br | Br | Cl | H | Me | H |
| Br | Br | $CH_3$ | H | Et | H | Br | Br | Cl | H | Et | H |
| Br | Br | $CH_3$ | H | i-Pr | H | Br | Br | Cl | H | i-Pr | H |
| Br | Br | $CH_3$ | H | t-Bu | H | Br | Br | Cl | H | t-Bu | H |
| Br | Br | $CH_3$ | H | Me | Me | Br | Br | Cl | H | Me | Me |
| Cl | $OCH_2CF_3$ | $CH_3$ | H | Me | H | Cl | $OCH_2CF_3$ | Cl | H | Me | H |
| Cl | $OCH_2CF_3$ | $CH_3$ | H | Et | H | Cl | $OCH_2CF_3$ | Cl | H | Et | H |
| Cl | $OCH_2CF_3$ | $CH_3$ | H | i-Pr | H | Cl | $OCH_2CF_3$ | Cl | H | i-Pr | H |
| Cl | $OCH_2CF_3$ | $CH_3$ | H | t-Bu | H | Cl | $OCH_2CF_3$ | Cl | H | t-Bu | H |
| Cl | $OCH_2CF_3$ | $CH_3$ | H | Me | Me | Cl | $OCH_2CF_3$ | Cl | H | Me | Me |
| Br | $OCH_2CF_3$ | $CH_3$ | H | Me | H | Br | $OCH_2CF_3$ | Cl | H | Me | H |
| Br | $OCH_2CF_3$ | $CH_3$ | H | Et | H | Br | $OCH_2CF_3$ | Cl | H | Et | H |
| Br | $OCH_2CF_3$ | $CH_3$ | H | i-Pr | H | Br | $OCH_2CF_3$ | Cl | H | i-Pr | H |
| Br | $OCH_2CF_3$ | $CH_3$ | H | t-Bu | H | Br | $OCH_2CF_3$ | Cl | H | t-Bu | H |
| Br | $OCH_2CF_3$ | $CH_3$ | H | Me | Me | Br | $OCH_2CF_3$ | Cl | H | Me | Me |
| Cl | $CF_3$ | $CH_3$ | F | Me | H | Cl | $CF_3$ | Cl | F | Me | H |
| Cl | $CF_3$ | $CH_3$ | F | Et | H | Cl | $CF_3$ | Cl | F | Et | H |
| Cl | $CF_3$ | $CH_3$ | F | i-Pr | H | Cl | $CF_3$ | Cl | F | i-Pr | H |
| Cl | $CF_3$ | $CH_3$ | F | t-Bu | H | Cl | $CF_3$ | Cl | F | t-Bu | H |
| Cl | $CF_3$ | $CH_3$ | F | Me | Me | Cl | $CF_3$ | Cl | F | Me | Me |
| Br | $CF_3$ | $CH_3$ | F | Me | H | Br | $CF_3$ | Cl | F | Me | H |
| Br | $CF_3$ | $CH_3$ | F | Et | H | Br | $CF_3$ | Cl | F | Et | H |
| Br | $CF_3$ | $CH_3$ | F | i-Pr | H | Br | $CF_3$ | Cl | F | i-Pr | H |
| Br | $CF_3$ | $CH_3$ | F | t-Bu | H | Br | $CF_3$ | Cl | F | t-Bu | H |
| Br | $CF_3$ | $CH_3$ | F | Me | Me | Br | $CF_3$ | Cl | F | Me | Me |
| Cl | Cl | $CH_3$ | F | Me | H | Cl | Cl | Cl | F | Me | H |
| Cl | Cl | $CH_3$ | F | Et | H | Cl | Cl | Cl | F | Et | H |
| Cl | Cl | $CH_3$ | F | i-Pr | H | Cl | Cl | Cl | F | i-Pr | H |
| Cl | Cl | $CH_3$ | F | t-Bu | H | Cl | Cl | Cl | F | t-Bu | H |
| Cl | Cl | $CH_3$ | F | Me | Me | Cl | Cl | Cl | F | Me | Me |
| Br | Cl | $CH_3$ | F | Me | H | Br | Cl | Cl | F | Me | H |
| Br | Cl | $CH_3$ | F | Et | H | Br | Cl | Cl | F | Et | H |
| Br | Cl | $CH_3$ | F | i-Pr | H | Br | Cl | Cl | F | i-Pr | H |
| Br | Cl | $CH_3$ | F | t-Bu | H | Br | Cl | Cl | F | t-Bu | H |
| Br | Cl | $CH_3$ | F | Me | Me | Br | Cl | Cl | F | Me | Me |

TABLE 2-continued

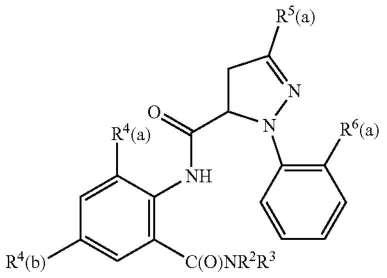

| $R^6$(a) | $R^5$(a) | $R^4$(a) | $R^4$(b) | $R^3$ | $R^2$ | $R^6$(a) | $R^5$(a) | $R^4$(a) | $R^4$(b) | $R^3$ | $R^2$ |
|---|---|---|---|---|---|---|---|---|---|---|---|
| Cl | Br | $CH_3$ | F | Me | H | Cl | Br | Cl | F | Me | H |
| Cl | Br | $CH_3$ | F | Et | H | Cl | Br | Cl | F | Et | H |
| Cl | Br | $CH_3$ | F | i-Pr | H | Cl | Br | Cl | F | i-Pr | H |
| Cl | Br | $CH_3$ | F | t-Bu | H | Cl | Br | Cl | F | t-Bu | H |
| Cl | Br | $CH_3$ | F | Me | Me | Cl | Br | Cl | F | Me | Me |
| Br | Br | $CH_3$ | F | Me | H | Br | Br | Cl | F | Me | H |
| Br | Br | $CH_3$ | F | Et | H | Br | Br | Cl | F | Et | H |
| Br | Br | $CH_3$ | F | i-Pr | H | Br | Br | Cl | F | i-Pr | H |
| Br | Br | $CH_3$ | F | t-Bu | H | Br | Br | Cl | F | t-Bu | H |
| Br | Br | $CH_3$ | F | Me | Me | Br | Br | Cl | F | Me | Me |
| Cl | $OCH_2CF_3$ | $CH_3$ | F | Me | H | Cl | $OCH_2CF_3$ | Cl | F | Me | H |
| Cl | $OCH_2CF_3$ | $CH_3$ | F | Et | H | Cl | $OCH_2CF_3$ | Cl | F | Et | H |
| Cl | $OCH_2CF_3$ | $CH_3$ | F | i-Pr | H | Cl | $OCH_2CF_3$ | Cl | F | i-Pr | H |
| Cl | $OCH_2CF_3$ | $CH_3$ | F | t-Bu | H | Cl | $OCH_2CF_3$ | Cl | F | t-Bu | H |
| Cl | $OCH_2CF_3$ | $CH_3$ | F | Me | Me | Cl | $OCH_2CF_3$ | Cl | F | Me | Me |
| Br | $OCH_2CF_3$ | $CH_3$ | F | Me | H | Br | $OCH_2CF_3$ | Cl | F | Me | H |
| Br | $OCH_2CF_3$ | $CH_3$ | F | Et | H | Br | $OCH_2CF_3$ | Cl | F | Et | H |
| Br | $OCH_2CF_3$ | $CH_3$ | F | i-Pr | H | Br | $OCH_2CF_3$ | Cl | F | i-Pr | H |
| Br | $OCH_2CF_3$ | $CH_3$ | F | t-Bu | H | Br | $OCH_2CF_3$ | Cl | F | t-Bu | H |
| Br | $OCH_2CF_3$ | $CH_3$ | F | Me | Me | Br | $OCH_2CF_3$ | Cl | F | Me | Me |
| Cl | $CF_3$ | $CH_3$ | Cl | Me | H | Cl | $CF_3$ | Cl | Cl | Me | H |
| Cl | $CF_3$ | $CH_3$ | Cl | Et | H | Cl | $CF_3$ | Cl | Cl | Et | H |
| Cl | $CF_3$ | $CH_3$ | Cl | i-Pr | H | Cl | $CF_3$ | Cl | Cl | i-Pr | H |
| Cl | $CF_3$ | $CH_3$ | Cl | t-Bu | H | Cl | $CF_3$ | Cl | Cl | t-Bu | H |
| Cl | $CF_3$ | $CH_3$ | Cl | Me | Me | Cl | $CF_3$ | Cl | Cl | Me | Me |
| Br | $CF_3$ | $CH_3$ | Cl | Me | H | Br | $CF_3$ | Cl | Cl | Me | H |
| Br | $CF_3$ | $CH_3$ | Cl | Et | H | Br | $CF_3$ | Cl | Cl | Et | H |
| Br | $CF_3$ | $CH_3$ | Cl | i-Pr | H | Br | $CF_3$ | Cl | Cl | i-Pr | H |
| Br | $CF_3$ | $CH_3$ | Cl | t-Bu | H | Br | $CF_3$ | Cl | Cl | t-Bu | H |
| Br | $CF_3$ | $CH_3$ | Cl | Me | Me | Br | $CF_3$ | Cl | Cl | Me | Me |
| Cl | Cl | $CH_3$ | Cl | Me | H | Cl | Cl | Cl | Cl | Me | H |
| Cl | Cl | $CH_3$ | Cl | Et | H | Cl | Cl | Cl | Cl | Et | H |
| Cl | Cl | $CH_3$ | Cl | i-Pr | H | Cl | Cl | Cl | Cl | i-Pr | H |
| Cl | Cl | $CH_3$ | Cl | t-Bu | H | Cl | Cl | Cl | Cl | t-Bu | H |
| Cl | Cl | $CH_3$ | Cl | Me | Me | Cl | Cl | Cl | Cl | Me | Me |
| Br | Cl | $CH_3$ | Cl | Me | H | Br | Cl | Cl | Cl | Me | H |
| Br | Cl | $CH_3$ | Cl | Et | H | Br | Cl | Cl | Cl | Et | H |
| Br | Cl | $CH_3$ | Cl | i-Pr | H | Br | Cl | Cl | Cl | i-Pr | H |
| Br | Cl | $CH_3$ | Cl | t-Bu | H | Br | Cl | Cl | Cl | t-Bu | H |
| Br | Cl | $CH_3$ | Cl | Me | Me | Br | Cl | Cl | Cl | Me | Me |
| Cl | Br | $CH_3$ | Cl | Me | H | Cl | Br | Cl | Cl | Me | H |
| Cl | Br | $CH_3$ | Cl | Et | H | Cl | Br | Cl | Cl | Et | H |
| Cl | Br | $CH_3$ | Cl | i-Pr | H | Cl | Br | Cl | Cl | i-Pr | H |
| Cl | Br | $CH_3$ | Cl | t-Bu | H | Cl | Br | Cl | Cl | t-Bu | H |
| Cl | Br | $CH_3$ | Cl | Me | Me | Cl | Br | Cl | Cl | Me | Me |
| Br | Br | $CH_3$ | Cl | Me | H | Br | Br | Cl | Cl | Me | H |
| Br | Br | $CH_3$ | Cl | Et | H | Br | Br | Cl | Cl | Et | H |
| Br | Br | $CH_3$ | Cl | i-Pr | H | Br | Br | Cl | Cl | i-Pr | H |
| Br | Br | $CH_3$ | Cl | t-Bu | H | Br | Br | Cl | Cl | t-Bu | H |
| Br | Br | $CH_3$ | Cl | Me | Me | Br | Br | Cl | Cl | Me | Me |
| Cl | $OCH_2CF_3$ | $CH_3$ | Cl | Me | H | Cl | $OCH_2CF_3$ | Cl | Cl | Me | H |
| Cl | $OCH_2CF_3$ | $CH_3$ | Cl | Et | H | Cl | $OCH_2CF_3$ | Cl | Cl | Et | H |
| Cl | $OCH_2CF_3$ | $CH_3$ | Cl | i-Pr | H | Cl | $OCH_2CF_3$ | Cl | Cl | i-Pr | H |
| Cl | $OCH_2CF_3$ | $CH_3$ | Cl | t-Bu | H | Cl | $OCH_2CF_3$ | Cl | Cl | t-Bu | H |
| Cl | $OCH_2CF_3$ | $CH_3$ | Cl | Me | Me | Cl | $OCH_2CF_3$ | Cl | Cl | Me | Me |
| Br | $OCH_2CF_3$ | $CH_3$ | Cl | Me | H | Br | $OCH_2CF_3$ | Cl | Cl | Me | H |
| Br | $OCH_2CF_3$ | $CH_3$ | Cl | Et | H | Br | $OCH_2CF_3$ | Cl | Cl | Et | H |
| Br | $OCH_2CF_3$ | $CH_3$ | Cl | i-Pr | H | Br | $OCH_2CF_3$ | Cl | Cl | i-Pr | H |
| Br | $OCH_2CF_3$ | $CH_3$ | Cl | t-Bu | H | Br | $OCH_2CF_3$ | Cl | Cl | t-Bu | H |
| Br | $OCH_2CF_3$ | $CH_3$ | Cl | Me | Me | Br | $OCH_2CF_3$ | Cl | Cl | Me | Me |

TABLE 2-continued

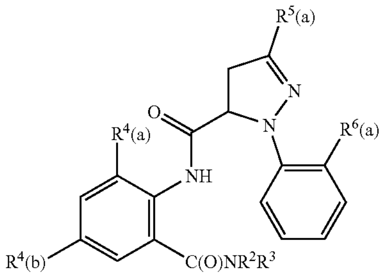

| $R^6$(a) | $R^5$(a) | $R^4$(a) | $R^4$(b) | $R^3$ | $R^2$ | $R^6$(a) | $R^5$(a) | $R^4$(a) | $R^4$(b) | $R^3$ | $R^2$ |
|---|---|---|---|---|---|---|---|---|---|---|---|
| Cl | $CF_3$ | $CH_3$ | Br | Me | H | Cl | $CF_3$ | Cl | Br | Me | H |
| Cl | $CF_3$ | $CH_3$ | Br | Et | H | Cl | $CF_3$ | Cl | Br | Et | H |
| Cl | $CF_3$ | $CH_3$ | Br | i-Pr | H | Cl | $CF_3$ | Cl | Br | i-Pr | H |
| Cl | $CF_3$ | $CH_3$ | Br | t-Bu | H | Cl | $CF_3$ | Cl | Br | t-Bu | H |
| Cl | $CF_3$ | $CH_3$ | Br | Me | Me | Cl | $CF_3$ | Cl | Br | Me | Me |
| Br | $CF_3$ | $CH_3$ | Br | Me | H | Br | $CF_3$ | Cl | Br | Me | H |
| Br | $CF_3$ | $CH_3$ | Br | Et | H | Br | $CF_3$ | Cl | Br | Et | H |
| Br | $CF_3$ | $CH_3$ | Br | i-Pr | H | Br | $CF_3$ | Cl | Br | i-Pr | H |
| Br | $CF_3$ | $CH_3$ | Br | t-Bu | H | Br | $CF_3$ | Cl | Br | t-Bu | H |
| Br | $CF_3$ | $CH_3$ | Br | Me | Me | Br | $CF_3$ | Cl | Br | Me | Me |
| Cl | Cl | $CH_3$ | Br | Me | H | Cl | Cl | Cl | Br | Me | H |
| Cl | Cl | $CH_3$ | Br | Et | H | Cl | Cl | Cl | Br | Et | H |
| Cl | Cl | $CH_3$ | Br | i-Pr | H | Cl | Cl | Cl | Br | i-Pr | H |
| Cl | Cl | $CH_3$ | Br | t-Bu | H | Cl | Cl | Cl | Br | t-Bu | H |
| Cl | Cl | $CH_3$ | Br | Me | Me | Cl | Cl | Cl | Br | Me | Me |
| Br | Cl | $CH_3$ | Br | Me | H | Br | Cl | Cl | Br | Me | H |
| Br | Cl | $CH_3$ | Br | Et | H | Br | Cl | Cl | Br | Et | H |
| Br | Cl | $CH_3$ | Br | i-Pr | H | Br | Cl | Cl | Br | i-Pr | H |
| Br | Cl | $CH_3$ | Br | t-Bu | H | Br | Cl | Cl | Br | t-Bu | H |
| Br | Cl | $CH_3$ | Br | Me | Me | Br | Cl | Cl | Br | Me | Me |
| Cl | Br | $CH_3$ | Br | Me | H | Cl | Br | Cl | Br | Me | H |
| Cl | Br | $CH_3$ | Br | Et | H | Cl | Br | Cl | Br | Et | H |
| Cl | Br | $CH_3$ | Br | i-Pr | H | Cl | Br | Cl | Br | i-Pr | H |
| Cl | Br | $CH_3$ | Br | t-Bu | H | Cl | Br | Cl | Br | t-Bu | H |
| Cl | Br | $CH_3$ | Br | Me | Me | Cl | Br | Cl | Br | Me | Me |
| Br | Br | $CH_3$ | Br | Me | H | Br | Br | Cl | Br | Me | H |
| Br | Br | $CH_3$ | Br | Et | H | Br | Br | Cl | Br | Et | H |
| Br | Br | $CH_3$ | Br | i-Pr | H | Br | Br | Cl | Br | i-Pr | H |
| Br | Br | $CH_3$ | Br | t-Bu | H | Br | Br | Cl | Br | t-Bu | H |
| Br | Br | $CH_3$ | Br | Me | Me | Br | Br | Cl | Br | Me | Me |
| Cl | $OCH_2CF_3$ | $CH_3$ | Br | Me | H | Cl | $OCH_2CF_3$ | Cl | Br | Me | H |
| Cl | $OCH_2CF_3$ | $CH_3$ | Br | Et | H | Cl | $OCH_2CF_3$ | Cl | Br | Et | H |
| Cl | $OCH_2CF_3$ | $CH_3$ | Br | i-Pr | H | Cl | $OCH_2CF_3$ | Cl | Br | i-Pr | H |
| Cl | $OCH_2CF_3$ | $CH_3$ | Br | t-Bu | H | Cl | $OCH_2CF_3$ | Cl | Br | t-Bu | H |
| Cl | $OCH_2CF_3$ | $CH_3$ | Br | Me | Me | Cl | $OCH_2CF_3$ | Cl | Br | Me | Me |
| Br | $OCH_2CF_3$ | $CH_3$ | Br | Me | H | Br | $OCH_2CF_3$ | Cl | Br | Me | H |
| Br | $OCH_2CF_3$ | $CH_3$ | Br | Et | H | Br | $OCH_2CF_3$ | Cl | Br | Et | H |
| Br | $OCH_2CF_3$ | $CH_3$ | Br | i-Pr | H | Br | $OCH_2CF_3$ | Cl | Br | i-Pr | H |
| Br | $OCH_2CF_3$ | $CH_3$ | Br | t-Bu | H | Br | $OCH_2CF_3$ | Cl | Br | t-Bu | H |
| Br | $OCH_2CF_3$ | $CH_3$ | Br | Me | Me | Br | $OCH_2CF_3$ | Cl | Br | Me | Me |
| Cl | $CF_3$ | $CH_3$ | I | Me | H | Cl | $CF_3$ | Cl | I | Me | H |
| Cl | $CF_3$ | $CH_3$ | I | Et | H | Cl | $CF_3$ | Cl | I | Et | H |
| Cl | $CF_3$ | $CH_3$ | I | i-Pr | H | Cl | $CF_3$ | Cl | I | i-Pr | H |
| Cl | $CF_3$ | $CH_3$ | I | t-Bu | H | Cl | $CF_3$ | Cl | I | t-Bu | H |
| Cl | $CF_3$ | $CH_3$ | I | Me | Me | Cl | $CF_3$ | Cl | I | Me | Me |
| Br | $CF_3$ | $CH_3$ | I | Me | H | Br | $CF_3$ | Cl | I | Me | H |
| Br | $CF_3$ | $CH_3$ | I | Et | H | Br | $CF_3$ | Cl | I | Et | H |
| Br | $CF_3$ | $CH_3$ | I | i-Pr | H | Br | $CF_3$ | Cl | I | i-Pr | H |
| Br | $CF_3$ | $CH_3$ | I | t-Bu | H | Br | $CF_3$ | Cl | I | t-Bu | H |
| Br | $CF_3$ | $CH_3$ | I | Me | Me | Br | $CF_3$ | Cl | I | Me | Me |
| Cl | Cl | $CH_3$ | I | Me | H | Cl | Cl | Cl | I | Me | H |
| Cl | Cl | $CH_3$ | I | Et | H | Cl | Cl | Cl | I | Et | H |
| Cl | Cl | $CH_3$ | I | i-Pr | H | Cl | Cl | Cl | I | i-Pr | H |
| Cl | Cl | $CH_3$ | I | t-Bu | H | Cl | Cl | Cl | I | t-Bu | H |
| Cl | Cl | $CH_3$ | I | Me | Me | Cl | Cl | Cl | I | Me | Me |
| Br | Cl | $CH_3$ | I | Me | H | Br | Cl | Cl | I | Me | H |
| Br | Cl | $CH_3$ | I | Et | H | Br | Cl | Cl | I | Et | H |
| Br | Cl | $CH_3$ | I | i-Pr | H | Br | Cl | Cl | I | i-Pr | H |
| Br | Cl | $CH_3$ | I | t-Bu | H | Br | Cl | Cl | I | t-Bu | H |
| Br | Cl | $CH_3$ | I | Me | Me | Br | Cl | Cl | I | Me | Me |

TABLE 2-continued

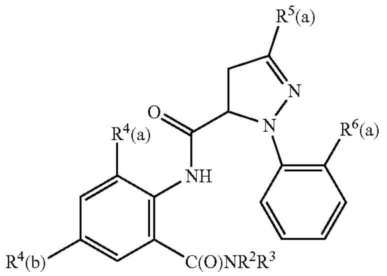

| $R^6$(a) | $R^5$(a) | $R^4$(a) | $R^4$(b) | $R^3$ | $R^2$ | $R^6$(a) | $R^5$(a) | $R^4$(a) | $R^4$(b) | $R^3$ | $R^2$ |
|---|---|---|---|---|---|---|---|---|---|---|---|
| Cl | Br | $CH_3$ | I | Me | H | Cl | Br | Cl | I | Me | H |
| Cl | Br | $CH_3$ | I | Et | H | Cl | Br | Cl | I | Et | H |
| Cl | Br | $CH_3$ | I | i-Pr | H | Cl | Br | Cl | I | i-Pr | H |
| Cl | Br | $CH_3$ | I | t-Bu | H | Cl | Br | Cl | I | t-Bu | H |
| Cl | Br | $CH_3$ | I | Me | Me | Cl | Br | Cl | I | Me | Me |
| Br | Br | $CH_3$ | I | Me | H | Br | Br | Cl | I | Me | H |
| Br | Br | $CH_3$ | I | Et | H | Br | Br | Cl | I | Et | H |
| Br | Br | $CH_3$ | I | i-Pr | H | Br | Br | Cl | I | i-Pr | H |
| Br | Br | $CH_3$ | I | t-Bu | H | Br | Br | Cl | I | t-Bu | H |
| Br | Br | $CH_3$ | I | Me | Me | Br | Br | Cl | I | Me | Me |
| Cl | $OCH_2CF_3$ | $CH_3$ | I | Me | H | Cl | $OCH_2CF_3$ | Cl | I | Me | H |
| Cl | $OCH_2CF_3$ | $CH_3$ | I | Et | H | Cl | $OCH_2CF_3$ | Cl | I | Et | H |
| Cl | $OCH_2CF_3$ | $CH_3$ | I | i-Pr | H | Cl | $OCH_2CF_3$ | Cl | I | i-Pr | H |
| Cl | $OCH_2CF_3$ | $CH_3$ | I | t-Bu | H | Cl | $OCH_2CF_3$ | Cl | I | t-Bu | H |
| Cl | $OCH_2CF_3$ | $CH_3$ | I | Me | Me | Cl | $OCH_2CF_3$ | Cl | I | Me | Me |
| Br | $OCH_2CF_3$ | $CH_3$ | I | Me | H | Br | $OCH_2CF_3$ | Cl | I | Me | H |
| Br | $OCH_2CF_3$ | $CH_3$ | I | Et | H | Br | $OCH_2CF_3$ | Cl | I | Et | H |
| Br | $OCH_2CF_3$ | $CH_3$ | I | i-Pr | H | Br | $OCH_2CF_3$ | Cl | I | i-Pr | H |
| Br | $OCH_2CF_3$ | $CH_3$ | I | t-Bu | H | Br | $OCH_2CF_3$ | Cl | I | t-Bu | H |
| Br | $OCH_2CF_3$ | $CH_3$ | I | Me | Me | Br | $OCH_2CF_3$ | Cl | I | Me | Me |
| Cl | $CF_3$ | $CH_3$ | $CF_3$ | Me | H | Cl | $CF_3$ | Cl | $CF_3$ | Me | H |
| Cl | $CF_3$ | $CH_3$ | $CF_3$ | Et | H | Cl | $CF_3$ | Cl | $CF_3$ | Et | H |
| Cl | $CF_3$ | $CH_3$ | $CF_3$ | i-Pr | H | Cl | $CF_3$ | Cl | $CF_3$ | i-Pr | H |
| Cl | $CF_3$ | $CH_3$ | $CF_3$ | t-Bu | H | Cl | $CF_3$ | Cl | $CF_3$ | t-Bu | H |
| Cl | $CF_3$ | $CH_3$ | $CF_3$ | Me | Me | Cl | $CF_3$ | Cl | $CF_3$ | Me | Me |
| Br | $CF_3$ | $CH_3$ | $CF_3$ | Me | H | Br | $CF_3$ | Cl | $CF_3$ | Me | H |
| Br | $CF_3$ | $CH_3$ | $CF_3$ | Et | H | Br | $CF_3$ | Cl | $CF_3$ | Et | H |
| Br | $CF_3$ | $CH_3$ | $CF_3$ | i-Pr | H | Br | $CF_3$ | Cl | $CF_3$ | i-Pr | H |
| Br | $CF_3$ | $CH_3$ | $CF_3$ | t-Bu | H | Br | $CF_3$ | Cl | $CF_3$ | t-Bu | H |
| Br | $CF_3$ | $CH_3$ | $CF_3$ | Me | Me | Br | $CF_3$ | Cl | $CF_3$ | Me | Me |
| Cl | Cl | $CH_3$ | $CF_3$ | Me | H | Cl | Cl | Cl | $CF_3$ | Me | H |
| Cl | Cl | $CH_3$ | $CF_3$ | Et | H | Cl | Cl | Cl | $CF_3$ | Et | H |
| Cl | Cl | $CH_3$ | $CF_3$ | i-Pr | H | Cl | Cl | Cl | $CF_3$ | i-Pr | H |
| Cl | Cl | $CH_3$ | $CF_3$ | t-Bu | H | Cl | Cl | Cl | $CF_3$ | t-Bu | H |
| Cl | Cl | $CH_3$ | $CF_3$ | Me | Me | Cl | Cl | Cl | $CF_3$ | Me | Me |
| Br | Cl | $CH_3$ | $CF_3$ | Me | H | Br | Cl | Cl | $CF_3$ | Me | H |
| Br | Cl | $CH_3$ | $CF_3$ | Et | H | Br | Cl | Cl | $CF_3$ | Et | H |
| Br | Cl | $CH_3$ | $CF_3$ | i-Pr | H | Br | Cl | Cl | $CF_3$ | i-Pr | H |
| Br | Cl | $CH_3$ | $CF_3$ | t-Bu | H | Br | Cl | Cl | $CF_3$ | t-Bu | H |
| Br | Cl | $CH_3$ | $CF_3$ | Me | Me | Br | Cl | Cl | $CF_3$ | Me | Me |
| Cl | Br | $CH_3$ | $CF_3$ | Me | H | Cl | Br | Cl | $CF_3$ | Me | H |
| Cl | Br | $CH_3$ | $CF_3$ | Et | H | Cl | Br | Cl | $CF_3$ | Et | H |
| Cl | Br | $CH_3$ | $CF_3$ | i-Pr | H | Cl | Br | Cl | $CF_3$ | i-Pr | H |
| Cl | Br | $CH_3$ | $CF_3$ | t-Bu | H | Cl | Br | Cl | $CF_3$ | t-Bu | H |
| Cl | Br | $CH_3$ | $CF_3$ | Me | Me | Cl | Br | Cl | $CF_3$ | Me | Me |
| Br | Br | $CH_3$ | $CF_3$ | Me | H | Br | Br | Cl | $CF_3$ | Me | H |
| Br | Br | $CH_3$ | $CF_3$ | Et | H | Br | Br | Cl | $CF_3$ | Et | H |
| Br | Br | $CH_3$ | $CF_3$ | i-Pr | H | Br | Br | Cl | $CF_3$ | i-Pr | H |
| Br | Br | $CH_3$ | $CF_3$ | t-Bu | H | Br | Br | Cl | $CF_3$ | t-Bu | H |
| Br | Br | $CH_3$ | $CF_3$ | Me | Me | Br | Br | Cl | $CF_3$ | Me | Me |
| Cl | $OCH_2CF_3$ | $CH_3$ | $CF_3$ | Me | H | Cl | $OCH_2CF_3$ | Cl | $CF_3$ | Me | H |
| Cl | $OCH_2CF_3$ | $CH_3$ | $CF_3$ | Et | H | Cl | $OCH_2CF_3$ | Cl | $CF_3$ | Et | H |
| Cl | $OCH_2CF_3$ | $CH_3$ | $CF_3$ | i-Pr | H | Cl | $OCH_2CF_3$ | Cl | $CF_3$ | i-Pr | H |
| Cl | $OCH_2CF_3$ | $CH_3$ | $CF_3$ | t-Bu | H | Cl | $OCH_2CF_3$ | Cl | $CF_3$ | t-Bu | H |
| Cl | $OCH_2CF_3$ | $CH_3$ | $CF_3$ | Me | Me | Cl | $OCH_2CF_3$ | Cl | $CF_3$ | Me | Me |
| Br | $OCH_2CF_3$ | $CH_3$ | $CF_3$ | Me | H | Br | $OCH_2CF_3$ | Cl | $CF_3$ | Me | H |
| Br | $OCH_2CF_3$ | $CH_3$ | $CF_3$ | Et | H | Br | $OCH_2CF_3$ | Cl | $CF_3$ | Et | H |
| Br | $OCH_2CF_3$ | $CH_3$ | $CF_3$ | i-Pr | H | Br | $OCH_2CF_3$ | Cl | $CF_3$ | i-Pr | H |
| Br | $OCH_2CF_3$ | $CH_3$ | $CF_3$ | t-Bu | H | Br | $OCH_2CF_3$ | Cl | $CF_3$ | t-Bu | H |
| Br | $OCH_2CF_3$ | $CH_3$ | $CF_3$ | Me | Me | Br | $OCH_2CF_3$ | Cl | $CF_3$ | Me | Me |

TABLE 2-continued

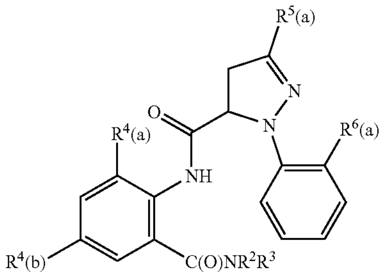

| $R^6(a)$ | $R^5(a)$ | $R^4(a)$ | $R^4(b)$ | $R^3$ | $R^2$ | $R^6(a)$ | $R^5(a)$ | $R^4(a)$ | $R^4(b)$ | $R^3$ | $R^2$ |
|---|---|---|---|---|---|---|---|---|---|---|---|
| Cl | Cl | $CH_3$ | Cl | n-Pr | H | Cl | Cl | Cl | Cl | n-Pr | H |
| Cl | Cl | $CH_3$ | Cl | n-Bu | H | Cl | Cl | Cl | Cl | n-Bu | H |
| Cl | Cl | $CH_3$ | Cl | s-Bu | H | Cl | Cl | Cl | Cl | s-Bu | H |
| Cl | Cl | $CH_3$ | Cl | i-Bu | H | Cl | Cl | Cl | Cl | i-Bu | H |
| Cl | Cl | $CH_3$ | Cl | Et | Me | Cl | Cl | Cl | Cl | Et | Et |
| Cl | $CF_3$ | F | H | Me | H | Cl | $CF_3$ | Br | H | Me | H |
| Cl | $CF_3$ | F | H | Et | H | Cl | $CF_3$ | Br | H | Et | H |
| Cl | $CF_3$ | F | H | i-Pr | H | Cl | $CF_3$ | Br | H | i-Pr | H |
| Cl | $CF_3$ | F | H | t-Bu | H | Cl | $CF_3$ | Br | H | t-Bu | H |
| Cl | $CF_3$ | F | H | Me | Me | Cl | $CF_3$ | Br | H | Me | Me |
| Br | $CF_3$ | F | H | Me | H | Br | $CF_3$ | Br | H | Me | H |
| Br | $CF_3$ | F | H | Et | H | Br | $CF_3$ | Br | H | Et | H |
| Br | $CF_3$ | F | H | i-Pr | H | Br | $CF_3$ | Br | H | i-Pr | H |
| Br | $CF_3$ | F | H | t-Bu | H | Br | $CF_3$ | Br | H | t-Bu | H |
| Br | $CF_3$ | F | H | Me | Me | Br | $CF_3$ | Br | H | Me | Me |
| Cl | Cl | F | H | Me | H | Cl | Cl | Br | H | Me | H |
| Cl | Cl | F | H | Et | H | Cl | Cl | Br | H | Et | H |
| Cl | Cl | F | H | i-Pr | H | Cl | Cl | Br | H | i-Pr | H |
| Cl | Cl | F | H | t-Bu | H | Cl | Cl | Br | H | t-Bu | H |
| Cl | Cl | F | H | Me | Me | Cl | Cl | Br | H | Me | Me |
| Br | Cl | F | H | Me | H | Br | Cl | Br | H | Me | H |
| Br | Cl | F | H | Et | H | Br | Cl | Br | H | Et | H |
| Br | Cl | F | H | i-Pr | H | Br | Cl | Br | H | i-Pr | H |
| Br | Cl | F | H | t-Bu | H | Br | Cl | Br | H | t-Bu | H |
| Br | Cl | F | H | Me | Me | Br | Cl | Br | H | Me | Me |
| Cl | Br | F | H | Me | H | Cl | Br | Br | H | Me | H |
| Cl | Br | F | H | Et | H | Cl | Br | Br | H | Et | H |
| Cl | Br | F | H | i-Pr | H | Cl | Br | Br | H | i-Pr | H |
| Cl | Br | F | H | t-Bu | H | Cl | Br | Br | H | t-Bu | H |
| Cl | Br | F | H | Me | Me | Cl | Br | Br | H | Me | Me |
| Br | Br | F | H | Me | H | Br | Br | Br | H | Me | H |
| Br | Br | F | H | Et | H | Br | Br | Br | H | Et | H |
| Br | Br | F | H | i-Pr | H | Br | Br | Br | H | i-Pr | H |
| Br | Br | F | H | t-Bu | H | Br | Br | Br | H | t-Bu | H |
| Br | Br | F | H | Me | Me | Br | Br | Br | H | Me | Me |
| Cl | $OCH_2CF_3$ | F | H | Me | H | Cl | $OCH_2CF_3$ | Br | H | Me | H |
| Cl | $OCH_2CF_3$ | F | H | Et | H | Cl | $OCH_2CF_3$ | Br | H | Et | H |
| Cl | $OCH_2CF_3$ | F | H | i-Pr | H | Cl | $OCH_2CF_3$ | Br | H | i-Pr | H |
| Cl | $OCH_2CF_3$ | F | H | t-Bu | H | Cl | $OCH_2CF_3$ | Br | H | t-Bu | H |
| Cl | $OCH_2CF_3$ | F | H | Me | Me | Cl | $OCH_2CF_3$ | Br | H | Me | Me |
| Br | $OCH_2CF_3$ | F | H | Me | H | Br | $OCH_2CF_3$ | Br | H | Me | H |
| Br | $OCH_2CF_3$ | F | H | Et | H | Br | $OCH_2CF_3$ | Br | H | Et | H |
| Br | $OCH_2CF_3$ | F | H | i-Pr | H | Br | $OCH_2CF_3$ | Br | H | i-Pr | H |
| Br | $OCH_2CF_3$ | F | H | t-Bu | H | Br | $OCH_2CF_3$ | Br | H | t-Bu | H |
| Br | $OCH_2CF_3$ | F | H | Me | Me | Br | $OCH_2CF_3$ | Br | H | Me | Me |
| Cl | $CF_3$ | F | F | Me | H | Cl | $CF_3$ | Br | F | Me | H |
| Cl | $CF_3$ | F | F | Et | H | Cl | $CF_3$ | Br | F | Et | H |
| Cl | $CF_3$ | F | F | i-Pr | H | Cl | $CF_3$ | Br | F | i-Pr | H |
| Cl | $CF_3$ | F | F | t-Bu | H | Cl | $CF_3$ | Br | F | t-Bu | H |
| Cl | $CF_3$ | F | F | Me | Me | Cl | $CF_3$ | Br | F | Me | Me |
| Br | $CF_3$ | F | F | Me | H | Br | $CF_3$ | Br | F | Me | H |
| Br | $CF_3$ | F | F | Et | H | Br | $CF_3$ | Br | F | Et | H |
| Br | $CF_3$ | F | F | i-Pr | H | Br | $CF_3$ | Br | F | i-Pr | H |
| Br | $CF_3$ | F | F | t-Bu | H | Br | $CF_3$ | Br | F | t-Bu | H |
| Br | $CF_3$ | F | F | Me | Me | Br | $CF_3$ | Br | F | Me | Me |
| Cl | Cl | F | F | Me | H | Cl | Cl | Br | F | Me | H |
| Cl | Cl | F | F | Et | H | Cl | Cl | Br | F | Et | H |
| Cl | Cl | F | F | i-Pr | H | Cl | Cl | Br | F | i-Pr | H |
| Cl | Cl | F | F | t-Bu | H | Cl | Cl | Br | F | t-Bu | H |
| Cl | Cl | F | F | Me | Me | Cl | Cl | Br | F | Me | Me |

TABLE 2-continued

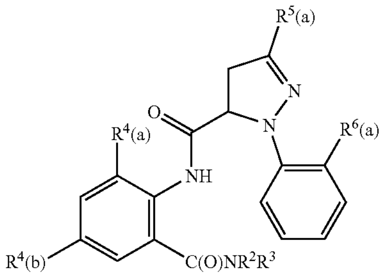

| $R^6$(a) | $R^5$(a) | $R^4$(a) | $R^4$(b) | $R^3$ | $R^2$ | $R^6$(a) | $R^5$(a) | $R^4$(a) | $R^4$(b) | $R^3$ | $R^2$ |
|---|---|---|---|---|---|---|---|---|---|---|---|
| Br | Cl | F | F | Me | H | Br | Cl | Br | F | Me | H |
| Br | Cl | F | F | EL | H | Br | Cl | Br | F | EL | H |
| Br | Cl | F | F | i-Pr | H | Br | Cl | Br | F | i-Pr | H |
| Br | Cl | F | F | t-Bu | H | Br | Cl | Br | F | t-Bu | H |
| Br | Cl | F | F | Me | Me | Br | Cl | Br | F | Me | Me |
| Cl | Br | F | F | Me | H | Cl | Br | Br | F | Me | H |
| Cl | Br | F | F | Et | H | Cl | Br | Br | F | EL | H |
| Cl | Br | F | F | i-Pr | H | Cl | Br | Br | F | i-Pr | H |
| Cl | Br | F | F | t-Bu | H | Cl | Br | Br | F | t-Bu | H |
| Cl | Br | F | F | Me | Me | Cl | Br | Br | F | Me | Me |
| Br | Br | F | F | Me | H | Br | Br | Br | F | Me | H |
| Br | Br | F | F | Et | H | Br | Br | Br | F | Et | H |
| Br | Br | F | F | i-Pr | H | Br | Br | Br | F | i-Pr | H |
| Br | Br | F | F | t-Bu | H | Br | Br | Br | F | t-Bu | H |
| Br | Br | F | F | Me | Me | Br | Br | Br | F | Me | Me |
| Cl | $OCH_2CF_3$ | F | F | Me | H | Cl | $OCH_2CF_3$ | Br | F | Me | H |
| Cl | $OCH_2CF_3$ | F | F | Et | H | Cl | $OCH_2CF_3$ | Br | F | Et | H |
| Cl | $OCH_2CF_3$ | F | F | i-Pr | H | Cl | $OCH_2CF_3$ | Br | F | i-Pr | H |
| Cl | $OCH_2CF_3$ | F | F | t-Bu | H | Cl | $OCH_2CF_3$ | Br | F | t-Bu | H |
| Cl | $OCH_2CF_3$ | F | F | Me | Me | Cl | $OCH_2CF_3$ | Br | F | Me | Me |
| Br | $OCH_2CF_3$ | F | F | Me | H | Br | $OCH_2CF_3$ | Br | F | Me | H |
| Br | $OCH_2CF_3$ | F | F | EL | H | Br | $OCH_2CF_3$ | Br | F | EL | H |
| Br | $OCH_2CF_3$ | F | F | i-Pr | H | Br | $OCH_2CF_3$ | Br | F | i-Pr | H |
| Br | $OCH_2CF_3$ | F | F | t-Bu | H | Br | $OCH_2CF_3$ | Br | F | t-Bu | H |
| Br | $OCH_2CF_3$ | F | F | Me | Me | Br | $OCH_2CF_3$ | Br | F | Me | Me |
| Cl | $CF_3$ | F | Cl | Me | H | Cl | $CF_3$ | Br | Cl | Me | H |
| Cl | $CF_3$ | F | Cl | Et | H | Cl | $CF_3$ | Br | Cl | Et | H |
| Cl | $CF_3$ | F | Cl | i-Pr | H | Cl | $CF_3$ | Br | Cl | i-Pr | H |
| Cl | $CF_3$ | F | Cl | t-Bu | H | Cl | $CF_3$ | Br | Cl | t-Bu | H |
| Cl | $CF_3$ | F | Cl | Me | Me | Cl | $CF_3$ | Br | Cl | Me | Me |
| Br | $CF_3$ | F | Cl | Me | H | Br | $CF_3$ | Br | Cl | Me | H |
| Br | $CF_3$ | F | Cl | EL | H | Br | $CF_3$ | Br | Cl | Et | H |
| Br | $CF_3$ | F | Cl | i-Pr | H | Br | $CF_3$ | Br | Cl | i-Pr | H |
| Br | $CF_3$ | F | Cl | t-Bu | H | Br | $CF_3$ | Br | Cl | t-Bu | H |
| Br | $CF_3$ | F | Cl | Me | Me | Br | $CF_3$ | Br | Cl | Me | Me |
| Cl | Cl | F | Cl | Me | H | Cl | Cl | Br | Cl | Me | H |
| Cl | Cl | F | Cl | Et | H | Cl | Cl | Br | Cl | Et | H |
| Cl | Cl | F | Cl | i-Pr | H | Cl | Cl | Br | Cl | i-Pr | H |
| Cl | Cl | F | Cl | t-Bu | H | Cl | Cl | Br | Cl | t-Bu | H |
| Cl | Cl | F | Cl | Me | Me | Cl | Cl | Br | Cl | Me | Me |
| Br | Cl | F | Cl | Me | H | Br | Cl | Br | Cl | Me | H |
| Br | Cl | F | Cl | Et | H | Br | Cl | Br | Cl | Et | H |
| Br | Cl | F | Cl | i-Pr | H | Br | Cl | Br | Cl | i-Pr | H |
| Br | Cl | F | Cl | t-Bu | H | Br | Cl | Br | Cl | t-Bu | H |
| Br | Cl | F | Cl | Me | Me | Br | Cl | Br | Cl | Me | Me |
| Cl | Br | F | Cl | Me | H | Cl | Br | Br | Cl | Me | H |
| Cl | Br | F | Cl | Et | H | Cl | Br | Br | Cl | Et | H |
| Cl | Br | F | Cl | i-Pr | H | Cl | Br | Br | Cl | i-Pr | H |
| Cl | Br | F | Cl | t-Bu | H | Cl | Br | Br | Cl | t-Bu | H |
| Cl | Br | F | Cl | Me | Me | Cl | Br | Br | Cl | Me | Me |
| Br | Br | F | Cl | Me | H | Br | Br | Br | Cl | Me | H |
| Br | Br | F | Cl | Et | H | Br | Br | Br | Cl | Et | H |
| Br | Br | F | Cl | i-Pr | H | Br | Br | Br | Cl | i-Pr | H |
| Br | Br | F | Cl | t-Bu | H | Br | Br | Br | Cl | t-Bu | H |
| Br | Br | F | Cl | Me | Me | Br | Br | Br | Cl | Me | Me |
| Cl | $OCH_2CF_3$ | F | Cl | Me | H | Cl | $OCH_2CF_3$ | Br | Cl | Me | H |
| Cl | $OCH_2CF_3$ | F | Cl | Et | H | Cl | $OCH_2CF_3$ | Br | Cl | Et | H |
| Cl | $OCH_2CF_3$ | F | Cl | i-Pr | H | Cl | $OCH_2CF_3$ | Br | Cl | i-Pr | H |
| Cl | $OCH_2CF_3$ | F | Cl | t-Bu | H | Cl | $OCH_2CF_3$ | Br | Cl | t-Bu | H |
| Cl | $OCH_2CF_3$ | F | Cl | Me | Me | Cl | $OCH_2CF_3$ | Br | Cl | Me | Me |

TABLE 2-continued

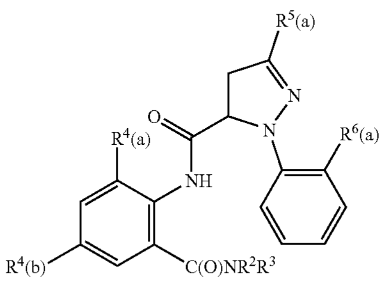

| $R^6(a)$ | $R^5(a)$ | $R^4(a)$ | $R^4(b)$ | $R^3$ | $R^2$ | $R^6(a)$ | $R^5(a)$ | $R^4(a)$ | $R^4(b)$ | $R^3$ | $R^2$ |
|---|---|---|---|---|---|---|---|---|---|---|---|
| Br | $OCH_2CF_3$ | F | Cl | Me | H | Br | $OCH_2CF_3$ | Br | Cl | Me | H |
| Br | $OCH_2CF_3$ | F | Cl | Et | H | Br | $OCH_2CF_3$ | Br | Cl | Et | H |
| Br | $OCH_2CF_3$ | F | Cl | i-Pr | H | Br | $OCH_2CF_3$ | Br | Cl | i-Pr | H |
| Br | $OCH_2CF_3$ | F | Cl | t-Bu | H | Br | $OCH_2CF_3$ | Br | Cl | t-Bu | H |
| Br | $OCH_2CF_3$ | F | Cl | Me | Me | Br | $OCH_2CF_3$ | Br | Cl | Me | Me |
| Cl | $CF_3$ | F | Br | Me | H | Cl | $CF_3$ | Br | Br | Me | H |
| Cl | $CF_3$ | F | Br | Et | H | Cl | $CF_3$ | Br | Br | Et | H |
| Cl | $CF_3$ | F | Br | i-Pr | H | Cl | $CF_3$ | Br | Br | i-Pr | H |
| Cl | $CF_3$ | F | Br | t-Bu | H | Cl | $CF_3$ | Br | Br | t-Bu | H |
| Cl | $CF_3$ | F | Br | Me | Me | Cl | $CF_3$ | Br | Br | Me | Me |
| Br | $CF_3$ | F | Br | Me | H | Br | $CF_3$ | Br | Br | Me | H |
| Br | $CF_3$ | F | Br | Et | H | Br | $CF_3$ | Br | Br | Et | H |
| Br | $CF_3$ | F | Br | i-Pr | H | Br | $CF_3$ | Br | Br | i-Pr | H |
| Br | $CF_3$ | F | Br | t-Bu | H | Br | $CF_3$ | Br | Br | t-Bu | H |
| Br | $CF_3$ | F | Br | Me | Me | Br | $CF_3$ | Br | Br | Me | Me |
| Cl | Cl | F | Br | Me | H | Cl | Cl | Br | Br | Me | H |
| Cl | Cl | F | Br | Et | H | Cl | Cl | Br | Br | Et | H |
| Cl | Cl | F | Br | i-Pr | H | Cl | Cl | Br | Br | i-Pr | H |
| Cl | Cl | F | Br | t-Bu | H | Cl | Cl | Br | Br | t-Bu | H |
| Cl | Cl | F | Br | Me | Me | Cl | Cl | Br | Br | Me | Me |
| Br | Cl | F | Br | Me | H | Br | Cl | Br | Br | Me | H |
| Br | Cl | F | Br | Et | H | Br | Cl | Br | Br | Et | H |
| Br | Cl | F | Br | i-Pr | H | Br | Cl | Br | Br | i-Pr | H |
| Br | Cl | F | Br | t-Bu | H | Br | Cl | Br | Br | t-Bu | H |
| Br | Cl | F | Br | Me | Me | Br | Cl | Br | Br | Me | Me |
| Cl | Br | F | Br | Me | H | Cl | Br | Br | Br | Me | H |
| Cl | Br | F | Br | Et | H | Cl | Br | Br | Br | Et | H |
| Cl | Br | F | Br | i-Pr | H | Cl | Br | Br | Br | i-Pr | H |
| Cl | Br | F | Br | t-Bu | H | Cl | Br | Br | Br | t-Bu | H |
| Cl | Br | F | Br | Me | Me | Cl | Br | Br | Br | Me | Me |
| Br | Br | F | Br | Me | H | Br | Br | Br | Br | Me | H |
| Br | Br | F | Br | Et | H | Br | Br | Br | Br | Et | H |
| Br | Br | F | Br | i-Pr | H | Br | Br | Br | Br | i-Pr | H |
| Br | Br | F | Br | t-Bu | H | Br | Br | Br | Br | t-Bu | H |
| Br | Br | F | Br | Me | Me | Br | Br | Br | Br | Me | Me |
| Cl | $OCH_2CF_3$ | F | Br | Me | H | Cl | $OCH_2CF_3$ | Br | Br | Me | H |
| Cl | $OCH_2CF_3$ | F | Br | Et | H | Cl | $OCH_2CF_3$ | Br | Br | Et | H |
| Cl | $OCH_2CF_3$ | F | Br | i-Pr | H | Cl | $OCH_2CF_3$ | Br | Br | i-Pr | H |
| Cl | $OCH_2CF_3$ | F | Br | t-Bu | H | Cl | $OCH_2CF_3$ | Br | Br | t-Bu | H |
| Cl | $OCH_2CF_3$ | F | Br | Me | Me | Cl | $OCH_2CF_3$ | Br | Br | Me | Me |
| Br | $OCH_2CF_3$ | F | Br | Me | H | Br | $OCH_2CF_3$ | Br | Br | Me | H |
| Br | $OCH_2CF_3$ | F | Br | Et | H | Br | $OCH_2CF_3$ | Br | Br | Et | H |
| Br | $OCH_2CF_3$ | F | Br | i-Pr | H | Br | $OCH_2CF_3$ | Br | Br | i-Pr | H |
| Br | $OCH_2CF_3$ | F | Br | t-Bu | H | Br | $OCH_2CF_3$ | Br | Br | t-Bu | H |
| Br | $OCH_2CF_3$ | F | Br | Me | Me | Br | $OCH_2CF_3$ | Br | Br | Me | Me |
| Cl | $CF_3$ | F | I | Me | H | Cl | $CF_3$ | Br | I | Me | H |
| Cl | $CF_3$ | F | I | Et | H | Cl | $CF_3$ | Br | I | Et | H |
| Cl | $CF_3$ | F | I | i-Pr | H | Cl | $CF_3$ | Br | I | i-Pr | H |
| Cl | $CF_3$ | F | I | t-Bu | H | Cl | $CF_3$ | Br | I | t-Bu | H |
| Cl | $CF_3$ | F | I | Me | Me | Cl | $CF_3$ | Br | I | Me | Me |
| Br | $CF_3$ | F | I | Me | H | Br | $CF_3$ | Br | I | Me | H |
| Br | $CF_3$ | F | I | Et | H | Br | $CF_3$ | Br | I | Et | H |
| Br | $CF_3$ | F | I | i-Pr | H | Br | $CF_3$ | Br | I | i-Pr | H |
| Br | $CF_3$ | F | I | t-Bu | H | Br | $CF_3$ | Br | I | t-Bu | H |
| Br | $CF_3$ | F | I | Me | Me | Br | $CF_3$ | Br | I | Me | Me |
| Cl | Cl | F | I | Me | H | Cl | Cl | Br | I | Me | H |
| Cl | Cl | F | I | Et | H | Cl | Cl | Br | I | Et | H |
| Cl | Cl | F | I | i-Pr | H | Cl | Cl | Br | I | i-Pr | H |
| Cl | Cl | F | I | t-Bu | H | Cl | Cl | Br | I | t-Bu | H |
| Cl | Cl | F | I | Me | Me | Cl | Cl | Br | I | Me | Me |
| Br | Cl | F | I | Me | H | Br | Cl | Br | I | Me | H |
| Br | Cl | F | I | Et | H | Br | Cl | Br | I | Et | H |
| Br | Cl | F | I | i-Pr | H | Br | Cl | Br | I | i-Pr | H |

TABLE 2-continued

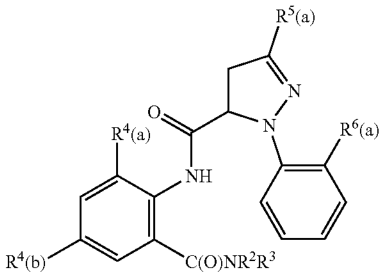

| $R^6$(a) | $R^5$(a) | $R^4$(a) | $R^4$(b) | $R^3$ | $R^2$ | $R^6$(a) | $R^5$(a) | $R^4$(a) | $R^4$(b) | $R^3$ | $R^2$ |
|---|---|---|---|---|---|---|---|---|---|---|---|
| Br | Cl | F | I | t-Bu | H | Br | Cl | Br | I | t-Bu | H |
| Br | Cl | F | I | Me | Me | Br | Cl | Br | I | Me | Me |
| Cl | Br | F | I | Me | H | Cl | Br | Br | I | Me | H |
| Cl | Br | F | I | Et | H | Cl | Br | Br | I | Et | H |
| Cl | Br | F | I | i-Pr | H | Cl | Br | Br | I | i-Pr | H |
| Cl | Br | F | I | t-Bu | H | Cl | Br | Br | I | t-Bu | H |
| Cl | Br | F | I | Me | Me | Cl | Br | Br | I | Me | Me |
| Br | Br | F | I | Me | H | Br | Br | Br | I | Me | H |
| Br | Br | F | I | Et | H | Br | Br | Br | I | Et | H |
| Br | Br | F | I | i-Pr | H | Br | Br | Br | I | i-Pr | H |
| Br | Br | F | I | t-Bu | H | Br | Br | Br | I | t-Bu | H |
| Br | Br | F | I | Me | Me | Br | Br | Br | I | Me | Me |
| Cl | $OCH_2CF_3$ | F | I | Me | H | Cl | $OCH_2CF_3$ | Br | I | Me | H |
| Cl | $OCH_2CF_3$ | F | I | Et | H | Cl | $OCH_2CF_3$ | Br | I | Et | H |
| Cl | $OCH_2CF_3$ | F | I | I-Pr | H | Cl | $OCH_2CF_3$ | Br | I | i-Pr | H |
| Cl | $OCH_2CF_3$ | F | I | t-Bu | H | Cl | $OCH_2CF_3$ | Br | I | t-Bu | H |
| Cl | $OCH_2CF_3$ | F | I | Me | Me | Cl | $OCH_2CF_3$ | Br | I | Me | Me |
| Br | $OCH_2CF_3$ | F | I | Me | H | Br | $OCH_2CF_3$ | Br | I | Me | H |
| Br | $OCH_2CF_3$ | F | I | Et | H | Br | $OCH_2CF_3$ | Br | I | Et | H |
| Br | $OCH_2CF_3$ | F | I | i-Pr | H | Br | $OCH_2CF_3$ | Br | I | i-Pr | H |
| Br | $OCH_2CF_3$ | F | I | t-Bu | H | Br | $OCH_2CF_3$ | Br | I | t-Bu | H |
| Br | $OCH_2CF_3$ | F | I | Me | Me | Br | $OCH_2CF_3$ | Br | I | Me | Me |
| Cl | $CF_3$ | F | $CF_3$ | Me | H | Cl | $CF_3$ | Br | $CF_3$ | Me | H |
| Cl | $CF_3$ | F | $CF_3$ | Et | H | Cl | $CF_3$ | Br | $CF_3$ | Et | H |
| Cl | $CF_3$ | F | $CF_3$ | i-Pr | H | Cl | $CF_3$ | Br | $CF_3$ | i-Pr | H |
| Cl | $CF_3$ | F | $CF_3$ | t-Bu | H | Cl | $CF_3$ | Br | $CF_3$ | t-Bu | H |
| Cl | $CF_3$ | F | $CF_3$ | Me | Me | Cl | $CF_3$ | Br | $CF_3$ | Me | Me |
| Br | $CF_3$ | F | $CF_3$ | Me | H | Br | $CF_3$ | Br | $CF_3$ | Me | H |
| Br | $CF_3$ | F | $CF_3$ | Et | H | Br | $CF_3$ | Br | $CF_3$ | Et | H |
| Br | $CF_3$ | F | $CF_3$ | i-Pr | H | Br | $CF_3$ | Br | $CF_3$ | i-Pr | H |
| Br | $CF_3$ | F | $CF_3$ | t-Bu | H | Br | $CF_3$ | Br | $CF_3$ | t-Bu | H |
| Br | $CF_3$ | F | $CF_3$ | Me | Me | Br | $CF_3$ | Br | $CF_3$ | Me | Me |
| Cl | Cl | F | $CF_3$ | Me | H | Cl | Cl | Br | $CF_3$ | Me | H |
| Cl | Cl | F | $CF_3$ | Et | H | Cl | Cl | Br | $CF_3$ | Et | H |
| Cl | Cl | F | $CF_3$ | i-Pr | H | Cl | Cl | Br | $CF_3$ | i-Pr | H |
| Cl | Cl | F | $CF_3$ | t-Bu | H | Cl | Cl | Br | $CF_3$ | t-Bu | H |
| Cl | Cl | F | $CF_3$ | Me | Me | Cl | Cl | Br | $CF_3$ | Me | Me |
| Br | Cl | F | $CF_3$ | Me | H | Br | Cl | Br | $CF_3$ | Me | H |
| Br | Cl | F | $CF_3$ | Et | H | Br | Cl | Br | $CF_3$ | Et | H |
| Br | Cl | F | $CF_3$ | i-Pr | H | Br | Cl | Br | $CF_3$ | i-Pr | H |
| Br | Cl | F | $CF_3$ | t-Bu | H | Br | Cl | Br | $CF_3$ | t-Bu | H |
| Br | Cl | F | $CF_3$ | Me | Me | Br | Cl | Br | $CF_3$ | Me | Me |
| Cl | Br | F | $CF_3$ | Me | H | Cl | Br | Br | $CF_3$ | Me | H |
| Cl | Br | F | $CF_3$ | Et | H | Cl | Br | Br | $CF_3$ | Et | H |
| Cl | Br | F | $CF_3$ | i-Pr | H | Cl | Br | Br | $CF_3$ | i-Pr | H |
| Cl | Br | F | $CF_3$ | t-Bu | H | Cl | Br | Br | $CF_3$ | t-Bu | H |
| Cl | Br | F | $CF_3$ | Me | Me | Cl | Br | Br | $CF_3$ | Me | Me |
| Br | Br | F | $CF_3$ | Me | H | Br | Br | Br | $CF_3$ | Me | H |
| Br | Br | F | $CF_3$ | Et | H | Br | Br | Br | $CF_3$ | Et | H |
| Br | Br | F | $CF_3$ | i-Pr | H | Br | Br | Br | $CF_3$ | i-Pr | H |
| Br | Br | F | $CF_3$ | t-Bu | H | Br | Br | Br | $CF_3$ | t-Bu | H |
| Br | Br | F | $CF_3$ | Me | Me | Br | Br | Br | $CF_3$ | Me | Me |
| Cl | $OCH_2CF_3$ | F | $CF_3$ | Me | H | Cl | $OCH_2CF_3$ | Br | $CF_3$ | Me | H |
| Cl | $OCH_2CF_3$ | F | $CF_3$ | Et | H | Cl | $OCH_2CF_3$ | Br | $CF_3$ | Et | H |
| Cl | $OCH_2CF_3$ | F | $CF_3$ | i-Pr | H | Cl | $OCH_2CF_3$ | Br | $CF_3$ | i-Pr | H |
| Cl | $OCH_2CF_3$ | F | $CF_3$ | t-Bu | H | Cl | $OCH_2CF_3$ | Br | $CF_3$ | t-Bu | H |
| Cl | $OCH_2CF_3$ | F | $CF_3$ | Me | Me | Cl | $OCH_2CF_3$ | Br | $CF_3$ | Me | Me |
| Br | $OCH_2CF_3$ | F | $CF_3$ | Me | H | Br | $OCH_2CF_3$ | Br | $CF_3$ | Me | H |
| Br | $OCH_2CF_3$ | F | $CF_3$ | Et | H | Br | $OCH_2CF_3$ | Br | $CF_3$ | Et | H |
| Br | $OCH_2CF_3$ | F | $CF_3$ | i-Pr | H | Br | $OCH_2CF_3$ | Br | $CF_3$ | i-Pr | H |
| Br | $OCH_2CF_3$ | F | $CF_3$ | t-Bu | H | Br | $OCH_2CF_3$ | Br | $CF_3$ | t-Bu | H |
| Br | $OCH_2CF_3$ | F | $CF_3$ | Me | Me | Br | $OCH_2CF_3$ | Br | $CF_3$ | Me | Me |

TABLE 3

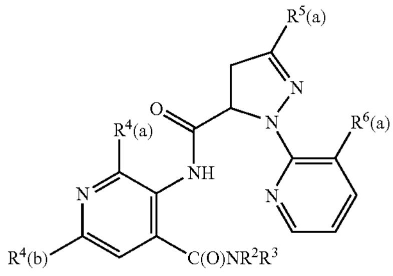

| $R^6$(a) | $R^5$(a) | $R^4$(a) | $R^4$(b) | $R^3$ | $R^2$ |
|---|---|---|---|---|---|
| Cl | $CF_3$ | $CH_3$ | H | Me | H |
| Cl | $CF_3$ | $CH_3$ | H | Et | H |
| Cl | $CF_3$ | $CH_3$ | H | i-Pr | H |
| Cl | $CF_3$ | $CH_3$ | H | t-Bu | H |
| Cl | $CF_3$ | $CH_3$ | H | Me | Me |
| Br | $CF_3$ | $CH_3$ | H | Me | H |
| Br | $CF_3$ | $CH_3$ | H | Et | H |
| Br | $CF_3$ | $CH_3$ | H | i-Pr | H |
| Br | $CF_3$ | $CH_3$ | H | t-Bu | H |
| Br | $CF_3$ | $CH_3$ | H | Me | Me |
| Cl | Cl | $CH_3$ | H | Me | H |
| Cl | Cl | $CH_3$ | H | Et | H |
| Cl | Cl | $CH_3$ | H | i-Pr | H |
| Cl | Cl | $CH_3$ | H | t-Bu | H |
| Cl | Cl | $CH_3$ | H | Me | Me |
| Br | Cl | $CH_3$ | H | Me | H |
| Br | Cl | $CH_3$ | H | Et | H |
| Br | Cl | $CH_3$ | H | i-Pr | H |
| Br | Cl | $CH_3$ | H | t-Bu | H |
| Br | Cl | $CH_3$ | H | Me | Me |
| Cl | Br | $CH_3$ | H | Me | H |
| Cl | Br | $CH_3$ | H | Et | H |
| Cl | Br | $CH_3$ | H | i-Pr | H |
| Cl | Br | $CH_3$ | H | t-Bu | H |
| Cl | Br | $CH_3$ | H | Me | Me |
| Br | Br | $CH_3$ | H | Me | H |
| Br | Br | $CH_3$ | H | Et | H |
| Br | Br | $CH_3$ | H | i-Pr | H |
| Br | Br | $CH_3$ | H | t-Bu | H |
| Br | Br | $CH_3$ | H | Me | Me |
| Cl | $OCH_2CF_3$ | $CH_3$ | H | Me | H |
| Cl | $OCH_2CF_3$ | $CH_3$ | H | Et | H |
| Cl | $OCH_2CF_3$ | $CH_3$ | H | i-Pr | H |
| Cl | $OCH_2CF_3$ | $CH_3$ | H | t-Bu | H |
| Cl | $OCH_2CF_3$ | $CH_3$ | H | Me | Me |
| Br | $OCH_2CF_3$ | $CH_3$ | H | Me | H |
| Br | $OCH_2CF_3$ | $CH_3$ | H | Et | H |
| Br | $OCH_2CF_3$ | $CH_3$ | H | i-Pr | H |
| Br | $OCH_2CF_3$ | $CH_3$ | H | t-Bu | H |
| Br | $OCH_2CF_3$ | $CH_3$ | H | Me | Me |
| Cl | $CF_3$ | $CH_3$ | F | Me | H |
| Cl | $CF_3$ | $CH_3$ | F | Et | H |
| Cl | $CF_3$ | $CH_3$ | F | i-Pr | H |
| Cl | $CF_3$ | $CH_3$ | F | t-Bu | H |
| Cl | $CF_3$ | $CH_3$ | F | Me | Me |
| Br | $CF_3$ | $CH_3$ | F | Me | H |
| Br | $CF_3$ | $CH_3$ | F | Et | H |
| Br | $CF_3$ | $CH_3$ | F | i-Pr | H |
| Br | $CF_3$ | $CH_3$ | F | t-Bu | H |
| Br | $CF_3$ | $CH_3$ | F | Me | Me |
| Cl | Cl | $CH_3$ | F | Me | H |
| Cl | Cl | $CH_3$ | F | Et | H |
| Cl | Cl | $CH_3$ | F | i-Pr | H |
| Cl | Cl | $CH_3$ | F | t-Bu | H |
| Cl | Cl | $CH_3$ | F | Me | Me |
| Br | Cl | $CH_3$ | F | Me | H |
| Br | Cl | $CH_3$ | F | Et | H |
| Br | Cl | $CH_3$ | F | i-Pr | H |
| Br | Cl | $CH_3$ | F | t-Bu | H |
| Br | Cl | $CH_3$ | F | Me | Me |
| Cl | Br | $CH_3$ | F | Me | H |
| Cl | Br | $CH_3$ | F | Et | H |
| Cl | Br | $CH_3$ | F | i-Pr | H |

TABLE 3-continued

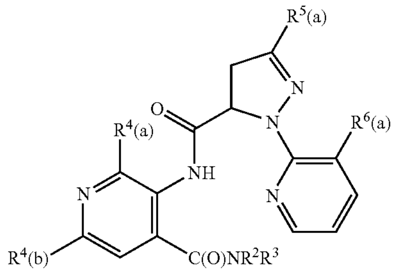

| $R^6$(a) | $R^5$(a) | $R^4$(a) | $R^4$(b) | $R^3$ | $R^2$ |
|---|---|---|---|---|---|
| Cl | Br | $CH_3$ | F | t-Bu | H |
| Cl | Br | $CH_3$ | F | Me | Me |
| Br | Br | $CH_3$ | F | Me | H |
| Br | Br | $CH_3$ | F | Et | H |
| Br | Br | $CH_3$ | F | i-Pr | H |
| Br | Br | $CH_3$ | F | t-Bu | H |
| Br | Br | $CH_3$ | F | Me | Me |
| Cl | $OCH_2CF_3$ | $CH_3$ | F | Me | H |
| Cl | $OCH_2CF_3$ | $CH_3$ | F | Et | H |
| Cl | $OCH_2CF_3$ | $CH_3$ | F | i-Pr | H |
| Cl | $OCH_2CF_3$ | $CH_3$ | F | t-Bu | H |
| Cl | $OCH_2CF_3$ | $CH_3$ | F | Me | Me |
| Br | $OCH_2CF_3$ | $CH_3$ | F | Me | H |
| Br | $OCH_2CF_3$ | $CH_3$ | F | Et | H |
| Br | $OCH_2CF_3$ | $CH_3$ | F | i-Pr | H |
| Br | $OCH_2CF_3$ | $CH_3$ | F | t-Bu | H |
| Br | $OCH_2CF_3$ | $CH_3$ | F | Me | Me |
| Cl | $CF_3$ | $CH_3$ | Cl | Me | H |
| Cl | $CF_3$ | $CH_3$ | Cl | Et | H |
| Cl | $CF_3$ | $CH_3$ | Cl | i-Pr | H |
| Cl | $CF_3$ | $CH_3$ | Cl | t-Bu | H |
| Cl | $CF_3$ | $CH_3$ | Cl | Me | Me |
| Br | $CF_3$ | $CH_3$ | Cl | Me | H |
| Br | $CF_3$ | $CH_3$ | Cl | Et | H |
| Br | $CF_3$ | $CH_3$ | Cl | i-Pr | H |
| Br | $CF_3$ | $CH_3$ | Cl | t-Bu | H |
| Br | $CF_3$ | $CH_3$ | Cl | Me | Me |
| Cl | Cl | $CH_3$ | Cl | Me | H |
| Cl | Cl | $CH_3$ | Cl | Et | H |
| Cl | Cl | $CH_3$ | Cl | i-Pr | H |
| Cl | Cl | $CH_3$ | Cl | t-Bu | H |
| Cl | Cl | $CH_3$ | Cl | Me | Me |
| Br | Cl | $CH_3$ | Cl | Me | H |
| Br | Cl | $CH_3$ | Cl | Et | H |
| Br | Cl | $CH_3$ | Cl | i-Pr | H |
| Br | Cl | $CH_3$ | Cl | t-Bu | H |
| Br | Cl | $CH_3$ | Cl | Me | Me |
| Cl | Br | $CH_3$ | Cl | Me | H |
| Cl | Br | $CH_3$ | Cl | Et | H |
| Cl | Br | $CH_3$ | Cl | i-Pr | H |
| Cl | Br | $CH_3$ | Cl | t-Bu | H |
| Cl | Br | $CH_3$ | Cl | Me | Me |
| Br | Br | $CH_3$ | Cl | Me | H |
| Br | Br | $CH_3$ | Cl | Et | H |
| Br | Br | $CH_3$ | Cl | i-Pr | H |
| Br | Br | $CH_3$ | Cl | t-Bu | H |
| Br | Br | $CH_3$ | Cl | Me | Me |
| Cl | $OCH_2CF_3$ | $CH_3$ | Cl | Me | H |
| Cl | $OCH_2CF_3$ | $CH_3$ | Cl | Et | H |
| Cl | $OCH_2CF_3$ | $CH_3$ | Cl | i-Pr | H |
| Cl | $OCH_2CF_3$ | $CH_3$ | Cl | t-Bu | H |
| Cl | $OCH_2CF_3$ | $CH_3$ | Cl | Me | Me |
| Br | $OCH_2CF_3$ | $CH_3$ | Cl | Me | H |
| Br | $OCH_2CF_3$ | $CH_3$ | Cl | Et | H |
| Br | $OCH_2CF_3$ | $CH_3$ | Cl | i-Pr | H |
| Br | $OCH_2CF_3$ | $CH_3$ | Cl | t-Bu | H |
| Br | $OCH_2CF_3$ | $CH_3$ | Cl | Me | Me |
| Cl | $CF_3$ | $CH_3$ | Br | Me | H |
| Cl | $CF_3$ | $CH_3$ | Br | Et | H |
| Cl | $CF_3$ | $CH_3$ | Br | i-Pr | H |
| Cl | $CF_3$ | $CH_3$ | Br | t-Bu | H |
| Cl | $CF_3$ | $CH_3$ | Br | Me | Me |
| Br | $CF_3$ | $CH_3$ | Br | Me | H |

TABLE 3-continued

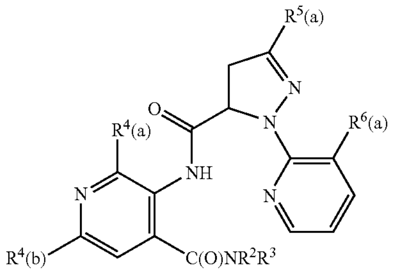

| $R^6$(a) | $R^5$(a) | $R^4$(a) | $R^4$(b) | $R^3$ | $R^2$ |
|---|---|---|---|---|---|
| Br | $CF_3$ | $CH_3$ | Br | Et | H |
| Br | $CF_3$ | $CH_3$ | Br | i-Pr | H |
| Br | $CF_3$ | $CH_3$ | Br | t-Bu | H |
| Br | $CF_3$ | $CH_3$ | Br | Me | Me |
| Cl | Cl | $CH_3$ | Br | Me | H |
| Cl | Cl | $CH_3$ | Br | Et | H |
| Cl | Cl | $CH_3$ | Br | i-Pr | H |
| Cl | Cl | $CH_3$ | Br | t-Bu | H |
| Cl | Cl | $CH_3$ | Br | Me | Me |
| Br | Cl | $CH_3$ | Br | Me | H |
| Br | Cl | $CH_3$ | Br | Et | H |
| Br | Cl | $CH_3$ | Br | i-Pr | H |
| Br | Cl | $CH_3$ | Br | t-Bu | H |
| Br | Cl | $CH_3$ | Br | Me | Me |
| Cl | Br | $CH_3$ | Br | Me | H |
| Cl | Br | $CH_3$ | Br | Et | H |
| Cl | Br | $CH_3$ | Br | i-Pr | H |
| Cl | Br | $CH_3$ | Br | t-Bu | H |
| Cl | Br | $CH_3$ | Br | Me | Me |
| Br | Br | $CH_3$ | Br | Me | H |
| Br | Br | $CH_3$ | Br | Et | H |
| Br | Br | $CH_3$ | Br | i-Pr | H |
| Br | Br | $CH_3$ | Br | t-Bu | H |
| Br | Br | $CH_3$ | Br | Me | Me |
| Cl | $OCH_2CF_3$ | $CH_3$ | Br | Me | H |
| Cl | $OCH_2CF_3$ | $CH_3$ | Br | Et | H |
| Cl | $OCH_2CF_3$ | $CH_3$ | Br | i-Pr | H |
| Cl | $OCH_2CF_3$ | $CH_3$ | Br | t-Bu | H |
| Cl | $OCH_2CF_3$ | $CH_3$ | Br | Me | Me |
| Br | $OCH_2CF_3$ | $CH_3$ | Br | Me | H |
| Br | $OCH_2CF_3$ | $CH_3$ | Br | Et | H |
| Br | $OCH_2CF_3$ | $CH_3$ | Br | i-Pr | H |
| Br | $OCH_2CF_3$ | $CH_3$ | Br | t-Bu | H |
| Br | $OCH_2CF_3$ | $CH_3$ | Br | Me | Me |
| Cl | $CF_3$ | $CH_3$ | I | Me | H |
| Cl | $CF_3$ | $CH_3$ | I | Et | H |
| Cl | $CF_3$ | $CH_3$ | I | i-Pr | H |
| Cl | $CF_3$ | $CH_3$ | I | t-Bu | H |
| Cl | $CF_3$ | $CH_3$ | I | Me | Me |
| Br | $CF_3$ | $CH_3$ | I | Me | H |
| Br | $CF_3$ | $CH_3$ | I | Et | H |
| Br | $CF_3$ | $CH_3$ | I | i-Pr | H |
| Br | $CF_3$ | $CH_3$ | I | t-Bu | H |
| Br | $CF_3$ | $CH_3$ | I | Me | Me |
| Cl | Cl | $CH_3$ | I | Me | H |
| Cl | Cl | $CH_3$ | I | Et | H |
| Cl | Cl | $CH_3$ | I | i-Pr | H |
| Cl | Cl | $CH_3$ | I | t-Bu | H |
| Cl | Cl | $CH_3$ | I | Me | Me |
| Br | Cl | $CH_3$ | I | Me | H |
| Br | Cl | $CH_3$ | I | Et | H |
| Br | Cl | $CH_3$ | I | i-Pr | H |
| Br | Cl | $CH_3$ | I | t-Bu | H |
| Br | Cl | $CH_3$ | I | Me | Me |
| Cl | Br | $CH_3$ | I | Me | H |
| Cl | Br | $CH_3$ | I | Et | H |
| Cl | Br | $CH_3$ | I | i-Pr | H |
| Cl | Br | $CH_3$ | I | t-Bu | H |
| Cl | Br | $CH_3$ | I | Me | Me |
| Br | Br | $CH_3$ | I | Me | H |
| Br | Br | $CH_3$ | I | Et | H |
| Br | Br | $CH_3$ | I | i-Pr | H |
| Br | Br | $CH_3$ | I | t-Bu | H |

TABLE 3-continued

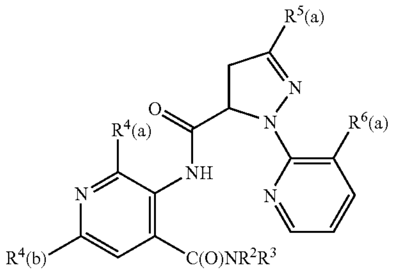

| $R^6$(a) | $R^5$(a) | $R^4$(a) | $R^4$(b) | $R^3$ | $R^2$ |
|---|---|---|---|---|---|
| Br | Br | $CH_3$ | I | Me | Me |
| Cl | $OCH_2CF_3$ | $CH_3$ | I | Me | H |
| Cl | $OCH_2CF_3$ | $CH_3$ | I | Et | H |
| Cl | $OCH_2CF_3$ | $CH_3$ | I | i-Pr | H |
| Cl | $OCH_2CF_3$ | $CH_3$ | I | t-Bu | H |
| Cl | $OCH_2CF_3$ | $CH_3$ | I | Me | Me |
| Br | $OCH_2CF_3$ | $CH_3$ | I | Me | H |
| Br | $OCH_2CF_3$ | $CH_3$ | I | Et | H |
| Br | $OCH_2CF_3$ | $CH_3$ | I | i-Pr | H |
| Br | $OCH_2CF_3$ | $CH_3$ | I | t-Bu | H |
| Br | $OCH_2CF_3$ | $CH_3$ | I | Me | Me |
| Cl | $CF_3$ | $CH_3$ | $CF_3$ | Me | H |
| Cl | $CF_3$ | $CH_3$ | $CF_3$ | Et | H |
| Cl | $CF_3$ | $CH_3$ | $CF_3$ | i-Pr | H |
| Cl | $CF_3$ | $CH_3$ | $CF_3$ | t-Bu | H |
| Cl | $CF_3$ | $CH_3$ | $CF_3$ | Me | Me |
| Br | $CF_3$ | $CH_3$ | $CF_3$ | Me | H |
| Br | $CF_3$ | $CH_3$ | $CF_3$ | Et | H |
| Br | $CF_3$ | $CH_3$ | $CF_3$ | i-Pr | H |
| Br | $CF_3$ | $CH_3$ | $CF_3$ | t-Bu | H |
| Br | $CF_3$ | $CH_3$ | $CF_3$ | Me | Me |
| Cl | Cl | $CH_3$ | $CF_3$ | Me | H |
| Cl | Cl | $CH_3$ | $CF_3$ | Et | H |
| Cl | Cl | $CH_3$ | $CF_3$ | i-Pr | H |
| Cl | Cl | $CH_3$ | $CF_3$ | t-Bu | H |
| Cl | Cl | $CH_3$ | $CF_3$ | Me | Me |
| Br | Cl | $CH_3$ | $CF_3$ | Me | H |
| Br | Cl | $CH_3$ | $CF_3$ | Et | H |
| Br | Cl | $CH_3$ | $CF_3$ | i-Pr | H |
| Br | Cl | $CH_3$ | $CF_3$ | t-Bu | H |
| Br | Cl | $CH_3$ | $CF_3$ | Me | Me |
| Cl | Br | $CH_3$ | $CF_3$ | Me | H |
| Cl | Br | $CH_3$ | $CF_3$ | Et | H |
| Cl | Br | $CH_3$ | $CF_3$ | i-Pr | H |
| Cl | Br | $CH_3$ | $CF_3$ | t-Bu | H |
| Cl | Br | $CH_3$ | $CF_3$ | Me | Me |
| Br | Br | $CH_3$ | $CF_3$ | Me | H |
| Br | Br | $CH_3$ | $CF_3$ | Et | H |
| Br | Br | $CH_3$ | $CF_3$ | i-Pr | H |
| Br | Br | $CH_3$ | $CF_3$ | t-Bu | H |
| Br | Br | $CH_3$ | $CF_3$ | Me | Me |
| Cl | $OCH_2CF_3$ | $CH_3$ | $CF_3$ | Me | H |
| Cl | $OCH_2CF_3$ | $CH_3$ | $CF_3$ | Et | H |
| Cl | $OCH_2CF_3$ | $CH_3$ | $CF_3$ | i-Pr | H |
| Cl | $OCH_2CF_3$ | $CH_3$ | $CF_3$ | t-Bu | H |
| Cl | $OCH_2CF_3$ | $CH_3$ | $CF_3$ | Me | Me |
| Br | $OCH_2CF_3$ | $CH_3$ | $CF_3$ | Me | H |
| Br | $OCH_2CF_3$ | $CH_3$ | $CF_3$ | Et | H |
| Br | $OCH_2CF_3$ | $CH_3$ | $CF_3$ | i-Pr | H |
| Br | $OCH_2CF_3$ | $CH_3$ | $CF_3$ | t-Bu | H |
| Br | $OCH_2CF_3$ | $CH_3$ | $CF_3$ | Me | Me |
| Cl | Cl | $CH_3$ | Cl | n-Pr | H |
| Cl | Cl | $CH_3$ | Cl | n-Bu | H |
| Cl | Cl | $CH_3$ | Cl | s-Bu | H |
| Cl | Cl | $CH_3$ | Cl | i-Bu | H |
| Cl | Cl | $CH_3$ | Cl | Et | Me |
| Cl | $CF_3$ | F | H | Me | H |
| Cl | $CF_3$ | F | H | Et | H |
| Cl | $CF_3$ | F | H | i-Pr | H |
| Cl | $CF_3$ | F | H | t-Bu | H |
| Cl | $CF_3$ | F | H | Me | Me |
| Br | $CF_3$ | F | H | Me | H |
| Br | $CF_3$ | F | H | Et | H |

TABLE 3-continued

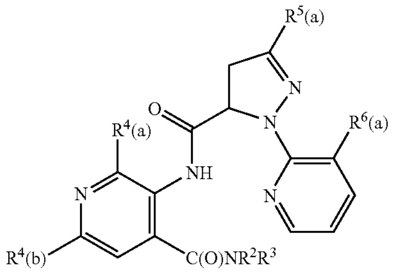

| $R^6$(a) | $R^5$(a) | $R^4$(a) | $R^4$(b) | $R^3$ | $R^2$ |
|---|---|---|---|---|---|
| Br | $CF_3$ | F | H | i-Pr | H |
| Br | $CF_3$ | F | H | t-Bu | H |
| Br | $CF_3$ | F | H | Me | Me |
| Cl | Cl | F | H | Me | H |
| Cl | Cl | F | H | Et | H |
| Cl | Cl | F | H | i-Pr | H |
| Cl | Cl | F | H | t-Bu | H |
| Cl | Cl | F | H | Me | Me |
| Br | Cl | F | H | Me | H |
| Br | Cl | F | H | Et | H |
| Br | Cl | F | H | i-Pr | H |
| Br | Cl | F | H | t-Bu | H |
| Br | Cl | F | H | Me | Me |
| Cl | Br | F | H | Me | H |
| Cl | Br | F | H | Et | H |
| Cl | Br | F | H | i-Pr | H |
| Cl | Br | F | H | t-Bu | H |
| Cl | Br | F | H | Me | Me |
| Br | Br | F | H | Me | H |
| Br | Br | F | H | Et | H |
| Br | Br | F | H | i-Pr | H |
| Br | Br | F | H | t-Bu | H |
| Br | Br | F | H | Me | Me |
| Cl | $OCH_2CF_3$ | F | H | Me | H |
| Cl | $OCH_2CF_3$ | F | H | Et | H |
| Cl | $OCH_2CF_3$ | F | H | i-Pr | H |
| Cl | $OCH_2CF_3$ | F | H | t-Bu | H |
| Cl | $OCH_2CF_3$ | F | H | Me | Me |
| Br | $OCH_2CF_3$ | F | H | Me | H |
| Br | $OCH_2CF_3$ | F | H | Et | H |
| Br | $OCH_2CF_3$ | F | H | i-Pr | H |
| Br | $OCH_2CF_3$ | F | H | t-Bu | H |
| Br | $OCH_2CF_3$ | F | H | Me | Me |
| Cl | $CF_3$ | F | F | Me | H |
| Cl | $CF_3$ | F | F | Et | H |
| Cl | $CF_3$ | F | F | i-Pr | H |
| Cl | $CF_3$ | F | F | t-Bu | H |
| Cl | $CF_3$ | F | F | Me | Me |
| Br | $CF_3$ | F | F | Me | H |
| Br | $CF_3$ | F | F | Et | H |
| Br | $CF_3$ | F | F | i-Pr | H |
| Br | $CF_3$ | F | F | t-Bu | H |
| Br | $CF_3$ | F | F | Me | Me |
| Cl | Cl | F | F | Me | H |
| Cl | Cl | F | F | Et | H |
| Cl | Cl | F | F | i-Pr | H |
| Cl | Cl | F | F | t-Bu | H |
| Cl | Cl | F | F | Me | Me |
| Br | Cl | F | F | Me | H |
| Br | Cl | F | F | Et | H |
| Br | Cl | F | F | i-Pr | H |
| Br | Cl | F | F | t-Bu | H |
| Br | Cl | F | F | Me | Me |
| Cl | Br | F | F | Me | H |
| Cl | Br | F | F | Et | H |
| Cl | Br | F | F | i-Pr | H |
| Cl | Br | F | F | t-Bu | H |
| Cl | Br | F | F | Me | Me |
| Br | Br | F | F | Me | H |
| Br | Br | F | F | Et | H |
| Br | Br | F | F | i-Pr | H |
| Br | Br | F | F | t-Bu | H |
| Br | Br | F | F | Me | Me |

TABLE 3-continued

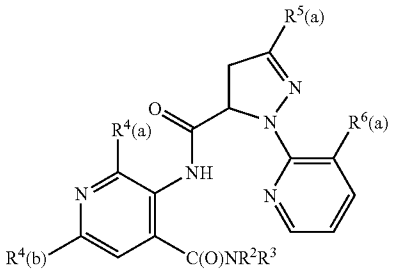

| $R^6$(a) | $R^5$(a) | $R^4$(a) | $R^4$(b) | $R^3$ | $R^2$ |
|---|---|---|---|---|---|
| Cl | $OCH_2CF_3$ | F | F | Me | H |
| Cl | $OCH_2CF_3$ | F | F | Et | H |
| Cl | $OCH_2CF_3$ | F | F | i-Pr | H |
| Cl | $OCH_2CF_3$ | F | F | t-Bu | H |
| Cl | $OCH_2CF_3$ | F | F | Me | Me |
| Br | $OCH_2CF_3$ | F | F | Me | H |
| Br | $OCH_2CF_3$ | F | F | Et | H |
| Br | $OCH_2CF_3$ | F | F | i-Pr | H |
| Br | $OCH_2CF_3$ | F | F | t-Bu | H |
| Br | $OCH_2CF_3$ | F | F | Me | Me |
| Cl | $CF_3$ | F | Cl | Me | H |
| Cl | $CF_3$ | F | Cl | Et | H |
| Cl | $CF_3$ | F | Cl | i-Pr | H |
| Cl | $CF_3$ | F | Cl | t-Bu | H |
| Cl | $CF_3$ | F | Cl | Me | Me |
| Br | $CF_3$ | F | Cl | Me | H |
| Br | $CF_3$ | F | Cl | Et | H |
| Br | $CF_3$ | F | Cl | i-Pr | H |
| Br | $CF_3$ | F | Cl | t-Bu | H |
| Br | $CF_3$ | F | Cl | Me | Me |
| Cl | Cl | F | Cl | Me | H |
| Cl | Cl | F | Cl | Et | H |
| Cl | Cl | F | Cl | i-Pr | H |
| Cl | Cl | F | Cl | t-Bu | H |
| Cl | Cl | F | Cl | Me | Me |
| Br | Cl | F | Cl | Me | H |
| Br | Cl | F | Cl | Et | H |
| Br | Cl | F | Cl | i-Pr | H |
| Br | Cl | F | Cl | t-Bu | H |
| Br | Cl | F | Cl | Me | Me |
| Cl | Br | F | Cl | Me | H |
| Cl | Br | F | Cl | Et | H |
| Cl | Br | F | Cl | i-Pr | H |
| Cl | Br | F | Cl | t-Bu | H |
| Cl | Br | F | Cl | Me | Me |
| Br | Br | F | Cl | Me | H |
| Br | Br | F | Cl | Et | H |
| Br | Br | F | Cl | i-Pr | H |
| Br | Br | F | Cl | t-Bu | H |
| Br | Br | F | Cl | Me | Me |
| Cl | $OCH_2CF_3$ | F | Cl | Me | H |
| Cl | $OCH_2CF_3$ | F | Cl | Et | H |
| Cl | $OCH_2CF_3$ | F | Cl | i-Pr | H |
| Cl | $OCH_2CF_3$ | F | Cl | t-Bu | H |
| Cl | $OCH_2CF_3$ | F | Cl | Me | Me |
| Br | $OCH_2CF_3$ | F | Cl | Me | H |
| Br | $OCH_2CF_3$ | F | Cl | Et | H |
| Br | $OCH_2CF_3$ | F | Cl | i-Pr | H |
| Br | $OCH_2CF_3$ | F | Cl | t-Bu | H |
| Br | $OCH_2CF_3$ | F | Cl | Me | Me |
| Cl | $CF_3$ | F | Br | Me | H |
| Cl | $CF_3$ | F | Br | Et | H |
| Cl | $CF_3$ | F | Br | i-Pr | H |
| Cl | $CF_3$ | F | Br | t-Bu | H |
| Cl | $CF_3$ | F | Br | Me | Me |
| Br | $CF_3$ | F | Br | Me | H |
| Br | $CF_3$ | F | Br | Et | H |
| Br | $CF_3$ | F | Br | i-Pr | H |
| Br | $CF_3$ | F | Br | t-Bu | H |
| Br | $CF_3$ | F | Br | Me | Me |
| Cl | Cl | F | Br | Me | H |
| Cl | Cl | F | Br | Et | H |
| Cl | Cl | F | Br | i-Pr | H |

TABLE 3-continued

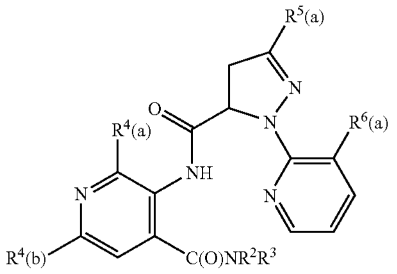

| $R^6$(a) | $R^5$(a) | $R^4$(a) | $R^4$(b) | $R^3$ | $R^2$ |
|---|---|---|---|---|---|
| Cl | Cl | F | Br | t-Bu | H |
| Cl | Cl | F | Br | Me | Me |
| Br | Cl | F | Br | Me | H |
| Br | Cl | F | Br | Et | H |
| Br | Cl | F | Br | i-Pr | H |
| Br | Cl | F | Br | t-Bu | H |
| Br | Cl | F | Br | Me | Me |
| Cl | Br | F | Br | Me | H |
| Cl | Br | F | Br | Et | H |
| Cl | Br | F | Br | i-Pr | H |
| Cl | Br | F | Br | t-Bu | H |
| Cl | Br | F | Br | Me | Me |
| Br | Br | F | Br | Me | H |
| Br | Br | F | Br | Et | H |
| Br | Br | F | Br | i-Pr | H |
| Br | Br | F | Br | t-Bu | H |
| Br | Br | F | Br | Me | Me |
| Cl | $OCH_2CF_3$ | F | Br | Me | H |
| Cl | $OCH_2CF_3$ | F | Br | Et | H |
| Cl | $OCH_2CF_3$ | F | Br | i-Pr | H |
| Cl | $OCH_2CF_3$ | F | Br | t-Bu | H |
| Cl | $OCH_2CF_3$ | F | Br | Me | Me |
| Br | $OCH_2CF_3$ | F | Br | Me | H |
| Br | $OCH_2CF_3$ | F | Br | Et | H |
| Br | $OCH_2CF_3$ | F | Br | i-Pr | H |
| Br | $OCH_2CF_3$ | F | Br | t-Bu | H |
| Br | $OCH_2CF_3$ | F | Br | Me | Me |
| Cl | $CF_3$ | F | I | Me | H |
| Cl | $CF_3$ | F | I | Et | H |
| Cl | $CF_3$ | F | I | i-Pr | H |
| Cl | $CF_3$ | F | I | t-Bu | H |
| Cl | $CF_3$ | F | I | Me | Me |
| Br | $CF_3$ | F | I | Me | H |
| Br | $CF_3$ | F | I | Et | H |
| Br | $CF_3$ | F | I | i-Pr | H |
| Br | $CF_3$ | F | I | t-Bu | H |
| Br | $CF_3$ | F | I | Me | Me |
| Cl | Cl | F | I | Me | H |
| Cl | Cl | F | I | Et | H |
| Cl | Cl | F | I | i-Pr | H |
| Cl | Cl | F | I | t-Bu | H |
| Cl | Cl | F | I | Me | Me |
| Br | Cl | F | I | Me | H |
| Br | Cl | F | I | Et | H |
| Br | Cl | F | I | i-Pr | H |
| Br | Cl | F | I | t-Bu | H |
| Br | Cl | F | I | Me | Me |
| Cl | Br | F | I | Me | H |
| Cl | Br | F | I | Et | H |
| Cl | Br | F | I | i-Pr | H |
| Cl | Br | F | I | t-Bu | H |
| Cl | Br | F | I | Me | Me |
| Br | Br | F | I | Me | H |
| Br | Br | F | I | Et | H |
| Br | Br | F | I | i-Pr | H |
| Br | Br | F | I | t-Bu | H |
| Br | Br | F | I | Me | Me |
| Cl | $OCH_2CF_3$ | F | I | Me | H |
| Cl | $OCH_2CF_3$ | F | I | Et | H |
| Cl | $OCH_2CF_3$ | F | I | i-Pr | H |
| Cl | $OCH_2CF_3$ | F | I | t-Bu | H |
| Cl | $OCH_2CF_3$ | F | I | Me | Me |
| Br | $OCH_2CF_3$ | F | I | Me | H |

TABLE 3-continued

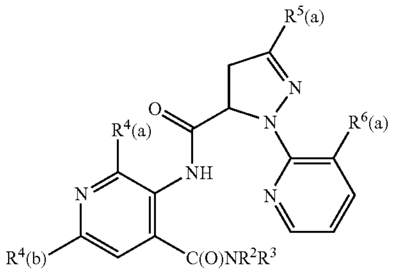

| $R^6$(a) | $R^5$(a) | $R^4$(a) | $R^4$(b) | $R^3$ | $R^2$ |
|---|---|---|---|---|---|
| Br | $OCH_2CF_3$ | F | I | Et | H |
| Br | $OCH_2CF_3$ | F | I | i-Pr | H |
| Br | $OCH_2CF_3$ | F | I | t-Bu | H |
| Br | $OCH_2CF_3$ | F | I | Me | Me |
| Cl | $CF_3$ | F | $CF_3$ | Me | H |
| Cl | $CF_3$ | F | $CF_3$ | Et | H |
| Cl | $CF_3$ | F | $CF_3$ | i-Pr | H |
| Cl | $CF_3$ | F | $CF_3$ | t-Bu | H |
| Cl | $CF_3$ | F | $CF_3$ | Me | Me |
| Br | $CF_3$ | F | $CF_3$ | Me | H |
| Br | $CF_3$ | F | $CF_3$ | Et | H |
| Br | $CF_3$ | F | $CF_3$ | i-Pr | H |
| Br | $CF_3$ | F | $CF_3$ | t-Bu | H |
| Br | $CF_3$ | F | $CF_3$ | Me | Me |
| Cl | Cl | F | $CF_3$ | Me | H |
| Cl | Cl | F | $CF_3$ | Et | H |
| Cl | Cl | F | $CF_3$ | i-Pr | H |
| Cl | Cl | F | $CF_3$ | t-Bu | H |
| Cl | Cl | F | $CF_3$ | Me | Me |
| Br | Cl | F | $CF_3$ | Me | H |
| Br | Cl | F | $CF_3$ | Et | H |
| Br | Cl | F | $CF_3$ | i-Pr | H |
| Br | Cl | F | $CF_3$ | t-Bu | H |
| Br | Cl | F | $CF_3$ | Me | Me |
| Cl | Br | F | $CF_3$ | Me | H |
| Cl | Br | F | $CF_3$ | Et | H |
| Cl | Br | F | $CF_3$ | i-Pr | H |
| Cl | Br | F | $CF_3$ | t-Bu | H |
| Cl | Br | F | $CF_3$ | Me | Me |
| Br | Br | F | $CF_3$ | Me | H |
| Br | Br | F | $CF_3$ | Et | H |
| Br | Br | F | $CF_3$ | i-Pr | H |
| Br | Br | F | $CF_3$ | t-Bu | H |
| Br | Br | F | $CF_3$ | Me | Me |
| Cl | $OCH_2CF_3$ | F | $CF_3$ | Me | H |
| Cl | $OCH_2CF_3$ | F | $CF_3$ | Et | H |
| Cl | $OCH_2CF_3$ | F | $CF_3$ | i-Pr | H |
| Cl | $OCH_2CF_3$ | F | $CF_3$ | t-Bu | H |
| Cl | $OCH_2CF_3$ | F | $CF_3$ | Me | Me |
| Br | $OCH_2CF_3$ | F | $CF_3$ | Me | H |
| Br | $OCH_2CF_3$ | F | $CF_3$ | Et | H |
| Br | $OCH_2CF_3$ | F | $CF_3$ | i-Pr | H |
| Br | $OCH_2CF_3$ | F | $CF_3$ | t-Bu | H |
| Br | $OCH_2CF_3$ | F | $CF_3$ | Me | Me |
| Cl | $CF_3$ | Cl | H | Me | H |
| Cl | $CF_3$ | Cl | H | Et | H |
| Cl | $CF_3$ | Cl | H | i-Pr | H |
| Cl | $CF_3$ | Cl | H | t-Bu | H |
| Cl | $CF_3$ | Cl | H | Me | Me |
| Br | $CF_3$ | Cl | H | Me | H |
| Br | $CF_3$ | Cl | H | Et | H |
| Br | $CF_3$ | Cl | H | i-Pr | H |
| Br | $CF_3$ | Cl | H | t-Bu | H |
| Br | $CF_3$ | Cl | H | Me | Me |
| Cl | Cl | Cl | H | Me | H |
| Cl | Cl | Cl | H | Et | H |
| Cl | Cl | Cl | H | i-Pr | H |
| Cl | Cl | Cl | H | t-Bu | H |
| Cl | Cl | Cl | H | Me | Me |
| Br | Cl | Cl | H | Me | H |
| Br | Cl | Cl | H | Et | H |
| Br | Cl | Cl | H | i-Pr | H |
| Br | Cl | Cl | H | t-Bu | H |

TABLE 3-continued

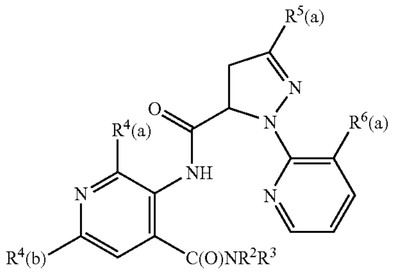

| $R^6$(a) | $R^5$(a) | $R^4$(a) | $R^4$(b) | $R^3$ | $R^2$ |
|---|---|---|---|---|---|
| Br | Cl | Cl | H | Me | Me |
| Cl | Br | Cl | H | Me | H |
| Cl | Br | Cl | H | Et | H |
| Cl | Br | Cl | H | i-Pr | H |
| Cl | Br | Cl | H | t-Bu | H |
| Cl | Br | Cl | H | Me | Me |
| Br | Br | Cl | H | Me | H |
| Br | Br | Cl | H | Et | H |
| Br | Br | Cl | H | i-Pr | H |
| Br | Br | Cl | H | t-Bu | H |
| Br | Br | Cl | H | Me | Me |
| Cl | $OCH_2CF_3$ | Cl | H | Me | H |
| Cl | $OCH_2CF_3$ | Cl | H | Et | H |
| Cl | $OCH_2CF_3$ | Cl | H | i-Pr | H |
| Cl | $OCH_2CF_3$ | Cl | H | t-Bu | H |
| Cl | $OCH_2CF_3$ | Cl | H | Me | Me |
| Br | $OCH_2CF_3$ | Cl | H | Me | H |
| Br | $OCH_2CF_3$ | Cl | H | Et | H |
| Br | $OCH_2CF_3$ | Cl | H | i-Pr | H |
| Br | $OCH_2CF_3$ | Cl | H | t-Bu | H |
| Br | $OCH_2CF_3$ | Cl | H | Me | Me |
| Cl | $CF_3$ | Cl | F | Me | H |
| Cl | $CF_3$ | Cl | F | Et | H |
| Cl | $CF_3$ | Cl | F | i-Pr | H |
| Cl | $CF_3$ | Cl | F | t-Bu | H |
| Cl | $CF_3$ | Cl | F | Me | Me |
| Br | $CF_3$ | Cl | F | Me | H |
| Br | $CF_3$ | Cl | F | Et | H |
| Br | $CF_3$ | Cl | F | i-Pr | H |
| Br | $CF_3$ | Cl | F | t-Bu | H |
| Br | $CF_3$ | Cl | F | Me | Me |
| Cl | Cl | Cl | F | Me | H |
| Cl | Cl | Cl | F | Et | H |
| Cl | Cl | Cl | F | i-Pr | H |
| Cl | Cl | Cl | F | t-Bu | H |
| Cl | Cl | Cl | F | Me | Me |
| Br | Cl | Cl | F | Me | H |
| Br | Cl | Cl | F | Et | H |
| Br | Cl | Cl | F | i-Pr | H |
| Br | Cl | Cl | F | t-Bu | H |
| Br | Cl | Cl | F | Me | Me |
| Cl | Br | Cl | F | Me | H |
| Cl | Br | Cl | F | Et | H |
| Cl | Br | Cl | F | i-Pr | H |
| Cl | Br | Cl | F | t-Bu | H |
| Cl | Br | Cl | F | Me | Me |
| Br | Br | Cl | F | Me | H |
| Br | Br | Cl | F | Et | H |
| Br | Br | Cl | F | i-Pr | H |
| Br | Br | Cl | F | t-Bu | H |
| Br | Br | Cl | F | Me | Me |
| Cl | $OCH_2CF_3$ | Cl | F | Me | H |
| Cl | $OCH_2CF_3$ | Cl | F | Et | H |
| Cl | $OCH_2CF_3$ | Cl | F | i-Pr | H |
| Cl | $OCH_2CF_3$ | Cl | F | t-Bu | H |
| Cl | $OCH_2CF_3$ | Cl | F | Me | Me |
| Br | $OCH_2CF_3$ | Cl | F | Me | H |
| Br | $OCH_2CF_3$ | Cl | F | Et | H |
| Br | $OCH_2CF_3$ | Cl | F | i-Pr | H |
| Br | $OCH_2CF_3$ | Cl | F | t-Bu | H |
| Br | $OCH_2CF_3$ | Cl | F | Me | Me |
| Cl | $CF_3$ | Cl | Cl | Me | H |
| Cl | $CF_3$ | Cl | Cl | Et | H |

TABLE 3-continued

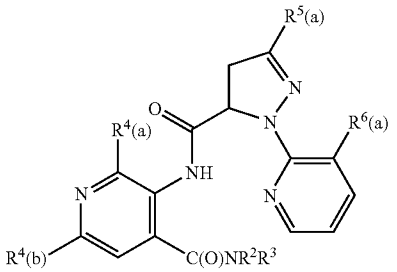

| $R^6$(a) | $R^5$(a) | $R^4$(a) | $R^4$(b) | $R^3$ | $R^2$ |
|---|---|---|---|---|---|
| Cl | $CF_3$ | Cl | Cl | i-Pr | H |
| Cl | $CF_3$ | Cl | Cl | t-Bu | H |
| Cl | $CF_3$ | Cl | Cl | Me | Me |
| Br | $CF_3$ | Cl | Cl | Me | H |
| Br | $CF_3$ | Cl | Cl | Et | H |
| Br | $CF_3$ | Cl | Cl | i-Pr | H |
| Br | $CF_3$ | Cl | Cl | t-Bu | H |
| Br | $CF_3$ | Cl | Cl | Me | Me |
| Cl | Cl | Cl | Cl | Me | H |
| Cl | Cl | Cl | Cl | Et | H |
| Cl | Cl | Cl | Cl | i-Pr | H |
| Cl | Cl | Cl | Cl | t-Bu | H |
| Cl | Cl | Cl | Cl | Me | Me |
| Br | Cl | Cl | Cl | Me | H |
| Br | Cl | Cl | Cl | Et | H |
| Br | Cl | Cl | Cl | i-Pr | H |
| Br | Cl | Cl | Cl | t-Bu | H |
| Br | Cl | Cl | Cl | Me | Me |
| Cl | Br | Cl | Cl | Me | H |
| Cl | Br | Cl | Cl | Et | H |
| Cl | Br | Cl | Cl | i-Pr | H |
| Cl | Br | Cl | Cl | t-Bu | H |
| Cl | Br | Cl | Cl | Me | Me |
| Br | Br | Cl | Cl | Me | H |
| Br | Br | Cl | Cl | Et | H |
| Br | Br | Cl | Cl | i-Pr | H |
| Br | Br | Cl | Cl | t-Bu | H |
| Br | Br | Cl | Cl | Me | Me |
| Cl | $OCH_2CF_3$ | Cl | Cl | Me | H |
| Cl | $OCH_2CF_3$ | Cl | Cl | Et | H |
| Cl | $OCH_2CF_3$ | Cl | Cl | i-Pr | H |
| Cl | $OCH_2CF_3$ | Cl | Cl | t-Bu | H |
| Cl | $OCH_2CF_3$ | Cl | Cl | Me | Me |
| Br | $OCH_2CF_3$ | Cl | Cl | Me | H |
| Br | $OCH_2CF_3$ | Cl | Cl | Et | H |
| Br | $OCH_2CF_3$ | Cl | Cl | i-Pr | H |
| Br | $OCH_2CF_3$ | Cl | Cl | t-Bu | H |
| Br | $OCH_2CF_3$ | Cl | Cl | Me | Me |
| Cl | $CF_3$ | Cl | Br | Me | H |
| Cl | $CF_3$ | Cl | Br | Et | H |
| Cl | $CF_3$ | Cl | Br | i-Pr | H |
| Cl | $CF_3$ | Cl | Br | t-Bu | H |
| Cl | $CF_3$ | Cl | Br | Me | Me |
| Br | $CF_3$ | Cl | Br | Me | H |
| Br | $CF_3$ | Cl | Br | Et | H |
| Br | $CF_3$ | Cl | Br | i-Pr | H |
| Br | $CF_3$ | Cl | Br | t-Bu | H |
| Br | $CF_3$ | Cl | Br | Me | Me |
| Cl | Cl | Cl | Br | Me | H |
| Cl | Cl | Cl | Br | Et | H |
| Cl | Cl | Cl | Br | i-Pr | H |
| Cl | Cl | Cl | Br | t-Bu | H |
| Cl | Cl | Cl | Br | Me | Me |
| Br | Cl | Cl | Br | Me | H |
| Br | Cl | Cl | Br | Et | H |
| Br | Cl | Cl | Br | i-Pr | H |
| Br | Cl | Cl | Br | t-Bu | H |
| Br | Cl | Cl | Br | Me | Me |
| Cl | Br | Cl | Br | Me | H |
| Cl | Br | Cl | Br | Et | H |
| Cl | Br | Cl | Br | i-Pr | H |
| Cl | Br | Cl | Br | t-Bu | H |
| Cl | Br | Cl | Br | Me | Me |

TABLE 3-continued

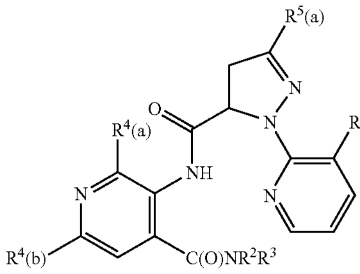

| $R^6$(a) | $R^5$(a) | $R^4$(a) | $R^4$(b) | $R^3$ | $R^2$ |
|---|---|---|---|---|---|
| Br | Br | Cl | Br | Me | H |
| Br | Br | Cl | Br | Et | H |
| Br | Br | Cl | Br | i-Pr | H |
| Br | Br | Cl | Br | t-Bu | H |
| Br | Br | Cl | Br | Me | Me |
| Cl | $OCH_2CF_3$ | Cl | Br | Me | H |
| Cl | $OCH_2CF_3$ | Cl | Br | Et | H |
| Cl | $OCH_2CF_3$ | Cl | Br | i-Pr | H |
| Cl | $OCH_2CF_3$ | Cl | Br | t-Bu | H |
| Cl | $OCH_2CF_3$ | Cl | Br | Me | Me |
| Br | $OCH_2CF_3$ | Cl | Br | Me | H |
| Br | $OCH_2CF_3$ | Cl | Br | Et | H |
| Br | $OCH_2CF_3$ | Cl | Br | i-Pr | H |
| Br | $OCH_2CF_3$ | Cl | Br | t-Bu | H |
| Br | $OCH_2CF_3$ | Cl | Br | Me | Me |
| Cl | $CF_3$ | Cl | I | Me | H |
| Cl | $CF_3$ | Cl | I | Et | H |
| Cl | $CF_3$ | Cl | I | i-Pr | H |
| Cl | $CF_3$ | Cl | I | t-Bu | H |
| Cl | $CF_3$ | Cl | I | Me | Me |
| Br | $CF_3$ | Cl | I | Me | H |
| Br | $CF_3$ | Cl | I | Et | H |
| Br | $CF_3$ | Cl | I | i-Pr | H |
| Br | $CF_3$ | Cl | I | t-Bu | H |
| Br | $CF_3$ | Cl | I | Me | Me |
| Cl | Cl | Cl | I | Me | H |
| Cl | Cl | Cl | I | Et | H |
| Cl | Cl | Cl | I | i-Pr | H |
| Cl | Cl | Cl | I | t-Bu | H |
| Cl | Cl | Cl | I | Me | Me |
| Br | Cl | Cl | I | Me | H |
| Br | Cl | Cl | I | Et | H |
| Br | Cl | Cl | I | i-Pr | H |
| Br | Cl | Cl | I | t-Bu | H |
| Br | Cl | Cl | I | Me | Me |
| Cl | Br | Cl | I | Me | H |
| Cl | Br | Cl | I | Et | H |
| Cl | Br | Cl | I | i-Pr | H |
| Cl | Br | Cl | I | t-Bu | H |
| Cl | Br | Cl | I | Me | Me |
| Br | Br | Cl | I | Me | H |
| Br | Br | Cl | I | Et | H |
| Br | Br | Cl | I | i-Pr | H |
| Br | Br | Cl | I | t-Bu | H |
| Br | Br | Cl | I | Me | Me |
| Cl | $OCH_2CF_3$ | Cl | I | Me | H |
| Cl | $OCH_2CF_3$ | Cl | I | Et | H |
| Cl | $OCH_2CF_3$ | Cl | I | i-Pr | H |
| Cl | $OCH_2CF_3$ | Cl | I | t-Bu | H |
| Cl | $OCH_2CF_3$ | Cl | I | Me | Me |
| Br | $OCH_2CF_3$ | Cl | I | Me | H |
| Br | $OCH_2CF_3$ | Cl | I | Et | H |
| Br | $OCH_2CF_3$ | Cl | I | i-Pr | H |
| Br | $OCH_2CF_3$ | Cl | I | t-Bu | H |
| Br | $OCH_2CF_3$ | Cl | I | Me | Me |
| Cl | $CF_3$ | Cl | $CF_3$ | Me | H |
| Cl | $CF_3$ | Cl | $CF_3$ | Et | H |
| Cl | $CF_3$ | Cl | $CF_3$ | i-Pr | H |
| Cl | $CF_3$ | Cl | $CF_3$ | t-Bu | H |
| Cl | $CF_3$ | Cl | $CF_3$ | Me | Me |
| Br | $CF_3$ | Cl | $CF_3$ | Me | H |
| Br | $CF_3$ | Cl | $CF_3$ | Et | H |
| Br | $CF_3$ | Cl | $CF_3$ | i-Pr | H |

TABLE 3-continued

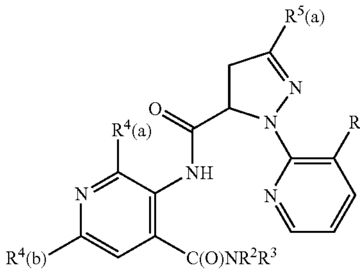

| $R^6$(a) | $R^5$(a) | $R^4$(a) | $R^4$(b) | $R^3$ | $R^2$ |
|---|---|---|---|---|---|
| Br | $CF_3$ | Cl | $CF_3$ | t-Bu | H |
| Br | $CF_3$ | Cl | $CF_3$ | Me | Me |
| Cl | Cl | Cl | $CF_3$ | Me | H |
| Cl | Cl | Cl | $CF_3$ | Et | H |
| Cl | Cl | Cl | $CF_3$ | i-Pr | H |
| Cl | Cl | Cl | $CF_3$ | t-Bu | H |
| Cl | Cl | Cl | $CF_3$ | Me | Me |
| Br | Cl | Cl | $CF_3$ | Me | H |
| Br | Cl | Cl | $CF_3$ | Et | H |
| Br | Cl | Cl | $CF_3$ | i-Pr | H |
| Br | Cl | Cl | $CF_3$ | t-Bu | H |
| Br | Cl | Cl | $CF_3$ | Me | Me |
| Cl | Br | Cl | $CF_3$ | Me | H |
| Cl | Br | Cl | $CF_3$ | Et | H |
| Cl | Br | Cl | $CF_3$ | i-Pr | H |
| Cl | Br | Cl | $CF_3$ | t-Bu | H |
| Cl | Br | Cl | $CF_3$ | Me | Me |
| Br | Br | Cl | $CF_3$ | Me | H |
| Br | Br | Cl | $CF_3$ | Et | H |
| Br | Br | Cl | $CF_3$ | i-Pr | H |
| Br | Br | Cl | $CF_3$ | t-Bu | H |
| Br | Br | Cl | $CF_3$ | Me | Me |
| Cl | $OCH_2CF_3$ | Cl | $CF_3$ | Me | H |
| Cl | $OCH_2CF_3$ | Cl | $CF_3$ | Et | H |
| Cl | $OCH_2CF_3$ | Cl | $CF_3$ | i-Pr | H |
| Cl | $OCH_2CF_3$ | Cl | $CF_3$ | t-Bu | H |
| Cl | $OCH_2CF_3$ | Cl | $CF_3$ | Me | Me |
| Br | $OCH_2CF_3$ | Cl | $CF_3$ | Me | H |
| Br | $OCH_2CF_3$ | Cl | $CF_3$ | Et | H |
| Br | $OCH_2CF_3$ | Cl | $CF_3$ | i-Pr | H |
| Br | $OCH_2CF_3$ | Cl | $CF_3$ | t-Bu | H |
| Br | $OCH_2CF_3$ | Cl | $CF_3$ | Me | Me |
| Cl | Cl | Cl | Cl | n-Pr | H |
| Cl | Cl | Cl | Cl | n-Bu | H |
| Cl | Cl | Cl | Cl | S-Bu | H |
| Cl | Cl | Cl | Cl | i-Bu | H |
| Cl | Cl | Cl | Cl | Et | Et |
| Cl | $CF_3$ | Br | H | Me | H |
| Cl | $CF_3$ | Br | H | Et | H |
| Cl | $CF_3$ | Br | H | i-Pr | H |
| Cl | $CF_3$ | Br | H | t-Bu | H |
| Cl | $CF_3$ | Br | H | Me | Me |
| Br | $CF_3$ | Br | H | Me | H |
| Br | $CF_3$ | Br | H | Et | H |
| Br | $CF_3$ | Br | H | i-Pr | H |
| Br | $CF_3$ | Br | H | t-Bu | H |
| Br | $CF_3$ | Br | H | Me | Me |
| Cl | Cl | Br | H | Me | H |
| Cl | Cl | Br | H | Et | H |
| Cl | Cl | Br | H | i-Pr | H |
| Cl | Cl | Br | H | t-Bu | H |
| Cl | Cl | Br | H | Me | Me |
| Br | Cl | Br | H | Me | H |
| Br | Cl | Br | H | Et | H |
| Br | Cl | Br | H | i-Pr | H |
| Br | Cl | Br | H | t-Bu | H |
| Br | Cl | Br | H | Me | Me |
| Cl | Br | Br | H | Me | H |
| Cl | Br | Br | H | Et | H |
| Cl | Br | Br | H | i-Pr | H |
| Cl | Br | Br | H | t-Bu | H |
| Cl | Br | Br | H | Me | Me |
| Br | Br | Br | H | Me | H |

TABLE 3-continued

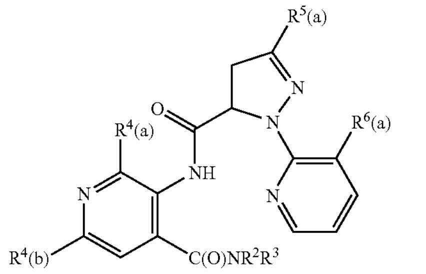

| $R^6(a)$ | $R^5(a)$ | $R^4(a)$ | $R^4(b)$ | $R^3$ | $R^2$ |
|---|---|---|---|---|---|
| Br | Br | Br | H | Et | H |
| Br | Br | Br | H | i-Pr | H |
| Br | Br | Br | H | t-Bu | H |
| Br | Br | Br | H | Me | Me |
| Cl | $OCH_2H_3$ | Br | H | Me | H |
| Cl | $OCH_2H_3$ | Br | H | Et | H |
| Cl | $OCH_2H_3$ | Br | H | i-Pr | H |
| Cl | $OCH_2H_3$ | Br | H | t-Bu | H |
| Cl | $OCH_2H_3$ | Br | H | Me | Me |
| Br | $OCH_2H_3$ | Br | H | Me | H |
| Br | $OCH_2H_3$ | Br | H | Et | H |
| Br | $OCH_2H_3$ | Br | H | i-Pr | H |
| Br | $OCH_2H_3$ | Br | H | t-Bu | H |
| Br | $OCH_2H_3$ | Br | H | Me | Me |
| Cl | $CF_3$ | Br | F | Me | H |
| Cl | $CF_3$ | Br | F | Et | H |
| Cl | $CF_3$ | Br | F | i-Pr | H |
| Cl | $CF_3$ | Br | F | t-Bu | H |
| Cl | $CF_3$ | Br | F | Me | Me |
| Br | $CF_3$ | Br | F | Me | H |
| Br | $CF_3$ | Br | F | Et | H |
| Br | $CF_3$ | Br | F | i-Pr | H |
| Br | $CF_3$ | Br | F | t-Bu | H |
| Br | $CF_3$ | Br | F | Me | Me |
| Cl | Cl | Br | F | Me | H |
| Cl | Cl | Br | F | Et | H |
| Cl | Cl | Br | F | i-Pr | H |
| Cl | Cl | Br | F | t-Bu | H |
| Cl | Cl | Br | F | Me | Me |
| Br | Cl | Br | F | Me | H |
| Br | Cl | Br | F | Et | H |
| Br | Cl | Br | F | i-Pr | H |
| Br | Cl | Br | F | t-Bu | H |
| Br | Cl | Br | F | Me | Me |
| Cl | Br | Br | F | Me | H |
| Cl | Br | Br | F | Et | H |
| Cl | Br | Br | F | i-Pr | H |
| Cl | Br | Br | F | t-Bu | H |
| Cl | Br | Br | F | Me | Me |
| Br | Br | Br | F | Me | H |
| Br | Br | Br | F | Et | H |
| Br | Br | Br | F | i-Pr | H |
| Br | Br | Br | F | t-Bu | H |
| Br | Br | Br | F | Me | Me |
| Cl | $OCH_2CF_3$ | Br | F | Me | H |
| Cl | $OCH_2CF_3$ | Br | F | Et | H |
| Cl | $OCH_2CF_3$ | Br | F | i-Pr | H |
| Cl | $OCH_2CF_3$ | Br | F | t-Bu | H |
| Cl | $OCH_2CF_3$ | Br | F | Me | Me |
| Br | $OCH_2CF_3$ | Br | F | Me | H |
| Br | $OCH_2CF_3$ | Br | F | Et | H |
| Br | $OCH_2CF_3$ | Br | F | i-Pr | H |
| Br | $OCH_2CF_3$ | Br | F | t-Bu | H |
| Br | $OCH_2CF_3$ | Br | F | Me | Me |
| Cl | $CF_3$ | Br | Cl | Me | H |
| Cl | $CF_3$ | Br | Cl | Et | H |
| Cl | $CF_3$ | Br | Cl | i-Pr | H |
| Cl | $CF_3$ | Br | Cl | t-Bu | H |
| Cl | $CF_3$ | Br | Cl | Me | Me |
| Br | $CF_3$ | Br | Cl | Me | H |
| Br | $CF_3$ | Br | Cl | Et | H |
| Br | $CF_3$ | Br | Cl | i-Pr | H |
| Br | $CF_3$ | Br | Cl | t-Bu | H |

TABLE 3-continued

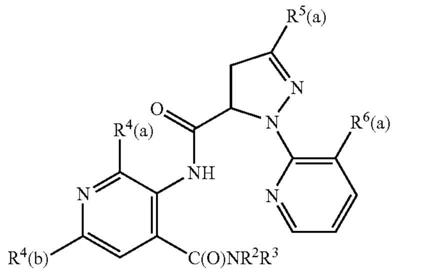

| $R^6(a)$ | $R^5(a)$ | $R^4(a)$ | $R^4(b)$ | $R^3$ | $R^2$ |
|---|---|---|---|---|---|
| Br | $CF_3$ | Br | Cl | Me | Me |
| Cl | Cl | Br | Cl | Me | H |
| Cl | Cl | Br | Cl | Et | H |
| Cl | Cl | Br | Cl | i-Pr | H |
| Cl | Cl | Br | Cl | t-Bu | H |
| Cl | Cl | Br | Cl | Me | Me |
| Br | Cl | Br | Cl | Me | H |
| Br | Cl | Br | Cl | Et | H |
| Br | Cl | Br | Cl | i-Pr | H |
| Br | Cl | Br | Cl | t-Bu | H |
| Br | Cl | Br | Cl | Me | Me |
| Cl | Br | Br | Cl | Me | H |
| Cl | Br | Br | Cl | Et | H |
| Cl | Br | Br | Cl | i-Pr | H |
| Cl | Br | Br | Cl | t-Bu | H |
| Cl | Br | Br | Cl | Me | Me |
| Br | Br | Br | Cl | Me | H |
| Br | Br | Br | Cl | Et | H |
| Br | Br | Br | Cl | i-Pr | H |
| Br | Br | Br | Cl | t-Bu | H |
| Br | Br | Br | Cl | Me | Me |
| Cl | $OCH_2CF_3$ | Br | Cl | Me | H |
| Cl | $OCH_2CF_3$ | Br | Cl | Et | H |
| Cl | $OCH_2CF_3$ | Br | Cl | i-Pr | H |
| Cl | $OCH_2CF_3$ | Br | Cl | t-Bu | H |
| Cl | $OCH_2CF_3$ | Br | Cl | Me | Me |
| Br | $OCH_2CF_3$ | Br | Cl | Me | H |
| Br | $OCH_2CF_3$ | Br | Cl | Et | H |
| Br | $OCH_2CF_3$ | Br | Cl | i-Pr | H |
| Br | $OCH_2CF_3$ | Br | Cl | t-Bu | H |
| Br | $OCH_2CF_3$ | Br | Cl | Me | Me |
| Cl | $CF_3$ | Br | Br | Me | H |
| Cl | $CF_3$ | Br | Br | Et | H |
| Cl | $CF_3$ | Br | Br | i-Pr | H |
| Cl | $CF_3$ | Br | Br | t-Bu | H |
| Cl | $CF_3$ | Br | Br | Me | Me |
| Br | $CF_3$ | Br | Br | Me | H |
| Br | $CF_3$ | Br | Br | Et | H |
| Br | $CF_3$ | Br | Br | i-Pr | H |
| Br | $CF_3$ | Br | Br | t-Bu | H |
| Br | $CF_3$ | Br | Br | Me | Me |
| Cl | Cl | Br | Br | Me | H |
| Cl | Cl | Br | Br | Et | H |
| Cl | Cl | Br | Br | i-Pr | H |
| Cl | Cl | Br | Br | t-Bu | H |
| Cl | Cl | Br | Br | Me | Me |
| Br | Cl | Br | Br | Me | H |
| Br | Cl | Br | Br | Et | H |
| Br | Cl | Br | Br | i-Pr | H |
| Br | Cl | Br | Br | t-Bu | H |
| Br | Cl | Br | Br | Me | Me |
| Cl | Br | Br | Br | Me | H |
| Cl | Br | Br | Br | Et | H |
| Cl | Br | Br | Br | i-Pr | H |
| Cl | Br | Br | Br | t-Bu | H |
| Cl | Br | Br | Br | Me | Me |
| Br | Br | Br | Br | Me | H |
| Br | Br | Br | Br | Et | H |
| Br | Br | Br | Br | i-Pr | H |
| Br | Br | Br | Br | t-Bu | H |
| Br | Br | Br | Br | Me | Me |
| Cl | $OCH_2CF_3$ | Br | Br | Me | H |
| Cl | $OCH_2CF_3$ | Br | Br | Et | H |

TABLE 3-continued

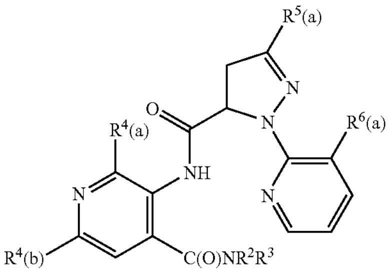

| $R^6$(a) | $R^5$(a) | $R^4$(a) | $R^4$(b) | $R^3$ | $R^2$ |
|---|---|---|---|---|---|
| Cl | $OCH_2CF_3$ | Br | Br | i-Pr | H |
| Cl | $OCH_2CF_3$ | Br | Br | t-Bu | H |
| Cl | $OCH_2CF_3$ | Br | Br | Me | Me |
| Br | $OCH_2CF_3$ | Br | Br | Me | H |
| Br | $OCH_2CF_3$ | Br | Br | Et | H |
| Br | $OCH_2CF_3$ | Br | Br | i-Pr | H |
| Br | $OCH_2CF_3$ | Br | Br | t-Bu | H |
| Br | $OCH_2CF_3$ | Br | Br | Me | Me |
| Cl | $CF_3$ | Br | I | Me | H |
| Cl | $CF_3$ | Br | I | Et | H |
| Cl | $CF_3$ | Br | I | i-Pr | H |
| Cl | $CF_3$ | Br | I | t-Bu | H |
| Cl | $CF_3$ | Br | I | Me | Me |
| Br | $CF_3$ | Br | I | Me | H |
| Br | $CF_3$ | Br | I | Et | H |
| Br | $CF_3$ | Br | I | i-Pr | H |
| Br | $CF_3$ | Br | I | t-Bu | H |
| Br | $CF_3$ | Br | I | Me | Me |
| Cl | Cl | Br | I | Me | H |
| Cl | Cl | Br | I | Et | H |
| Cl | Cl | Br | I | i-Pr | H |
| Cl | Cl | Br | I | t-Bu | H |
| Cl | Cl | Br | I | Me | Me |
| Br | Cl | Br | I | Me | H |
| Br | Cl | Br | I | Et | H |
| Br | Cl | Br | I | i-Pr | H |
| Br | Cl | Br | I | t-Bu | H |
| Br | Cl | Br | I | Me | Me |
| Cl | Br | Br | I | Me | H |
| Cl | Br | Br | I | Et | H |
| Cl | Br | Br | I | i-Pr | H |
| Cl | Br | Br | I | t-Bu | H |
| Cl | Br | Br | I | Me | Me |
| Br | Br | Br | I | Me | H |
| Br | Br | Br | I | Et | H |
| Br | Br | Br | I | i-Pr | H |
| Br | Br | Br | I | t-Bu | H |
| Br | Br | Br | I | Me | Me |
| Cl | $OCH_2CF_3$ | Br | I | Me | H |
| Cl | $OCH_2CF_3$ | Br | I | Et | H |
| Cl | $OCH_2CF_3$ | Br | I | i-Pr | H |
| Cl | $OCH_2CF_3$ | Br | I | t-Bu | H |
| Cl | $OCH_2CF_3$ | Br | I | Me | Me |
| Br | $OCH_2CF_3$ | Br | I | Me | H |
| Br | $OCH_2CF_3$ | Br | I | Et | H |
| Br | $OCH_2CF_3$ | Br | I | i-Pr | H |
| Br | $OCH_2CF_3$ | Br | I | t-Bu | H |
| Br | $OCH_2CF_3$ | Br | I | Me | Me |
| Cl | $CF_3$ | Br | $CF_3$ | Me | H |
| Cl | $CF_3$ | Br | $CF_3$ | Et | H |
| Cl | $CF_3$ | Br | $CF_3$ | i-Pr | H |
| Cl | $CF_3$ | Br | $CF_3$ | t-Bu | H |
| Cl | $CF_3$ | Br | $CF_3$ | Me | Me |
| Br | $CF_3$ | Br | $CF_3$ | Me | H |
| Br | $CF_3$ | Br | $CF_3$ | Et | H |
| Br | $CF_3$ | Br | $CF_3$ | i-Pr | H |
| Br | $CF_3$ | Br | $CF_3$ | t-Bu | H |
| Br | $CF_3$ | Br | $CF_3$ | Me | Me |
| Cl | Cl | Br | $CF_3$ | Me | H |
| Cl | Cl | Br | $CF_3$ | Et | H |
| Cl | Cl | Br | $CF_3$ | i-Pr | H |
| Cl | Cl | Br | $CF_3$ | t-Bu | H |
| Cl | Cl | Br | $CF_3$ | Me | Me |

TABLE 3-continued

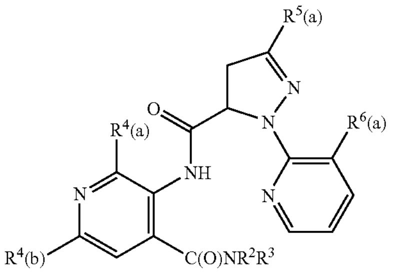

| $R^6$(a) | $R^5$(a) | $R^4$(a) | $R^4$(b) | $R^3$ | $R^2$ |
|---|---|---|---|---|---|
| Br | Cl | Br | $CF_3$ | Me | H |
| Br | Cl | Br | $CF_3$ | Et | H |
| Br | Cl | Br | $CF_3$ | i-Pr | H |
| Br | Cl | Br | $CF_3$ | t-Bu | H |
| Br | Cl | Br | $CF_3$ | Me | Me |
| Cl | Br | Br | $CF_3$ | Me | H |
| Cl | Br | Br | $CF_3$ | Et | H |
| Cl | Br | Br | $CF_3$ | i-Pr | H |
| Cl | Br | Br | $CF_3$ | t-Bu | H |
| Cl | Br | Br | $CF_3$ | Me | Me |
| Br | Br | Br | $CF_3$ | Me | H |
| Br | Br | Br | $CF_3$ | Et | H |
| Br | Br | Br | $CF_3$ | i-Pr | H |
| Br | Br | Br | $CF_3$ | t-Bu | H |
| Br | Br | Br | $CF_3$ | Me | Me |
| Cl | $OCH_2CF_3$ | Br | $CF_3$ | Me | H |
| Cl | $OCH_2CF_3$ | Br | $CF_3$ | Et | H |
| Cl | $OCH_2CF_3$ | Br | $CF_3$ | i-Pr | H |
| Cl | $OCH_2CF_3$ | Br | $CF_3$ | t-Bu | H |
| Cl | $OCH_2CF_3$ | Br | $CF_3$ | Me | Me |
| Br | $OCH_2CF_3$ | Br | $CF_3$ | Me | H |
| Br | $OCH_2CF_3$ | Br | $CF_3$ | Et | H |
| Br | $OCH_2CF_3$ | Br | $CF_3$ | i-Pr | H |
| Br | $OCH_2CF_3$ | Br | $CF_3$ | t-Bu | H |
| Br | $OCH_2CF_3$ | Br | $CF_3$ | Me | Me |

TABLE 4

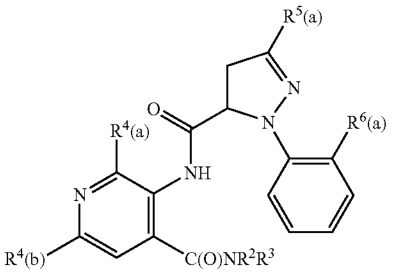

| $R^6$(a) | $R^5$(a) | $R^4$(a) | $R^4$(b) | $R^3$ | $R^2$ |
|---|---|---|---|---|---|
| Cl | $CF_3$ | $CH_3$ | H | Me | H |
| Cl | $CF_3$ | $CH_3$ | H | Et | H |
| Cl | $CF_3$ | $CH_3$ | H | i-Pr | H |
| Cl | $CF_3$ | $CH_3$ | H | t-Bu | H |
| Cl | $CF_3$ | $CH_3$ | H | Me | Me |
| Br | $CF_3$ | $CH_3$ | H | Me | H |
| Br | $CF_3$ | $CH_3$ | H | Et | H |
| Br | $CF_3$ | $CH_3$ | H | i-Pr | H |
| Br | $CF_3$ | $CH_3$ | H | t-Bu | H |
| Br | $CF_3$ | $CH_3$ | H | Me | Me |
| Cl | Cl | $CH_3$ | H | Me | H |
| Cl | Cl | $CH_3$ | H | Et | H |
| Cl | Cl | $CH_3$ | H | i-Pr | H |
| Cl | Cl | $CH_3$ | H | t-Bu | H |
| Cl | Cl | $CH_3$ | H | Me | Me |
| Br | Cl | $CH_3$ | H | Me | H |
| Br | Cl | $CH_3$ | H | Et | H |

TABLE 4-continued

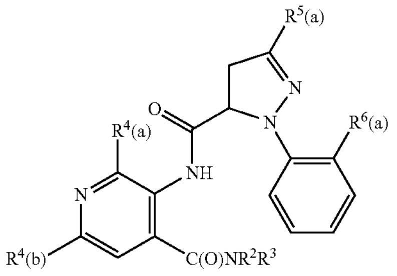

| $R^6$(a) | $R^5$(a) | $R^4$(a) | $R^4$(b) | $R^3$ | $R^2$ |
|---|---|---|---|---|---|
| Br | Cl | $CH_3$ | H | i-Pr | H |
| Br | Cl | $CH_3$ | H | t-Bu | H |
| Br | Cl | $CH_3$ | H | Me | Me |
| Cl | Br | $CH_3$ | H | Me | H |
| Cl | Br | $CH_3$ | H | Et | H |
| Cl | Br | $CH_3$ | H | i-Pr | H |
| Cl | Br | $CH_3$ | H | t-Bu | H |
| Cl | Br | $CH_3$ | H | Me | Me |
| Br | Br | $CH_3$ | H | Me | H |
| Br | Br | $CH_3$ | H | Et | H |
| Br | Br | $CH_3$ | H | i-Pr | H |
| Br | Br | $CH_3$ | H | t-Bu | H |
| Br | Br | $CH_3$ | H | Me | Me |
| Cl | $OCH_2CF_3$ | $CH_3$ | H | Me | H |
| Cl | $OCH_2CF_3$ | $CH_3$ | H | Et | H |
| Cl | $OCH_2CF_3$ | $CH_3$ | H | i-Pr | H |
| Cl | $OCH_2CF_3$ | $CH_3$ | H | t-Bu | H |
| Cl | $OCH_2CF_3$ | $CH_3$ | H | Me | Me |
| Br | $OCH_2CF_3$ | $CH_3$ | H | Me | H |
| Br | $OCH_2CF_3$ | $CH_3$ | H | Et | H |
| Br | $OCH_2CF_3$ | $CH_3$ | H | i-Pr | H |
| Br | $OCH_2CF_3$ | $CH_3$ | H | t-Bu | H |
| Br | $OCH_2CF_3$ | $CH_3$ | H | Me | Me |
| Cl | $CF_3$ | $CH_3$ | F | Me | H |
| Cl | $CF_3$ | $CH_3$ | F | Et | H |
| Cl | $CF_3$ | $CH_3$ | F | i-Pr | H |
| Cl | $CF_3$ | $CH_3$ | F | t-Bu | H |
| Cl | $CF_3$ | $CH_3$ | F | Me | Me |
| Br | $CF_3$ | $CH_3$ | F | Me | H |
| Br | $CF_3$ | $CH_3$ | F | Et | H |
| Br | $CF_3$ | $CH_3$ | F | i-Pr | H |
| Br | $CF_3$ | $CH_3$ | F | t-Bu | H |
| Br | $CF_3$ | $CH_3$ | F | Me | Me |
| Cl | Cl | $CH_3$ | F | Me | H |
| Cl | Cl | $CH_3$ | F | Et | H |
| Cl | Cl | $CH_3$ | F | i-Pr | H |
| Cl | Cl | $CH_3$ | F | t-Bu | H |
| Cl | Cl | $CH_3$ | F | Me | Me |
| Br | Cl | $CH_3$ | F | Me | H |
| Br | Cl | $CH_3$ | F | Et | H |
| Br | Cl | $CH_3$ | F | i-Pr | H |
| Br | Cl | $CH_3$ | F | t-Bu | H |
| Br | Cl | $CH_3$ | F | Me | Me |
| Cl | Br | $CH_3$ | F | Me | H |
| Cl | Br | $CH_3$ | F | Et | H |
| Cl | Br | $CH_3$ | F | i-Pr | H |
| Cl | Br | $CH_3$ | F | t-Bu | H |
| Cl | Br | $CH_3$ | F | Me | Me |
| Br | Br | $CH_3$ | F | Me | H |
| Br | Br | $CH_3$ | F | Et | H |
| Br | Br | $CH_3$ | F | i-Pr | H |
| Br | Br | $CH_3$ | F | t-Bu | H |
| Br | Br | $CH_3$ | F | Me | Me |
| Cl | $OCH_2CF_3$ | $CH_3$ | F | Me | H |
| Cl | $OCH_2CF_3$ | $CH_3$ | F | Et | H |
| Cl | $OCH_2CF_3$ | $CH_3$ | F | i-Pr | H |
| Cl | $OCH_2CF_3$ | $CH_3$ | F | t-Bu | H |
| Cl | $OCH_2CF_3$ | $CH_3$ | F | Me | Me |
| Br | $OCH_2CF_3$ | $CH_3$ | F | Me | H |
| Br | $OCH_2CF_3$ | $CH_3$ | F | Et | H |
| Br | $OCH_2CF_3$ | $CH_3$ | F | i-Pr | H |
| Br | $OCH_2CF_3$ | $CH_3$ | F | t-Bu | H |
| Br | $OCH_2CF_3$ | $CH_3$ | F | Me | Me |

TABLE 4-continued

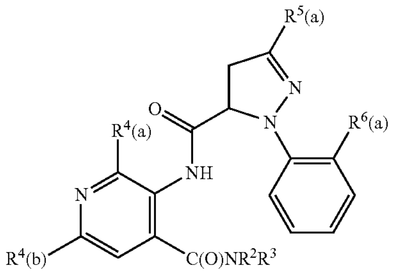

| $R^6$(a) | $R^5$(a) | $R^4$(a) | $R^4$(b) | $R^3$ | $R^2$ |
|---|---|---|---|---|---|
| Cl | $CF_3$ | $CH_3$ | Cl | Me | H |
| Cl | $CF_3$ | $CH_3$ | Cl | Et | H |
| Cl | $CF_3$ | $CH_3$ | Cl | i-Pr | H |
| Cl | $CF_3$ | $CH_3$ | Cl | t-Bu | H |
| Cl | $CF_3$ | $CH_3$ | Cl | Me | Me |
| Br | $CF_3$ | $CH_3$ | Cl | Me | H |
| Br | $CF_3$ | $CH_3$ | Cl | Et | H |
| Br | $CF_3$ | $CH_3$ | Cl | i-Pr | H |
| Br | $CF_3$ | $CH_3$ | Cl | t-Bu | H |
| Br | Cl | $CH_3$ | Cl | Me | Me |
| Cl | Cl | $CH_3$ | Cl | Me | H |
| Cl | Cl | $CH_3$ | Cl | Et | H |
| Cl | Cl | $CH_3$ | Cl | i-Pr | H |
| Cl | Cl | $CH_3$ | Cl | t-Bu | H |
| Cl | Cl | $CH_3$ | Cl | Me | Me |
| Br | Cl | $CH_3$ | Cl | Me | H |
| Br | Cl | $CH_3$ | Cl | Et | H |
| Br | Cl | $CH_3$ | Cl | i-Pr | H |
| Br | Cl | $CH_3$ | Cl | t-Bu | H |
| Br | Cl | $CH_3$ | Cl | Me | Me |
| Cl | Br | $CH_3$ | Cl | Me | H |
| Cl | Br | $CH_3$ | Cl | Et | H |
| Cl | Br | $CH_3$ | Cl | i-Pr | H |
| Cl | Br | $CH_3$ | Cl | t-Bu | H |
| Cl | Br | $CH_3$ | Cl | Me | Me |
| Br | Br | $CH_3$ | Cl | Me | H |
| Br | Br | $CH_3$ | Cl | Et | H |
| Br | Br | $CH_3$ | Cl | i-Pr | H |
| Br | Br | $CH_3$ | Cl | t-Bu | H |
| Br | Br | $CH_3$ | Cl | Me | Me |
| Cl | $OCH_2CF_3$ | $CH_3$ | Cl | Me | H |
| Cl | $OCH_2CF_3$ | $CH_3$ | Cl | Et | H |
| Cl | $OCH_2CF_3$ | $CH_3$ | Cl | i-Pr | H |
| Cl | $OCH_2CF_3$ | $CH_3$ | Cl | t-Bu | H |
| Cl | $OCH_2CF_3$ | $CH_3$ | Cl | Me | Me |
| Br | $OCH_2CF_3$ | $CH_3$ | Cl | Me | H |
| Br | $OCH_2CF_3$ | $CH_3$ | Cl | Et | H |
| Br | $OCH_2CF_3$ | $CH_3$ | Cl | i-Pr | H |
| Br | $OCH_2CF_3$ | $CH_3$ | Cl | t-Bu | H |
| Br | $OCH_2CF_3$ | $CH_3$ | Cl | Me | Me |
| Cl | $CF_3$ | $CH_3$ | Br | Me | H |
| Cl | $CF_3$ | $CH_3$ | Br | Et | H |
| Cl | $CF_3$ | $CH_3$ | Br | i-Pr | H |
| Cl | $CF_3$ | $CH_3$ | Br | t-Bu | H |
| Cl | $CF_3$ | $CH_3$ | Br | Me | Me |
| Br | $CF_3$ | $CH_3$ | Br | Me | H |
| Br | $CF_3$ | $CH_3$ | Br | Et | H |
| Br | $CF_3$ | $CH_3$ | Br | i-Pr | H |
| Br | $CF_3$ | $CH_3$ | Br | t-Bu | H |
| Br | $CF_3$ | $CH_3$ | Br | Me | Me |
| Cl | Cl | $CH_3$ | Br | Me | H |
| Cl | Cl | $CH_3$ | Br | Et | H |
| Cl | Cl | $CH_3$ | Br | i-Pr | H |
| Cl | Cl | $CH_3$ | Br | t-Bu | H |
| Cl | Cl | $CH_3$ | Br | Me | Me |
| Br | Cl | $CH_3$ | Br | Me | H |
| Br | Cl | $CH_3$ | Br | Et | H |
| Br | Cl | $CH_3$ | Br | i-Pr | H |
| Br | Cl | $CH_3$ | Br | t-Bu | H |
| Br | Cl | $CH_3$ | Br | Me | Me |
| Cl | Br | $CH_3$ | Br | Me | H |
| Cl | Br | $CH_3$ | Br | Et | H |
| Cl | Br | $CH_3$ | Br | i-Pr | H |

TABLE 4-continued

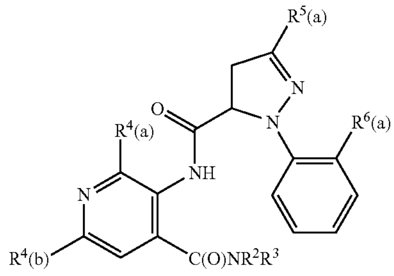

| $R^6$(a) | $R^5$(a) | $R^4$(a) | $R^4$(b) | $R^3$ | $R^2$ |
|---|---|---|---|---|---|
| Cl | Br | $CH_3$ | Br | t-Bu | H |
| Cl | Br | $CH_3$ | Br | Me | Me |
| Br | Br | $CH_3$ | Br | Me | H |
| Br | Br | $CH_3$ | Br | Et | H |
| Br | Br | $CH_3$ | Br | i-Pr | H |
| Br | Br | $CH_3$ | Br | t-Bu | H |
| Br | Br | $CH_3$ | Br | Me | Me |
| Cl | $OCH_2CF_3$ | $CH_3$ | Br | Me | H |
| Cl | $OCH_2CF_3$ | $CH_3$ | Br | Et | H |
| Cl | $OCH_2CF_3$ | $CH_3$ | Br | i-Pr | H |
| Cl | $OCH_2CF_3$ | $CH_3$ | Br | t-Bu | H |
| Cl | $OCH_2CF_3$ | $CH_3$ | Br | Me | Me |
| Br | $OCH_2CF_3$ | $CH_3$ | Br | Me | H |
| Br | $OCH_2CF_3$ | $CH_3$ | Br | Et | H |
| Br | $OCH_2CF_3$ | $CH_3$ | Br | i-Pr | H |
| Br | $OCH_2CF_3$ | $CH_3$ | Br | t-Bu | H |
| Br | $OCH_2CF_3$ | $CH_3$ | Br | Me | Me |
| Cl | $CF_3$ | $CH_3$ | I | Me | H |
| Cl | $CF_3$ | $CH_3$ | I | Et | H |
| Cl | $CF_3$ | $CH_3$ | I | i-Pr | H |
| Cl | $CF_3$ | $CH_3$ | I | t-Bu | H |
| Cl | $CF_3$ | $CH_3$ | I | Me | Me |
| Br | $CF_3$ | $CH_3$ | I | Me | H |
| Br | $CF_3$ | $CH_3$ | I | Et | H |
| Br | $CF_3$ | $CH_3$ | I | i-Pr | H |
| Br | $CF_3$ | $CH_3$ | I | t-Bu | H |
| Br | $CF_3$ | $CH_3$ | I | Me | Me |
| Cl | Cl | $CH_3$ | I | Me | H |
| Cl | Cl | $CH_3$ | I | Et | H |
| Cl | Cl | $CH_3$ | I | i-Pr | H |
| Cl | Cl | $CH_3$ | I | t-Bu | H |
| Cl | Cl | $CH_3$ | I | Me | Me |
| Br | Cl | $CH_3$ | I | Me | H |
| Br | Cl | $CH_3$ | I | Et | H |
| Br | Cl | $CH_3$ | I | i-Pr | H |
| Br | Cl | $CH_3$ | I | t-Bu | H |
| Br | Cl | $CH_3$ | I | Me | Me |
| Cl | Br | $CH_3$ | I | Me | H |
| Cl | Br | $CH_3$ | I | Et | H |
| Cl | Br | $CH_3$ | I | i-Pr | H |
| Cl | Br | $CH_3$ | I | t-Bu | H |
| Cl | Br | $CH_3$ | I | Me | Me |
| Br | Br | $CH_3$ | I | Me | H |
| Br | Br | $CH_3$ | I | Et | H |
| Br | Br | $CH_3$ | I | i-Pr | H |
| Br | Br | $CH_3$ | I | t-Bu | H |
| Br | Br | $CH_3$ | I | Me | Me |
| Cl | $OCH_2CF_3$ | $CH_3$ | I | Me | H |
| Cl | $OCH_2CF_3$ | $CH_3$ | I | Et | H |
| Cl | $OCH_2CF_3$ | $CH_3$ | I | i-Pr | H |
| Cl | $OCH_2CF_3$ | $CH_3$ | I | t-Bu | H |
| Cl | $OCH_2CF_3$ | $CH_3$ | I | Me | Me |
| Br | $OCH_2CF_3$ | $CH_3$ | I | Me | H |
| Br | $OCH_2CF_3$ | $CH_3$ | I | Et | H |
| Br | $OCH_2CF_3$ | $CH_3$ | I | i-Pr H | |
| Br | $OCH_2CF_3$ | $CH_3$ | I | t-Bu | H |
| Br | $OCH_2CF_3$ | $CH_3$ | I | Me | Me |
| Cl | $CF_3$ | $CH_3$ | $CF_3$ | Me | H |
| Cl | $CF_3$ | $CH_3$ | $CF_3$ | Et | H |
| Cl | $CF_3$ | $CH_3$ | $CF_3$ | i-Pr H | |
| Cl | $CF_3$ | $CH_3$ | $CF_3$ | t-Bu | H |
| Cl | $CF_3$ | $CH_3$ | $CF_3$ | Me | Me |
| Br | $CF_3$ | $CH_3$ | $CF_3$ | Me | H |

TABLE 4-continued

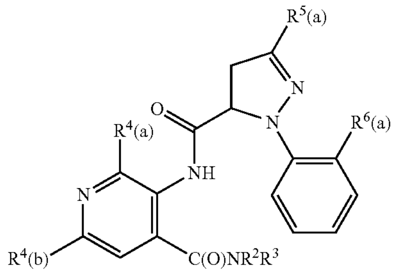

| $R^6$(a) | $R^5$(a) | $R^4$(a) | $R^4$(b) | $R^3$ | $R^2$ |
|---|---|---|---|---|---|
| Br | $CF_3$ | $CH_3$ | $CF_3$ | Et | H |
| Br | $CF_3$ | $CH_3$ | $CF_3$ | i-Pr H | |
| Br | $CF_3$ | $CH_3$ | $CF_3$ | t-Bu | H |
| Br | $CF_3$ | $CH_3$ | $CF_3$ | Me | Me |
| Cl | Cl | $CH_3$ | $CF_3$ | Me | H |
| Cl | Cl | $CH_3$ | $CF_3$ | Et | H |
| Cl | Cl | $CH_3$ | $CF_3$ | i-Pr H | |
| Cl | Cl | $CH_3$ | $CF_3$ | t-Bu | H |
| Cl | Cl | $CH_3$ | $CF_3$ | Me | Me |
| Br | Cl | $CH_3$ | $CF_3$ | Me | H |
| Br | Cl | $CH_3$ | $CF_3$ | Et | H |
| Br | Cl | $CH_3$ | $CF_3$ | i-Pr H | |
| Br | Cl | $CH_3$ | $CF_3$ | t-Bu | H |
| Br | Cl | $CH_3$ | $CF_3$ | Me | Me |
| Cl | Br | $CH_3$ | $CF_3$ | Me | H |
| Cl | Br | $CH_3$ | $CF_3$ | Et | H |
| Cl | Br | $CH_3$ | $CF_3$ | i-Pr H | |
| Cl | Br | $CH_3$ | $CF_3$ | t-Bu | H |
| Cl | Br | $CH_3$ | $CF_3$ | Me | Me |
| Br | Br | $CH_3$ | $CF_3$ | Me | H |
| Br | Br | $CH_3$ | $CF_3$ | Et | H |
| Br | Br | $CH_3$ | $CF_3$ | i-Pr H | |
| Br | Br | $CH_3$ | $CF_3$ | t-Bu | H |
| Br | Br | $CH_3$ | $CF_3$ | Me | Me |
| Cl | $OCH_2CF_3$ | $CH_3$ | $CF_3$ | Me | H |
| Cl | $OCH_2CF_3$ | $CH_3$ | $CF_3$ | Et | H |
| Cl | $OCH_2CF_3$ | $CH_3$ | $CF_3$ | i-Pr | H |
| Cl | $OCH_2CF_3$ | $CH_3$ | $CF_3$ | t-Bu | H |
| Cl | $OCH_2CF_3$ | $CH_3$ | $CF_3$ | Me | Me |
| Br | $OCH_2CF_3$ | $CH_3$ | $CF_3$ | Me | H |
| Br | $OCH_2CF_3$ | $CH_3$ | $CF_3$ | Et | H |
| Br | $OCH_2CF_3$ | $CH_3$ | $CF_3$ | i-Pr | H |
| Br | $OCH_2CF_3$ | $CH_3$ | $CF_3$ | t-Bu | H |
| Br | $OCH_2CF_3$ | $CH_3$ | $CF_3$ | Me | Me |
| Cl | Cl | $CH_3$ | Cl | n-Pr | H |
| Cl | Cl | $CH_3$ | Cl | n-Bu | H |
| Cl | Cl | $CH_3$ | Cl | s-Bu | H |
| Cl | Cl | $CH_3$ | Cl | i-Bu | H |
| Cl | Cl | $CH_3$ | Cl | Et | Me |
| Cl | $CF_3$ | F | H | Me | H |
| Cl | $CF_3$ | F | H | Et | H |
| Cl | $CF_3$ | F | H | i-Pr | H |
| Cl | $CF_3$ | F | H | t-Bu | H |
| Cl | $CF_3$ | F | H | Me | Me |
| Br | $CF_3$ | F | H | Me | H |
| Br | $CF_3$ | F | H | Et | H |
| Br | $CF_3$ | F | H | i-Pr | H |
| Br | $CF_3$ | F | H | t-Bu | H |
| Br | $CF_3$ | F | H | Me | Me |
| Cl | Cl | F | H | Me | H |
| Cl | Cl | F | H | Et | H |
| Cl | Cl | F | H | i-Pr | H |
| Cl | Cl | F | H | t-Bu | H |
| Cl | Cl | F | H | Me | Me |
| Br | Cl | F | H | Me | H |
| Br | Cl | F | H | Et | H |
| Br | Cl | F | H | i-Pr | H |
| Br | Cl | F | H | t-Bu | H |
| Br | Cl | F | H | Me | Me |
| Cl | Br | F | H | Me | H |
| Cl | Br | F | H | Et | H |
| Cl | Br | F | H | i-Pr | H |
| Cl | Br | F | H | t-Bu | H |

TABLE 4-continued

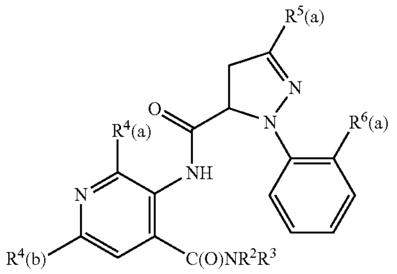

| $R^6$(a) | $R^5$(a) | $R^4$(a) | $R^4$(b) | $R^3$ | $R^2$ |
|---|---|---|---|---|---|
| Cl | Br | F | H | Me | Me |
| Br | Br | F | H | Me | H |
| Br | Br | F | H | Et | H |
| Br | Br | F | H | i-Pr | H |
| Br | Br | F | H | t-Bu | H |
| Br | Br | F | H | Me | Me |
| Cl | $OC_2CF_3$ | F | H | Me | H |
| Cl | $OCH_2CF_3$ | F | H | Et | H |
| Cl | $OCH_2CF_3$ | F | H | i-Pr | H |
| Cl | $OCH_2CF_3$ | F | H | t-Bu | H |
| Cl | $OCH_2CF_3$ | F | H | Me | Me |
| Br | $OCH_2CF_3$ | F | H | Me | H |
| Br | $OCH_2CF_3$ | F | H | Et | H |
| Br | $OCH_2CF_3$ | F | H | i-Pr | H |
| Br | $OCH_2CF_3$ | F | H | t-Bu | H |
| Br | $OCH_2CF_3$ | F | H | Me | Me |
| Cl | $CF_3$ | F | F | Me | H |
| Cl | $CF_3$ | F | F | Et | H |
| Cl | $CF_3$ | F | F | i-Pr | H |
| Cl | $CF_3$ | F | F | t-Bu | H |
| Cl | $CF_3$ | F | F | Me | Me |
| Br | $CF_3$ | F | F | Me | H |
| Br | $CF_3$ | F | F | Et | H |
| Br | $CF_3$ | F | F | i-Pr | H |
| Br | $CF_3$ | F | F | t-Bu | H |
| Br | $CF_3$ | F | F | Me | Me |
| Cl | Cl | F | F | Me | H |
| Cl | Cl | F | F | Et | H |
| Cl | Cl | F | F | i-Pr | H |
| Cl | Cl | F | F | t-Bu | H |
| Cl | Cl | F | F | Me | Me |
| Br | Cl | F | F | Me | H |
| Br | Cl | F | F | Et | H |
| Br | Cl | F | F | i-Pr | H |
| Br | Cl | F | F | t-Bu | H |
| Br | Cl | F | F | Me | Me |
| Cl | Br | F | F | Me | H |
| Cl | Br | F | F | Et | H |
| Cl | Br | F | F | i-Pr | H |
| Cl | Br | F | F | t-Bu | H |
| Cl | Br | F | F | Me | Me |
| Br | Br | F | F | Me | H |
| Br | Br | F | F | Et | H |
| Br | Br | F | F | i-Pr | H |
| Br | Br | F | F | t-Bu | H |
| Br | Br | F | F | Me | Me |
| Cl | $OCH_2CF_3$ | F | F | Me | H |
| Cl | $OCH_2CF_3$ | F | F | Et | H |
| Cl | $OCH_2CF_3$ | F | F | i-Pr | H |
| Cl | $OCH_2CF_3$ | F | F | t-Bu | H |
| Cl | $OCH_2CF_3$ | F | F | Me | Me |
| Br | $OCH_2CF_3$ | F | F | Me | H |
| Br | $OCH_2CF_3$ | F | F | Et | H |
| Br | $OCH_2CF_3$ | F | F | i-Pr | H |
| Br | $OCH_2CF_3$ | F | F | t-Bu | H |
| Br | $OCH_2CF_3$ | F | F | Me | Me |
| Cl | $CF_3$ | F | Cl | Me | H |
| Cl | $CF_3$ | F | Cl | Et | H |
| Cl | $CF_3$ | F | Cl | i-Pr | H |
| Cl | $CF_3$ | F | Cl | t-Bu | H |
| Cl | $CF_3$ | F | Cl | Me | Me |
| Br | $CF_3$ | F | Cl | Me | H |
| Br | $CF_3$ | F | Cl | Et | H |

TABLE 4-continued

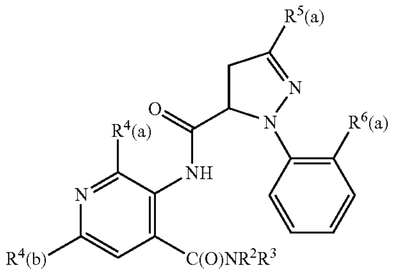

| $R^6$(a) | $R^5$(a) | $R^4$(a) | $R^4$(b) | $R^3$ | $R^2$ |
|---|---|---|---|---|---|
| Br | $CF_3$ | F | Cl | i-Pr | H |
| Br | $CF_3$ | F | Cl | t-Bu | H |
| Br | $CF_3$ | F | Cl | Me | Me |
| Cl | Cl | F | Cl | Me | H |
| Cl | Cl | F | Cl | Et | H |
| Cl | Cl | F | Cl | i-Pr | H |
| Cl | Cl | F | Cl | t-Bu | H |
| Cl | Cl | F | Cl | Me | Me |
| Br | Cl | F | Cl | Me | H |
| Br | Cl | F | Cl | Et | H |
| Br | Cl | F | Cl | i-Pr | H |
| Br | Cl | F | Cl | t-Bu | H |
| Br | Cl | F | Cl | Me | Me |
| Cl | Br | F | Cl | Me | H |
| Cl | Br | F | Cl | Et | H |
| Cl | Br | F | Cl | i-Pr | H |
| Cl | Br | F | Cl | t-Bu | H |
| Cl | Br | F | Cl | Me | Me |
| Br | Br | F | Cl | Me | H |
| Br | Br | F | Cl | Et | H |
| Br | Br | F | Cl | i-Pr | H |
| Br | Br | F | Cl | t-Bu | H |
| Br | Br | F | Cl | Me | Me |
| Cl | $OCH_2CF_3$ | F | Cl | Me | H |
| Cl | $OCH_2CF_3$ | F | Cl | Et | H |
| Cl | $OCH_2CF_3$ | F | Cl | i-Pr | H |
| Cl | $OCH_2CF_3$ | F | Cl | t-Bu | H |
| Cl | $OCH_2CF_3$ | F | Cl | Me | Me |
| Br | $OCH_2CF_3$ | F | Cl | Me | H |
| Br | $OCH_2CF_3$ | F | Cl | Et | H |
| Br | $OCH_2CF_3$ | F | Cl | i-Pr | H |
| Br | $OCH_2CF_3$ | F | Cl | t-Bu | H |
| Br | $OCH_2CF_3$ | F | Cl | Me | Me |
| Cl | $CF_3$ | F | Br | Me | H |
| Cl | $CF_3$ | F | Br | Et | H |
| Cl | $CF_3$ | F | Br | i-Pr | H |
| Cl | $CF_3$ | F | Br | t-Bu | H |
| Cl | $CF_3$ | F | Br | Me | Me |
| Br | $CF_3$ | F | Br | Me | H |
| Br | $CF_3$ | F | Br | Et | H |
| Br | $CF_3$ | F | Br | i-Pr | H |
| Br | $CF_3$ | F | Br | t-Bu | H |
| Br | $CF_3$ | F | Br | Me | Me |
| Cl | Cl | F | Br | Me | H |
| Cl | Cl | F | Br | Et | H |
| Cl | Cl | F | Br | i-Pr | H |
| Cl | Cl | F | Br | t-Bu | H |
| Cl | Cl | F | Br | Me | Me |
| Br | Cl | F | Br | Me | H |
| Br | Cl | F | Br | Et | H |
| Br | Cl | F | Br | i-Pr | H |
| Br | Cl | F | Br | t-Bu | H |
| Br | Cl | F | Br | Me | Me |
| Cl | Br | F | Br | Me | H |
| Cl | Br | F | Br | Et | H |
| Cl | Br | F | Br | i-Pr | H |
| Cl | Br | F | Br | t-Bu | H |
| Cl | Br | F | Br | Me | Me |
| Br | Br | F | Br | Me | H |
| Br | Br | F | Br | Et | H |
| Br | Br | F | Br | i-Pr | H |
| Br | Br | F | Br | t-Bu | H |
| Br | Br | F | Br | Me | Me |

TABLE 4-continued

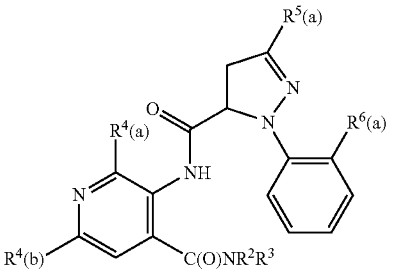

| $R^6$(a) | $R^5$(a) | $R^4$(a) | $R^4$(b) | $R^3$ | $R^2$ |
|---|---|---|---|---|---|
| Cl | $OCH_2CF_3$ | F | Br | Me | H |
| Cl | $OCH_2CF_3$ | F | Br | Et | H |
| Cl | $OCH_2CF_3$ | F | Br | i-Pr | H |
| Cl | $OCH_2CF_3$ | F | Br | t-Bu | H |
| Cl | $OCH_2CF_3$ | F | Br | Me | Me |
| Br | $OCH_2CF_3$ | F | Br | Me | H |
| Br | $OCH_2CF_3$ | F | Br | Et | H |
| Br | $OCH_2CF_3$ | F | Br | i-Pr | H |
| Br | $OCH_2CF_3$ | F | Br | t-Bu | H |
| Br | $OCH_2CF_3$ | F | Br | Me | Me |
| Cl | $CF_3$ | F | I | Me | H |
| Cl | $CF_3$ | F | I | Et | H |
| Cl | $CF_3$ | F | I | i-Pr | H |
| Cl | $CF_3$ | F | I | t-Bu | H |
| Cl | $CF_3$ | F | I | Me | Me |
| Br | $CF_3$ | F | I | Me | H |
| Br | $CF_3$ | F | I | Et | H |
| Br | $CF_3$ | F | I | i-Pr | H |
| Br | $CF_3$ | F | I | t-Bu | H |
| Br | $CF_3$ | F | I | Me | Me |
| Cl | Cl | F | I | Me | H |
| Cl | Cl | F | I | Et | H |
| Cl | Cl | F | I | i-Pr | H |
| Cl | Cl | F | I | t-Bu | H |
| Cl | Cl | F | I | Me | Me |
| Br | Cl | F | I | Me | H |
| Br | Cl | F | I | Et | H |
| Br | Cl | F | I | i-Pr | H |
| Br | Cl | F | I | t-Bu | H |
| Br | Cl | F | I | Me | Me |
| Cl | Br | F | I | Me | H |
| Cl | Br | F | I | Et | H |
| Cl | Br | F | I | i-Pr | H |
| Cl | Br | F | I | t-Bu | H |
| Cl | Br | F | I | Me | Me |
| Br | Br | F | I | Me | H |
| Br | Br | F | I | Et | H |
| Br | Br | F | I | i-Pr | H |
| Br | Br | F | I | t-Bu | H |
| Br | Br | F | I | Me | Me |
| Cl | $OCH_2CF_3$ | F | I | Me | H |
| Cl | $OCH_2CF_3$ | F | I | Et | H |
| Cl | $OCH_2CF_3$ | F | I | i-Pr | H |
| Cl | $OCH_2CF_3$ | F | I | t-Bu | H |
| Cl | $OCH_2CF_3$ | F | I | Me | Me |
| Br | $OCH_2CF_3$ | F | I | Me | H |
| Br | $OCH_2CF_3$ | F | I | Et | H |
| Br | $OCH_2CF_3$ | F | I | i-Pr | H |
| Br | $OCH_2CF_3$ | F | I | t-Bu | H |
| Br | $OCH_2CF_3$ | F | I | Me | Me |
| Cl | $CF_3$ | F | $CF_3$ | Me | H |
| Cl | $CF_3$ | F | $CF_3$ | Et | H |
| Cl | $CF_3$ | F | $CF_3$ | i-Pr | H |
| Cl | $CF_3$ | F | $CF_3$ | t-Bu | H |
| Cl | $CF_3$ | F | $CF_3$ | Me | Me |
| Br | $CF_3$ | F | $CF_3$ | Me | H |
| Br | $CF_3$ | F | $CF_3$ | Et | H |
| Br | $CF_3$ | F | $CF_3$ | i-Pr | H |
| Br | $CF_3$ | F | $CF_3$ | t-Bu | H |
| Br | $CF_3$ | F | $CF_3$ | Me | Me |
| Cl | Cl | F | $CF_3$ | Me | H |
| Cl | Cl | F | $CF_3$ | Et | H |
| Cl | Cl | F | $CF_3$ | i-Pr | H |

TABLE 4-continued

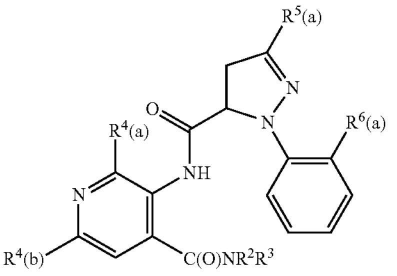

| $R^6$(a) | $R^5$(a) | $R^4$(a) | $R^4$(b) | $R^3$ | $R^2$ |
|---|---|---|---|---|---|
| Cl | Cl | F | $CF_3$ | t-Bu | H |
| Cl | Cl | F | $CF_3$ | Me | Me |
| Br | Cl | F | $CF_3$ | Me | H |
| Br | Cl | F | $CF_3$ | Et | H |
| Br | Cl | F | $CF_3$ | i-Pr | H |
| Br | Cl | F | $CF_3$ | t-Bu | H |
| Br | Cl | F | $CF_3$ | Me | Me |
| Cl | Br | F | $CF_3$ | Me | H |
| Cl | Br | F | $CF_3$ | Et | H |
| Cl | Br | F | $CF_3$ | i-Pr | H |
| Cl | Br | F | $CF_3$ | t-Bu | H |
| Cl | Br | F | $CF_3$ | Me | Me |
| Br | Br | F | $CF_3$ | Me | H |
| Br | Br | F | $CF_3$ | Et | H |
| Br | Br | F | $CF_3$ | i-Pr | H |
| Br | Br | F | $CF_3$ | t-Bu | H |
| Br | Br | F | $CF_3$ | Me | Me |
| Cl | $OCH_2CF_3$ | F | $CF_3$ | Me | H |
| Cl | $OCH_2CF_3$ | F | $CF_3$ | Et | H |
| Cl | $OCH_2CF_3$ | F | $CF_3$ | i-Pr | H |
| Cl | $OCH_2CF_3$ | F | $CF_3$ | t-Bu | H |
| Cl | $OCH_2CF_3$ | F | $CF_3$ | Me | Me |
| Br | $OCH_2CF_3$ | F | $CF_3$ | Me | H |
| Br | $OCH_2CF_3$ | F | $CF_3$ | Et | H |
| Br | $OCH_2CF_3$ | F | $CF_3$ | i-Pr | H |
| Br | $OCH_2CF_3$ | F | $CF_3$ | t-Bu | H |
| Br | $OCH_2CF_3$ | F | $CF_3$ | Me | Me |
| Cl | $CF_3$ | Cl | H | Me | H |
| Cl | $CF_3$ | Cl | H | Et | H |
| Cl | $CF_3$ | Cl | H | i-Pr | H |
| Cl | $CF_3$ | Cl | H | t-Bu | H |
| Cl | $CF_3$ | Cl | H | Me | Me |
| Br | $CF_3$ | Cl | H | Me | H |
| Br | $CF_3$ | Cl | H | Et | H |
| Br | $CF_3$ | Cl | H | i-Pr | H |
| Br | $CF_3$ | Cl | H | t-Bu | H |
| Br | $CF_3$ | Cl | H | Me | Me |
| Cl | Cl | Cl | H | Me | H |
| Cl | Cl | Cl | H | Et | H |
| Cl | Cl | Cl | H | i-Pr | H |
| Cl | Cl | Cl | H | t-Bu | H |
| Cl | Cl | Cl | H | Me | Me |
| Br | Cl | Cl | H | Me | H |
| Br | Cl | Cl | H | Et | H |
| Br | Cl | Cl | H | i-Pr | H |
| Br | Cl | Cl | H | t-Bu | H |
| Br | Cl | Cl | H | Me | Me |
| Cl | Br | Cl | H | Me | H |
| Cl | Br | Cl | H | Et | H |
| Cl | Br | Cl | H | i-Pr | H |
| Cl | Br | Cl | H | t-Bu | H |
| Cl | Br | Cl | H | Me | Me |
| Br | Br | Cl | H | Me | H |
| Br | Br | Cl | H | Et | H |
| Br | Br | Cl | H | i-Pr | H |
| Br | Br | Cl | H | t-Bu | H |
| Br | Br | Cl | H | Me | Me |
| Cl | $OCH_2CF_3$ | Cl | H | Me | H |
| Cl | $OCH_2CF_3$ | Cl | H | Et | H |
| Cl | $OCH_2CF_3$ | Cl | H | i-Pr | H |
| Cl | $OCH_2CF_3$ | Cl | H | t-Bu | H |
| Cl | $OCH_2CF_3$ | Cl | H | Me | Me |
| Br | $OCH_2CF_3$ | Cl | H | Me | H |

TABLE 4-continued

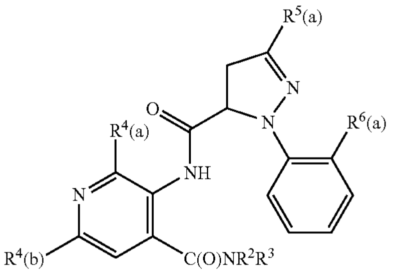

| $R^6$(a) | $R^5$(a) | $R^4$(a) | $R^4$(b) | $R^3$ | $R^2$ |
|---|---|---|---|---|---|
| Br | $OCH_2CF_3$ | Cl | H | Et | H |
| Br | $OCH_2CF_3$ | Cl | H | i-Pr | H |
| Br | $OCH_2CF_3$ | Cl | H | t-Bu | H |
| Br | $OCH_2CF_3$ | Cl | H | Me | Me |
| Cl | $CF_3$ | Cl | F | Me | H |
| Cl | $CF_3$ | Cl | F | Et | H |
| Cl | $CF_3$ | Cl | F | i-Pr | H |
| Cl | $CF_3$ | Cl | F | t-Bu | H |
| Cl | $CF_3$ | Cl | F | Me | Me |
| Br | $CF_3$ | Cl | F | Me | H |
| Br | $CF_3$ | Cl | F | Et | H |
| Br | $CF_3$ | Cl | F | i-Pr | H |
| Br | $CF_3$ | Cl | F | t-Bu | H |
| Br | $CF_3$ | Cl | F | Me | Me |
| Cl | Cl | Cl | F | Me | H |
| Cl | Cl | Cl | F | Et | H |
| Cl | Cl | Cl | F | i-Pr | H |
| Cl | Cl | Cl | F | t-Bu | H |
| Cl | Cl | Cl | F | Me | Me |
| Br | Cl | Cl | F | Me | H |
| Br | Cl | Cl | F | Et | H |
| Br | Cl | Cl | F | i-Pr | H |
| Br | Cl | Cl | F | t-Bu | H |
| Br | Cl | Cl | F | Me | Me |
| Cl | Br | Cl | F | Me | H |
| Cl | Br | Cl | F | Et | H |
| Cl | Br | Cl | F | i-Pr | H |
| Cl | Br | Cl | F | t-Bu | H |
| Cl | Br | Cl | F | Me | Me |
| Br | Br | Cl | F | Me | H |
| Br | Br | Cl | F | Et | H |
| Br | Br | Cl | F | i-Pr | H |
| Br | Br | Cl | F | t-Bu | H |
| Br | Br | Cl | F | Me | Me |
| Cl | $OCH_2CF_3$ | Cl | F | Me | H |
| Cl | $OCH_2CF_3$ | Cl | F | Et | H |
| Cl | $OCH_2CF_3$ | Cl | F | i-Pr | H |
| Cl | $OCH_2CF_3$ | Cl | F | t-Bu | H |
| Cl | $OCH_2CF_3$ | Cl | F | Me | Me |
| Br | $OCH_2CF_3$ | Cl | F | Me | H |
| Br | $OCH_2CF_3$ | Cl | F | Et | H |
| Br | $OCH_2CF_3$ | Cl | F | i-Pr | H |
| Br | $OCH_2CF_3$ | Cl | F | t-Bu | H |
| Br | $OCH_2CF_3$ | Cl | F | Me | Me |
| Cl | $CF_3$ | Cl | Cl | Me | H |
| Cl | $CF_3$ | Cl | Cl | Et | H |
| Cl | $CF_3$ | Cl | Cl | i-Pr | H |
| Cl | $CF_3$ | Cl | Cl | t-Bu | H |
| Cl | $CF_3$ | Cl | Cl | Me | Me |
| Br | $CF_3$ | Cl | Cl | Me | H |
| Br | $CF_3$ | Cl | Cl | Et | H |
| Br | $CF_3$ | Cl | Cl | i-Pr | H |
| Br | $CF_3$ | Cl | Cl | t-Bu | H |
| Br | $CF_3$ | Cl | Cl | Me | Me |
| Cl | Cl | Cl | Cl | Me | H |
| Cl | Cl | Cl | Cl | Et | H |
| Cl | Cl | Cl | Cl | i-Pr | H |
| Cl | Cl | Cl | Cl | t-Bu | H |
| Cl | Cl | Cl | Cl | Me | Me |
| Br | Cl | Cl | Cl | Me | H |
| Br | Cl | Cl | Cl | Et | H |
| Br | Cl | Cl | Cl | i-Pr | H |
| Br | Cl | Cl | Cl | t-Bu | H |

TABLE 4-continued

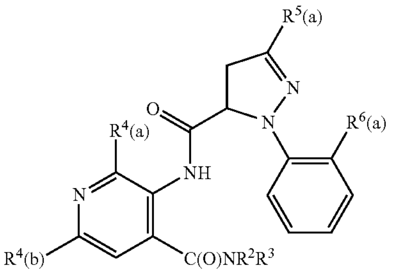

| $R^6$(a) | $R^5$(a) | $R^4$(a) | $R^4$(b) | $R^3$ | $R^2$ |
|---|---|---|---|---|---|
| Br | Cl | Cl | Cl | Me | Me |
| Cl | Br | Cl | Cl | Me | H |
| Cl | Br | Cl | Cl | Et | H |
| Cl | Br | Cl | Cl | i-Pr | H |
| Cl | Br | Cl | Cl | t-Bu | H |
| Cl | Br | Cl | Cl | Me | Me |
| Br | Br | Cl | Cl | Me | H |
| Br | Br | Cl | Cl | Et | H |
| Br | Br | Cl | Cl | i-Pr | H |
| Br | Br | Cl | Cl | t-Bu | H |
| Br | Br | Cl | Cl | Me | Me |
| Cl | $OCH_2CF_3$ | Cl | Cl | Me | H |
| Cl | $OCH_2CF_3$ | Cl | Cl | Et | H |
| Cl | $OCH_2CF_3$ | Cl | Cl | i-Pr | H |
| Cl | $OCH_2CF_3$ | Cl | Cl | t-Bu | H |
| Cl | $OCH_2CF_3$ | Cl | Cl | Me | Me |
| Br | $OCH_2CF_3$ | Cl | Cl | Me | H |
| Br | $OCH_2CF_3$ | Cl | Cl | Et | H |
| Br | $OCH_2CF_3$ | Cl | Cl | i-Pr | H |
| Br | $OCH_2CF_3$ | Cl | Cl | t-Bu | H |
| Br | $OCH_2CF_3$ | Cl | Cl | Me | Me |
| Cl | $CF_3$ | Cl | Br | Me | H |
| Cl | $CF_3$ | Cl | Br | Et | H |
| Cl | $CF_3$ | Cl | Br | i-Pr | H |
| Cl | $CF_3$ | Cl | Br | t-Bu | H |
| Cl | $CF_3$ | Cl | Br | Me | Me |
| Br | $CF_3$ | Cl | Br | Me | H |
| Br | $CF_3$ | Cl | Br | Et | H |
| Br | $CF_3$ | Cl | Br | i-Pr | H |
| Br | $CF_3$ | Cl | Br | t-Bu | H |
| Br | $CF_3$ | Cl | Br | Me | Me |
| Cl | Cl | Cl | Br | Me | H |
| Cl | Cl | Cl | Br | Et | H |
| Cl | Cl | Cl | Br | i-Pr | H |
| Cl | Cl | Cl | Br | t-Bu | H |
| Cl | Cl | Cl | Br | Me | Me |
| Br | Cl | Cl | Br | Me | H |
| Br | Cl | Cl | Br | Et | H |
| Br | Cl | Cl | Br | i-Pr | H |
| Br | Cl | Cl | Br | t-Bu | H |
| Br | Cl | Cl | Br | Me | Me |
| Cl | Br | Cl | Br | Me | H |
| Cl | Br | Cl | Br | Et | H |
| Cl | Br | Cl | Br | i-Pr | H |
| Cl | Br | Cl | Br | t-Bu | H |
| Cl | Br | Cl | Br | Me | Me |
| Br | Br | Cl | Br | Me | H |
| Br | Br | Cl | Br | Et | H |
| Br | Br | Cl | Br | i-Pr | H |
| Br | Br | Cl | Br | t-Bu | H |
| Br | Br | Cl | Br | Me | Me |
| Cl | $OCH_2CF_3$ | Cl | Br | Me | H |
| Cl | $OCH_2CF_3$ | Cl | Br | Et | H |
| Cl | $OCH_2CF_3$ | Cl | Br | i-Pr | H |
| Cl | $OCH_2CF_3$ | Cl | Br | t-Bu | H |
| Cl | $OCH_2CF_3$ | Cl | Br | Me | Me |
| Br | $OCH_2CF_3$ | Cl | Br | Me | H |
| Br | $OCH_2CF_3$ | Cl | Br | Et | H |
| Br | $OCH_2CF_3$ | Cl | Br | i-Pr | H |
| Br | $OCH_2CF_3$ | Cl | Br | t-Bu | H |
| Br | $OCH_2CF_3$ | Cl | Br | Me | Me |
| Cl | $CF_3$ | Cl | I | Me | H |
| Cl | $CF_3$ | Cl | I | Et | H |

TABLE 4-continued

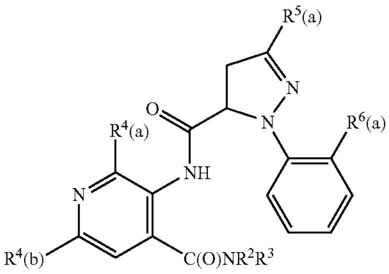

| $R^6$(a) | $R^5$(a) | $R^4$(a) | $R^4$(b) | $R^3$ | $R^2$ |
|---|---|---|---|---|---|
| Cl | $CF_3$ | Cl | I | i-Pr | H |
| Cl | $CF_3$ | Cl | I | t-Bu | H |
| Cl | $CF_3$ | Cl | I | Me | Me |
| Br | $CF_3$ | Cl | I | Me | H |
| Br | $CF_3$ | Cl | I | Et | H |
| Br | $CF_3$ | Cl | I | i-Pr | H |
| Br | $CF_3$ | Cl | I | t-Bu | H |
| Br | $CF_3$ | Cl | I | Me | Me |
| Cl | Cl | Cl | I | Me | H |
| Cl | Cl | Cl | I | Et | H |
| Cl | Cl | Cl | I | i-Pr | H |
| Cl | Cl | Cl | I | t-Bu | H |
| Cl | Cl | Cl | I | Me | Me |
| Br | Cl | Cl | I | Me | H |
| Br | Cl | Cl | I | Et | H |
| Br | Cl | Cl | I | i-Pr | H |
| Br | Cl | Cl | I | t-Bu | H |
| Br | Cl | Cl | I | Me | Me |
| Cl | Br | Cl | I | Me | H |
| Cl | Br | Cl | I | Et | H |
| Cl | Br | Cl | I | i-Pr | H |
| Cl | Br | Cl | I | t-Bu | H |
| Cl | Br | Cl | I | Me | Me |
| Br | Br | Cl | I | Me | H |
| Br | Br | Cl | I | Et | H |
| Br | Br | Cl | I | i-Pr | H |
| Br | Br | Cl | I | t-Bu | H |
| Br | Br | Cl | I | Me | Me |
| Cl | $OCH_2CF_3$ | Cl | I | Me | H |
| Cl | $OCH_2CF_3$ | Cl | I | Et | H |
| Cl | $OCH_2CF_3$ | Cl | I | i-Pr | H |
| Cl | $OCH_2CF_3$ | Cl | I | t-Bu | H |
| Cl | $OCH_2CF_3$ | Cl | I | Me | Me |
| Br | $OCH_2CF_3$ | Cl | I | Me | H |
| Br | $OCH_2CF_3$ | Cl | I | Et | H |
| Br | $OCH_2CF_3$ | Cl | I | i-Pr | H |
| Br | $OCH_2CF_3$ | Cl | I | t-Bu | H |
| Br | $OCH_2CF_3$ | Cl | I | Me | Me |
| Cl | $CF_3$ | Cl | $CF_3$ | Me | H |
| Cl | $CF_3$ | Cl | $CF_3$ | Et | H |
| Cl | $CF_3$ | Cl | $CF_3$ | i-Pr | H |
| Cl | $CF_3$ | Cl | $CF_3$ | t-Bu | H |
| Cl | $CF_3$ | Cl | $CF_3$ | Me | Me |
| Br | $CF_3$ | Cl | $CF_3$ | Me | H |
| Br | $CF_3$ | Cl | $CF_3$ | Et | H |
| Br | $CF_3$ | Cl | $CF_3$ | i-Pr | H |
| Br | $CF_3$ | Cl | $CF_3$ | t-Bu | H |
| Br | $CF_3$ | Cl | $CF_3$ | Me | Me |
| Cl | Cl | Cl | $CF_3$ | Me | H |
| Cl | Cl | Cl | $CF_3$ | Et | H |
| Cl | Cl | Cl | $CF_3$ | i-Pr | H |
| Cl | Cl | Cl | $CF_3$ | t-Bu | H |
| Cl | Cl | Cl | $CF_3$ | Me | Me |
| Br | Cl | Cl | $CF_3$ | Me | H |
| Br | Cl | Cl | $CF_3$ | Et | H |
| Br | Cl | Cl | $CF_3$ | i-Pr | H |
| Br | Cl | Cl | $CF_3$ | t-Bu | H |
| Br | Cl | Cl | $CF_3$ | Me | Me |
| Cl | Br | Cl | $CF_3$ | Me | H |
| Cl | Br | Cl | $CF_3$ | Et | H |
| Cl | Br | Cl | $CF_3$ | i-Pr | H |
| Cl | Br | Cl | $CF_3$ | t-Bu | H |
| Cl | Br | Cl | $CF_3$ | Me | Me |

TABLE 4-continued

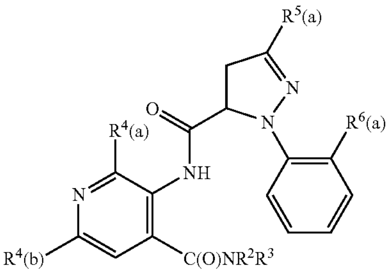

| $R^6$(a) | $R^5$(a) | $R^4$(a) | $R^4$(b) | $R^3$ | $R^2$ |
|---|---|---|---|---|---|
| Br | Br | Cl | $CF_3$ | Me | H |
| Br | Br | Cl | $CF_3$ | Et | H |
| Br | Br | Cl | $CF_3$ | i-Pr | H |
| Br | Br | Cl | $CF_3$ | t-Bu | H |
| Br | Br | Cl | $CF_3$ | Me | Me |
| Cl | $OCH_2CF_3$ | Cl | $CF_3$ | Me | H |
| Cl | $OCH_2CF_3$ | Cl | $CF_3$ | Et | H |
| Cl | $OCH_2CF_3$ | Cl | $CF_3$ | i-Pr | H |
| Cl | $OCH_2CF_3$ | Cl | $CF_3$ | t-Bu | H |
| Cl | $OCH_2CF_3$ | Cl | $CF_3$ | Me | Me |
| Br | $OCH_2CF_3$ | Cl | $CF_3$ | Me | H |
| Br | $OCH_2CF_3$ | Cl | $CF_3$ | Et | H |
| Br | $OCH_2CF_3$ | Cl | $CF_3$ | i-Pr | H |
| Br | $OCH_2CF_3$ | Cl | $CF_3$ | t-Bu | H |
| Br | $OCH_2CF_3$ | Cl | $CF_3$ | Me | Me |
| Cl | Cl | Cl | Cl | n-Pr | H |
| Cl | Cl | Cl | Cl | n-Bu | H |
| Cl | Cl | Cl | Cl | s-Bu | H |
| Cl | Cl | Cl | Cl | i-Bu | H |
| Cl | Cl | Cl | Cl | Et | Me |
| Cl | $CF_3$ | Br | H | Me | H |
| Cl | $CF_3$ | Br | H | Et | H |
| Cl | $CF_3$ | Br | H | i-Pr | H |
| Cl | $CF_3$ | Br | H | t-Bu | H |
| Cl | $CF_3$ | Br | H | Me | Me |
| Br | $CF_3$ | Br | H | Me | H |
| Br | $CF_3$ | Br | H | Et | H |
| Br | $CF_3$ | Br | H | i-Pr | H |
| Br | $CF_3$ | Br | H | t-Bu | H |
| Br | $CF_3$ | Br | H | Me | Me |
| Cl | Cl | Br | H | Me | H |
| Cl | Cl | Br | H | Et | H |
| Cl | Cl | Br | H | i-Pr | H |
| Cl | Cl | Br | H | t-Bu | H |
| Cl | Cl | Br | H | Me | Me |
| Br | Cl | Br | H | Me | H |
| Br | Cl | Br | H | Et | H |
| Br | Cl | Br | H | i-Pr | H |
| Br | Cl | Br | H | t-Bu | H |
| Br | Cl | Br | H | Me | Me |
| Cl | Br | Br | H | Me | H |
| Cl | Br | Br | H | Et | H |
| Cl | Br | Br | H | i-Pr | H |
| Cl | Br | Br | H | t-Bu | H |
| Cl | Br | Br | H | Me | Me |
| Br | Br | Br | H | Me | H |
| Br | Br | Br | H | Et | H |
| Br | Br | Br | H | i-Pr | H |
| Br | Br | Br | H | t-Bu | H |
| Br | Br | Br | H | Me | Me |
| Cl | $OCH_2CF_3$ | Br | H | Me | H |
| Cl | $OCH_2CF_3$ | Br | H | Et | H |
| Cl | $OCH_2CF_3$ | Br | H | i-Pr | H |
| Cl | $OCH_2CF_3$ | Br | H | t-Bu | H |
| Cl | $OCH_2CF_3$ | Br | H | Me | Me |
| Br | $OCH_2CF_3$ | Br | H | Me | H |
| Br | $OCH_2CF_3$ | Br | H | Et | H |
| Br | $OCH_2CF_3$ | Br | H | i-Pr | H |
| Br | $OCH_2CF_3$ | Br | H | t-Bu | H |
| Br | $OCH_2CF_3$ | Br | H | Me | Me |
| Cl | $CF_3$ | Br | F | Me | H |
| Cl | $CF_3$ | Br | F | Et | H |
| Cl | $CF_3$ | Br | F | i-Pr | H |

TABLE 4-continued

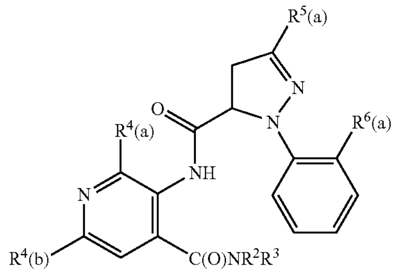

| $R^6$(a) | $R^5$(a) | $R^4$(a) | $R^4$(b) | $R^3$ | $R^2$ |
|---|---|---|---|---|---|
| Cl | $CF_3$ | Br | F | t-Bu | H |
| Cl | $CF_3$ | Br | F | Me | Me |
| Br | $CF_3$ | Br | F | Me | H |
| Br | $CF_3$ | Br | F | Et | H |
| Br | $CF_3$ | Br | F | i-Pr | H |
| Br | $CF_3$ | Br | F | t-Bu | H |
| Br | $CF_3$ | Br | F | Me | Me |
| Cl | Cl | Br | F | Me | H |
| Cl | Cl | Br | F | Et | H |
| Cl | Cl | Br | F | i-Pr | H |
| Cl | Cl | Br | F | t-Bu | H |
| Cl | Cl | Br | F | Me | Me |
| Br | Cl | Br | F | Me | H |
| Br | Cl | Br | F | Et | H |
| Br | Cl | Br | F | i-Pr | H |
| Br | Cl | Br | F | t-Bu | H |
| Br | Cl | Br | F | Me | Me |
| Cl | Br | Br | F | Me | H |
| Cl | Br | Br | F | Et | H |
| Cl | Br | Br | F | i-Pr | H |
| Cl | Br | Br | F | t-Bu | H |
| Cl | Br | Br | F | Me | Me |
| Br | Br | Br | F | Me | H |
| Br | Br | Br | F | Et | H |
| Br | Br | Br | F | i-Pr | H |
| Br | Br | Br | F | t-Bu | H |
| Br | Br | Br | F | Me | Me |
| Cl | $OCH_2CF_3$ | Br | F | Me | H |
| Cl | $OCH_2CF_3$ | Br | F | Et | H |
| Cl | $OCH_2CF_3$ | Br | F | i-Pr | H |
| Cl | $OCH_2CF_3$ | Br | F | t-Bu | H |
| Cl | $OCH_2CF_3$ | Br | F | Me | Me |
| Br | $OCH_2CF_3$ | Br | F | Me | H |
| Br | $OCH_2CF_3$ | Br | F | Et | H |
| Br | $OCH_2CF_3$ | Br | F | i-Pr | H |
| Br | $OCH_2CF_3$ | Br | F | t-Bu | H |
| Br | $OCH_2CF_3$ | Br | F | Me | Me |
| Cl | $CF_3$ | Br | Cl | Me | H |
| Cl | $CF_3$ | Br | Cl | Et | H |
| Cl | $CF_3$ | Br | Cl | i-Pr | H |
| Cl | $CF_3$ | Br | Cl | t-Bu | H |
| Cl | $CF_3$ | Br | Cl | Me | Me |
| Br | $CF_3$ | Br | Cl | Me | H |
| Br | $CF_3$ | Br | Cl | Et | H |
| Br | $CF_3$ | Br | Cl | i-Pr | H |
| Br | $CF_3$ | Br | Cl | t-Bu | H |
| Br | $CF_3$ | Br | Cl | Me | Me |
| Cl | Cl | Br | Cl | Me | H |
| Cl | Cl | Br | Cl | Et | H |
| Cl | Cl | Br | Cl | i-Pr | H |
| Cl | Cl | Br | Cl | t-Bu | H |
| Cl | Cl | Br | Cl | Me | Me |
| Br | Cl | Br | Cl | Me | H |
| Br | Cl | Br | Cl | Et | H |
| Br | Cl | Br | Cl | i-Pr | H |
| Br | Cl | Br | Cl | t-Bu | H |
| Br | Cl | Br | Cl | Me | Me |
| Cl | Br | Br | Cl | Me | H |
| Cl | Br | Br | Cl | Et | H |
| Cl | Br | Br | Cl | i-Pr | H |
| Cl | Br | Br | Cl | t-Bu | H |
| Cl | Br | Br | Cl | Me | Me |
| Br | Br | Br | Cl | Me | H |

TABLE 4-continued

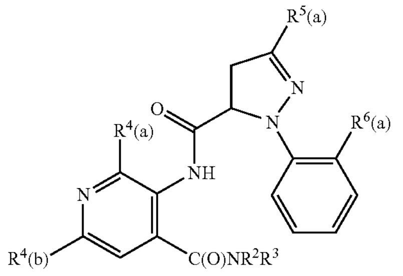

| $R^6$(a) | $R^5$(a) | $R^4$(a) | $R^4$(b) | $R^3$ | $R^2$ |
|---|---|---|---|---|---|
| Br | Br | Br | Cl | Et | H |
| Br | Br | Br | Cl | i-Pr | H |
| Br | Br | Br | Cl | t-Bu | H |
| Br | Br | Br | Cl | Me | Me |
| Cl | $OCH_2CF_3$ | Br | Cl | Me | H |
| Cl | $OCH_2CF_3$ | Br | Cl | Et | H |
| Cl | $OCH_2CF_3$ | Br | Cl | i-Pr | H |
| Cl | $OCH_2CF_3$ | Br | Cl | t-Bu | H |
| Cl | $OCH_2CF_3$ | Br | Cl | Me | Me |
| Br | $OCH_2CF_3$ | Br | Cl | Me | H |
| Br | $OCH_2CF_3$ | Br | Cl | Et | H |
| Br | $OCH_2CF_3$ | Br | Cl | i-Pr | H |
| Br | $OCH_2CF_3$ | Br | Cl | t-Bu | H |
| Br | $OCH_2CF_3$ | Br | Cl | Me | Me |
| Cl | $CF_3$ | Br | Br | Me | H |
| Cl | $CF_3$ | Br | Br | Et | H |
| Cl | $CF_3$ | Br | Br | i-Pr | H |
| Cl | $CF_3$ | Br | Br | t-Bu | H |
| Cl | $CF_3$ | Br | Br | Me | Me |
| Br | $CF_3$ | Br | Br | Me | H |
| Br | $CF_3$ | Br | Br | Et | H |
| Br | $CF_3$ | Br | Br | i-Pr | H |
| Br | $CF_3$ | Br | Br | t-Bu | H |
| Br | $CF_3$ | Br | Br | Me | Me |
| Cl | Cl | Br | Br | Me | H |
| Cl | Cl | Br | Br | Et | H |
| Cl | Cl | Br | Br | i-Pr | H |
| Cl | Cl | Br | Br | t-Bu | H |
| Cl | Cl | Br | Br | Me | Me |
| Br | Cl | Br | Br | Me | H |
| Br | Cl | Br | Br | Et | H |
| Br | Cl | Br | Br | i-Pr | H |
| Br | Cl | Br | Br | t-Bu | H |
| Br | Cl | Br | Br | Me | Me |
| Cl | Br | Br | Br | Me | H |
| Cl | Br | Br | Br | Et | H |
| Cl | Br | Br | Br | i-Pr | H |
| Cl | Br | Br | Br | t-Bu | H |
| Cl | Br | Br | Br | Me | Me |
| Br | Br | Br | Br | Me | H |
| Br | Br | Br | Br | Et | H |
| Br | Br | Br | Br | i-Pr | H |
| Br | Br | Br | Br | t-Bu | H |
| Br | Br | Br | Br | Me | Me |
| Cl | $OCH_2CF_3$ | Br | Br | Me | H |
| Cl | $OCH_2CF_3$ | Br | Br | Et | H |
| Cl | $OCH_2CF_3$ | Br | Br | i-Pr | H |
| Cl | $OCH_2CF_3$ | Br | Br | t-Bu | H |
| Cl | $OCH_2CF_3$ | Br | Br | Me | Me |
| Br | $OCH_2CF_3$ | Br | Br | Me | H |
| Br | $OCH_2CF_3$ | Br | Br | Et | H |
| Br | $OCH_2CF_3$ | Br | Br | i-Pr | H |
| Br | $OCH_2CF_3$ | Br | Br | t-Bu | H |
| Br | $OCH_2CF_3$ | Br | Br | Me | Me |
| Cl | $CF_3$ | Br | I | Me | H |
| Cl | $CF_3$ | Br | I | Et | H |
| Cl | $CF_3$ | Br | I | i-Pr | H |
| Cl | $CF_3$ | Br | I | t-Bu | H |
| Cl | $CF_3$ | Br | I | Me | Me |
| Br | $CF_3$ | Br | I | Me | H |
| Br | $CF_3$ | Br | I | Et | H |
| Br | $CF_3$ | Br | I | i-Pr | H |
| Br | $CF_3$ | Br | I | t-Bu | H |

TABLE 4-continued

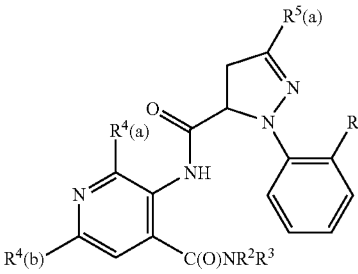

| $R^6(a)$ | $R^5(a)$ | $R^4(a)$ | $R^4(b)$ | $R^3$ | $R^2$ |
|---|---|---|---|---|---|
| Br | $CF_3$ | Br | I | Me | Me |
| Cl | Cl | Br | I | Me | H |
| Cl | Cl | Br | I | Et | H |
| Cl | Cl | Br | I | i-Pr | H |
| Cl | Cl | Br | I | t-Bu | H |
| Cl | Cl | Br | I | Me | Me |
| Br | Cl | Br | I | Me | H |
| Br | Cl | Br | I | Et | H |
| Br | Cl | Br | I | i-Pr | H |
| Br | Cl | Br | I | t-Bu | H |
| Br | Cl | Br | I | Me | Me |
| Cl | Br | Br | I | Me | H |
| Cl | Br | Br | I | Et | H |
| Cl | Br | Br | I | i-Pr | H |
| Cl | Br | Br | I | t-Bu | H |
| Cl | Br | Br | I | Me | Me |
| Br | Br | Br | I | Me | H |
| Br | Br | Br | I | Et | H |
| Br | Br | Br | I | i-Pr | H |
| Br | Br | Br | I | t-Bu | H |
| Br | Br | Br | I | Me | Me |
| Cl | $OCH_2CF_3$ | Br | I | Me | H |
| Cl | $OCH_2CF_3$ | Br | I | Et | H |
| Cl | $OCH_2CF_3$ | Br | I | i-Pr | H |
| Cl | $OCH_2CF_3$ | Br | I | t-Bu | H |
| Cl | $OCH_2CF_3$ | Br | I | Me | Me |
| Br | $OCH_2CF_3$ | Br | I | Me | H |
| Br | $OCH_2CF_3$ | Br | I | Et | H |
| Br | $OCH_2CF_3$ | Br | I | i-Pr | H |
| Br | $OCH_2CF_3$ | Br | I | t-Bu | H |
| Br | $OCH_2CF_3$ | Br | I | Me | Me |
| Cl | $CF_3$ | Br | $CF_3$ | Me | H |
| Cl | $CF_3$ | Br | $CF_3$ | Et | H |
| Cl | $CF_3$ | Br | $CF_3$ | i-Pr | H |
| Cl | $CF_3$ | Br | $CF_3$ | t-Bu | H |
| Cl | $CF_3$ | Br | $CF_3$ | Me | Me |
| Br | $CF_3$ | Br | $CF_3$ | Me | H |
| Br | $CF_3$ | Br | $CF_3$ | Et | H |
| Br | $CF_3$ | Br | $CF_3$ | i-Pr | H |
| Br | $CF_3$ | Br | $CF_3$ | t-Bu | H |
| Br | $CF_3$ | Br | $CF_3$ | Me | Me |
| Cl | Cl | Br | $CF_3$ | Me | H |
| Cl | Cl | Br | $CF_3$ | Et | H |
| Cl | Cl | Br | $CF_3$ | i-Pr | H |
| Cl | Cl | Br | $CF_3$ | t-Bu | H |
| Cl | Cl | Br | $CF_3$ | Me | Me |
| Br | Cl | Br | $CF_3$ | Me | H |
| Br | Cl | Br | $CF_3$ | Et | H |
| Br | Cl | Br | $CF_3$ | i-Pr | H |
| Br | Cl | Br | $CF_3$ | t-Bu | H |
| Br | Cl | Br | $CF_3$ | Me | Me |
| Cl | Br | Br | $CF_3$ | Me | H |
| Cl | Br | Br | $CF_3$ | Et | H |
| Cl | Br | Br | $CF_3$ | i-Pr | H |
| Cl | Br | Br | $CF_3$ | t-Bu | H |
| Cl | Br | Br | $CF_3$ | Me | Me |
| Br | Br | Br | $CF_3$ | Me | H |
| Br | Br | Br | $CF_3$ | Et | H |
| Br | Br | Br | $CF_3$ | i-Pr | H |
| Br | Br | Br | $CF_3$ | t-Bu | H |
| Br | Br | Br | $CF_3$ | Me | Me |
| Cl | $OCH_2CF_3$ | Br | $CF_3$ | Me | H |
| Cl | $OCH_2CF_3$ | Br | $CF_3$ | Et | H |

TABLE 4-continued

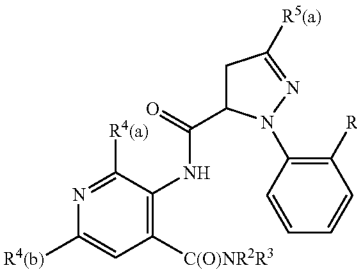

| $R^6(a)$ | $R^5(a)$ | $R^4(a)$ | $R^4(b)$ | $R^3$ | $R^2$ |
|---|---|---|---|---|---|
| Cl | $OCH_2CF_3$ | Br | $CF_3$ | i-Pr | H |
| Cl | $OCH_2CF_3$ | Br | $CF_3$ | t-Bu | H |
| Cl | $OCH_2CF_3$ | Br | $CF_3$ | Me | Me |
| Br | $OCH_2CF_3$ | Br | $CF_3$ | Me | H |
| Br | $OCH_2CF_3$ | Br | $CF_3$ | Et | H |
| Br | $OCH_2CF_3$ | Br | $CF_3$ | i-Pr | H |
| Br | $OCH_2CF_3$ | Br | $CF_3$ | t-Bu | H |
| Br | $OCH_2CF_3$ | Br | $CF_3$ | Me | Me |

TABLE 5

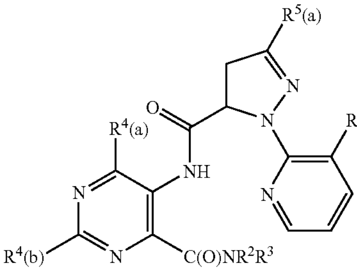

| $R^6(a)$ | $R^5(a)$ | $R^4(a)$ | $R^4(b)$ | $R^3$ | $R^2$ |
|---|---|---|---|---|---|
| Cl | $CF_3$ | $CH_3$ | H | Me | H |
| Cl | $CF_3$ | $CH_3$ | H | Et | H |
| Cl | $CF_3$ | $CH_3$ | H | i-Pr | H |
| Cl | $CF_3$ | $CH_3$ | H | t-Bu | H |
| Cl | $CF_3$ | $CH_3$ | H | Me | Me |
| Br | $CF_3$ | $CH_3$ | H | Me | H |
| Br | $CF_3$ | $CH_3$ | H | Et | H |
| Br | $CF_3$ | $CH_3$ | H | i-Pr | H |
| Br | $CF_3$ | $CH_3$ | H | t-Bu | H |
| Br | $CF_3$ | $CH_3$ | H | Me | Me |
| Cl | Cl | $CH_3$ | H | Me | H |
| Cl | Cl | $CH_3$ | H | Et | H |
| Cl | Cl | $CH_3$ | H | i-Pr | H |
| Cl | Cl | $CH_3$ | H | t-Bu | H |
| Cl | Cl | $CH_3$ | H | Me | Me |
| Br | Cl | $CH_3$ | H | Me | H |
| Br | Cl | $CH_3$ | H | Et | H |
| Br | Cl | $CH_3$ | H | i-Pr | H |
| Br | Cl | $CH_3$ | H | t-Bu | H |
| Br | Cl | $CH_3$ | H | Me | Me |
| Cl | Br | $CH_3$ | H | Me | H |
| Cl | Br | $CH_3$ | H | Et | H |
| Cl | Br | $CH_3$ | H | i-Pr | H |
| Cl | Br | $CH_3$ | H | t-Bu | H |
| Cl | Br | $CH_3$ | H | Me | Me |
| Br | Br | $CH_3$ | H | Me | H |
| Br | Br | $CH_3$ | H | Et | H |
| Br | Br | $CH_3$ | H | i-Pr | H |
| Br | Br | $CH_3$ | H | t-Bu | H |
| Br | Br | $CH_3$ | H | Me | Me |
| Cl | $OCH_2CF_3$ | $CH_3$ | H | Me | H |
| Cl | $OCH_2CF_3$ | $CH_3$ | H | Et | H |
| Cl | $OCH_2CF_3$ | $CH_3$ | H | i-Pr | H |
| Cl | $OCH_2CF_3$ | $CH_3$ | H | t-Bu | H |

TABLE 5-continued

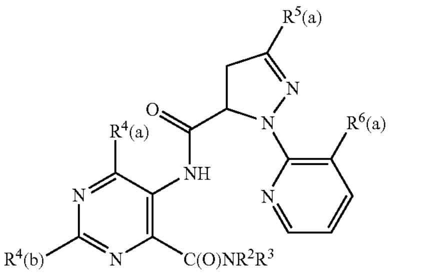

| $R^6$(a) | $R^5$(a) | $R^4$(a) | $R^4$(b) | $R^3$ | $R^2$ |
|---|---|---|---|---|---|
| Cl | $OCH_2CF_3$ | $CH_3$ | H | Me | Me |
| Br | $OCH_2CF_3$ | $CH_3$ | H | Me | H |
| Br | $OCH_2CF_3$ | $CH_3$ | H | Et | H |
| Br | $OCH_2CF_3$ | $CH_3$ | H | i-Pr | H |
| Br | $OCH_2CF_3$ | $CH_3$ | H | t-Bu | H |
| Br | $OCH_2CF_3$ | $CH_3$ | H | Me | Me |
| Cl | $CF_3$ | $CH_3$ | F | Me | H |
| Cl | $CF_3$ | $CH_3$ | F | Et | H |
| Cl | $CF_3$ | $CH_3$ | F | i-Pr | H |
| Cl | $CF_3$ | $CH_3$ | F | t-Bu | H |
| Cl | $CF_3$ | $CH_3$ | F | Me | Me |
| Br | $CF_3$ | $CH_3$ | F | Me | H |
| Br | $CF_3$ | $CH_3$ | F | Et | H |
| Br | $CF_3$ | $CH_3$ | F | i-Pr | H |
| Br | $CF_3$ | $CH_3$ | F | t-Bu | H |
| Br | $CF_3$ | $CH_3$ | F | Me | Me |
| Cl | Cl | $CH_3$ | F | Me | H |
| Cl | Cl | $CH_3$ | F | Et | H |
| Cl | Cl | $CH_3$ | F | i-Pr | H |
| Cl | Cl | $CH_3$ | F | t-Bu | H |
| Cl | Cl | $CH_3$ | F | Me | Me |
| Br | Cl | $CH_3$ | F | Me | H |
| Br | Cl | $CH_3$ | F | Et | H |
| Br | Cl | $CH_3$ | F | i-Pr | H |
| Br | Cl | $CH_3$ | F | t-Bu | H |
| Br | Cl | $CH_3$ | F | Me | Me |
| Cl | Br | $CH_3$ | F | Me | H |
| Cl | Br | $CH_3$ | F | Et | H |
| Cl | Br | $CH_3$ | F | i-Pr | H |
| Cl | Br | $CH_3$ | F | t-Bu | H |
| Cl | Br | $CH_3$ | F | Me | Me |
| Br | Br | $CH_3$ | F | Me | H |
| Br | Br | $CH_3$ | F | Et | H |
| Br | Br | $CH_3$ | F | i-Pr | H |
| Br | Br | $CH_3$ | F | t-Bu | H |
| Br | Br | $CH_3$ | F | Me | Me |
| Cl | $OCH_2CF_3$ | $CH_3$ | F | Me | H |
| Cl | $OCH_2CF_3$ | $CH_3$ | F | Et | H |
| Cl | $OCH_2CF_3$ | $CH_3$ | F | i-Pr | H |
| Cl | $OCH_2CF_3$ | $CH_3$ | F | t-Bu | H |
| Cl | $OCH_2CF_3$ | $CH_3$ | F | Me | Me |
| Br | $OCH_2CF_3$ | $CH_3$ | F | Me | H |
| Br | $OCH_2CF_3$ | $CH_3$ | F | Et | H |
| Br | $OCH_2CF_3$ | $CH_3$ | F | i-Pr | H |
| Br | $OCH_2CF_3$ | $CH_3$ | F | t-Bu | H |
| Br | $OCH_2CF_3$ | $CH_3$ | F | Me | Me |
| Cl | $CF_3$ | $CH_3$ | Cl | Me | H |
| Cl | $CF_3$ | $CH_3$ | Cl | Et | H |
| Cl | $CF_3$ | $CH_3$ | Cl | i-Pr | H |
| Cl | $CF_3$ | $CH_3$ | Cl | t-Bu | H |
| Cl | $CF_3$ | $CH_3$ | Cl | Me | Me |
| Br | $CF_3$ | $CH_3$ | Cl | Me | H |
| Br | $CF_3$ | $CH_3$ | Cl | Et | H |
| Br | $CF_3$ | $CH_3$ | Cl | i-Pr | H |
| Br | $CF_3$ | $CH_3$ | Cl | t-Bu | H |
| Br | $CF_3$ | $CH_3$ | Cl | Me | Me |
| Cl | Cl | $CH_3$ | Cl | Me | H |
| Cl | Cl | $CH_3$ | Cl | Et | H |
| Cl | Cl | $CH_3$ | Cl | i-Pr | H |
| Cl | Cl | $CH_3$ | Cl | t-Bu | H |
| Cl | Cl | $CH_3$ | Cl | Me | Me |
| Br | Cl | $CH_3$ | Cl | Me | H |
| Br | Cl | $CH_3$ | Cl | Et | H |

TABLE 5-continued

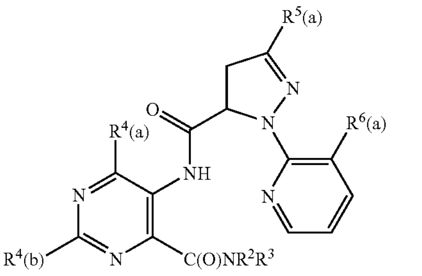

| $R^6$(a) | $R^5$(a) | $R^4$(a) | $R^4$(b) | $R^3$ | $R^2$ |
|---|---|---|---|---|---|
| Br | Cl | $CH_3$ | Cl | i-Pr | H |
| Br | Cl | $CH_3$ | Cl | t-Bu | H |
| Br | Cl | $CH_3$ | Cl | Me | Me |
| Cl | Br | $CH_3$ | Cl | Me | H |
| Cl | Br | $CH_3$ | Cl | Et | H |
| Cl | Br | $CH_3$ | Cl | i-Pr | H |
| Cl | Br | $CH_3$ | Cl | t-Bu | H |
| Cl | Br | $CH_3$ | Cl | Me | Me |
| Br | Br | $CH_3$ | Cl | Me | H |
| Br | Br | $CH_3$ | Cl | Et | H |
| Br | Br | $CH_3$ | Cl | i-Pr | H |
| Br | Br | $CH_3$ | Cl | t-Bu | H |
| Br | Br | $CH_3$ | Cl | Me | Me |
| Cl | $OCH_2CF_3$ | $CH_3$ | Cl | Me | H |
| Cl | $OCH_2CF_3$ | $CH_3$ | Cl | Et | H |
| Cl | $OCH_2CF_3$ | $CH_3$ | Cl | i-Pr | H |
| Cl | $OCH_2CF_3$ | $CH_3$ | Cl | t-Bu | H |
| Cl | $OCH_2CF_3$ | $CH_3$ | Cl | Me | Me |
| Br | $OCH_2CF_3$ | $CH_3$ | Cl | Me | H |
| Br | $OCH_2CF_3$ | $CH_3$ | Cl | Et | H |
| Br | $OCH_2CF_3$ | $CH_3$ | Cl | i-Pr | H |
| Br | $OCH_2CF_3$ | $CH_3$ | Cl | t-Bu | H |
| Br | $OCH_2CF_3$ | $CH_3$ | Cl | Me | Me |
| Cl | $CF_3$ | $CH_3$ | Br | Me | H |
| Cl | $CF_3$ | $CH_3$ | Br | Et | H |
| Cl | $CF_3$ | $CH_3$ | Br | i-Pr | H |
| Cl | $CF_3$ | $CH_3$ | Br | t-Bu | H |
| Cl | $CF_3$ | $CH_3$ | Br | Me | Me |
| Br | $CF_3$ | $CH_3$ | Br | Me | H |
| Br | $CF_3$ | $CH_3$ | Br | Et | H |
| Br | $CF_3$ | $CH_3$ | Br | i-Pr | H |
| Br | $CF_3$ | $CH_3$ | Br | t-Bu | H |
| Br | $CF_3$ | $CH_3$ | Br | Me | Me |
| Cl | Cl | $CH_3$ | Br | Me | H |
| Cl | Cl | $CH_3$ | Br | Et | H |
| Cl | Cl | $CH_3$ | Br | i-Pr | H |
| Cl | Cl | $CH_3$ | Br | t-Bu | H |
| Cl | Cl | $CH_3$ | Br | Me | Me |
| Br | Cl | $CH_3$ | Br | Me | H |
| Br | Cl | $CH_3$ | Br | Et | H |
| Br | Cl | $CH_3$ | Br | i-Pr | H |
| Br | Cl | $CH_3$ | Br | t-Bu | H |
| Br | Cl | $CH_3$ | Br | Me | Me |
| Cl | Br | $CH_3$ | Br | Me | H |
| Cl | Br | $CH_3$ | Br | Et | H |
| Cl | Br | $CH_3$ | Br | i-Pr | H |
| Cl | Br | $CH_3$ | Br | t-Bu | H |
| Cl | Br | $CH_3$ | Br | Me | Me |
| Br | Br | $CH_3$ | Br | Me | H |
| Br | Br | $CH_3$ | Br | Et | H |
| Br | Br | $CH_3$ | Br | i-Pr | H |
| Br | Br | $CH_3$ | Br | t-Bu | H |
| Br | Br | $CH_3$ | Br | Me | Me |
| Cl | $OCH_2CF_3$ | $CH_3$ | Br | Me | H |
| Cl | $OCH_2CF_3$ | $CH_3$ | Br | Et | H |
| Cl | $OCH_2CF_3$ | $CH_3$ | Br | i-Pr | H |
| Cl | $OCH_2CF_3$ | $CH_3$ | Br | t-Bu | H |
| Cl | $OCH_2CF_3$ | $CH_3$ | Br | Me | Me |
| Br | $OCH_2CF_3$ | $CH_3$ | Br | Me | H |
| Br | $OCH_2CF_3$ | $CH_3$ | Br | Et | H |
| Br | $OCH_2CF_3$ | $CH_3$ | Br | i-Pr | H |
| Br | $OCH_2CF_3$ | $CH_3$ | Br | t-Bu | H |
| Br | $OCH_2CF_3$ | $CH_3$ | Br | Me | Me |

TABLE 5-continued

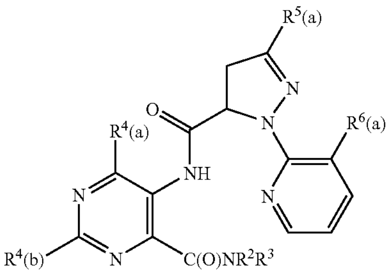

| $R^6$(a) | $R^5$(a) | $R^4$(a) | $R^4$(b) | $R^3$ | $R^2$ |
|---|---|---|---|---|---|
| Cl | $CF_3$ | $CH_3$ | I | Me | H |
| Cl | $CF_3$ | $CH_3$ | I | Et | H |
| Cl | $CF_3$ | $CH_3$ | I | i-Pr | H |
| Cl | $CF_3$ | $CH_3$ | I | t-Bu | H |
| Cl | $CF_3$ | $CH_3$ | I | Me | Me |
| Br | $CF_3$ | $CH_3$ | I | Me | H |
| Br | $CF_3$ | $CH_3$ | I | Et | H |
| Br | $CF_3$ | $CH_3$ | I | i-Pr | H |
| Br | $CF_3$ | $CH_3$ | I | t-Bu | H |
| Br | $CF_3$ | $CH_3$ | I | Me | Me |
| Cl | Cl | $CH_3$ | I | Me | H |
| Cl | Cl | $CH_3$ | I | Et | H |
| Cl | Cl | $CH_3$ | I | i-Pr | H |
| Cl | Cl | $CH_3$ | I | t-Bu | H |
| Cl | Cl | $CH_3$ | I | Me | Me |
| Br | Cl | $CH_3$ | I | Me | H |
| Br | Cl | $CH_3$ | I | Et | H |
| Br | Cl | $CH_3$ | I | i-Pr | H |
| Br | Cl | $CH_3$ | I | t-Bu | H |
| Br | Cl | $CH_3$ | I | Me | Me |
| Cl | Br | $CH_3$ | I | Me | H |
| Cl | Br | $CH_3$ | I | Et | H |
| Cl | Br | $CH_3$ | I | i-Pr | H |
| Cl | Br | $CH_3$ | I | t-Bu | H |
| Cl | Br | $CH_3$ | I | Me | Me |
| Br | Br | $CH_3$ | I | Me | H |
| Br | Br | $CH_3$ | I | Et | H |
| Br | Br | $CH_3$ | I | i-Pr | H |
| Br | Br | $CH_3$ | I | t-Bu | H |
| Br | Br | $CH_3$ | I | Me | Me |
| Cl | $OCH_2CF_3$ | $CH_3$ | I | Me | H |
| Cl | $OCH_2CF_3$ | $CH_3$ | I | Et | H |
| Cl | $OCH_2CF_3$ | $CH_3$ | I | i-Pr | H |
| Cl | $OCH_2CF_3$ | $CH_3$ | I | t-Bu | H |
| Cl | $OCH_2CF_3$ | $CH_3$ | I | Me | Me |
| Br | $OCH_2CF_3$ | $CH_3$ | I | Me | H |
| Br | $OCH_2CF_3$ | $CH_3$ | I | Et | H |
| Br | $OCH_2CF_3$ | $CH_3$ | I | i-Pr | H |
| Br | $OCH_2CF_3$ | $CH_3$ | I | t-Bu | H |
| Br | $OCH_2CF_3$ | $CH_3$ | I | Me | Me |
| Cl | $CF_3$ | $CH_3$ | $CH_3$ | Me | H |
| Cl | $CF_3$ | $CH_3$ | $CH_3$ | Et | H |
| Cl | $CF_3$ | $CH_3$ | $CH_3$ | i-Pr | H |
| Cl | $CF_3$ | $CH_3$ | $CH_3$ | t-Bu | H |
| Cl | $CF_3$ | $CH_3$ | $CH_3$ | Me | Me |
| Br | $CF_3$ | $CH_3$ | $CH_3$ | Me | H |
| Br | $CF_3$ | $CH_3$ | $CH_3$ | Et | H |
| Br | $CF_3$ | $CH_3$ | $CH_3$ | i-Pr | H |
| Br | $CF_3$ | $CH_3$ | $CH_3$ | t-Bu | H |
| Br | $CF_3$ | $CH_3$ | $CH_3$ | Me | Me |
| Cl | Cl | $CH_3$ | $CH_3$ | Me | H |
| Cl | Cl | $CH_3$ | $CH_3$ | Et | H |
| Cl | Cl | $CH_3$ | $CH_3$ | i-Pr | H |
| Cl | Cl | $CH_3$ | $CF_3$ | t-Bu | H |
| Cl | Cl | $CH_3$ | $CF_3$ | Me | Me |
| Br | Cl | $CH_3$ | $CF_3$ | Me | H |
| Br | Cl | $CH_3$ | $CF_3$ | Et | H |
| Br | Cl | $CH_3$ | $CF_3$ | i-Pr | H |
| Br | Cl | $CH_3$ | $CF_3$ | t-Bu | H |
| Br | Cl | $CH_3$ | $CF_3$ | Me | Me |
| Cl | Br | $CH_3$ | $CF_3$ | Me | H |
| Cl | Br | $CH_3$ | $CF_3$ | Et | H |
| Cl | Br | $CH_3$ | $CF_3$ | i-Pr | H |

TABLE 5-continued

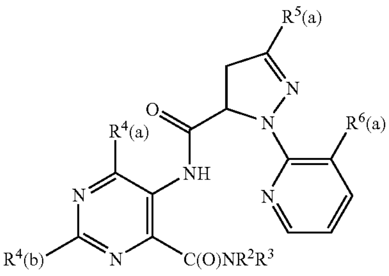

| $R^6$(a) | $R^5$(a) | $R^4$(a) | $R^4$(b) | $R^3$ | $R^2$ |
|---|---|---|---|---|---|
| Cl | Br | $CH_3$ | $CF_3$ | t-Bu | H |
| Cl | Br | $CH_3$ | $CF_3$ | Me | Me |
| Br | Br | $CH_3$ | $CF_3$ | Me | H |
| Br | Br | $CH_3$ | $CF_3$ | Et | H |
| Br | Br | $CH_3$ | $CF_3$ | i-Pr | H |
| Br | Br | $CH_3$ | $CF_3$ | t-Bu | H |
| Br | Br | $CH_3$ | $CF_3$ | Me | Me |
| Cl | $OCH_2CF_3$ | $CH_3$ | $CF_3$ | Me | H |
| Cl | $OCH_2CF_3$ | $CH_3$ | $CF_3$ | Et | H |
| Cl | $OCH_2CF_3$ | $CH_3$ | $CF_3$ | i-Pr | H |
| Cl | $OCH_2CF_3$ | $CH_3$ | $CF_3$ | t-Bu | H |
| Cl | $OCH_2CF_3$ | $CH_3$ | $CF_3$ | Me | Me |
| Br | $OCH_2CF_3$ | $CH_3$ | $CF_3$ | Me | H |
| Br | $OCH_2CF_3$ | $CH_3$ | $CF_3$ | Et | H |
| Br | $OCH_2CF_3$ | $CH_3$ | $CF_3$ | i-Pr | H |
| Br | $OCH_2CF_3$ | $CH_3$ | $CF_3$ | t-Bu | H |
| Br | $OCH_2CF_3$ | $CH_3$ | $CF_3$ | Me | Me |
| Cl | Cl | $CH_3$ | Cl | n-Pr | H |
| Cl | Cl | $CH_3$ | Cl | n-Bu | H |
| Cl | Cl | $CH_3$ | Cl | s-Bu | H |
| Cl | Cl | $CH_3$ | Cl | i-Bu | H |
| Cl | Cl | $CH_3$ | Cl | Et | Me |
| Cl | $CF_3$ | F | H | Me | H |
| Cl | $CF_3$ | F | H | Et | H |
| Cl | $CF_3$ | F | H | i-Pr | H |
| Cl | $CF_3$ | F | H | t-Bu | H |
| Cl | $CF_3$ | F | H | Me | Me |
| Br | $CF_3$ | F | H | Me | H |
| Br | $CF_3$ | F | H | Et | H |
| Br | $CF_3$ | F | H | i-Pr | H |
| Br | $CF_3$ | F | H | t-Bu | H |
| Br | $CF_3$ | F | H | Me | Me |
| Cl | Cl | F | H | Me | H |
| Cl | Cl | F | H | Et | H |
| Cl | Cl | F | H | i-Pr | H |
| Cl | Cl | F | H | t-Bu | H |
| Cl | Cl | F | H | Me | Me |
| Br | Cl | F | H | Me | H |
| Br | Cl | F | H | Et | H |
| Br | Cl | F | H | i-Pr | H |
| Br | Cl | F | H | t-Bu | H |
| Br | Cl | F | H | Me | Me |
| Cl | Br | F | H | Me | H |
| Cl | Br | F | H | Et | H |
| Cl | Br | F | H | i-Pr | H |
| Cl | Br | F | H | t-Bu | H |
| Cl | Br | F | H | Me | Me |
| Br | Br | F | H | Me | H |
| Br | Br | F | H | Et | H |
| Br | Br | F | H | i-Pr | H |
| Br | Br | F | H | t-Bu | H |
| Br | Br | F | H | Me | Me |
| Cl | $OCH_2CF_3$ | F | H | Me | H |
| Cl | $OCH_2CF_3$ | F | H | Et | H |
| Cl | $OCH_2CF_3$ | F | H | i-Pr | H |
| Cl | $OCH_2CF_3$ | F | H | t-Bu | H |
| Cl | $OCH_2CF_3$ | F | H | Me | Me |
| Br | $OCH_2CF_3$ | F | H | Me | H |
| Br | $OCH_2CF_3$ | F | H | Et | H |
| Br | $OCH_2CF_3$ | F | H | i-Pr | H |
| Br | $OCH_2CF_3$ | F | H | t-Bu | H |
| Br | $OCH_2CF_3$ | F | H | Me | Me |
| Cl | $CF_3$ | F | F | Me | H |

TABLE 5-continued

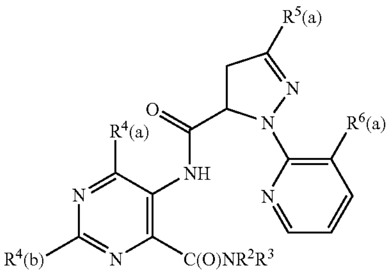

| $R^6$(a) | $R^5$(a) | $R^4$(a) | $R^4$(b) | $R^3$ | $R^2$ |
|---|---|---|---|---|---|
| Cl | $CF_3$ | F | F | Et | H |
| Cl | $CF_3$ | F | F | i-Pr | H |
| Cl | $CF_3$ | F | F | t-Bu | H |
| Cl | $CF_3$ | F | F | Me | Me |
| Br | $CF_3$ | F | F | Me | H |
| Br | $CF_3$ | F | F | Et | H |
| Br | $CF_3$ | F | F | i-Pr | H |
| Br | $CF_3$ | F | F | t-Bu | H |
| Br | $CF_3$ | F | F | Me | Me |
| Cl | Cl | F | F | Me | H |
| Cl | Cl | F | F | Et | H |
| Cl | Cl | F | F | i-Pr | H |
| Cl | Cl | F | F | t-Bu | H |
| Cl | Cl | F | F | Me | Me |
| Br | Cl | F | F | Me | H |
| Br | Cl | F | F | Et | H |
| Br | Cl | F | F | i-Pr | H |
| Br | Cl | F | F | t-Bu | H |
| Br | Cl | F | F | Me | Me |
| Cl | Br | F | F | Me | H |
| Cl | Br | F | F | Et | H |
| Cl | Br | F | F | i-Pr | H |
| Cl | Br | F | F | t-Bu | H |
| Cl | Br | F | F | Me | Me |
| Br | Br | F | F | Me | H |
| Br | Br | F | F | Et | H |
| Br | Br | F | F | i-Pr | H |
| Br | Br | F | F | t-Bu | H |
| Br | Br | F | F | Me | Me |
| Cl | $OCH_2CF_3$ | F | F | Me | H |
| Cl | $OCH_2CF_3$ | F | F | Et | H |
| Cl | $OCH_2CF_3$ | F | F | i-Pr | H |
| Cl | $OCH_2CF_3$ | F | F | t-Bu | H |
| Cl | $OCH_2CF_3$ | F | F | Me | Me |
| Br | $OCH_2CF_3$ | F | F | Me | H |
| Br | $OCH_2CF_3$ | F | F | Et | H |
| Br | $OCH_2CF_3$ | F | F | i-Pr | H |
| Br | $OCH_2CF_3$ | F | F | t-Bu | H |
| Br | $OCH_2CF_3$ | F | Cl | Me | Me |
| Cl | $CF_3$ | F | Cl | Me | H |
| Cl | $CF_3$ | F | Cl | Et | H |
| Cl | $CF_3$ | F | Cl | i-Pr | H |
| Cl | $CF_3$ | F | Cl | t-Bu | H |
| Cl | $CF_3$ | F | Cl | Me | Me |
| Br | $CF_3$ | F | Cl | Me | H |
| Br | $CF_3$ | F | Cl | Et | H |
| Br | $CF_3$ | F | Cl | i-Pr | H |
| Br | $CF_3$ | F | Cl | t-Bu | H |
| Br | $CF_3$ | F | Cl | Me | Me |
| Cl | Cl | F | Cl | Me | H |
| Cl | Cl | F | Cl | Et | H |
| Cl | Cl | F | Cl | i-Pr | H |
| Cl | Cl | F | Cl | t-Bu | H |
| Cl | Cl | F | Cl | Me | Me |
| Br | Cl | F | Cl | Me | H |
| Br | Cl | F | Cl | Et | H |
| Br | Cl | F | Cl | i-Pr | H |
| Br | Cl | F | Cl | t-Bu | H |
| Br | Cl | F | Cl | Me | Me |
| Cl | Br | F | Cl | Me | H |
| Cl | Br | F | Cl | Et | H |
| Cl | Br | F | Cl | i-Pr | H |
| Cl | Br | F | Cl | t-Bu | H |

TABLE 5-continued

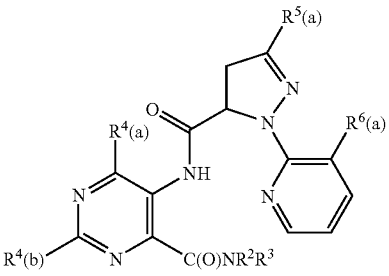

| $R^6$(a) | $R^5$(a) | $R^4$(a) | $R^4$(b) | $R^3$ | $R^2$ |
|---|---|---|---|---|---|
| Cl | Br | F | Cl | Me | Me |
| Br | Br | F | Cl | Me | H |
| Br | Br | F | Cl | Et | H |
| Br | Br | F | Cl | i-Pr | H |
| Br | Br | F | Cl | t-Bu | H |
| Br | Br | F | Cl | Me | Me |
| Cl | $OCH_2CF_3$ | F | Cl | Me | H |
| Cl | $OCH_2CF_3$ | F | Cl | Et | H |
| Cl | $OCH_2CF_3$ | F | Cl | i-Pr | H |
| Cl | $OCH_2CF_3$ | F | Cl | t-Bu | H |
| Cl | $OCH_2CF_3$ | F | Cl | Me | Me |
| Br | $OCH_2CF_3$ | F | Cl | Me | H |
| Br | $OCH_2CF_3$ | F | Cl | Et | H |
| Br | $OCH_2CF_3$ | F | Cl | i-Pr | H |
| Br | $OCH_2CF_3$ | F | Cl | t-Bu | H |
| Br | $OCH_2CF_3$ | F | Cl | Me | Me |
| Cl | $CF_3$ | F | Br | Me | H |
| Cl | $CF_3$ | F | Br | Et | H |
| Cl | $CF_3$ | F | Br | i-Pr | H |
| Cl | $CF_3$ | F | Br | t-Bu | H |
| Cl | $CF_3$ | F | Br | Me | Me |
| Br | $CF_3$ | F | Br | Me | H |
| Br | $CF_3$ | F | Br | Et | H |
| Br | $CF_3$ | F | Br | i-Pr | H |
| Br | $CF_3$ | F | Br | t-Bu | H |
| Br | $CF_3$ | F | Br | Me | Me |
| Cl | Cl | F | Br | Me | H |
| Cl | Cl | F | Br | Et | H |
| Cl | Cl | F | Br | i-Pr | H |
| Cl | Cl | F | Br | t-Bu | H |
| Cl | Cl | F | Br | Me | Me |
| Br | Cl | F | Br | Me | H |
| Br | Cl | F | Br | Et | H |
| Br | Cl | F | Br | i-Pr | H |
| Br | Cl | F | Br | t-Bu | H |
| Br | Cl | F | Br | Me | Me |
| Cl | Br | F | Br | Me | H |
| Cl | Br | F | Br | Et | H |
| Cl | Br | F | Br | i-Pr | H |
| Cl | Br | F | Br | t-Bu | H |
| Cl | Br | F | Br | Me | Me |
| Br | Br | F | Br | Me | H |
| Br | Br | F | Br | Et | H |
| Br | Br | F | Br | i-Pr | H |
| Br | Br | F | Br | t-Bu | H |
| Br | Br | F | Br | Me | Me |
| Cl | $OCH_2CF_3$ | F | Br | Me | H |
| Cl | $OCH_2CF_3$ | F | Br | Et | H |
| Cl | $OCH_2CF_3$ | F | Br | i-Pr | H |
| Cl | $OCH_2CF_3$ | F | Br | t-Bu | H |
| Cl | $OCH_2CF_3$ | F | Br | Me | Me |
| Br | $OCH_2CF_3$ | F | Br | Me | H |
| Br | $OCH_2CF_3$ | F | Br | Et | H |
| Br | $OCH_2CF_3$ | F | Br | i-Pr | H |
| Br | $OCH_2CF_3$ | F | Br | t-Bu | H |
| Br | $OCH_2CF_3$ | F | Br | Me | Me |
| Cl | $CF_3$ | F | I | Me | H |
| Cl | $CF_3$ | F | I | Et | H |
| Cl | $CF_3$ | F | I | i-Pr | H |
| Cl | $CF_3$ | F | I | t-Bu | H |
| Cl | $CF_3$ | F | I | Me | Me |
| Br | $CF_3$ | F | I | Me | H |
| Br | $CF_3$ | F | I | Et | H |

TABLE 5-continued

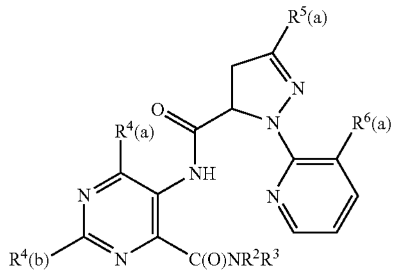

| $R^6$(a) | $R^5$(a) | $R^4$(a) | $R^4$(b) | $R^3$ | $R^2$ |
|---|---|---|---|---|---|
| Br | $CF_3$ | F | I | i-Pr | H |
| Br | $CF_3$ | F | I | t-Bu | H |
| Br | $CF_3$ | F | I | Me | Me |
| Cl | Cl | F | I | Me | H |
| Cl | Cl | F | I | Et | H |
| Cl | Cl | F | I | i-Pr | H |
| Cl | Cl | F | I | t-Bu | H |
| Cl | Cl | F | I | Me | Me |
| Br | Cl | F | I | Me | H |
| Br | Cl | F | I | Et | H |
| Br | Cl | F | I | i-Pr | H |
| Br | Cl | F | I | t-Bu | H |
| Br | Cl | F | I | Me | Me |
| Cl | Br | F | I | Me | H |
| Cl | Br | F | I | Et | H |
| Cl | Br | F | I | i-Pr | H |
| Cl | Br | F | I | t-Bu | H |
| Cl | Br | F | I | Me | Me |
| Br | Br | F | I | Me | H |
| Br | Br | F | I | Et | H |
| Br | Br | F | I | i-Pr | H |
| Br | Br | F | I | t-Bu | H |
| Br | Br | F | I | Me | Me |
| Cl | $OCH_2CF_3$ | F | I | Me | H |
| Cl | $OCH_2CF_3$ | F | I | Et | H |
| Cl | $OCH_2CF_3$ | F | I | i-Pr | H |
| Cl | $OCH_2CF_3$ | F | I | t-Bu | H |
| Cl | $OCH_2CF_3$ | F | I | Me | Me |
| Br | $OCH_2CF_3$ | F | I | Me | H |
| Br | $OCH_2CF_3$ | F | I | Et | H |
| Br | $OCH_2CF_3$ | F | I | i-Pr | H |
| Br | $OCH_2CF_3$ | F | I | t-Bu | H |
| Br | $OCH_2CF_3$ | F | I | Me | Me |
| Cl | $CF_3$ | F | $CF_3$ | Me | H |
| Cl | $CF_3$ | F | $CF_3$ | Et | H |
| Cl | $CF_3$ | F | $CF_3$ | i-Pr | H |
| Cl | $CF_3$ | F | $CF_3$ | t-Bu | H |
| Cl | $CF_3$ | F | $CF_3$ | Me | Me |
| Br | $CF_3$ | F | $CF_3$ | Me | H |
| Br | $CF_3$ | F | $CF_3$ | Et | H |
| Br | $CF_3$ | F | $CF_3$ | i-Pr | H |
| Br | $CF_3$ | F | $CF_3$ | t-Bu | H |
| Br | $CF_3$ | F | $CF_3$ | Me | Me |
| Cl | Cl | F | $CF_3$ | Me | H |
| Cl | Cl | F | $CF_3$ | Et | H |
| Cl | Cl | F | $CF_3$ | i-Pr | H |
| Cl | Cl | F | $CF_3$ | t-Bu | H |
| Cl | Cl | F | $CF_3$ | Me | Me |
| Br | Cl | F | $CF_3$ | Me | H |
| Br | Cl | F | $CF_3$ | Et | H |
| Br | Cl | F | $CF_3$ | i-Pr | H |
| Br | Cl | F | $CF_3$ | t-Bu | H |
| Br | Cl | F | $CF_3$ | Me | Me |
| Cl | Br | F | $CF_3$ | Me | H |
| Cl | Br | F | $CF_3$ | Et | H |
| Cl | Br | F | $CF_3$ | i-Pr | H |
| Cl | Br | F | $CF_3$ | t-Bu | H |
| Cl | Br | F | $CF_3$ | Me | Me |
| Br | Br | F | $CF_3$ | Me | H |
| Br | Br | F | $CF_3$ | Et | H |
| Br | Br | F | $CF_3$ | i-Pr | H |
| Br | Br | F | $CF_3$ | t-Bu | H |
| Br | Br | F | $CF_3$ | Me | Me |

TABLE 5-continued

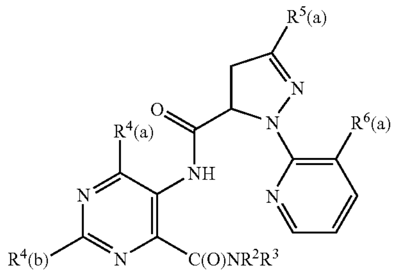

| $R^6$(a) | $R^5$(a) | $R^4$(a) | $R^4$(b) | $R^3$ | $R^2$ |
|---|---|---|---|---|---|
| Cl | $OCH_2CF_3$ | F | $CF_3$ | Me | H |
| Cl | $OCH_2CF_3$ | F | $CF_3$ | Et | H |
| Cl | $OCH_2CF_3$ | F | $CF_3$ | i-Pr | H |
| Cl | $OCH_2CF_3$ | F | $CF_3$ | t-Bu | H |
| Cl | $OCH_2CF_3$ | F | $CF_3$ | Me | Me |
| Br | $OCH_2CF_3$ | F | $CF_3$ | Me | H |
| Br | $OCH_2CF_3$ | F | $CF_3$ | Et | H |
| Br | $OCH_2CF_3$ | F | $CF_3$ | i-Pr | H |
| Br | $OCH_2CF_3$ | F | $CF_3$ | t-Bu | H |
| Br | $OCH_2CF_3$ | F | $CF_3$ | Me | Me |
| Cl | $CF_3$ | Cl | H | Me | H |
| Cl | $CF_3$ | Cl | H | Et | H |
| Cl | $CF_3$ | Cl | H | i-Pr | H |
| Cl | $CF_3$ | Cl | H | t-Bu | H |
| Cl | $CF_3$ | Cl | H | Me | Me |
| Br | $CF_3$ | Cl | H | Me | H |
| Br | $CF_3$ | Cl | H | Et | H |
| Br | $CF_3$ | Cl | H | i-Pr | H |
| Br | $CF_3$ | Cl | H | t-Bu | H |
| Br | $CF_3$ | Cl | H | Me | Me |
| Cl | Cl | Cl | H | Me | H |
| Cl | Cl | Cl | H | Et | H |
| Cl | Cl | Cl | H | i-Pr | H |
| Cl | Cl | Cl | H | t-Bu | H |
| Cl | Cl | Cl | H | Me | Me |
| Br | Cl | Cl | H | Me | H |
| Br | Cl | Cl | H | Et | H |
| Br | Cl | Cl | H | i-Pr | H |
| Br | Cl | Cl | H | t-Bu | H |
| Br | Cl | Cl | H | Me | Me |
| Cl | Br | Cl | H | Me | H |
| Cl | Br | Cl | H | Et | H |
| Cl | Br | Cl | H | i-Pr | H |
| Cl | Br | Cl | H | t-Bu | H |
| Cl | Br | Cl | H | Me | Me |
| Br | Br | Cl | H | Me | H |
| Br | Br | Cl | H | Et | H |
| Br | Br | Cl | H | i-Pr | H |
| Br | Br | Cl | H | t-Bu | H |
| Br | Br | Cl | H | Me | Me |
| Cl | $OCH_2CF_3$ | Cl | H | Me | H |
| Cl | $OCH_2CF_3$ | Cl | H | Et | H |
| Cl | $OCH_2CF_3$ | Cl | H | i-Pr | H |
| Cl | $OCH_2CF_3$ | Cl | H | t-Bu | H |
| Cl | $OCH_2CF_3$ | Cl | H | Me | Me |
| Br | $OCH_2CF_3$ | Cl | H | Me | H |
| Br | $OCH_2CF_3$ | Cl | H | Et | H |
| Br | $OCH_2CF_3$ | Cl | H | i-Pr | H |
| Br | $OCH_2CF_3$ | Cl | H | t-Bu | H |
| Br | $OCH_2CF_3$ | Cl | H | Me | Me |
| Cl | $CF_3$ | Cl | F | Me | H |
| Cl | $CF_3$ | Cl | F | Et | H |
| Cl | $CF_3$ | Cl | F | i-Pr | H |
| Cl | $CF_3$ | Cl | F | t-Bu | H |
| Cl | $CF_3$ | Cl | F | Me | Me |
| Br | $CF_3$ | Cl | F | Me | H |
| Br | $CF_3$ | Cl | F | Et | H |
| Br | $CF_3$ | Cl | F | i-Pr | H |
| Br | $CF_3$ | Cl | F | t-Bu | H |
| Br | $CF_3$ | Cl | F | Me | Me |
| Cl | Cl | Cl | F | Me | H |
| Cl | Cl | Cl | F | Et | H |
| Cl | Cl | Cl | F | i-Pr | H |

TABLE 5-continued

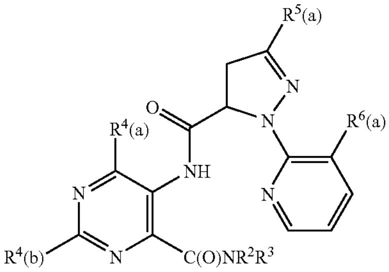

| $R^6(a)$ | $R^5(a)$ | $R^4(a)$ | $R^4(b)$ | $R^3$ | $R^2$ |
|---|---|---|---|---|---|
| Cl | Cl | Cl | F | t-Bu | H |
| Cl | Cl | Cl | F | Me | Me |
| Br | Cl | Cl | F | Me | H |
| Br | Cl | Cl | F | Et | H |
| Br | Cl | Cl | F | i-Pr | H |
| Br | Cl | Cl | F | t-Bu | H |
| Br | Cl | Cl | F | Me | Me |
| Cl | Br | Cl | F | Me | H |
| Cl | Br | Cl | F | Et | H |
| Cl | Br | Cl | F | i-Pr | H |
| Cl | Br | Cl | F | t-Bu | H |
| Cl | Br | Cl | F | Me | Me |
| Br | Br | Cl | F | Me | H |
| Br | Br | Cl | F | Et | H |
| Br | Br | Cl | F | i-Pr | H |
| Br | Br | Cl | F | t-Bu | H |
| Br | Br | Cl | F | Me | Me |
| Cl | $OCH_2CF_3$ | Cl | F | Me | H |
| Cl | $OCH_2CF_3$ | Cl | F | Et | H |
| Cl | $OCH_2CF_3$ | Cl | F | i-Pr | H |
| Cl | $OCH_2CF_3$ | Cl | F | t-Bu | H |
| Cl | $OCH_2CF_3$ | Cl | F | Me | Me |
| Br | $OCH_2CF_3$ | Cl | F | Me | H |
| Br | $OCH_2CF_3$ | Cl | F | Et | H |
| Br | $OCH_2CF_3$ | Cl | F | i-Pr | H |
| Br | $OCH_2CF_3$ | Cl | F | t-Bu | H |
| Br | $OCH_2CF_3$ | Cl | F | Me | Me |
| Cl | $CF_3$ | Cl | Cl | Me | H |
| Cl | $CF_3$ | Cl | Cl | Et | H |
| Cl | $CF_3$ | Cl | Cl | i-Pr | H |
| Cl | $CF_3$ | Cl | Cl | t-Bu | H |
| Cl | $CF_3$ | Cl | Cl | Me | Me |
| Br | $CF_3$ | Cl | Cl | Me | H |
| Br | $CF_3$ | Cl | Cl | Et | H |
| Br | $CF_3$ | Cl | Cl | i-Pr | H |
| Br | $CF_3$ | Cl | Cl | t-Bu | H |
| Br | $CF_3$ | Cl | Cl | Me | Me |
| Cl | Cl | Cl | Cl | Me | H |
| Cl | Cl | Cl | Cl | Et | H |
| Cl | Cl | Cl | Cl | i-Pr | H |
| Cl | Cl | Cl | Cl | t-Bu | H |
| Cl | Cl | Cl | Cl | Me | Me |
| Br | Cl | Cl | Cl | Me | H |
| Br | Cl | Cl | Cl | Et | H |
| Br | Cl | Cl | Cl | i-Pr | H |
| Br | Cl | Cl | Cl | t-Bu | H |
| Br | Cl | Cl | Cl | Me | Me |
| Cl | Br | Cl | Cl | Me | H |
| Cl | Br | Cl | Cl | Et | H |
| Cl | Br | Cl | Cl | i-Pr | H |
| Cl | Br | Cl | Cl | t-Bu | H |
| Cl | Br | Cl | Cl | Me | Me |
| Br | Br | Cl | Cl | Me | H |
| Br | Br | Cl | Cl | Et | H |
| Br | Br | Cl | Cl | i-Pr | H |
| Br | Br | Cl | Cl | t-Bu | H |
| Br | Br | Cl | Cl | Me | Me |
| Cl | $OCH_2CF_3$ | Cl | Cl | Me | H |
| Cl | $OCH_2CF_3$ | Cl | Cl | Et | H |
| Cl | $OCH_2CF_3$ | Cl | Cl | i-Pr | H |
| Cl | $OCH_2CF_3$ | Cl | Cl | t-Bu | H |
| Cl | $OCH_2CF_3$ | Cl | Cl | Me | Me |
| Br | $OCH_2CF_3$ | Cl | Cl | Me | H |

TABLE 5-continued

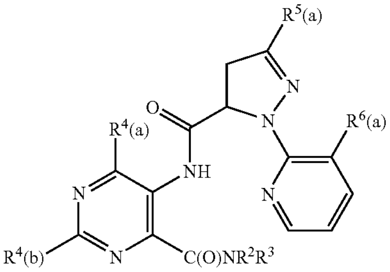

| $R^6(a)$ | $R^5(a)$ | $R^4(a)$ | $R^4(b)$ | $R^3$ | $R^2$ |
|---|---|---|---|---|---|
| Br | $OCH_2CF_3$ | Cl | Cl | Et | H |
| Br | $OCH_2CF_3$ | Cl | Cl | i-Pr | H |
| Br | $OCH_2CF_3$ | Cl | Cl | t-Bu | H |
| Br | $OCH_2CF_3$ | Cl | Cl | Me | Me |
| Cl | $CF_3$ | Cl | Br | Me | H |
| Cl | $CF_3$ | Cl | Br | Et | H |
| Cl | $CF_3$ | Cl | Br | i-Pr | H |
| Cl | $CF_3$ | Cl | Br | t-Bu | H |
| Cl | $CF_3$ | Cl | Br | Me | Me |
| Br | $CF_3$ | Cl | Br | Me | H |
| Br | $CF_3$ | Cl | Br | Et | H |
| Br | $CF_3$ | Cl | Br | i-Pr | H |
| Br | $CF_3$ | Cl | Br | t-Bu | H |
| Br | $CF_3$ | Cl | Br | Me | Me |
| Cl | Cl | Cl | Br | Me | H |
| Cl | Cl | Cl | Br | Et | H |
| Cl | Cl | Cl | Br | i-Pr | H |
| Cl | Cl | Cl | Br | t-Bu | H |
| Cl | Cl | Cl | Br | Me | Me |
| Br | Cl | Cl | Br | Me | H |
| Br | Cl | Cl | Br | Et | H |
| Br | Cl | Cl | Br | i-Pr | H |
| Br | Cl | Cl | Br | t-Bu | H |
| Br | Cl | Cl | Br | Me | Me |
| Cl | Br | Cl | Br | Me | H |
| Cl | Br | Cl | Br | Et | H |
| Cl | Br | Cl | Br | i-Pr | H |
| Cl | Br | Cl | Br | t-Bu | H |
| Cl | Br | Cl | Br | Me | Me |
| Br | Br | Cl | Br | Me | H |
| Br | Br | Cl | Br | Et | H |
| Br | Br | Cl | Br | i-Pr | H |
| Br | Br | Cl | Br | t-Bu | H |
| Br | Br | Cl | Br | Me | Me |
| Cl | $OCH_2CF_3$ | Cl | Br | Me | H |
| Cl | $OCH_2CF_3$ | Cl | Br | Et | H |
| Cl | $OCH_2CF_3$ | Cl | Br | i-Pr | H |
| Cl | $OCH_2CF_3$ | Cl | Br | t-Bu | H |
| Cl | $OCH_2CF_3$ | Cl | Br | Me | Me |
| Br | $OCH_2CF_3$ | Cl | Br | Me | H |
| Br | $OCH_2CF_3$ | Cl | Br | Et | H |
| Br | $OCH_2CF_3$ | Cl | Br | i-Pr | H |
| Br | $OCH_2CF_3$ | Cl | Br | t-Bu | H |
| Br | $OCH_2CF_3$ | Cl | Br | Me | Me |
| Cl | $CF_3$ | Cl | I | Me | H |
| Cl | $CF_3$ | Cl | I | Et | H |
| Cl | $CF_3$ | Cl | I | i-Pr | H |
| Cl | $CF_3$ | Cl | I | t-Bu | H |
| Cl | $CF_3$ | Cl | I | Me | Me |
| Br | $CF_3$ | Cl | I | Me | H |
| Br | $CF_3$ | Cl | I | Et | H |
| Br | $CF_3$ | Cl | I | i-Pr | H |
| Br | $CF_3$ | Cl | I | t-Bu | H |
| Br | $CF_3$ | Cl | I | Me | Me |
| Cl | Cl | Cl | I | Me | H |
| Cl | Cl | Cl | I | Et | H |
| Cl | Cl | Cl | I | i-Pr | H |
| Cl | Cl | Cl | I | t-Bu | H |
| Cl | Cl | Cl | I | Me | Me |
| Br | Cl | Cl | I | Me | H |
| Br | Cl | Cl | I | Et | H |
| Br | Cl | Cl | I | i-Pr | H |
| Br | Cl | Cl | I | t-Bu | H |

TABLE 5-continued

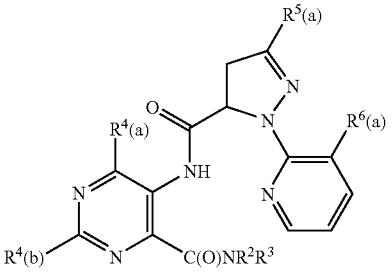

| $R^6$(a) | $R^5$(a) | $R^4$(a) | $R^4$(b) | $R^3$ | $R^2$ |
|---|---|---|---|---|---|
| Br | Cl | Cl | I | Me | Me |
| Cl | Br | Cl | I | Me | H |
| Cl | Br | Cl | I | Et | H |
| Cl | Br | Cl | I | i-Pr | H |
| Cl | Br | Cl | I | t-Bu | H |
| Cl | Br | Cl | I | Me | Me |
| Br | Br | Cl | I | Me | H |
| Br | Br | Cl | I | Et | H |
| Br | Br | Cl | I | i-Pr | H |
| Br | Br | Cl | I | t-Bu | H |
| Br | Br | Cl | I | Me | Me |
| Cl | $OCH_2CF_3$ | Cl | I | Me | H |
| Cl | $OCH_2CF_3$ | Cl | I | Et | H |
| Cl | $OCH_2CF_3$ | Cl | I | i-Pr | H |
| Cl | $OCH_2CF_3$ | Cl | I | t-Bu | H |
| Cl | $OCH_2CF_3$ | Cl | I | Me | Me |
| Br | $OCH_2CF_3$ | Cl | I | Me | H |
| Br | $OCH_2CF_3$ | Cl | I | Et | H |
| Br | $OCH_2CF_3$ | Cl | I | i-Pr | H |
| Br | $OCH_2CF_3$ | Cl | I | t-Bu | H |
| Br | $OCH_2CF_3$ | Cl | I | Me | Me |
| Cl | $CF_3$ | Cl | $CF_3$ | Me | H |
| Cl | $CF_3$ | Cl | $CF_3$ | Et | H |
| Cl | $CF_3$ | Cl | $CF_3$ | i-Pr | H |
| Cl | $CF_3$ | Cl | $CF_3$ | t-Bu | H |
| Cl | $CF_3$ | Cl | $CF_3$ | Me | Me |
| Br | $CF_3$ | Cl | $CF_3$ | Me | H |
| Br | $CF_3$ | Cl | $CF_3$ | Et | H |
| Br | $CF_3$ | Cl | $CF_3$ | i-Pr | H |
| Br | $CF_3$ | Cl | $CF_3$ | t-Bu | H |
| Br | $CF_3$ | Cl | $CF_3$ | Me | Me |
| Cl | Cl | Cl | $CF_3$ | Me | H |
| Cl | Cl | Cl | $CF_3$ | Et | H |
| Cl | Cl | Cl | $CF_3$ | i-Pr | H |
| Cl | Cl | Cl | $CF_3$ | t-Bu | H |
| Cl | Cl | Cl | $CF_3$ | Me | Me |
| Br | Cl | Cl | $CF_3$ | Me | H |
| Br | Cl | Cl | $CF_3$ | Et | H |
| Br | Cl | Cl | $CF_3$ | i-Pr | H |
| Br | Cl | Cl | $CF_3$ | t-Bu | H |
| Br | Cl | Cl | $CF_3$ | Me | Me |
| Cl | Br | Cl | $CF_3$ | Me | H |
| Cl | Br | Cl | $CF_3$ | Et | H |
| Cl | Br | Cl | $CF_3$ | i-Pr | H |
| Cl | Br | Cl | $CF_3$ | t-Bu | H |
| Cl | Br | Cl | $CF_3$ | Me | Me |
| Br | Br | Cl | $CF_3$ | Me | H |
| Br | Br | Cl | $CF_3$ | Et | H |
| Br | Br | Cl | $CF_3$ | i-Pr | H |
| Br | Br | Cl | $CF_3$ | t-Bu | H |
| Br | Br | Cl | $CF_3$ | Me | Me |
| Cl | $OCH_2CF_3$ | Cl | $CF_3$ | Me | H |
| Cl | $OCH_2CF_3$ | Cl | $CF_3$ | Et | H |
| Cl | $OCH_2CF_3$ | Cl | $CF_3$ | i-Pr | H |
| Cl | $OCH_2CF_3$ | Cl | $CF_3$ | t-Bu | H |
| Cl | $OCH_2CF_3$ | Cl | $CF_3$ | Me | Me |
| Br | $OCH_2CF_3$ | Cl | $CF_3$ | Me | H |
| Br | $OCH_2CF_3$ | Cl | $CF_3$ | Et | H |
| Br | $OCH_2CF_3$ | Cl | $CF_3$ | i-Pr | H |
| Br | $OCH_2CF_3$ | Cl | $CF_3$ | t-Bu | H |
| Br | $OCH_2CF_3$ | Cl | $CF_3$ | Me | Me |
| Cl | Cl | Cl | Cl | n-Pr | H |
| Cl | Cl | Cl | Cl | n-Bu | H |

TABLE 5-continued

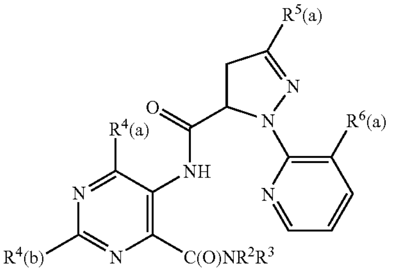

| $R^6$(a) | $R^5$(a) | $R^4$(a) | $R^4$(b) | $R^3$ | $R^2$ |
|---|---|---|---|---|---|
| Cl | Cl | Cl | Cl | s-Bu | H |
| Cl | Cl | Cl | Cl | i-Bu | H |
| Cl | Cl | Cl | Cl | Et | Me |
| Cl | $CF_3$ | Br | H | Me | H |
| Cl | $CF_3$ | Br | H | Et | H |
| Cl | $CF_3$ | Br | H | i-Pr | H |
| Cl | $CF_3$ | Br | H | t-Bu | H |
| Cl | $CF_3$ | Br | H | Me | Me |
| Br | $CF_3$ | Br | H | Me | H |
| Br | $CF_3$ | Br | H | Et | H |
| Br | $CF_3$ | Br | H | i-Pr | H |
| Br | $CF_3$ | Br | H | t-Bu | H |
| Br | $CF_3$ | Br | H | Me | Me |
| Cl | Cl | Br | H | Me | H |
| Cl | Cl | Br | H | Et | H |
| Cl | Cl | Br | H | i-Pr | H |
| Cl | Cl | Br | H | t-Bu | H |
| Cl | Cl | Br | H | Me | Me |
| Br | Cl | Br | H | Me | H |
| Br | Cl | Br | H | Et | H |
| Br | Cl | Br | H | i-Pr | H |
| Br | Cl | Br | H | t-Bu | H |
| Br | Cl | Br | H | Me | Me |
| Cl | Br | Br | H | Me | H |
| Cl | Br | Br | H | Et | H |
| Cl | Br | Br | H | i-Pr | H |
| Cl | Br | Br | H | t-Bu | H |
| Cl | Br | Br | H | Me | Me |
| Br | Br | Br | H | Me | H |
| Br | Br | Br | H | Et | H |
| Br | Br | Br | H | i-Pr | H |
| Br | Br | Br | H | t-Bu | H |
| Br | Br | Br | H | Me | Me |
| Cl | $OCH_2CF_3$ | Br | H | Me | H |
| Cl | $OCH_2CF_3$ | Br | H | Et | H |
| Cl | $OCH_2CF_3$ | Br | H | i-Pr | H |
| Cl | $OCH_2CF_3$ | Br | H | t-Bu | H |
| Cl | $OCH_2CF_3$ | Br | H | Me | Me |
| Br | $OCH_2CF_3$ | Br | H | Me | H |
| Br | $OCH_2CF_3$ | Br | H | Et | H |
| Br | $OCH_2CF_3$ | Br | H | i-Pr | H |
| Br | $OCH_2CF_3$ | Br | H | t-Bu | H |
| Br | $OCH_2CF_3$ | Br | H | Me | Me |
| Cl | $CF_3$ | Br | F | Me | H |
| Cl | $CF_3$ | Br | F | Et | H |
| Cl | $CF_3$ | Br | F | i-Pr | H |
| Cl | $CF_3$ | Br | F | t-Bu | H |
| Cl | $CF_3$ | Br | F | Me | Me |
| Br | $CF_3$ | Br | F | Me | H |
| Br | $CF_3$ | Br | F | Et | H |
| Br | $CF_3$ | Br | F | i-Pr | H |
| Br | $CF_3$ | Br | F | t-Bu | H |
| Br | $CF_3$ | Br | F | Me | Me |
| Cl | Cl | Br | F | Me | H |
| Cl | Cl | Br | F | Et | H |
| Cl | Cl | Br | F | i-Pr | H |
| Cl | Cl | Br | F | t-Bu | H |
| Cl | Cl | Br | F | Me | Me |
| Br | Cl | Br | F | Me | H |
| Br | Cl | Br | F | Et | H |
| Br | Cl | Br | F | i-Pr | H |
| Br | Cl | Br | F | t-Bu | H |
| Br | Cl | Br | F | Me | Me |

TABLE 5-continued

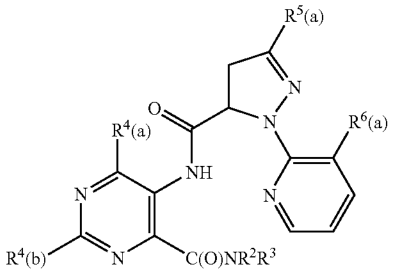

| $R^6$(a) | $R^5$(a) | $R^4$(a) | $R^4$(b) | $R^3$ | $R^2$ |
|---|---|---|---|---|---|
| Cl | Br | Br | F | Me | H |
| Cl | Br | Br | F | Et | H |
| Cl | Br | Br | F | i-Pr | H |
| Cl | Br | Br | F | t-Bu | H |
| Cl | Br | Br | F | Me | Me |
| Br | Br | Br | F | Me | H |
| Br | Br | Br | F | Et | H |
| Br | Br | Br | F | i-Pr | H |
| Br | Br | Br | F | t-Bu | H |
| Br | Br | Br | F | Me | Me |
| Cl | $OCH_2CF_3$ | Br | F | Me | H |
| Cl | $OCH_2CF_3$ | Br | F | Et | H |
| Cl | $OCH_2CF_3$ | Br | F | i-Pr | H |
| Cl | $OCH_2CF_3$ | Br | F | t-Bu | H |
| Cl | $OCH_2CF_3$ | Br | F | Me | Me |
| Br | $OCH_2CF_3$ | Br | F | Me | H |
| Br | $OCH_2CF_3$ | Br | F | Et | H |
| Br | $OCH_2CF_3$ | Br | F | i-Pr | H |
| Br | $OCH_2CF_3$ | Br | F | t-Bu | H |
| Br | $OCH_2CF_3$ | Br | F | Me | Me |
| Cl | $CF_3$ | Br | Cl | Me | H |
| Cl | $CF_3$ | Br | Cl | Et | H |
| Cl | $CF_3$ | Br | Cl | i-Pr | H |
| Cl | $CF_3$ | Br | Cl | t-Bu | H |
| Cl | $CF_3$ | Br | Cl | Me | Me |
| Br | $CF_3$ | Br | Cl | Me | H |
| Br | $CF_3$ | Br | Cl | Et | H |
| Br | $CF_3$ | Br | Cl | i-Pr | H |
| Br | $CF_3$ | Br | Cl | t-Bu | H |
| Br | $CF_3$ | Br | Cl | Me | Me |
| Cl | Cl | Br | Cl | Me | H |
| Cl | Cl | Br | Cl | Et | H |
| Cl | Cl | Br | Cl | i-Pr | H |
| Cl | Cl | Br | Cl | t-Bu | H |
| Cl | Cl | Br | Cl | Me | Me |
| Br | Cl | Br | Cl | Me | H |
| Br | Cl | Br | Cl | Et | H |
| Br | Cl | Br | Cl | i-Pr | H |
| Br | Cl | Br | Cl | t-Bu | H |
| Br | Cl | Br | Cl | Me | Me |
| Cl | Br | Br | Cl | Me | H |
| Cl | Br | Br | Cl | Et | H |
| Cl | Br | Br | Cl | i-Pr | H |
| Cl | Br | Br | Cl | t-Bu | H |
| Cl | Br | Br | Cl | Me | Me |
| Br | Br | Br | Cl | Me | H |
| Br | Br | Br | Cl | Et | H |
| Br | Br | Br | Cl | i-Pr | H |
| Br | Br | Br | Cl | t-Bu | H |
| Br | Br | Br | Cl | Me | Me |
| Cl | $OCH_2CF_3$ | Br | Cl | Me | H |
| Cl | $OCH_2CF_3$ | Br | Cl | Et | H |
| Cl | $OCH_2CF_3$ | Br | Cl | i-Pr | H |
| Cl | $OCH_2CF_3$ | Br | Cl | t-Bu | H |
| Cl | $OCH_2CF_3$ | Br | Cl | Me | Me |
| Br | $OCH_2CF_3$ | Br | Cl | Me | H |
| Br | $OCH_2CF_3$ | Br | Cl | Et | H |
| Br | $OCH_2CF_3$ | Br | Cl | i-Pr | H |
| Br | $OCH_2CF_3$ | Br | Cl | t-Bu | H |
| Br | $OCH_2CF_3$ | Br | Cl | Me | Me |

TABLE 5-continued

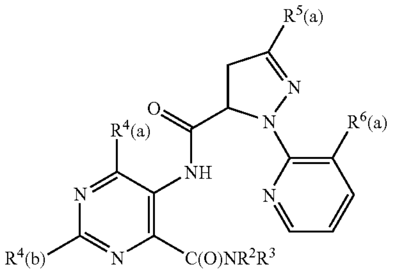

| $R^6$(a) | $R^5$(a) | $R^4$(a) | $R^4$(b) | $R^3$ | $R^2$ |
|---|---|---|---|---|---|
| Cl | $CF_3$ | Br | Br | Me | H |
| Cl | $CF_3$ | Br | Br | Et | H |
| Cl | $CF_3$ | Br | Br | i-Pr | H |
| Cl | $CF_3$ | Br | Br | t-Bu | H |
| Cl | $CF_3$ | Br | Br | Me | Me |
| Br | $CF_3$ | Br | Br | Me | H |
| Br | $CF_3$ | Br | Br | Et | H |
| Br | $CF_3$ | Br | Br | i-Pr | H |
| Br | $CF_3$ | Br | Br | t-Bu | H |
| Br | $CF_3$ | Br | Br | Me | Me |
| Cl | Cl | Br | Br | Me | H |
| Cl | Cl | Br | Br | Et | H |
| Cl | Cl | Br | Br | i-Pr | H |
| Cl | Cl | Br | Br | t-Bu | H |
| Cl | Cl | Br | Br | Me | Me |
| Br | Cl | Br | Br | Me | H |
| Br | Cl | Br | Br | Et | H |
| Br | Cl | Br | Br | i-Pr | H |
| Br | Cl | Br | Br | t-Bu | H |
| Br | Cl | Br | Br | Me | Me |
| Cl | Br | Br | Br | Me | H |
| Cl | Br | Br | Br | Et | H |
| Cl | Br | Br | Br | i-Pr | H |
| Cl | Br | Br | Br | t-Bu | H |
| Cl | Br | Br | Br | Me | Me |
| Br | Br | Br | Br | Me | H |
| Br | Br | Br | Br | Et | H |
| Br | Br | Br | Br | i-Pr | H |
| Br | Br | Br | Br | t-Bu | H |
| Br | Br | Br | Br | Me | Me |
| Cl | $OCH_2CF_3$ | Br | Br | Me | H |
| Cl | $OCH_2CF_3$ | Br | Br | Et | H |
| Cl | $OCH_2CF_3$ | Br | Br | i-Pr | H |
| Cl | $OCH_2CF_3$ | Br | Br | t-Bu | H |
| Cl | $OCH_2CF_3$ | Br | Br | Me | Me |
| Br | $OCH_2CF_3$ | Br | Br | Me | H |
| Br | $OCH_2CF_3$ | Br | Br | Et | H |
| Br | $OCH_2CF_3$ | Br | Br | i-Pr | H |
| Br | $OCH_2CF_3$ | Br | Br | t-Bu | H |
| Br | $OCH_2CF_3$ | Br | Br | Me | Me |
| Cl | $CF_3$ | Br | I | Me | H |
| Cl | $CF_3$ | Br | I | Et | H |
| Cl | $CF_3$ | Br | I | i-Pr | H |
| Cl | $CF_3$ | Br | I | t-Bu | H |
| Cl | $CF_3$ | Br | I | Me | Me |
| Br | $CF_3$ | Br | I | Me | H |
| Br | $CF_3$ | Br | I | Et | H |
| Br | $CF_3$ | Br | I | i-Pr | H |
| Br | $CF_3$ | Br | I | t-Bu | H |
| Br | $CF_3$ | Br | I | Me | Me |
| Cl | Cl | Br | I | Me | H |
| Cl | Cl | Br | I | Et | H |
| Cl | Cl | Br | I | i-Pr | H |
| Cl | Cl | Br | I | t-Bu | H |
| Cl | Cl | Br | I | Me | Me |
| Br | Cl | Br | I | Me | H |
| Br | Cl | Br | I | Et | H |
| Br | Cl | Br | I | i-Pr | H |
| Br | Cl | Br | I | t-Bu | H |
| Br | Cl | Br | I | Me | Me |

TABLE 5-continued

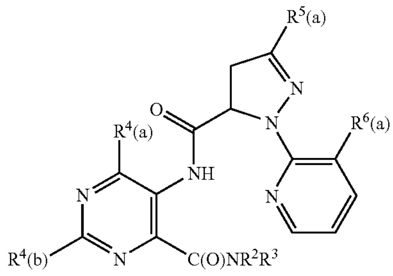

| $R^6$(a) | $R^5$(a) | $R^4$(a) | $R^4$(b) | $R^3$ | $R^2$ |
|---|---|---|---|---|---|
| Cl | Br | Br | I | Me | H |
| Cl | Br | Br | I | Et | H |
| Cl | Br | Br | I | i-Pr | H |
| Cl | Br | Br | I | t-Bu | H |
| Cl | Br | Br | I | Me | Me |
| Br | Br | Br | I | Me | H |
| Br | Br | Br | I | Et | H |
| Br | Br | Br | I | i-Pr | H |
| Br | Br | Br | I | t-Bu | H |
| Br | Br | Br | I | Me | Me |
| Cl | $OCH_2CF_3$ | Br | I | Me | H |
| Cl | $OCH_2CF_3$ | Br | I | Et | H |
| Cl | $OCH_2CF_3$ | Br | I | i-Pr | H |
| Cl | $OCH_2CF_3$ | Br | I | t-Bu | H |
| Cl | $OCH_2CF_3$ | Br | I | Me | Me |
| Br | $OCH_2CF_3$ | Br | I | Me | H |
| Br | $OCH_2CF_3$ | Br | I | Et | H |
| Br | $OCH_2CF_3$ | Br | I | i-Pr | H |
| Br | $OCH_2CF_3$ | Br | I | t-Bu | H |
| Br | $OCH_2CF_3$ | Br | I | Me | Me |
| Cl | $CF_3$ | Br | $CF_3$ | Me | H |
| Cl | $CF_3$ | Br | $CF_3$ | Et | H |
| Cl | $CF_3$ | Br | $CF_3$ | i-Pr | H |
| Cl | $CF_3$ | Br | $CF_3$ | t-Bu | H |
| Cl | $CF_3$ | Br | $CF_3$ | Me | Me |
| Br | $CF_3$ | Br | $CF_3$ | Me | H |
| Br | $CF_3$ | Br | $CF_3$ | Et | H |
| Br | $CF_3$ | Br | $CF_3$ | i-Pr | H |
| Br | $CF_3$ | Br | $CF_3$ | t-Bu | H |
| Br | $CF_3$ | Br | $CF_3$ | Me | Me |
| Cl | Cl | Br | $CF_3$ | Me | H |
| Cl | Cl | Br | $CF_3$ | Et | H |
| Cl | Cl | Br | $CF_3$ | i-Pr | H |
| Cl | Cl | Br | $CF_3$ | t-Bu | H |
| Cl | Cl | Br | $CF_3$ | Me | Me |
| Br | Cl | Br | $CF_3$ | Me | H |
| Br | Cl | Br | $CF_3$ | Et | H |
| Br | Cl | Br | $CF_3$ | i-Pr | H |
| Br | Cl | Br | $CF_3$ | t-Bu | H |
| Br | Cl | Br | $CF_3$ | Me | Me |
| Cl | Br | Br | $CF_3$ | Me | H |
| Cl | Br | Br | $CF_3$ | Et | H |
| Cl | Br | Br | $CF_3$ | i-Pr | H |
| Cl | Br | Br | $CF_3$ | t-Bu | H |
| Cl | Br | Br | $CF_3$ | Me | Me |
| Br | Br | Br | $CF_3$ | Me | H |
| Br | Br | Br | $CF_3$ | Et | H |
| Br | Br | Br | $CF_3$ | i-Pr | H |
| Br | Br | Br | $CF_3$ | t-Bu | H |
| Br | Br | Br | $CF_3$ | Me | Me |
| Cl | $OCH_2CF_3$ | Br | $CF_3$ | Me | H |
| Cl | $OCH_2CF_3$ | Br | $CF_3$ | Et | H |
| Cl | $OCH_2CF_3$ | Br | $CF_3$ | i-Pr | H |
| Cl | $OCH_2CF_3$ | Br | $CF_3$ | t-Bu | H |
| Cl | $OCH_2CF_3$ | Br | $CF_3$ | Me | Me |
| Br | $OCH_2CF_3$ | Br | $CF_3$ | Me | H |
| Br | $OCH_2CF_3$ | Br | $CF_3$ | Et | H |
| Br | $OCH_2CF_3$ | Br | $CF_3$ | i-Pr | H |
| Br | $OCH_2CF_3$ | Br | $CF_3$ | t-Bu | H |
| Br | $OCH_2CF_3$ | Br | $CF_3$ | Me | Me |

TABLE 6

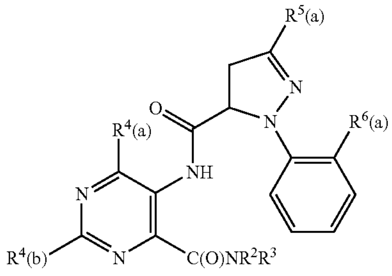

| $R^6$(a) | $R^5$(a) | $R^4$(a) | $R^4$(b) | $R^3$ | $R^2$ |
|---|---|---|---|---|---|
| Cl | $CF_3$ | $CH_3$ | H | Me | H |
| Cl | $CF_3$ | $CH_3$ | H | Et | H |
| Cl | $CF_3$ | $CH_3$ | H | i-Pr | H |
| Cl | $CF_3$ | $CH_3$ | H | t-Bu | H |
| Cl | $CF_3$ | $CH_3$ | H | Me | Me |
| Br | $CF_3$ | $CH_3$ | H | Me | H |
| Br | $CF_3$ | $CH_3$ | H | Et | H |
| Br | $CF_3$ | $CH_3$ | H | i-Pr | H |
| Br | $CF_3$ | $CH_3$ | H | t-Bu | H |
| Br | $CF_3$ | $CH_3$ | H | Me | Me |
| Cl | Cl | $CH_3$ | H | Me | H |
| Cl | Cl | $CH_3$ | H | Et | H |
| Cl | Cl | $CH_3$ | H | i-Pr | H |
| Cl | Cl | $CH_3$ | H | t-Bu | H |
| Cl | Cl | $CH_3$ | H | Me | Me |
| Br | Cl | $CH_3$ | H | Me | H |
| Br | Cl | $CH_3$ | H | Et | H |
| Br | Cl | $CH_3$ | H | i-Pr | H |
| Br | Cl | $CH_3$ | H | t-Bu | H |
| Br | Cl | $CH_3$ | H | Me | Me |
| Cl | Br | $CH_3$ | H | Me | H |
| Cl | Br | $CH_3$ | H | Et | H |
| Cl | Br | $CH_3$ | H | i-Pr | H |
| Cl | Br | $CH_3$ | H | t-Bu | H |
| Cl | Br | $CH_3$ | H | Me | Me |
| Br | Br | $CH_3$ | H | Me | H |
| Br | Br | $CH_3$ | H | Et | H |
| Br | Br | $CH_3$ | H | i-Pr | H |
| Br | Br | $CH_3$ | H | t-Bu | H |
| Br | Br | $CH_3$ | H | Me | Me |
| Cl | $OCH_2CF_3$ | $CH_3$ | H | Me | H |
| Cl | $OCH_2CF_3$ | $CH_3$ | H | Et | H |
| Cl | $OCH_2CF_3$ | $CH_3$ | H | i-Pr | H |
| Cl | $OCH_2CF_3$ | $CH_3$ | H | t-Bu | H |
| Cl | $OCH_2CF_3$ | $CH_3$ | H | Me | Me |
| Br | $OCH_2CF_3$ | $CH_3$ | H | Me | H |
| Br | $OCH_2CF_3$ | $CH_3$ | H | Et | H |
| Br | $OCH_2CF_3$ | $CH_3$ | H | i-Pr | H |
| Br | $OCH_2CF_3$ | $CH_3$ | H | t-Bu | H |
| Br | $OCH_2CF_3$ | $CH_3$ | H | Me | Me |
| Cl | $CF_3$ | $CH_3$ | F | Me | H |
| Cl | $CF_3$ | $CH_3$ | F | Et | H |
| Cl | $CF_3$ | $CH_3$ | F | i-Pr | H |
| Cl | $CF_3$ | $CH_3$ | F | t-Bu | H |
| Cl | $CF_3$ | $CH_3$ | F | Me | Me |
| Br | $CF_3$ | $CH_3$ | F | Me | H |
| Br | $CF_3$ | $CH_3$ | F | Et | H |
| Br | $CF_3$ | $CH_3$ | F | i-Pr | H |
| Br | $CF_3$ | $CH_3$ | F | t-Bu | H |
| Br | $CF_3$ | $CH_3$ | F | Me | Me |
| Cl | Cl | $CH_3$ | F | Me | H |
| Cl | Cl | $CH_3$ | F | Et | H |
| Cl | Cl | $CH_3$ | F | i-Pr | H |
| Cl | Cl | $CH_3$ | F | t-Bu | H |
| Cl | Cl | $CH_3$ | F | Me | Me |
| Br | Cl | $CH_3$ | F | Me | H |
| Br | Cl | $CH_3$ | F | Et | H |
| Br | Cl | $CH_3$ | F | i-Pr | H |
| Br | Cl | $CH_3$ | F | t-Bu | H |
| Br | Cl | $CH_3$ | F | Me | Me |
| Cl | Br | $CH_3$ | F | Me | H |
| Cl | Br | $CH_3$ | F | Et | H |
| Cl | Br | $CH_3$ | F | i-Pr | H |

TABLE 6-continued

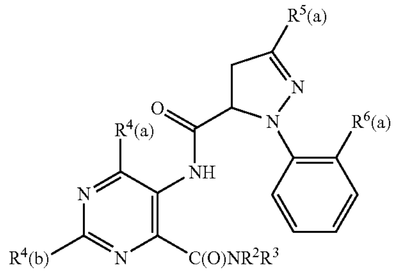

| $R^6(a)$ | $R^5(a)$ | $R^4(a)$ | $R^4(b)$ | $R^3$ | $R^2$ |
|---|---|---|---|---|---|
| Cl | Br | $CH_3$ | F | t-Bu | H |
| Cl | Br | $CH_3$ | F | Me | Me |
| Br | Br | $CH_3$ | F | Me | H |
| Br | Br | $CH_3$ | F | Et | H |
| Br | Br | $CH_3$ | F | i-Pr | H |
| Br | Br | $CH_3$ | F | t-Bu | H |
| Br | Br | $CH_3$ | F | Me | Me |
| Cl | $OCH_2CF_3$ | $CH_3$ | F | Me | H |
| Cl | $OCH_2CF_3$ | $CH_3$ | F | Et | H |
| Cl | $OCH_2CF_3$ | $CH_3$ | F | i-Pr | H |
| Cl | $OCH_2CF_3$ | $CH_3$ | F | t-Bu | H |
| Cl | $OCH_2CF_3$ | $CH_3$ | F | Me | Me |
| Br | $OCH_2CF_3$ | $CH_3$ | F | Me | H |
| Br | $OCH_2CF_3$ | $CH_3$ | F | Et | H |
| Br | $OCH_2CF_3$ | $CH_3$ | F | i-Pr | H |
| Br | $OCH_2CF_3$ | $CH_3$ | F | t-Bu | H |
| Br | $OCH_2CF_3$ | $CH_3$ | F | Me | Me |
| Cl | $CF_3$ | $CH_3$ | Cl | Me | H |
| Cl | $CF_3$ | $CH_3$ | Cl | Et | H |
| Cl | $CF_3$ | $CH_3$ | Cl | i-Pr | H |
| Cl | $CF_3$ | $CH_3$ | Cl | t-Bu | H |
| Cl | $CF_3$ | $CH_3$ | Cl | Me | Me |
| Br | $CF_3$ | $CH_3$ | Cl | Me | H |
| Br | $CF_3$ | $CH_3$ | Cl | Et | H |
| Br | $CF_3$ | $CH_3$ | Cl | i-Pr | H |
| Br | $CF_3$ | $CH_3$ | Cl | t-Bu | H |
| Br | $CF_3$ | $CH_3$ | Cl | Me | Me |
| Cl | Cl | $CH_3$ | Cl | Me | H |
| Cl | Cl | $CH_3$ | Cl | Et | H |
| Cl | Cl | $CH_3$ | Cl | i-Pr | H |
| Cl | Cl | $CH_3$ | Cl | t-Bu | H |
| Cl | Cl | $CH_3$ | Cl | Me | Me |
| Br | Cl | $CH_3$ | Cl | Me | H |
| Br | Cl | $CH_3$ | Cl | Et | H |
| Br | Cl | $CH_3$ | Cl | i-Pr | H |
| Br | Cl | $CH_3$ | Cl | t-Bu | H |
| Br | Cl | $CH_3$ | Cl | Me | Me |
| Cl | Br | $CH_3$ | Cl | Me | H |
| Cl | Br | $CH_3$ | Cl | Et | H |
| Cl | Br | $CH_3$ | Cl | i-Pr | H |
| Cl | Br | $CH_3$ | Cl | t-Bu | H |
| Cl | Br | $CH_3$ | Cl | Me | Me |
| Br | Br | $CH_3$ | Cl | Me | H |
| Br | Br | $CH_3$ | Cl | Et | H |
| Br | Br | $CH_3$ | Cl | i-Pr | H |
| Br | Br | $CH_3$ | Cl | t-Bu | H |
| Br | Br | $CH_3$ | Cl | Me | Me |
| Cl | $OCH_2CF_3$ | $CH_3$ | Cl | Me | H |
| Cl | $OCH_2CF_3$ | $CH_3$ | Cl | Et | H |
| Cl | $OCH_2CF_3$ | $CH_3$ | Cl | i-Pr | H |
| Cl | $OCH_2CF_3$ | $CH_3$ | Cl | t-Bu | H |
| Cl | $OCH_2CF_3$ | $CH_3$ | Cl | Me | Me |
| Br | $OCH_2CF_3$ | $CH_3$ | Cl | Me | H |
| Br | $OCH_2CF_3$ | $CH_3$ | Cl | Et | H |
| Br | $OCH_2CF_3$ | $CH_3$ | Cl | i-Pr | H |
| Br | $OCH_2CF_3$ | $CH_3$ | Cl | t-Bu | H |
| Br | $OCH_2CF_3$ | $CH_3$ | Cl | Me | Me |
| Cl | $CF_3$ | $CH_3$ | Br | Me | H |
| Cl | $CF_3$ | $CH_3$ | Br | Et | H |
| Cl | $CF_3$ | $CH_3$ | Br | i-Pr | H |
| Cl | $CF_3$ | $CH_3$ | Br | t-Bu | H |
| Cl | $CF_3$ | $CH_3$ | Br | Me | Me |
| Br | $CF_3$ | $CH_3$ | Br | Me | H |

TABLE 6-continued

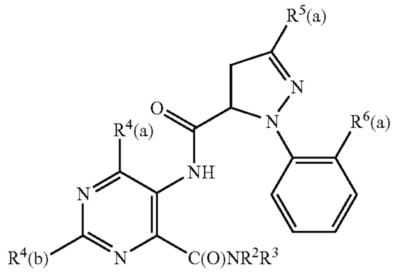

| $R^6(a)$ | $R^5(a)$ | $R^4(a)$ | $R^4(b)$ | $R^3$ | $R^2$ |
|---|---|---|---|---|---|
| Br | $CF_3$ | $CH_3$ | Br | Et | H |
| Br | $CF_3$ | $CH_3$ | Br | i-Pr | H |
| Br | $CF_3$ | $CH_3$ | Br | t-Bu | H |
| Br | $CF_3$ | $CH_3$ | Br | Me | Me |
| Cl | Cl | $CH_3$ | Br | Me | H |
| Cl | Cl | $CH_3$ | Br | Et | H |
| Cl | Cl | $CH_3$ | Br | i-Pr | H |
| Cl | Cl | $CH_3$ | Br | t-Bu | H |
| Cl | Cl | $CH_3$ | Br | Me | Me |
| Br | Cl | $CH_3$ | Br | Me | H |
| Br | Cl | $CH_3$ | Br | Et | H |
| Br | Cl | $CH_3$ | Br | i-Pr | H |
| Br | Cl | $CH_3$ | Br | t-Bu | H |
| Br | Cl | $CH_3$ | Br | Me | Me |
| Cl | Br | $CH_3$ | Br | Me | H |
| Cl | Br | $CH_3$ | Br | Et | H |
| Cl | Br | $CH_3$ | Br | i-Pr | H |
| Cl | Br | $CH_3$ | Br | t-Bu | H |
| Cl | Br | $CH_3$ | Br | Me | Me |
| Br | Br | $CH_3$ | Br | Me | H |
| Br | Br | $CH_3$ | Br | Et | H |
| Br | Br | $CH_3$ | Br | i-Pr | H |
| Br | Br | $CH_3$ | Br | t-Bu | H |
| Br | Br | $CH_3$ | Br | Me | Me |
| Cl | $OCH_2CF_3$ | $CH_3$ | Br | Me | H |
| Cl | $OCH_2CF_3$ | $CH_3$ | Br | Et | H |
| Cl | $OCH_2CF_3$ | $CH_3$ | Br | i-Pr | H |
| Cl | $OCH_2CF_3$ | $CH_3$ | Br | t-Bu | H |
| Cl | $OCH_2CF_3$ | $CH_3$ | Br | Me | Me |
| Br | $OCH_2CF_3$ | $CH_3$ | Br | Me | H |
| Br | $OCH_2CF_3$ | $CH_3$ | Br | Et | H |
| Br | $OCH_2CF_3$ | $CH_3$ | Br | i-Pr | H |
| Br | $OCH_2CF_3$ | $CH_3$ | Br | t-Bu | H |
| Br | $OCH_2CF_3$ | $CH_3$ | Br | Me | Me |
| Cl | $CF_3$ | $CH_3$ | I | Me | H |
| Cl | $CF_3$ | $CH_3$ | I | Et | H |
| Cl | $CF_3$ | $CH_3$ | I | i-Pr | H |
| Cl | $CF_3$ | $CH_3$ | I | t-Bu | H |
| Cl | $CF_3$ | $CH_3$ | I | Me | Me |
| Br | $CF_3$ | $CH_3$ | I | Me | H |
| Br | $CF_3$ | $CH_3$ | I | Et | H |
| Br | $CF_3$ | $CH_3$ | I | i-Pr | H |
| Br | $CF_3$ | $CH_3$ | I | t-Bu | H |
| Br | $CF_3$ | $CH_3$ | I | Me | Me |
| Cl | Cl | $CH_3$ | I | Me | H |
| Cl | Cl | $CH_3$ | I | Et | H |
| Cl | Cl | $CH_3$ | I | i-Pr | H |
| Cl | Cl | $CH_3$ | I | t-Bu | H |
| Cl | Cl | $CH_3$ | I | Me | Me |
| Br | Cl | $CH_3$ | I | Me | H |
| Br | Cl | $CH_3$ | I | Et | H |
| Br | Cl | $CH_3$ | I | i-Pr | H |
| Br | Cl | $CH_3$ | I | t-Bu | H |
| Br | Cl | $CH_3$ | I | Me | Me |
| Cl | Br | $CH_3$ | I | Me | H |
| Cl | Br | $CH_3$ | I | Et | H |
| Cl | Br | $CH_3$ | I | i-Pr | H |
| Cl | Br | $CH_3$ | I | t-Bu | H |
| Cl | Br | $CH_3$ | I | Me | Me |
| Br | Br | $CH_3$ | I | Me | H |
| Br | Br | $CH_3$ | I | Et | H |
| Br | Br | $CH_3$ | I | i-Pr | H |
| Br | Br | $CH_3$ | I | t-Bu | H |

TABLE 6-continued

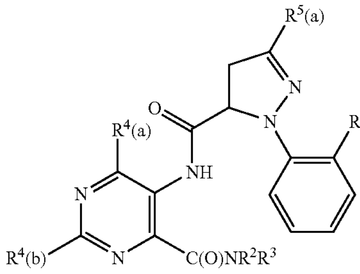

| $R^6(a)$ | $R^5(a)$ | $R^4(a)$ | $R^4(b)$ | $R^3$ | $R^2$ |
|---|---|---|---|---|---|
| Br | Br | $CH_3$ | I | Me | Me |
| Cl | $OCH_2CF_3$ | $CH_3$ | I | Me | H |
| Cl | $OCH_2CF_3$ | $CH_3$ | I | Et | H |
| Cl | $OCH_2CF_3$ | $CH_3$ | I | i-Pr | H |
| Cl | $OCH_2CF_3$ | $CH_3$ | I | t-Bu | H |
| Cl | $OCH_2CF_3$ | $CH_3$ | I | Me | Me |
| Br | $OCH_2CF_3$ | $CH_3$ | I | Me | H |
| Br | $OCH_2CF_3$ | $CH_3$ | I | Et | H |
| Br | $OCH_2CF_3$ | $CH_3$ | I | i-Pr | H |
| Br | $OCH_2CF_3$ | $CH_3$ | I | t-Bu | H |
| Br | $OCH_2CF_3$ | $CH_3$ | I | Me | Me |
| Cl | $CF_3$ | $CH_3$ | $CF_3$ | Me | H |
| Cl | $CF_3$ | $CH_3$ | $CF_3$ | Et | H |
| Cl | $CF_3$ | $CH_3$ | $CF_3$ | i-Pr | H |
| Cl | $CF_3$ | $CH_3$ | $CF_3$ | t-Bu | H |
| Cl | $CF_3$ | $CH_3$ | $CF_3$ | Me | Me |
| Br | $CF_3$ | $CH_3$ | $CF_3$ | Me | H |
| Br | $CF_3$ | $CH_3$ | $CF_3$ | Et | H |
| Br | $CF_3$ | $CH_3$ | $CF_3$ | i-Pr | H |
| Br | $CF_3$ | $CH_3$ | $CF_3$ | t-Bu | H |
| Br | $CF_3$ | $CH_3$ | $CF_3$ | Me | Me |
| Cl | Cl | $CH_3$ | $CF_3$ | Me | H |
| Cl | Cl | $CH_3$ | $CF_3$ | Et | H |
| Cl | Cl | $CH_3$ | $CF_3$ | i-Pr | H |
| Cl | Cl | $CH_3$ | $CF_3$ | t-Bu | H |
| Cl | Cl | $CH_3$ | $CF_3$ | Me | Me |
| Br | Cl | $CH_3$ | $CF_3$ | Me | H |
| Br | Cl | $CH_3$ | $CF_3$ | Et | H |
| Br | Cl | $CH_3$ | $CF_3$ | i-Pr | H |
| Br | Cl | $CH_3$ | $CF_3$ | t-Bu | H |
| Br | Cl | $CH_3$ | $CF_3$ | Me | Me |
| Cl | Br | $CH_3$ | $CF_3$ | Me | H |
| Cl | Br | $CH_3$ | $CF_3$ | Et | H |
| Cl | Br | $CH_3$ | $CF_3$ | i-Pr | H |
| Cl | Br | $CH_3$ | $CF_3$ | t-Bu | H |
| Cl | Br | $CH_3$ | $CF_3$ | Me | Me |
| Br | Br | $CH_3$ | $CF_3$ | Me | H |
| Br | Br | $CH_3$ | $CF_3$ | Et | H |
| Br | Br | $CH_3$ | $CF_3$ | i-Pr | H |
| Br | Br | $CH_3$ | $CF_3$ | t-Bu | H |
| Br | Br | $CH_3$ | $CF_3$ | Me | Me |
| Cl | $OCH_2CF_3$ | $CH_3$ | $CF_3$ | Me | H |
| Cl | $OCH_2CF_3$ | $CH_3$ | $CF_3$ | Et | H |
| Cl | $OCH_2CF_3$ | $CH_3$ | $CF_3$ | i-Pr | H |
| Cl | $OCH_2CF_3$ | $CH_3$ | $CF_3$ | t-Bu | H |
| Cl | $OCH_2CF_3$ | $CH_3$ | $CF_3$ | Me | Me |
| Br | $OCH_2CF_3$ | $CH_3$ | $CF_3$ | Me | H |
| Br | $OCH_2CF_3$ | $CH_3$ | $CF_3$ | Et | H |
| Br | $OCH_2CF_3$ | $CH_3$ | $CF_3$ | i-Pr | H |
| Br | $OCH_2CF_3$ | $CH_3$ | $CF_3$ | t-Bu | H |
| Br | $OCH_2CF_3$ | $CH_3$ | $CF_3$ | Me | Me |
| Cl | Cl | $CH_3$ | Cl | n-Pr | H |
| Cl | Cl | $CH_3$ | Cl | n-Bu | H |
| Cl | Cl | $CH_3$ | Cl | s-Bu | H |
| Cl | Cl | $CH_3$ | Cl | i-Bu | H |
| Cl | Cl | $CH_3$ | Cl | Et | Me |
| Cl | $CF_3$ | F | H | Me | H |
| Cl | $CF_3$ | F | H | Et | H |
| Cl | $CF_3$ | F | H | i-Pr | H |
| Cl | $CF_3$ | F | H | t-Bu | H |
| Cl | $CF_3$ | F | H | Me | Me |
| Br | $CF_3$ | F | H | Me | H |
| Br | $CF_3$ | F | H | Et | H |

TABLE 6-continued

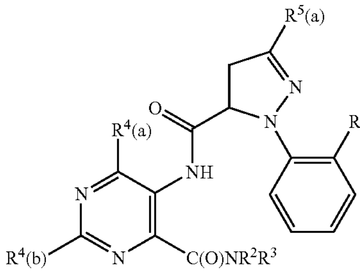

| $R^6(a)$ | $R^5(a)$ | $R^4(a)$ | $R^4(b)$ | $R^3$ | $R^2$ |
|---|---|---|---|---|---|
| Br | $CF_3$ | F | H | i-Pr | H |
| Br | $CF_3$ | F | H | t-Bu | H |
| Br | $CF_3$ | F | H | Me | Me |
| Cl | Cl | F | H | Me | H |
| Cl | Cl | F | H | Et | H |
| Cl | Cl | F | H | i-Pr | H |
| Cl | Cl | F | H | t-Bu | H |
| Cl | Cl | F | H | Me | Me |
| Br | Cl | F | H | Me | H |
| Br | Cl | F | H | Et | H |
| Br | Cl | F | H | i-Pr | H |
| Br | Cl | F | H | t-Bu | H |
| Br | Cl | F | H | Me | Me |
| Cl | Br | F | H | Me | H |
| Cl | Br | F | H | Et | H |
| Cl | Br | F | H | i-Pr | H |
| Cl | Br | F | H | t-Bu | H |
| Cl | Br | F | H | Me | Me |
| Br | Br | F | H | Me | H |
| Br | Br | F | H | Et | H |
| Br | Br | F | H | i-Pr | H |
| Br | Br | F | H | t-Bu | H |
| Br | Br | F | H | Me | Me |
| Cl | $OCH_2CF_3$ | F | H | Me | H |
| Cl | $OCH_2CF_3$ | F | H | Et | H |
| Cl | $OCH_2CF_3$ | F | H | i-Pr | H |
| Cl | $OCH_2CF_3$ | F | H | t-Bu | H |
| Cl | $OCH_2CF_3$ | F | H | Me | Me |
| Br | $OCH_2CF_3$ | F | H | Me | H |
| Br | $OCH_2CF_3$ | F | H | Et | H |
| Br | $OCH_2CF_3$ | F | H | i-Pr | H |
| Br | $OCH_2CF_3$ | F | H | t-Bu | H |
| Br | $OCH_2CF_3$ | F | H | Me | Me |
| Cl | $CF_3$ | F | F | Me | H |
| Cl | $CF_3$ | F | F | Et | H |
| Cl | $CF_3$ | F | F | i-Pr | H |
| Cl | $CF_3$ | F | F | t-Bu | H |
| Cl | $CF_3$ | F | F | Me | Me |
| Br | $CF_3$ | F | F | Me | H |
| Br | $CF_3$ | F | F | Et | H |
| Br | $CF_3$ | F | F | i-Pr | H |
| Br | $CF_3$ | F | F | t-Bu | H |
| Br | $CF_3$ | F | F | Me | Me |
| Cl | Cl | F | F | Me | H |
| Cl | Cl | F | F | Et | H |
| Cl | Cl | F | F | i-Pr | H |
| Cl | Cl | F | F | t-Bu | H |
| Cl | Cl | F | F | Me | Me |
| Br | Cl | F | F | Me | H |
| Br | Cl | F | F | Et | H |
| Br | Cl | F | F | i-Pr | H |
| Br | Cl | F | F | t-Bu | H |
| Br | Cl | F | F | Me | Me |
| Cl | Br | F | F | Me | H |
| Cl | Br | F | F | Et | H |
| Cl | Br | F | F | i-Pr | H |
| Cl | Br | F | F | t-Bu | H |
| Cl | Br | F | F | Me | Me |
| Br | Br | F | F | Me | H |
| Br | Br | F | F | Et | H |
| Br | Br | F | F | i-Pr | H |
| Br | Br | F | F | t-Bu | H |
| Br | Br | F | F | Me | Me |

TABLE 6-continued

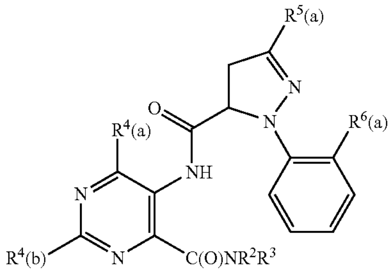

| R⁶(a) | R⁵(a) | R⁴(a) | R⁴(b) | R³ | R² |
|---|---|---|---|---|---|
| Cl | $OCH_2CF_3$ | F | F | Me | H |
| Cl | $OCH_2CF_3$ | F | F | Et | H |
| Cl | $OCH_2CF_3$ | F | F | i-Pr | H |
| Cl | $OCH_2CF_3$ | F | F | t-Bu | H |
| Cl | $OCH_2CF_3$ | F | F | Me | Me |
| Br | $OCH_2CF_3$ | F | F | Me | H |
| Br | $OCH_2CF_3$ | F | F | Et | H |
| Br | $OCH_2CF_3$ | F | F | i-Pr | H |
| Br | $OCH_2CF_3$ | F | F | t-Bu | H |
| Br | $OCH_2CF_3$ | F | F | Me | Me |
| Cl | $CF_3$ | F | Cl | Me | H |
| Cl | $CF_3$ | F | Cl | Et | H |
| Cl | $CF_3$ | F | Cl | i-Pr | H |
| Cl | $CF_3$ | F | Cl | t-Bu | H |
| Cl | $CF_3$ | F | Cl | Me | Me |
| Br | $CF_3$ | F | Cl | Me | H |
| Br | $CF_3$ | F | Cl | Et | H |
| Br | $CF_3$ | F | Cl | i-Pr | H |
| Br | $CF_3$ | F | Cl | t-Bu | H |
| Br | $CF_3$ | F | Cl | Me | Me |
| Cl | Cl | F | Cl | Me | H |
| Cl | Cl | F | Cl | Et | H |
| Cl | Cl | F | Cl | i-Pr | H |
| Cl | Cl | F | Cl | t-Bu | H |
| Cl | Cl | F | Cl | Me | Me |
| Br | Cl | F | Cl | Me | H |
| Br | Cl | F | Cl | Et | H |
| Br | Cl | F | Cl | i-Pr | H |
| Br | Cl | F | Cl | t-Bu | H |
| Br | Cl | F | Cl | Me | Me |
| Cl | Br | F | Cl | Me | H |
| Cl | Br | F | Cl | Et | H |
| Cl | Br | F | Cl | i-Pr | H |
| Cl | Br | F | Cl | t-Bu | H |
| Cl | Br | F | Cl | Me | Me |
| Br | Br | F | Cl | Me | H |
| Br | Br | F | Cl | Et | H |
| Br | Br | F | Cl | i-Pr | H |
| Br | Br | F | Cl | t-Bu | H |
| Br | Br | F | Cl | Me | Me |
| Cl | $OCH_2CF_3$ | F | Cl | Me | H |
| Cl | $OCH_2CF_3$ | F | Cl | Et | H |
| Cl | $OCH_2CF_3$ | F | Cl | i-Pr | H |
| Cl | $OCH_2CF_3$ | F | Cl | t-Bu | H |
| Cl | $OCH_2CF_3$ | F | Cl | Me | Me |
| Br | $OCH_2CF_3$ | F | Cl | Me | H |
| Br | $OCH_2CF_3$ | F | Cl | Et | H |
| Br | $OCH_2CF_3$ | F | Cl | i-Pr | H |
| Br | $OCH_2CF_3$ | F | Cl | t-Bu | H |
| Br | $OCH_2CF_3$ | F | Cl | Me | Me |
| Cl | $CF_3$ | F | Br | Me | H |
| Cl | $CF_3$ | F | Br | Et | H |
| Cl | $CF_3$ | F | Br | i-Pr | H |
| Cl | $CF_3$ | F | Br | t-Bu | H |
| Cl | $CF_3$ | F | Br | Me | Me |
| Br | $CF_3$ | F | Br | Me | H |
| Br | $CF_3$ | F | Br | Et | H |
| Br | $CF_3$ | F | Br | i-Pr | H |
| Br | $CF_3$ | F | Br | t-Bu | H |
| Br | $CF_3$ | F | Br | Me | Me |
| Cl | Cl | F | Br | Me | H |
| Cl | Cl | F | Br | Et | H |
| Cl | Cl | F | Br | i-Pr | H |

TABLE 6-continued

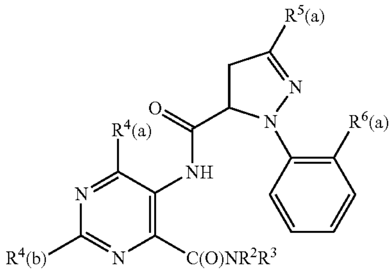

| R⁶(a) | R⁵(a) | R⁴(a) | R⁴(b) | R³ | R² |
|---|---|---|---|---|---|
| Cl | Cl | F | Br | t-Bu | H |
| Cl | Cl | F | Br | Me | Me |
| Br | Cl | F | Br | Me | H |
| Br | Cl | F | Br | Et | H |
| Br | Cl | F | Br | i-Pr | H |
| Br | Cl | F | Br | t-Bu | H |
| Br | Cl | F | Br | Me | Me |
| Cl | Br | F | Br | Me | H |
| Cl | Br | F | Br | Et | H |
| Cl | Br | F | Br | i-Pr | H |
| Cl | Br | F | Br | t-Bu | H |
| Cl | Br | F | Br | Me | Me |
| Br | Br | F | Br | Me | H |
| Br | Br | F | Br | Et | H |
| Br | Br | F | Br | i-Pr | H |
| Br | Br | F | Br | t-Bu | H |
| Br | Br | F | Br | Me | Me |
| Cl | $OCH_2CF_3$ | F | Br | Me | H |
| Cl | $OCH_2CF_3$ | F | Br | Et | H |
| Cl | $OCH_2CF_3$ | F | Br | i-Pr | H |
| Cl | $OCH_2CF_3$ | F | Br | t-Bu | H |
| Cl | $OCH_2CF_3$ | F | Br | Me | Me |
| Br | $OCH_2CF_3$ | F | Br | Me | H |
| Br | $OCH_2CF_3$ | F | Br | Et | H |
| Br | $OCH_2CF_3$ | F | Br | i-Pr | H |
| Br | $OCH_2CF_3$ | F | Br | t-Bu | H |
| Br | $OCH_2CF_3$ | F | Br | Me | Me |
| Cl | $CF_3$ | F | I | Me | H |
| Cl | $CF_3$ | F | I | Et | H |
| Cl | $CF_3$ | F | I | i-Pr | H |
| Cl | $CF_3$ | F | I | t-Bu | H |
| Cl | $CF_3$ | F | I | Me | Me |
| Br | $CF_3$ | F | I | Me | H |
| Br | $CF_3$ | F | I | Et | H |
| Br | $CF_3$ | F | I | i-Pr | H |
| Br | $CF_3$ | F | I | t-Bu | H |
| Br | $CF_3$ | F | I | Me | Me |
| Cl | Cl | F | I | Me | H |
| Cl | Cl | F | I | Et | H |
| Cl | Cl | F | I | i-Pr | H |
| Cl | Cl | F | I | t-Bu | H |
| Cl | Cl | F | I | Me | Me |
| Br | Cl | F | I | Me | H |
| Br | Cl | F | I | Et | H |
| Br | Cl | F | I | i-Pr | H |
| Br | Cl | F | I | t-Bu | H |
| Br | Cl | F | I | Me | Me |
| Cl | Br | F | I | Me | H |
| Cl | Br | F | I | Et | H |
| Cl | Br | F | I | i-Pr | H |
| Cl | Br | F | I | t-Bu | H |
| Cl | Br | F | I | Me | Me |
| Br | Br | F | I | Me | H |
| Br | Br | F | I | Et | H |
| Br | Br | F | I | i-Pr | H |
| Br | Br | F | I | t-Bu | H |
| Br | Br | F | I | Me | Me |
| Cl | $OCH_2CF_3$ | F | I | Me | H |
| Cl | $OCH_2CF_3$ | F | I | Et | H |
| Cl | $OCH_2CF_3$ | F | I | i-Pr | H |
| Cl | $OCH_2CF_3$ | F | I | t-Bu | H |
| Cl | $OCH_2CF_3$ | F | I | Me | Me |
| Br | $OCH_2CF_3$ | F | I | Me | H |

TABLE 6-continued

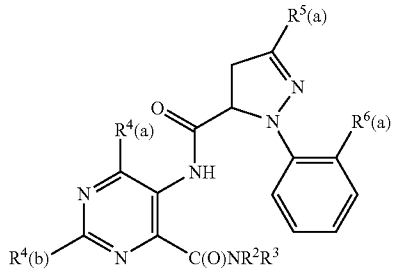

| $R^6$(a) | $R^5$(a) | $R^4$(a) | $R^4$(b) | $R^3$ | $R^2$ |
|---|---|---|---|---|---|
| Br | $OCH_2CF_3$ | F | I | Et | H |
| Br | $OCH_2CF_3$ | F | I | i-Pr | H |
| Br | $OCH_2CF_3$ | F | I | t-Bu | H |
| Br | $OCH_2CF_3$ | F | I | Me | Me |
| Cl | $CF_3$ | F | $CF_3$ | Me | H |
| Cl | $CF_3$ | F | $CF_3$ | Et | H |
| Cl | $CF_3$ | F | $CF_3$ | i-Pr | H |
| Cl | $CF_3$ | F | $CF_3$ | t-Bu | H |
| Cl | $CF_3$ | F | $CF_3$ | Me | Me |
| Br | $CF_3$ | F | $CF_3$ | Me | H |
| Br | $CF_3$ | F | $CF_3$ | Et | H |
| Br | $CF_3$ | F | $CF_3$ | i-Pr | H |
| Br | $CF_3$ | F | $CF_3$ | t-Bu | H |
| Br | $CF_3$ | F | $CF_3$ | Me | Me |
| Cl | Cl | F | $CF_3$ | Me | H |
| Cl | Cl | F | $CF_3$ | Et | H |
| Cl | Cl | F | $CF_3$ | i-Pr | H |
| Cl | Cl | F | $CF_3$ | t-Bu | H |
| Cl | Cl | F | $CF_3$ | Me | Me |
| Br | Cl | F | $CF_3$ | Me | H |
| Br | Cl | F | $CF_3$ | Et | H |
| Br | Cl | F | $CF_3$ | i-Pr | H |
| Br | Cl | F | $CF_3$ | t-Bu | H |
| Br | Cl | F | $CF_3$ | Me | Me |
| Cl | Br | F | $CF_3$ | Me | H |
| Cl | Br | F | $CF_3$ | Et | H |
| Cl | Br | F | $CF_3$ | i-Pr | H |
| Cl | Br | F | $CF_3$ | t-Bu | H |
| Cl | Br | F | $CF_3$ | Me | Me |
| Br | Br | F | $CF_3$ | Me | H |
| Br | Br | F | $CF_3$ | Et | H |
| Br | Br | F | $CF_3$ | i-Pr | H |
| Br | Br | F | $CF_3$ | t-Bu | H |
| Br | Br | F | $CF_3$ | Me | Me |
| Cl | $OCH_2CF_3$ | F | $CF_3$ | Me | H |
| Cl | $OCH_2CF_3$ | F | $CF_3$ | Et | H |
| Cl | $OCH_2CF_3$ | F | $CF_3$ | i-Pr | H |
| Cl | $OCH_2CF_3$ | F | $CF_3$ | t-Bu | H |
| Cl | $OCH_2CF_3$ | F | $CF_3$ | Me | Me |
| Br | $OCH_2CF_3$ | F | $CF_3$ | Me | H |
| Br | $OCH_2CF_3$ | F | $CF_3$ | Et | H |
| Br | $OCH_2CF_3$ | F | $CF_3$ | i-Pr | H |
| Br | $OCH_2CF_3$ | F | $CF_3$ | t-Bu | H |
| Br | $OCH_2CF_3$ | F | $CF_3$ | Me | Me |
| Cl | $CF_3$ | Cl | H | Me | H |
| Cl | $CF_3$ | Cl | H | Et | H |
| Cl | $CF_3$ | Cl | H | i-Pr | H |
| Cl | $CF_3$ | Cl | H | t-Bu | H |
| Cl | $CF_3$ | Cl | H | Me | Me |
| Br | $CF_3$ | Cl | H | Me | H |
| Br | $CF_3$ | Cl | H | Et | H |
| Br | $CF_3$ | Cl | H | i-Pr | H |
| Br | $CF_3$ | Cl | H | t-Bu | H |
| Br | $CF_3$ | Cl | H | Me | Me |
| Cl | Cl | Cl | H | Me | H |
| Cl | Cl | Cl | H | Et | H |
| Cl | Cl | Cl | H | i-Pr | H |
| Cl | Cl | Cl | H | t-Bu | H |
| Cl | Cl | Cl | H | Me | Me |
| Br | Cl | Cl | H | Me | H |
| Br | Cl | Cl | H | Et | H |
| Br | Cl | Cl | H | i-Pr | H |
| Br | Cl | Cl | H | t-Bu | H |

TABLE 6-continued

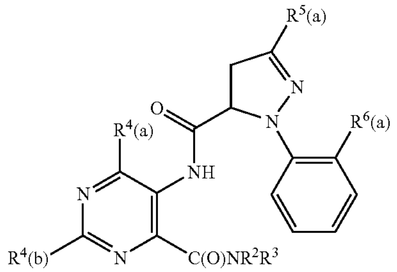

| $R^6$(a) | $R^5$(a) | $R^4$(a) | $R^4$(b) | $R^3$ | $R^2$ |
|---|---|---|---|---|---|
| Br | Cl | Cl | H | Me | Me |
| Cl | Br | Cl | H | Me | H |
| Cl | Br | Cl | H | Et | H |
| Cl | Br | Cl | H | i-Pr | H |
| Cl | Br | Cl | H | t-Bu | H |
| Cl | Br | Cl | H | Me | Me |
| Br | Br | Cl | H | Me | H |
| Br | Br | Cl | H | Et | H |
| Br | Br | Cl | H | i-Pr | H |
| Br | Br | Cl | H | t-Bu | H |
| Br | Br | Cl | H | Me | Me |
| Cl | $OCH_2CF_3$ | Cl | H | Me | H |
| Cl | $OCH_2CF_3$ | Cl | H | Et | H |
| Cl | $OCH_2CF_3$ | Cl | H | i-Pr | H |
| Cl | $OCH_2CF_3$ | Cl | H | t-Bu | H |
| Cl | $OCH_2CF_3$ | Cl | H | Me | Me |
| Br | $OCH_2CF_3$ | Cl | H | Me | H |
| Br | $OCH_2CF_3$ | Cl | H | Et | H |
| Br | $OCH_2CF_3$ | Cl | H | i-Pr | H |
| Br | $OCH_2CF_3$ | Cl | H | t-Bu | H |
| Br | $OCH_2CF_3$ | Cl | H | Me | Me |
| Cl | $CF_3$ | Cl | F | Me | H |
| Cl | $CF_3$ | Cl | F | Et | H |
| Cl | $CF_3$ | Cl | F | i-Pr | H |
| Cl | $CF_3$ | Cl | F | t-Bu | H |
| Cl | $CF_3$ | Cl | F | Me | Me |
| Br | $CF_3$ | Cl | F | Me | H |
| Br | $CF_3$ | Cl | F | Et | H |
| Br | $CF_3$ | Cl | F | i-Pr | H |
| Br | $CF_3$ | Cl | F | t-Bu | H |
| Br | $CF_3$ | Cl | F | Me | Me |
| Cl | Cl | Cl | F | Me | H |
| Cl | Cl | Cl | F | Et | H |
| Cl | Cl | Cl | F | i-Pr | H |
| Cl | Cl | Cl | F | t-Bu | H |
| Cl | Cl | Cl | F | Me | Me |
| Br | Cl | Cl | F | Me | H |
| Br | Cl | Cl | F | Et | H |
| Br | Cl | Cl | F | i-Pr | H |
| Br | Cl | Cl | F | t-Bu | H |
| Br | Cl | Cl | F | Me | Me |
| Cl | Br | Cl | F | Me | H |
| Cl | Br | Cl | F | Et | H |
| Cl | Br | Cl | F | i-Pr | H |
| Cl | Br | Cl | F | t-Bu | H |
| Cl | Br | Cl | F | Me | Me |
| Br | Br | Cl | F | Me | H |
| Br | Br | Cl | F | Et | H |
| Br | Br | Cl | F | i-Pr | H |
| Br | Br | Cl | F | t-Bu | H |
| Br | Br | Cl | F | Me | Me |
| Cl | $OCH_2CF_3$ | Cl | F | Me | H |
| Cl | $OCH_2CF_3$ | Cl | F | Et | H |
| Cl | $OCH_2CF_3$ | Cl | F | i-Pr | H |
| Cl | $OCH_2CF_3$ | Cl | F | t-Bu | H |
| Cl | $OCH_2CF_3$ | Cl | F | Me | Me |
| Br | $OCH_2CF_3$ | Cl | F | Me | H |
| Br | $OCH_2CF_3$ | Cl | F | Et | H |
| Br | $OCH_2CF_3$ | Cl | F | i-Pr | H |
| Br | $OCH_2CF_3$ | Cl | F | t-Bu | H |
| Br | $OCH_2CF_3$ | Cl | F | Me | Me |
| Cl | $CF_3$ | Cl | Cl | Me | H |
| Cl | $CF_3$ | Cl | Cl | Et | H |

TABLE 6-continued

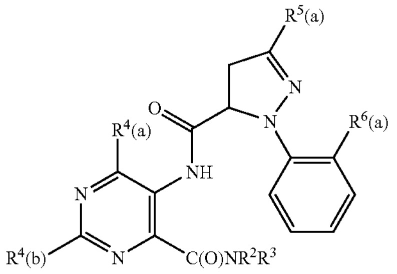

| $R^6$(a) | $R^5$(a) | $R^4$(a) | $R^4$(b) | $R^3$ | $R^2$ |
|---|---|---|---|---|---|
| Cl | $CF_3$ | Cl | Cl | i-Pr | H |
| Cl | $CF_3$ | Cl | Cl | t-Bu | H |
| Cl | $CF_3$ | Cl | Cl | Me | Me |
| Br | $CF_3$ | Cl | Cl | Me | H |
| Br | $CF_3$ | Cl | Cl | Et | H |
| Br | $CF_3$ | Cl | Cl | i-Pr | H |
| Br | $CF_3$ | Cl | Cl | t-Bu | H |
| Br | $CF_3$ | Cl | Cl | Me | Me |
| Cl | Cl | Cl | Cl | Me | H |
| Cl | Cl | Cl | Cl | Et | H |
| Cl | Cl | Cl | Cl | i-Pr | H |
| Cl | Cl | Cl | Cl | t-Bu | H |
| Cl | Cl | Cl | Cl | Me | Me |
| Br | Cl | Cl | Cl | Me | H |
| Br | Cl | Cl | Cl | Et | H |
| Br | Cl | Cl | Cl | i-Pr | H |
| Br | Cl | Cl | Cl | t-Bu | H |
| Br | Cl | Cl | Cl | Me | Me |
| Cl | Br | Cl | Cl | Me | H |
| Cl | Br | Cl | Cl | Et | H |
| Cl | Br | Cl | Cl | i-Pr | H |
| Cl | Br | Cl | Cl | t-Bu | H |
| Cl | Br | Cl | Cl | Me | Me |
| Br | Br | Cl | Cl | Me | H |
| Br | Br | Cl | Cl | Et | H |
| Br | Br | Cl | Cl | i-Pr | H |
| Br | Br | Cl | Cl | t-Bu | H |
| Br | Br | Cl | Cl | Me | Me |
| Cl | $OCH_2CF_3$ | Cl | Cl | Me | H |
| Cl | $OCH_2CF_3$ | Cl | Cl | Et | H |
| Cl | $OCH_2CF_3$ | Cl | Cl | i-Pr | H |
| Cl | $OCH_2CF_3$ | Cl | Cl | t-Bu | H |
| Cl | $OCH_2CF_3$ | Cl | Cl | Me | Me |
| Br | $OCH_2CF_3$ | Cl | Cl | Me | H |
| Br | $OCH_2CF_3$ | Cl | Cl | Et | H |
| Br | $OCH_2CF_3$ | Cl | Cl | i-Pr | H |
| Br | $OCH_2CF_3$ | Cl | Cl | t-Bu | H |
| Br | $OCH_2CF_3$ | Cl | Cl | Me | Me |
| Cl | $CF_3$ | Cl | Br | Me | H |
| Cl | $CF_3$ | Cl | Br | Et | H |
| Cl | $CF_3$ | Cl | Br | i-Pr | H |
| Cl | $CF_3$ | Cl | Br | t-Bu | H |
| Cl | $CF_3$ | Cl | Br | Me | Me |
| Br | $CF_3$ | Cl | Br | Me | H |
| Br | $CF_3$ | Cl | Br | Et | H |
| Br | $CF_3$ | Cl | Br | i-Pr | H |
| Br | $CF_3$ | Cl | Br | t-Bu | H |
| Br | $CF_3$ | Cl | Br | Me | Me |
| Cl | Cl | Cl | Br | Me | H |
| Cl | Cl | Cl | Br | Et | H |
| Cl | Cl | Cl | Br | i-Pr | H |
| Cl | Cl | Cl | Br | t-Bu | H |
| Cl | Cl | Cl | Br | Me | Me |
| Br | Cl | Cl | Br | Me | H |
| Br | Cl | Cl | Br | Et | H |
| Br | Cl | Cl | Br | i-Pr | H |
| Br | Cl | Cl | Br | t-Bu | H |
| Br | Cl | Cl | Br | Me | Me |
| Cl | Br | Cl | Br | Me | H |
| Cl | Br | Cl | Br | Et | H |
| Cl | Br | Cl | Br | i-Pr | H |
| Cl | Br | Cl | Br | t-Bu | H |
| Cl | Br | Cl | Br | Me | Me |

TABLE 6-continued

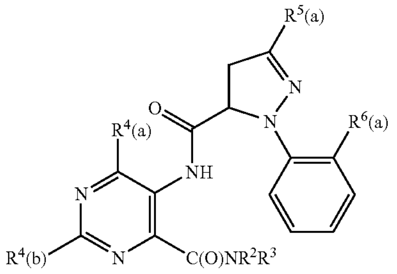

| $R^6$(a) | $R^5$(a) | $R^4$(a) | $R^4$(b) | $R^3$ | $R^2$ |
|---|---|---|---|---|---|
| Br | Br | Cl | Br | Me | H |
| Br | Br | Cl | Br | Et | H |
| Br | Br | Cl | Br | i-Pr | H |
| Br | Br | Cl | Br | t-Bu | H |
| Br | Br | Cl | Br | Me | Me |
| Cl | $OCH_2CF_3$ | Cl | Br | Me | H |
| Cl | $OCH_2CF_3$ | Cl | Br | Et | H |
| Cl | $OCH_2CF_3$ | Cl | Br | i-Pr | H |
| Cl | $OCH_2CF_3$ | Cl | Br | t-Bu | H |
| Cl | $OCH_2CF_3$ | Cl | Br | Me | Me |
| Br | $OCH_2CF_3$ | Cl | Br | Me | H |
| Br | $OCH_2CF_3$ | Cl | Br | Et | H |
| Br | $OCH_2CF_3$ | Cl | Br | i-Pr | H |
| Br | $OCH_2CF_3$ | Cl | Br | t-Bu | H |
| Br | $OCH_2CF_3$ | Cl | Br | Me | Me |
| Cl | $CF_3$ | Cl | I | Me | H |
| Cl | $CF_3$ | Cl | I | Et | H |
| Cl | $CF_3$ | Cl | I | i-Pr | H |
| Cl | $CF_3$ | Cl | I | t-Bu | H |
| Cl | $CF_3$ | Cl | I | Me | Me |
| Br | $CF_3$ | Cl | I | Me | H |
| Br | $CF_3$ | Cl | I | Et | H |
| Br | $CF_3$ | Cl | I | i-Pr | H |
| Br | $CF_3$ | Cl | I | t-Bu | H |
| Br | $CF_3$ | Cl | I | Me | Me |
| Cl | Cl | Cl | I | Me | H |
| Cl | Cl | Cl | I | Et | H |
| Cl | Cl | Cl | I | i-Pr | H |
| Cl | Cl | Cl | I | t-Bu | H |
| Cl | Cl | Cl | I | Me | Me |
| Br | Cl | Cl | I | Me | H |
| Br | Cl | Cl | I | Et | H |
| Br | Cl | Cl | I | i-Pr | H |
| Br | Cl | Cl | I | t-Bu | H |
| Br | Cl | Cl | I | Me | Me |
| Cl | Br | Cl | I | Me | H |
| Cl | Br | Cl | I | Et | H |
| Cl | Br | Cl | I | i-Pr | H |
| Cl | Br | Cl | I | t-Bu | H |
| Cl | Br | Cl | I | Me | Me |
| Br | Br | Cl | I | Me | H |
| Br | Br | Cl | I | Et | H |
| Br | Br | Cl | I | i-Pr | H |
| Br | Br | Cl | I | t-Bu | H |
| Br | Br | Cl | I | Me | Me |
| Cl | $OCH_2CF_3$ | Cl | I | Me | H |
| Cl | $OCH_2CF_3$ | Cl | I | Et | H |
| Cl | $OCH_2CF_3$ | Cl | I | i-Pr | H |
| Cl | $OCH_2CF_3$ | Cl | I | t-Bu | H |
| Cl | $OCH_2CF_3$ | Cl | I | Me | Me |
| Br | $OCH_2CF_3$ | Cl | I | Me | H |
| Br | $OCH_2CF_3$ | Cl | I | Et | H |
| Br | $OCH_2CF_3$ | Cl | I | i-Pr | H |
| Br | $OCH_2CF_3$ | Cl | I | t-Bu | H |
| Br | $OCH_2CF_3$ | Cl | I | Me | Me |
| Cl | $CF_3$ | Cl | $CF_3$ | Me | H |
| Cl | $CF_3$ | Cl | $CF_3$ | Et | H |
| Cl | $CF_3$ | Cl | $CF_3$ | i-Pr | H |
| Cl | $CF_3$ | Cl | $CF_3$ | t-Bu | H |
| Cl | $CF_3$ | Cl | $CF_3$ | Me | Me |
| Br | $CF_3$ | Cl | $CF_3$ | Me | H |
| Br | $CF_3$ | Cl | $CF_3$ | Et | H |
| Br | $CF_3$ | Cl | $CF_3$ | i-Pr | H |

TABLE 6-continued

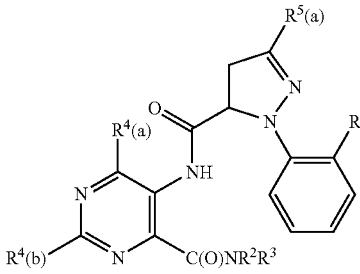

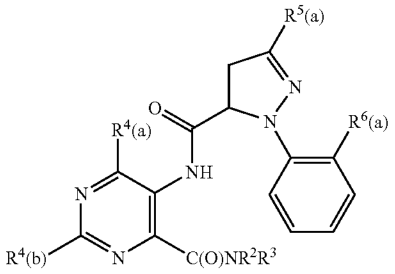

| $R^6(a)$ | $R^5(a)$ | $R^4(a)$ | $R^4(b)$ | $R^3$ | $R^2$ |
|---|---|---|---|---|---|
| Br | $CF_3$ | Cl | $CF_3$ | t-Bu | H |
| Br | $CF_3$ | Cl | $CF_3$ | Me | Me |
| Cl | Cl | Cl | $CF_3$ | Me | H |
| Cl | Cl | Cl | $CF_3$ | Et | H |
| Cl | Cl | Cl | $CF_3$ | i-Pr | H |
| Cl | Cl | Cl | $CF_3$ | t-Bu | H |
| Cl | Cl | Cl | $CF_3$ | Me | Me |
| Br | Cl | Cl | $CF_3$ | Me | H |
| Br | Cl | Cl | $CF_3$ | Et | H |
| Br | Cl | Cl | $CF_3$ | i-Pr | H |
| Br | Cl | Cl | $CF_3$ | t-Bu | H |
| Br | Cl | Cl | $CF_3$ | Me | Me |
| Cl | Br | Cl | $CF_3$ | Me | H |
| Cl | Br | Cl | $CF_3$ | Et | H |
| Cl | Br | Cl | $CF_3$ | i-Pr | H |
| Cl | Br | Cl | $CF_3$ | t-Bu | H |
| Cl | Br | Cl | $CF_3$ | Me | Me |
| Br | Br | Cl | $CF_3$ | Me | H |
| Br | Br | Cl | $CF_3$ | Et | H |
| Br | Br | Cl | $CF_3$ | i-Pr | H |
| Br | Br | Cl | $CF_3$ | t-Bu | H |
| Br | Br | Cl | $CF_3$ | Me | Me |
| Cl | $OCH_2CF_3$ | Cl | $CF_3$ | Me | H |
| Cl | $OCH_2CF_3$ | Cl | $CF_3$ | Et | H |
| Cl | $OCH_2CF_3$ | Cl | $CF_3$ | i-Pr | H |
| Cl | $OCH_2CF_3$ | Cl | $CF_3$ | t-Bu | H |
| Cl | $OCH_2CF_3$ | Cl | $CF_3$ | Me | Me |
| Br | $OCH_2CF_3$ | Cl | $CF_3$ | Me | H |
| Br | $OCH_2CF_3$ | Cl | $CF_3$ | Et | H |
| Br | $OCH_2CF_3$ | Cl | $CF_3$ | i-Pr | H |
| Br | $OCH_2CF_3$ | Cl | $CF_3$ | t-Bu | H |
| Br | $OCH_2CF_3$ | Cl | $CF_3$ | Me | Me |
| Cl | Cl | Cl | Cl | n-Pr | H |
| Cl | Cl | Cl | Cl | n-Bu | H |
| Cl | Cl | Cl | Cl | s-Bu | H |
| Cl | Cl | Cl | Cl | i-Bu | H |
| Cl | Cl | Cl | Cl | Et | Et |
| Cl | $CF_3$ | Br | H | Me | H |
| Cl | $CF_3$ | Br | H | Et | H |
| Cl | $CF_3$ | Br | H | i-Pr | H |
| Cl | $CF_3$ | Br | H | t-Bu | H |
| Cl | $CF_3$ | Br | H | Me | Me |
| Br | $CF_3$ | Br | H | Me | H |
| Br | $CF_3$ | Br | H | Et | H |
| Br | $CF_3$ | Br | H | i-Pr | H |
| Br | $CF_3$ | Br | H | t-Bu | H |
| Br | $CF_3$ | Br | H | Me | Me |
| Cl | Cl | Br | H | Me | H |
| Cl | Cl | Br | H | Et | H |
| Cl | Cl | Br | H | i-Pr | H |
| Cl | Cl | Br | H | t-Bu | H |
| Cl | Cl | Br | H | Me | Me |
| Br | Cl | Br | H | Me | H |
| Br | Cl | Br | H | Et | H |
| Br | Cl | Br | H | i-Pr | H |
| Br | Cl | Br | H | t-Bu | H |
| Br | Cl | Br | H | Me | Me |
| Cl | Br | Br | H | Me | H |
| Cl | Br | Br | H | Et | H |
| Cl | Br | Br | H | i-Pr | H |
| Cl | Br | Br | H | t-Bu | H |
| Cl | Br | Br | H | Me | Me |
| Br | Br | Br | H | Me | H |
| Br | Br | Br | H | Et | H |
| Br | Br | Br | H | i-Pr | H |
| Br | Br | Br | H | t-Bu | H |
| Br | Br | Br | H | Me | Me |
| Cl | $OCH_2CF_3$ | Br | H | Me | H |
| Cl | $OCH_2CF_3$ | Br | H | Et | H |
| Cl | $OCH_2CF_3$ | Br | H | i-Pr | H |
| Cl | $OCH_2CF_3$ | Br | H | t-Bu | H |
| Cl | $OCH_2CF_3$ | Br | H | Me | Me |
| Br | $OCH_2CF_3$ | Br | H | Me | H |
| Br | $OCH_2CF_3$ | Br | H | Et | H |
| Br | $OCH_2CF_3$ | Br | H | i-Pr | H |
| Br | $OCH_2CF_3$ | Br | H | t-Bu | H |
| Br | $OCH_2CF_3$ | Br | H | Me | Me |
| Cl | $CF_3$ | Br | F | Me | H |
| Cl | $CF_3$ | Br | F | Et | H |
| Cl | $CF_3$ | Br | F | i-Pr | H |
| Cl | $CF_3$ | Br | F | t-Bu | H |
| Cl | $CF_3$ | Br | F | Me | Me |
| Br | $CF_3$ | Br | F | Me | H |
| Br | $CF_3$ | Br | F | Et | H |
| Br | $CF_3$ | Br | F | i-Pr | H |
| Br | $CF_3$ | Br | F | t-Bu | H |
| Br | $CF_3$ | Br | F | Me | Me |
| Cl | Cl | Br | F | Me | H |
| Cl | Cl | Br | F | Et | H |
| Cl | Cl | Br | F | i-Pr | H |
| Cl | Cl | Br | F | t-Bu | H |
| Cl | Cl | Br | F | Me | Me |
| Br | Cl | Br | F | Me | H |
| Br | Cl | Br | F | Et | H |
| Br | Cl | Br | F | i-Pr | H |
| Br | Cl | Br | F | t-Bu | H |
| Br | Cl | Br | F | Me | Me |
| Cl | Br | Br | F | Me | H |
| Cl | Br | Br | F | Et | H |
| Cl | Br | Br | F | i-Pr | H |
| Cl | Br | Br | F | t-Bu | H |
| Cl | Br | Br | F | Me | Me |
| Br | Br | Br | F | Me | H |
| Br | Br | Br | F | Et | H |
| Br | Br | Br | F | i-Pr | H |
| Br | Br | Br | F | t-Bu | H |
| Br | Br | Br | F | Me | Me |
| Cl | $OCH_2CF_3$ | Br | F | Me | H |
| Cl | $OCH_2CF_3$ | Br | F | Et | H |
| Cl | $OCH_2CF_3$ | Br | F | i-Pr | H |
| Cl | $OCH_2CF_3$ | Br | F | t-Bu | H |
| Cl | $OCH_2CF_3$ | Br | F | Me | Me |
| Br | $OCH_2CF_3$ | Br | F | Me | H |
| Br | $OCH_2CF_3$ | Br | F | Et | H |
| Br | $OCH_2CF_3$ | Br | F | i-Pr | H |
| Br | $OCH_2CF_3$ | Br | F | t-Bu | H |
| Br | $OCH_2CF_3$ | Br | F | Me | Me |
| Cl | $CF_3$ | Br | Cl | Me | H |
| Cl | $CF_3$ | Br | Cl | Et | H |
| Cl | $CF_3$ | Br | Cl | i-Pr | H |
| Cl | $CF_3$ | Br | Cl | t-Bu | H |
| Cl | $CF_3$ | Br | Cl | Me | Me |
| Br | $CF_3$ | Br | Cl | Me | H |
| Br | $CF_3$ | Br | Cl | Et | H |
| Br | $CF_3$ | Br | Cl | i-Pr | H |
| Br | $CF_3$ | Br | Cl | t-Bu | H |

TABLE 6-continued

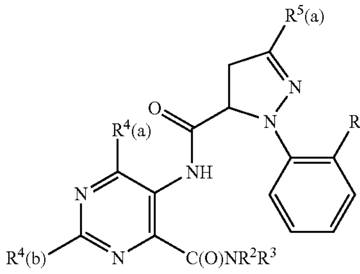

| $R^6$(a) | $R^5$(a) | $R^4$(a) | $R^4$(b) | $R^3$ | $R^2$ |
|---|---|---|---|---|---|
| Br | $CF_3$ | Br | Cl | Me | Me |
| Cl | Cl | Br | Cl | Me | H |
| Cl | Cl | Br | Cl | Et | H |
| Cl | Cl | Br | Cl | i-Pr | H |
| Cl | Cl | Br | Cl | t-Bu | H |
| Cl | Cl | Br | Cl | Me | Me |
| Br | Cl | Br | Cl | Me | H |
| Br | Cl | Br | Cl | Et | H |
| Br | Cl | Br | Cl | i-Pr | H |
| Br | Cl | Br | Cl | t-Bu | H |
| Br | Cl | Br | Cl | Me | Me |
| Cl | Br | Br | Cl | Me | H |
| Cl | Br | Br | Cl | Et | H |
| Cl | Br | Br | Cl | i-Pr | H |
| Cl | Br | Br | Cl | t-Bu | H |
| Cl | Br | Br | Cl | Me | Me |
| Br | Br | Br | Cl | Me | H |
| Br | Br | Br | Cl | Et | H |
| Br | Br | Br | Cl | i-Pr | H |
| Br | Br | Br | Cl | t-Bu | H |
| Br | Br | Br | Cl | Me | Me |
| Cl | $OCH_2CF_3$ | Br | Cl | Me | H |
| Cl | $OCH_2CF_3$ | Br | Cl | Et | H |
| Cl | $OCH_2CF_3$ | Br | Cl | i-Pr | H |
| Cl | $OCH_2CF_3$ | Br | Cl | t-Bu | H |
| Cl | $OCH_2CF_3$ | Br | Cl | Me | Me |
| Br | $OCH_2CF_3$ | Br | Cl | Me | H |
| Br | $OCH_2CF_3$ | Br | Cl | Et | H |
| Br | $OCH_2CF_3$ | Br | Cl | i-Pr | H |
| Br | $OCH_2CF_3$ | Br | Cl | t-Bu | H |
| Br | $OCH_2CF_3$ | Br | Cl | Me | Me |
| Cl | $CF_3$ | Br | Br | Me | H |
| Cl | $CF_3$ | Br | Br | Et | H |
| Cl | $CF_3$ | Br | Br | i-Pr | H |
| Cl | $CF_3$ | Br | Br | t-Bu | H |
| Cl | $CF_3$ | Br | Br | Me | Me |
| Br | $CF_3$ | Br | Br | Me | H |
| Br | $CF_3$ | Br | Br | Et | H |
| Br | $CF_3$ | Br | Br | i-Pr | H |
| Br | $CF_3$ | Br | Br | t-Bu | H |
| Br | $CF_3$ | Br | Br | Me | Me |
| Cl | Cl | Br | Br | Me | H |
| Cl | Cl | Br | Br | Et | H |
| Cl | Cl | Br | Br | i-Pr | H |
| Cl | Cl | Br | Br | t-Bu | H |
| Cl | Cl | Br | Br | Me | Me |
| Br | Cl | Br | Br | Me | H |
| Br | Cl | Br | Br | Et | H |
| Br | Cl | Br | Br | i-Pr | H |
| Br | Cl | Br | Br | t-Bu | H |
| Br | Cl | Br | Br | Me | Me |
| Cl | Br | Br | Br | Me | H |
| Cl | Br | Br | Br | Et | H |
| Cl | Br | Br | Br | i-Pr | H |
| Cl | Br | Br | Br | t-Bu | H |
| Cl | Br | Br | Br | Me | Me |
| Br | Br | Br | Br | Me | H |
| Br | Br | Br | Br | Et | H |
| Br | Br | Br | Br | i-Pr | H |
| Br | Br | Br | Br | t-Bu | H |
| Br | Br | Br | Br | Me | Me |
| Cl | $OCH_2CF_3$ | Br | Br | Me | H |
| Cl | $OCH_2CF_3$ | Br | Br | Et | H |

TABLE 6-continued

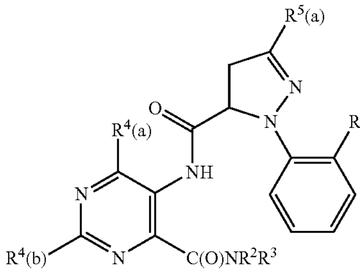

| $R^6$(a) | $R^5$(a) | $R^4$(a) | $R^4$(b) | $R^3$ | $R^2$ |
|---|---|---|---|---|---|
| Cl | $OCH_2CF_3$ | Br | Br | i-Pr | H |
| Cl | $OCH_2CF_3$ | Br | Br | t-Bu | H |
| Cl | $OCH_2CF_3$ | Br | Br | Me | Me |
| Br | $OCH_2CF_3$ | Br | Br | Me | H |
| Br | $OCH_2CF_3$ | Br | Br | Et | H |
| Br | $OCH_2CF_3$ | Br | Br | i-Pr | H |
| Br | $OCH_2CF_3$ | Br | Br | t-Bu | H |
| Br | $OCH_2CF_3$ | Br | Br | Me | Me |
| Cl | $CF_3$ | Br | I | Me | H |
| Cl | $CF_3$ | Br | I | Et | H |
| Cl | $CF_3$ | Br | I | i-Pr | H |
| Cl | $CF_3$ | Br | I | t-Bu | H |
| Cl | $CF_3$ | Br | I | Me | Me |
| Br | $CF_3$ | Br | I | Me | H |
| Br | $CF_3$ | Br | I | Et | H |
| Br | $CF_3$ | Br | I | i-Pr | H |
| Br | $CF_3$ | Br | I | t-Bu | H |
| Br | $CF_3$ | Br | I | Me | Me |
| Cl | Cl | Br | I | Me | H |
| Cl | Cl | Br | I | Et | H |
| Cl | Cl | Br | I | i-Pr | H |
| Cl | Cl | Br | I | t-Bu | H |
| Cl | Cl | Br | I | Me | Me |
| Br | Cl | Br | I | Me | H |
| Br | Cl | Br | I | Et | H |
| Br | Cl | Br | I | i-Pr | H |
| Br | Cl | Br | I | t-Bu | H |
| Br | Cl | Br | I | Me | Me |
| Cl | Br | Br | I | Me | H |
| Cl | Br | Br | I | Et | H |
| Cl | Br | Br | I | i-Pr | H |
| Cl | Br | Br | I | t-Bu | H |
| Cl | Br | Br | I | Me | Me |
| Br | Br | Br | I | Me | H |
| Br | Br | Br | I | Et | H |
| Br | Br | Br | I | i-Pr | H |
| Br | Br | Br | I | t-Bu | H |
| Br | Br | Br | I | Me | Me |
| Cl | $OCH_2CF_3$ | Br | I | Me | H |
| Cl | $OCH_2CF_3$ | Br | I | Et | H |
| Cl | $OCH_2CF_3$ | Br | I | i-Pr | H |
| Cl | $OCH_2CF_3$ | Br | I | t-Bu | H |
| Cl | $OCH_2CF_3$ | Br | I | Me | Me |
| Br | $OCH_2CF_3$ | Br | I | Me | H |
| Br | $OCH_2CF_3$ | Br | I | Et | H |
| Br | $OCH_2CF_3$ | Br | I | i-Pr | H |
| Br | $OCH_2CF_3$ | Br | I | t-Bu | H |
| Br | $OCH_2CF_3$ | Br | I | Me | Me |
| Cl | $CF_3$ | Br | $CF_3$ | Me | H |
| Cl | $CF_3$ | Br | $CF_3$ | Et | H |
| Cl | $CF_3$ | Br | $CF_3$ | i-Pr | H |
| Cl | $CF_3$ | Br | $CF_3$ | t-Bu | H |
| Cl | $CF_3$ | Br | $CF_3$ | Me | Me |
| Br | $CF_3$ | Br | $CF_3$ | Me | H |
| Br | $CF_3$ | Br | $CF_3$ | Et | H |
| Br | $CF_3$ | Br | $CF_3$ | i-Pr | H |
| Br | $CF_3$ | Br | $CF_3$ | t-Bu | H |
| Br | $CF_3$ | Br | $CF_3$ | Me | Me |
| Cl | Cl | Br | $CF_3$ | Me | H |
| Cl | Cl | Br | $CF_3$ | Et | H |
| Cl | Cl | Br | $CF_3$ | i-Pr | H |
| Cl | Cl | Br | $CF_3$ | t-Bu | H |
| Cl | Cl | Br | $CF_3$ | Me | Me |

TABLE 6-continued

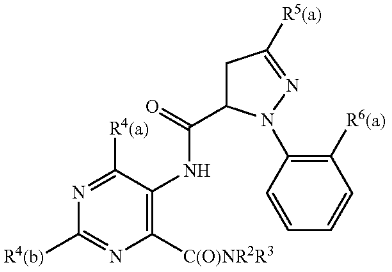

| $R^6$(a) | $R^5$(a) | $R^4$(a) | $R^4$(b) | $R^3$ | $R^2$ |
|---|---|---|---|---|---|
| Br | Cl | Br | $CF_3$ | Me | H |
| Br | Cl | Br | $CF_3$ | Et | H |
| Br | Cl | Br | $CF_3$ | i-Pr | H |
| Br | Cl | Br | $CF_3$ | t-Bu | H |
| Br | Cl | Br | $CF_3$ | Me | Me |
| Cl | Br | Br | $CF_3$ | Me | H |
| Cl | Br | Br | $CF_3$ | Et | H |
| Cl | Br | Br | $CF_3$ | i-Pr | H |
| Cl | Br | Br | $CF_3$ | t-Bu | H |
| Cl | Br | Br | $CF_3$ | Me | Me |
| Br | Br | Br | $CF_3$ | Me | H |
| Br | Br | Br | $CF_3$ | Et | H |
| Br | Br | Br | $CF_3$ | i-Pr | H |
| Br | Br | Br | $CF_3$ | t-Bu | H |
| Br | Br | Br | $CF_3$ | Me | Me |

TABLE 6-continued

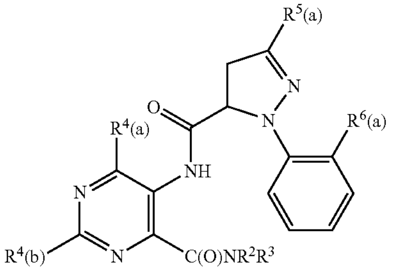

| $R^6$(a) | $R^5$(a) | $R^4$(a) | $R^4$(b) | $R^3$ | $R^2$ |
|---|---|---|---|---|---|
| Cl | $OCH_2CF_3$ | Br | $CF_3$ | Me | H |
| Cl | $OCH_2CF_3$ | Br | $CF_3$ | Et | H |
| Cl | $OCH_2CF_3$ | Br | $CF_3$ | i-Pr | H |
| Cl | $OCH_2CF_3$ | Br | $CF_3$ | t-Bu | H |
| Cl | $OCH_2CF_3$ | Br | $CF_3$ | Me | Me |
| Br | $OCH_2CF_3$ | Br | $CF_3$ | Me | H |
| Br | $OCH_2CF_3$ | Br | $CF_3$ | Et | H |
| Br | $OCH_2CF_3$ | Br | $CF_3$ | i-Pr | H |
| Br | $OCH_2CF_3$ | Br | $CF_3$ | t-Bu | H |
| Br | $OCH_2CF_3$ | Br | $CF_3$ | Me | Me |

TABLE 7

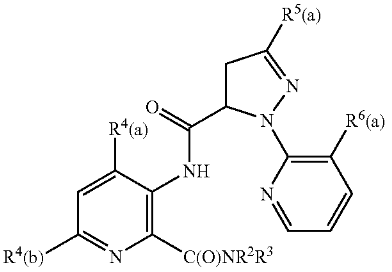

| $R^6$(a) | $R^5$(a) | $R^4$(a) | $R^4$(b) | $R^3$ | $R^2$ | $R^6$(a) | $R^5$(a) | $R^4$(a) | $R^4$(b) | $R^3$ | $R^2$ |
|---|---|---|---|---|---|---|---|---|---|---|---|
| Cl | $CF_3$ | $CH_3$ | H | Me | H | Cl | $CF_3$ | Cl | H | Me | H |
| Cl | $CF_3$ | $CH_3$ | H | Et | H | Cl | $CF_3$ | Cl | H | Et | H |
| Cl | $CF_3$ | $CH_3$ | H | i-Pr | H | Cl | $CF_3$ | Cl | H | i-Pr | H |
| Cl | $CF_3$ | $CH_3$ | H | t-Bu | H | Cl | $CF_3$ | Cl | H | t-Bu | H |
| Cl | $CF_3$ | $CH_3$ | H | Me | Me | Cl | $CF_3$ | Cl | H | Me | Me |
| Br | $CF_3$ | $CH_3$ | H | Me | H | Br | $CF_3$ | Cl | H | Me | H |
| Br | $CF_3$ | $CH_3$ | H | Et | H | Br | $CF_3$ | Cl | H | Et | H |
| Br | $CF_3$ | $CH_3$ | H | i-Pr | H | Br | $CF_3$ | Cl | H | i-Pr | H |
| Br | $CF_3$ | $CH_3$ | H | t-Bu | H | Br | $CF_3$ | Cl | H | t-Bu | H |
| Br | $CF_3$ | $CH_3$ | H | Me | Me | Br | $CF_3$ | Cl | H | Me | Me |
| Cl | Cl | $CH_3$ | H | Me | H | Cl | Cl | Cl | H | Me | H |
| Cl | Cl | $CH_3$ | H | Et | H | Cl | Cl | Cl | H | Et | H |
| Cl | Cl | $CH_3$ | H | i-Pr | H | Cl | Cl | Cl | H | i-Pr | H |
| Cl | Cl | $CH_3$ | H | t-Bu | H | Cl | Cl | Cl | H | t-Bu | H |
| Cl | Cl | $CH_3$ | H | Me | Me | Cl | Cl | Cl | H | Me | Me |
| Br | Cl | $CH_3$ | H | Me | H | Br | Cl | Cl | H | Me | H |
| Br | Cl | $CH_3$ | H | Et | H | Br | Cl | Cl | H | Et | H |
| Br | Cl | $CH_3$ | H | i-Pr | H | Br | Cl | Cl | H | i-Pr | H |
| Br | Cl | $CH_3$ | H | t-Bu | H | Br | Cl | Cl | H | t-Bu | H |
| Br | Cl | $CH_3$ | H | Me | Me | Br | Cl | Cl | H | Me | Me |
| Cl | Br | $CH_3$ | H | Me | H | Cl | Br | Cl | H | Me | H |
| Cl | Br | $CH_3$ | H | Et | H | Cl | Br | Cl | H | Et | H |
| Cl | Br | $CH_3$ | H | i-Pr | H | Cl | Br | Cl | H | i-Pr | H |
| Cl | Br | $CH_3$ | H | t-Bu | H | Cl | Br | Cl | H | t-Bu | H |
| Cl | Br | $CH_3$ | H | Me | Me | Cl | Br | Cl | H | Me | Me |

TABLE 7-continued

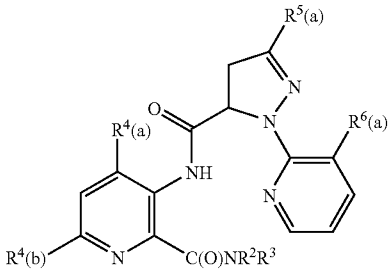

| $R^6$(a) | $R^5$(a) | $R^4$(a) | $R^4$(b) | $R^3$ | $R^2$ | $R^6$(a) | $R^5$(a) | $R^4$(a) | $R^4$(b) | $R^3$ | $R^2$ |
|---|---|---|---|---|---|---|---|---|---|---|---|
| Br | Br | $CH_3$ | H | Me | H | Br | Br | Cl | H | Me | H |
| Br | Br | $CH_3$ | H | Et | H | Br | Br | Cl | H | Et | H |
| Br | Br | $CH_3$ | H | i-Pr | H | Br | Br | Cl | H | i-Pr | H |
| Br | Br | $CH_3$ | H | t-Bu | H | Br | Br | Cl | H | t-Bu | H |
| Br | Br | $CH_3$ | H | Me | Me | Br | Br | Cl | H | Me | Me |
| Cl | $OCH_2CF_3$ | $CH_3$ | H | Me | H | Cl | $OCH_2CF_3$ | Cl | H | Me | H |
| Cl | $OCH_2CF_3$ | $CH_3$ | H | Et | H | Cl | $OCH_2CF_3$ | Cl | H | Et | H |
| Cl | $OCH_2CF_3$ | $CH_3$ | H | i-Pr | H | Cl | $OCH_2CF_3$ | Cl | H | i-Pr | H |
| Cl | $OCH_2CF_3$ | $CH_3$ | H | t-Bu | H | Cl | $OCH_2CF_3$ | Cl | H | t-Bu | H |
| Cl | $OCH_2CF_3$ | $CH_3$ | H | Me | Me | Cl | $OCH_2CF_3$ | Cl | H | Me | Me |
| Br | $OCH_2CF_3$ | $CH_3$ | H | Me | H | Br | $OCH_2CF_3$ | Cl | H | Me | H |
| Br | $OCH_2CF_3$ | $CH_3$ | H | Et | H | Br | $OCH_2CF_3$ | Cl | H | Et | H |
| Br | $OCH_2CF_3$ | $CH_3$ | H | i-Pr | H | Br | $OCH_2CF_3$ | Cl | H | i-Pr | H |
| Br | $OCH_2CF_3$ | $CH_3$ | H | t-Bu | H | Br | $OCH_2CF_3$ | Cl | H | t-Bu | H |
| Br | $OCH_2CF_3$ | $CH_3$ | H | Me | Me | Br | $OCH_2CF_3$ | Cl | H | Me | Me |
| Cl | $CF_3$ | $CH_3$ | F | Me | H | Cl | $CF_3$ | Cl | F | Me | H |
| Cl | $CF_3$ | $CH_3$ | F | Et | H | Cl | $CF_3$ | Cl | F | Et | H |
| Cl | $CF_3$ | $CH_3$ | F | i-Pr | H | Cl | $CF_3$ | Cl | F | i-Pr | H |
| Cl | $CF_3$ | $CH_3$ | F | t-Bu | H | Cl | $CF_3$ | Cl | F | t-Bu | H |
| Cl | $CF_3$ | $CH_3$ | F | Me | Me | Cl | $CF_3$ | Cl | F | Me | Me |
| Br | $CF_3$ | $CH_3$ | F | Me | H | Br | $CF_3$ | Cl | F | Me | H |
| Br | $CF_3$ | $CH_3$ | F | Et | H | Br | $CF_3$ | Cl | F | Et | H |
| Br | $CF_3$ | $CH_3$ | F | i-Pr | H | Br | $CF_3$ | Cl | F | i-Pr | H |
| Br | $CF_3$ | $CH_3$ | F | t-Bu | H | Br | $CF_3$ | Cl | F | t-Bu | H |
| Br | $CF_3$ | $CH_3$ | F | Me | Me | Br | $CF_3$ | Cl | F | Me | Me |
| Cl | Cl | $CH_3$ | F | Me | H | Cl | Cl | Cl | F | Me | H |
| Cl | Cl | $CH_3$ | F | Et | H | Cl | Cl | Cl | F | Et | H |
| Cl | Cl | $CH_3$ | F | i-Pr | H | Cl | Cl | Cl | F | i-Pr | H |
| Cl | Cl | $CH_3$ | F | t-Bu | H | Cl | Cl | Cl | F | t-Bu | H |
| Cl | Cl | $CH_3$ | F | Me | Me | Cl | Cl | Cl | F | Me | Me |
| Br | Cl | $CH_3$ | F | Me | H | Br | Cl | Cl | F | Me | H |
| Br | Cl | $CH_3$ | F | Et | H | Br | Cl | Cl | F | Et | H |
| Br | Cl | $CH_3$ | F | i-Pr | H | Br | Cl | Cl | F | i-Pr | H |
| Br | Cl | $CH_3$ | F | t-Bu | H | Br | Cl | Cl | F | t-Bu | H |
| Br | Cl | $CH_3$ | F | Me | Me | Br | Cl | Cl | F | Me | Me |
| Cl | Br | $CH_3$ | F | Me | H | Cl | Br | Cl | F | Me | H |
| Cl | Br | $CH_3$ | F | Et | H | Cl | Br | Cl | F | Ft | H |
| Cl | Br | $CH_3$ | F | i-Pr | H | Cl | Br | Cl | F | i-Pr | H |
| Cl | Br | $CH_3$ | F | t-Bu | H | Cl | Br | Cl | F | t-Bu | H |
| Cl | Br | $CH_3$ | F | Me | Me | Cl | Br | Cl | F | Me | Me |
| Br | Br | $CH_3$ | F | Me | H | Br | Br | Cl | F | Me | H |
| Br | Br | $CH_3$ | F | Et | H | Br | Br | Cl | F | Et | H |
| Br | Br | $CH_3$ | F | i-Pr | H | Br | Br | Cl | F | i-Pr | H |
| Br | Br | $CH_3$ | F | t-Bu | H | Br | Br | Cl | F | t-Bu | H |
| Br | Br | $CH_3$ | F | Me | Me | Br | Br | Cl | F | Me | Me |
| Cl | $OCH_2CF_3$ | $CH_3$ | F | Me | H | Cl | $OCH_2CF_3$ | Cl | F | Me | H |
| Cl | $OCH_2CF_3$ | $CH_3$ | F | Et | H | Cl | $OCH_2CF_3$ | Cl | F | Et | H |
| Cl | $OCH_2CF_3$ | $CH_3$ | F | i-Pr | H | Cl | $OCH_2CF_3$ | Cl | F | i-Pr | H |
| Cl | $OCH_2CF_3$ | $CH_3$ | F | t-Bu | H | Cl | $OCH_2CF_3$ | Cl | F | t-Bu | H |
| Cl | $OCH_2CF_3$ | $CH_3$ | F | Me | Me | Cl | $OCH_2CF_3$ | Cl | F | Me | Me |
| Br | $OCH_2CF_3$ | $CH_3$ | F | Me | H | Br | $OCH_2CF_3$ | Cl | F | Me | H |
| Br | $OCH_2CF_3$ | $CH_3$ | F | Et | H | Br | $OCH_2CF_3$ | Cl | F | Et | H |
| Br | $OCH_2CF_3$ | $CH_3$ | F | i-Pr | H | Br | $OCH_2CF_3$ | Cl | F | i-Pr | H |
| Br | $OCH_2CF_3$ | $CH_3$ | F | t-Bu | H | Br | $OCH_2CF_3$ | Cl | F | t-Bu | H |
| Br | $OCH_2CF_3$ | $CH_3$ | F | Me | Me | Br | $OCH_2CF_3$ | Cl | F | Me | Me |
| Cl | $CF_3$ | $CH_3$ | Cl | Me | H | Cl | $CF_3$ | Cl | Cl | Me | H |
| Cl | $CF_3$ | $CH_3$ | Cl | Et | H | Cl | $CF_3$ | Cl | Cl | Et | H |
| Cl | $CF_3$ | $CH_3$ | Cl | i-Pr | H | Cl | $CF_3$ | Cl | Cl | i-Pr | H |
| Cl | $CF_3$ | $CH_3$ | Cl | t-Bu | H | Cl | $CF_3$ | Cl | Cl | t-Bu | H |
| Cl | $CF_3$ | $CH_3$ | Cl | Me | Me | Cl | $CF_3$ | Cl | Cl | Me | Me |
| Br | $CF_3$ | $CH_3$ | Cl | Me | H | Br | $CF_3$ | Cl | Cl | Me | H |
| Br | $CF_3$ | $CH_3$ | Cl | Et | H | Br | $CF_3$ | Cl | Cl | Et | H |
| Br | $CF_3$ | $CH_3$ | Cl | i-Pr | H | Br | $CF_3$ | Cl | Cl | i-Pr | H |

TABLE 7-continued

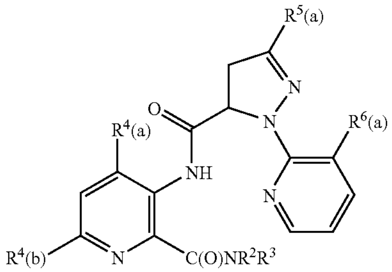

| $R^6$(a) | $R^5$(a) | $R^4$(a) | $R^4$(b) | $R^3$ | $R^2$ | $R^6$(a) | $R^5$(a) | $R^4$(a) | $R^4$(b) | $R^3$ | $R^2$ |
|---|---|---|---|---|---|---|---|---|---|---|---|
| Br | $CF_3$ | $CH_3$ | Cl | t-Bu | H | Br | $CF_3$ | Cl | Cl | t-Bu | H |
| Br | $CF_3$ | $CH_3$ | Cl | Me | Me | Br | $CF_3$ | Cl | Cl | Me | Me |
| Cl | Cl | $CH_3$ | Cl | Me | H | Cl | Cl | Cl | Cl | Me | H |
| Cl | Cl | $CH_3$ | Cl | Et | H | Cl | Cl | Cl | Cl | Et | H |
| Cl | Cl | $CH_3$ | Cl | i-Pr | H | Cl | Cl | Cl | Cl | i-Pr | H |
| Cl | Cl | $CH_3$ | Cl | t-Bu | H | Cl | Cl | Cl | Cl | t-Bu | H |
| Cl | Cl | $CH_3$ | Cl | Me | Me | Cl | Cl | Cl | Cl | Me | Me |
| Br | Cl | $CH_3$ | Cl | Me | H | Br | Cl | Cl | Cl | Me | H |
| Br | Cl | $CH_3$ | Cl | Et | H | Br | Cl | Cl | Cl | Et | H |
| Br | Cl | $CH_3$ | Cl | i-Pr | H | Br | Cl | Cl | Cl | i-Pr | H |
| Br | Cl | $CH_3$ | Cl | t-Bu | H | Br | Cl | Cl | Cl | t-Bu | H |
| Br | Cl | $CH_3$ | Cl | Me | Me | Br | Cl | Cl | Cl | Me | Me |
| Cl | Br | $CH_3$ | Cl | Me | H | Cl | Br | Cl | Cl | Me | H |
| Cl | Br | $CH_3$ | Cl | Et | H | Cl | Br | Cl | Cl | Et | H |
| Cl | Br | $CH_3$ | Cl | i-Pr | H | Cl | Br | Cl | Cl | i-Pr | H |
| Cl | Br | $CH_3$ | Cl | t-Bu | H | Cl | Br | Cl | Cl | t-Bu | H |
| Cl | Br | $CH_3$ | Cl | Me | Me | Cl | Br | Cl | Cl | Me | Me |
| Br | Br | $CH_3$ | Cl | Me | H | Br | Br | Cl | Cl | Me | H |
| Br | Br | $CH_3$ | Cl | Et | H | Br | Br | Cl | Cl | Et | H |
| Br | Br | $CH_3$ | Cl | i-Pr | H | Br | Br | Cl | Cl | i-Pr | H |
| Br | Br | $CH_3$ | Cl | t-Bu | H | Br | Br | Cl | Cl | t-Bu | H |
| Br | Br | $CH_3$ | Cl | Me | Me | Br | Br | Cl | Cl | Me | Me |
| Cl | $OCH_2CF_3$ | $CH_3$ | Cl | Me | H | Cl | $OCH_2CF_3$ | Cl | Cl | Me | H |
| Cl | $OCH_2CF_3$ | $CH_3$ | Cl | Et | H | Cl | $OCH_2CF_3$ | Cl | Cl | Et | H |
| Cl | $OCH_2CF_3$ | $CH_3$ | Cl | i-Pr | H | Cl | $OCH_2CF_3$ | Cl | Cl | i-Pr | H |
| Cl | $OCH_2CF_3$ | $CH_3$ | Cl | t-Bu | H | Cl | $OCH_2CF_3$ | Cl | Cl | t-Bu | H |
| Cl | $OCH_2CF_3$ | $CH_3$ | Cl | Me | Me | Cl | $OCH_2CF_3$ | Cl | Cl | Me | Me |
| Br | $OCH_2CF_3$ | $CH_3$ | Cl | Me | H | Br | $OCH_2CF_3$ | Cl | Cl | Me | H |
| Br | $OCH_2CF_3$ | $CH_3$ | Cl | Et | H | Br | $OCH_2CF_3$ | Cl | Cl | Et | H |
| Br | $OCH_2CF_3$ | $CH_3$ | Cl | i-Pr | H | Br | $OCH_2CF_3$ | Cl | Cl | i-Pr | H |
| Br | $OCH_2CF_3$ | $CH_3$ | Cl | t-Bu | H | Br | $OCH_2CF_3$ | Cl | Cl | t-Bu | H |
| Br | $OCH_2CF_3$ | $CH_3$ | Cl | Me | Me | Br | $OCH_2CF_3$ | Cl | Cl | Me | Me |
| Cl | $CF_3$ | $CH_3$ | Br | Me | H | Cl | $CF_3$ | Cl | Br | Me | H |
| Cl | $CF_3$ | $CH_3$ | Br | Et | H | Cl | $CF_3$ | Cl | Br | Et | H |
| Cl | $CF_3$ | $CH_3$ | Br | i-Pr | H | Cl | $CF_3$ | Cl | Br | i-Pr | H |
| Cl | $CF_3$ | $CH_3$ | Br | t-Bu | H | Cl | $CF_3$ | Cl | Br | t-Bu | H |
| Cl | $CF_3$ | $CH_3$ | Br | Me | Me | Cl | $CF_3$ | Cl | Br | Me | Me |
| Br | $CF_3$ | $CH_3$ | Br | Me | H | Br | $CF_3$ | Cl | Br | Me | H |
| Br | $CF_3$ | $CH_3$ | Br | Et | H | Br | $CF_3$ | Cl | Br | Et | H |
| Br | $CF_3$ | $CH_3$ | Br | i-Pr | H | Br | $CF_3$ | Cl | Br | i-Pr | H |
| Br | $CF_3$ | $CH_3$ | Br | t-Bu | H | Br | $CF_3$ | Cl | Br | t-Bu | H |
| Br | $CF_3$ | $CH_3$ | Br | Me | Me | Br | $CF_3$ | Cl | Br | Me | Me |
| Cl | Cl | $CH_3$ | Br | Me | H | Cl | Cl | Cl | Br | Me | H |
| Cl | Cl | $CH_3$ | Br | Et | H | Cl | Cl | Cl | Br | Et | H |
| Cl | Cl | $CH_3$ | Br | i-Pr | H | Cl | Cl | Cl | Br | i-Pr | H |
| Cl | Cl | $CH_3$ | Br | t-Bu | H | Cl | Cl | Cl | Br | t-Bu | H |
| Cl | Cl | $CH_3$ | Br | Me | Me | Cl | Cl | Cl | Br | Me | Me |
| Br | Cl | $CH_3$ | Br | Me | H | Br | Cl | Cl | Br | Me | H |
| Br | Cl | $CH_3$ | Br | Et | H | Br | Cl | Cl | Br | Et | H |
| Br | Cl | $CH_3$ | Br | i-Pr | H | Br | Cl | Cl | Br | i-Pr | H |
| Br | Cl | $CH_3$ | Br | t-Bu | H | Br | Cl | Cl | Br | t-Bu | H |
| Br | Cl | $CH_3$ | Br | Me | Me | Br | Cl | Cl | Br | Me | Me |
| Cl | Br | $CH_3$ | Br | Me | H | Cl | Br | Cl | Br | Me | H |
| Cl | Br | $CH_3$ | Br | Et | H | Cl | Br | Cl | Br | Et | H |
| Cl | Br | $CH_3$ | Br | i-Pr | H | Cl | Br | Cl | Br | i-Pr | H |
| Cl | Br | $CH_3$ | Br | t-Bu | H | Cl | Br | Cl | Br | t-Bu | H |
| Cl | Br | $CH_3$ | Br | Me | Me | Cl | Br | Cl | Br | Me | Me |
| Br | Br | $CH_3$ | Br | Me | H | Br | Br | Cl | Br | Me | H |
| Br | Br | $CH_3$ | Br | Et | H | Br | Br | Cl | Br | Et | H |
| Br | Br | $CH_3$ | Br | i-Pr | H | Br | Br | Cl | Br | i-Pr | H |
| Br | Br | $CH_3$ | Br | t-Bu | H | Br | Br | Cl | Br | t-Bu | H |
| Br | Br | $CH_3$ | Br | Me | Me | Br | Br | Cl | Br | Me | Me |
| Cl | $OCH_2CF_3$ | $CH_3$ | Br | Me | H | Cl | $OCH_2CF_3$ | Cl | Br | Me | H |

TABLE 7-continued

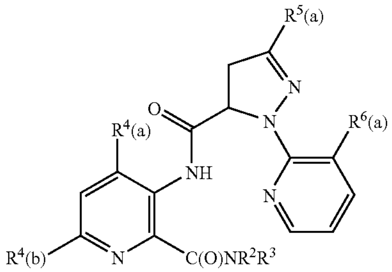

| $R^6$(a) | $R^5$(a) | $R^4$(a) | $R^4$(b) | $R^3$ | $R^2$ | $R^6$(a) | $R^5$(a) | $R^4$(a) | $R^4$(b) | $R^3$ | $R^2$ |
|---|---|---|---|---|---|---|---|---|---|---|---|
| Cl | $OCH_2CF_3$ | $CH_3$ | Br | Et | H | Cl | $OCH_2CF_3$ | Cl | Br | Et | H |
| Cl | $OCH_2CF_3$ | $CH_3$ | Br | i-Pr | H | Cl | $OCH_2CF_3$ | Cl | Br | i-Pr | H |
| Cl | $OCH_2CF_3$ | $CH_3$ | Br | t-Bu | H | Cl | $OCH_2CF_3$ | Cl | Br | t-Bu | H |
| Cl | $OCH_2CF_3$ | $CH_3$ | Br | Me | Me | Cl | $OCH_2CF_3$ | Cl | Br | Me | Me |
| Br | $OCH_2CF_3$ | $CH_3$ | Br | Me | H | Br | $OCH_2CF_3$ | Cl | Br | Me | H |
| Br | $OCH_2CF_3$ | $CH_3$ | Br | Et | H | Br | $OCH_2CF_3$ | Cl | Br | Et | H |
| Br | $OCH_2CF_3$ | $CH_3$ | Br | i-Pr | H | Br | $OCH_2CF_3$ | Cl | Br | i-Pr | H |
| Br | $OCH_2CF_3$ | $CH_3$ | Br | t-Bu | H | Br | $OCH_2CF_3$ | Cl | Br | t-Bu | H |
| Br | $OCH_2CF_3$ | $CH_3$ | Br | Me | Me | Br | $OCH_2CF_3$ | Cl | Br | Me | Me |
| Cl | $CF_3$ | $CH_3$ | I | Me | H | Cl | $CF_3$ | Cl | I | Me | H |
| Cl | $CF_3$ | $CH_3$ | I | Et | H | Cl | $CF_3$ | Cl | I | Et | H |
| Cl | $CF_3$ | $CH_3$ | I | i-Pr | H | Cl | $CF_3$ | Cl | I | i-Pr | H |
| Cl | $CF_3$ | $CH_3$ | I | t-Bu | H | Cl | $CF_3$ | Cl | I | t-Bu | H |
| Cl | $CF_3$ | $CH_3$ | I | Me | Me | Cl | $CF_3$ | Cl | I | Me | Me |
| Br | $CF_3$ | $CH_3$ | I | Me | H | Br | $CF_3$ | Cl | I | Me | H |
| Br | $CF_3$ | $CH_3$ | I | Et | H | Br | $CF_3$ | Cl | I | Et | H |
| Br | $CF_3$ | $CH_3$ | I | i-Pr | H | Br | $CF_3$ | Cl | I | i-Pr | H |
| Br | $CF_3$ | $CH_3$ | I | t-Bu | H | Br | $CF_3$ | Cl | I | t-Bu | H |
| Br | $CF_3$ | $CH_3$ | I | Me | Me | Br | $CF_3$ | Cl | I | Me | Me |
| Cl | Cl | $CH_3$ | I | Me | H | Cl | Cl | Cl | I | Me | H |
| Cl | Cl | $CH_3$ | I | Et | H | Cl | Cl | Cl | I | Et | H |
| Cl | Cl | $CH_3$ | I | i-Pr | H | Cl | Cl | Cl | I | i-Pr | H |
| Cl | Cl | $CH_3$ | I | t-Bu | H | Cl | Cl | Cl | I | t-Bu | H |
| Cl | Cl | $CH_3$ | I | Me | Me | Cl | Cl | Cl | I | Me | Me |
| Br | Cl | $CH_3$ | I | Me | H | Br | Cl | Cl | I | Me | H |
| Br | Cl | $CH_3$ | I | Et | H | Br | Cl | Cl | I | Et | H |
| Br | Cl | $CH_3$ | I | i-Pr | H | Br | Cl | Cl | I | i-Pr | H |
| Br | Cl | $CH_3$ | I | t-Bu | H | Br | Cl | Cl | I | t-Bu | H |
| Br | Cl | $CH_3$ | I | Me | Me | Br | Cl | Cl | I | Me | Me |
| Cl | Br | $CH_3$ | I | Me | H | Cl | Br | Cl | I | Me | H |
| Cl | Br | $CH_3$ | I | Et | H | Cl | Br | Cl | I | Et | H |
| Cl | Br | $CH_3$ | I | i-Pr | H | Cl | Br | Cl | I | i-Pr | H |
| Cl | Br | $CH_3$ | I | t-Bu | H | Cl | Br | Cl | I | t-Bu | H |
| Cl | Br | $CH_3$ | I | Me | Me | Cl | Br | Cl | I | Me | Me |
| Br | Br | $CH_3$ | I | Me | H | Br | Br | Cl | I | Me | H |
| Br | Br | $CH_3$ | I | Et | H | Br | Br | Cl | I | Et | H |
| Br | Br | $CH_3$ | I | i-Pr | H | Br | Br | Cl | I | i-Pr | H |
| Br | Br | $CH_3$ | I | t-Bu | H | Br | Br | Cl | I | t-Bu | H |
| Br | Br | $CH_3$ | I | Me | Me | Br | Br | Cl | I | Me | Me |
| Cl | $OCH_2CF_3$ | $CH_3$ | I | Me | H | Cl | $OCH_2CF_3$ | Cl | I | Me | H |
| Cl | $OCH_2CF_3$ | $CH_3$ | I | Et | H | Cl | $OCH_2CF_3$ | Cl | I | Et | H |
| Cl | $OCH_2CF_3$ | $CH_3$ | I | i-Pr | H | Cl | $OCH_2CF_3$ | Cl | I | i-Pr | H |
| Cl | $OCH_2CF_3$ | $CH_3$ | I | t-Bu | H | Cl | $OCH_2CF_3$ | Cl | I | t-Bu | H |
| Cl | $OCH_2CF_3$ | $CH_3$ | I | Me | Me | Cl | $OCH_2CF_3$ | Cl | I | Me | Me |
| Br | $OCH_2CF_3$ | $CH_3$ | I | Me | H | Br | $OCH_2CF_3$ | Cl | I | Me | H |
| Br | $OCH_2CF_3$ | $CH_3$ | I | Et | H | Br | $OCH_2CF_3$ | Cl | I | Et | H |
| Br | $OCH_2CF_3$ | $CH_3$ | I | i-Pr | H | Br | $OCH_2CF_3$ | Cl | I | i-Pr | H |
| Br | $OCH_2CF_3$ | $CH_3$ | I | t-Bu | H | Br | $OCH_2CF_3$ | Cl | I | t-Bu | H |
| Br | $OCH_2CF_3$ | $CH_3$ | I | Me | Me | Br | $OCH_2CF_3$ | Cl | I | Me | Me |
| Cl | $CF_3$ | $CH_3$ | $CF_3$ | Me | H | Cl | $CF_3$ | Cl | $CF_3$ | Me | H |
| Cl | $CF_3$ | $CH_3$ | $CF_3$ | Et | H | Cl | $CF_3$ | Cl | $CF_3$ | Et | H |
| Cl | $CF_3$ | $CH_3$ | $CF_3$ | i-Pr | H | Cl | $CF_3$ | Cl | $CF_3$ | i-Pr | H |
| Cl | $CF_3$ | $CH_3$ | $CF_3$ | t-Bu | H | Cl | $CF_3$ | Cl | $CF_3$ | t-Bu | H |
| Cl | $CF_3$ | $CH_3$ | $CF_3$ | Me | Me | Cl | $CF_3$ | Cl | $CF_3$ | Me | Me |
| Br | $CF_3$ | $CH_3$ | $CF_3$ | Me | H | Br | $CF_3$ | Cl | $CF_3$ | Me | H |
| Br | $CF_3$ | $CH_3$ | $CF_3$ | Et | H | Br | $CF_3$ | Cl | $CF_3$ | Et | H |
| Br | $CF_3$ | $CH_3$ | $CF_3$ | i-Pr | H | Br | $CF_3$ | Cl | $CF_3$ | i-Pr | H |
| Br | $CF_3$ | $CH_3$ | $CF_3$ | t-Bu | H | Br | $CF_3$ | Cl | $CF_3$ | t-Bu | H |
| Br | $CF_3$ | $CH_3$ | $CF_3$ | Me | Me | Br | $CF_3$ | Cl | $CF_3$ | Me | Me |
| Cl | Cl | $CH_3$ | $CF_3$ | Me | H | Cl | Cl | Cl | $CF_3$ | Me | H |
| Cl | Cl | $CH_3$ | $CF_3$ | Et | H | Cl | Cl | Cl | $CF_3$ | Et | H |
| Cl | Cl | $CH_3$ | $CF_3$ | i-Pr | H | Cl | Cl | Cl | $CF_3$ | i-Pr | H |
| Cl | Cl | $CH_3$ | $CF_3$ | t-Bu | H | Cl | Cl | Cl | $CF_3$ | t-Bu | H |

TABLE 7-continued

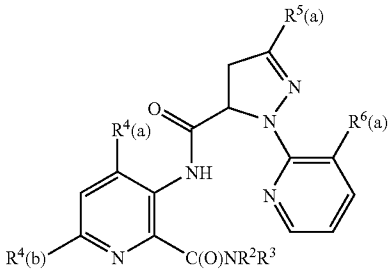

| $R^6$(a) | $R^5$(a) | $R^4$(a) | $R^4$(b) | $R^3$ | $R^2$ | $R^6$(a) | $R^5$(a) | $R^4$(a) | $R^4$(b) | $R^3$ | $R^2$ |
|---|---|---|---|---|---|---|---|---|---|---|---|
| Cl | Cl | $CH_3$ | $CF_3$ | Me | Me | Cl | Cl | Cl | $CF_3$ | Me | Me |
| Br | Cl | $CH_3$ | $CF_3$ | Me | H | Br | Cl | Cl | $CF_3$ | Me | H |
| Br | Cl | $CH_3$ | $CF_3$ | Et | H | Br | Cl | Cl | $CF_3$ | Et | H |
| Br | Cl | $CH_3$ | $CF_3$ | i-Pr | H | Br | Cl | Cl | $CF_3$ | i-Pr | H |
| Br | Cl | $CH_3$ | $CF_3$ | t-Bu | H | Br | Cl | Cl | $CF_3$ | t-Bu | H |
| Br | Cl | $CH_3$ | $CF_3$ | Me | Me | Br | Cl | Cl | $CF_3$ | Me | Me |
| Cl | Br | $CH_3$ | $CF_3$ | Me | H | Cl | Br | Cl | $CF_3$ | Me | H |
| Cl | Br | $CH_3$ | $CF_3$ | Et | H | Cl | Br | Cl | $CF_3$ | Et | H |
| Cl | Br | $CH_3$ | $CF_3$ | i-Pr | H | Cl | Br | Cl | $CF_3$ | i-Pr | H |
| Cl | Br | $CH_3$ | $CF_3$ | t-Bu | H | Cl | Br | Cl | $CF_3$ | t-Bu | H |
| Cl | Br | $CH_3$ | $CF_3$ | Me | Me | Cl | Br | Cl | $CF_3$ | Me | Me |
| Br | Br | $CH_3$ | $CF_3$ | Me | H | Br | Br | Cl | $CF_3$ | Me | H |
| Br | Br | $CH_3$ | $CF_3$ | Et | H | Br | Br | Cl | $CF_3$ | Et | H |
| Br | Br | $CH_3$ | $CF_3$ | i-Pr | H | Br | Br | Cl | $CF_3$ | i-Pr | H |
| Br | Br | $CH_3$ | $CF_3$ | t-Bu | H | Br | Br | Cl | $CF_3$ | t-Bu | H |
| Br | Br | $CH_3$ | $CF_3$ | Me | Me | Br | Br | Cl | $CF_3$ | Me | Me |
| Cl | $OCH_2CF_3$ | $CH_3$ | $CF_3$ | Me | H | Cl | $OCH_2CF_3$ | Cl | $CF_3$ | Me | H |
| Cl | $OCH_2CF_3$ | $CH_3$ | $CF_3$ | Et | H | Cl | $OCH_2CF_3$ | Cl | $CF_3$ | Et | H |
| Cl | $OCH_2CF_3$ | $CH_3$ | $CF_3$ | i-Pr | H | Cl | $OCH_2CF_3$ | Cl | $CF_3$ | i-Pr | H |
| Cl | $OCH_2CF_3$ | $CH_3$ | $CF_3$ | t-Bu | H | Cl | $OCH_2CF_3$ | Cl | $CF_3$ | t-Bu | H |
| Cl | $OCH_2CF_3$ | $CH_3$ | $CF_3$ | Me | Me | Cl | $OCH_2CF_3$ | Cl | $CF_3$ | Me | Me |
| Br | $OCH_2CF_3$ | $CH_3$ | $CF_3$ | Me | H | Br | $OCH_2CF_3$ | Cl | $CF_3$ | Me | H |
| Br | $OCH_2CF_3$ | $CH_3$ | $CF_3$ | Et | H | Br | $OCH_2CF_3$ | Cl | $CF_3$ | Et | H |
| Br | $OCH_2CF_3$ | $CH_3$ | $CF_3$ | i-Pr | H | Br | $OCH_2CF_3$ | Cl | $CF_3$ | i-Pr | H |
| Br | $OCH_2CF_3$ | $CH_3$ | $CF_3$ | t-Bu | H | Br | $OCH_2CF_3$ | Cl | $CF_3$ | t-Bu | H |
| Br | $OCH_2CF_3$ | $CH_3$ | $CF_3$ | Me | Me | Br | $OCH_2CF_3$ | Cl | $CF_3$ | Me | Me |
| Cl | Cl | $CH_3$ | Cl | n-Pr | H | Cl | Cl | Cl | Cl | n-Pr | H |
| Cl | Cl | $CH_3$ | Cl | n-Bu | H | Cl | Cl | Cl | Cl | n-Bu | H |
| Cl | Cl | $CH_3$ | Cl | s-Bu | H | Cl | Cl | Cl | Cl | s-Bu | H |
| Cl | Cl | $CH_3$ | Cl | i-Bu | H | Cl | Cl | Cl | Cl | i-Bu | H |
| Cl | Cl | $CH_3$ | Cl | Et | Me | Cl | Cl | Cl | Cl | Et | Et |
| Cl | $CF_3$ | F | H | Me | H | Cl | $CF_3$ | Br | H | Me | H |
| Cl | $CF_3$ | F | H | Et | H | Cl | $CF_3$ | Br | H | Et | H |
| Cl | $CF_3$ | F | H | i-Pr | H | Cl | $CF_3$ | Br | H | i-Pr | H |
| Cl | $CF_3$ | F | H | t-Bu | H | Cl | $CF_3$ | Br | H | t-Bu | H |
| Cl | $CF_3$ | F | H | Me | Me | Cl | $CF_3$ | Br | H | Me | Me |
| Br | $CF_3$ | F | H | Me | H | Br | $CF_3$ | Br | H | Me | H |
| Br | $CF_3$ | F | H | Et | H | Br | $CF_3$ | Br | H | Et | H |
| Br | $CF_3$ | F | H | i-Pr | H | Br | $CF_3$ | Br | H | i-Pr | H |
| Br | $CF_3$ | F | H | t-Bu | H | Br | $CF_3$ | Br | H | t-Bu | H |
| Br | $CF_3$ | F | H | Me | Me | Br | $CF_3$ | Br | H | Me | Me |
| Cl | Cl | F | H | Me | H | Cl | Cl | Br | H | Me | H |
| Cl | Cl | F | H | Et | H | Cl | Cl | Br | H | Et | H |
| Cl | Cl | F | H | i-Pr | H | Cl | Cl | Br | H | i-Pr | H |
| Cl | Cl | F | H | t-Bu | H | Cl | Cl | Br | H | t-Bu | H |
| Cl | Cl | F | H | Me | Me | Cl | Cl | Br | H | Me | Me |
| Br | Cl | F | H | Me | H | Br | Cl | Br | H | Me | H |
| Br | Cl | F | H | Et | H | Br | Cl | Br | H | Et | H |
| Br | Cl | F | H | i-Pr | H | Br | Cl | Br | H | i-Pr | H |
| Br | Cl | F | H | t-Bu | H | Br | Cl | Br | H | t-Bu | H |
| Br | Cl | F | H | Me | Me | Br | Cl | Br | H | Me | Me |
| Cl | Br | F | H | Me | H | Cl | Br | Br | H | Me | H |
| Cl | Br | F | H | Et | H | Cl | Br | Br | H | Et | H |
| Cl | Br | F | H | i-Pr | H | Cl | Br | Br | H | i-Pr | H |
| Cl | Br | F | H | t-Bu | H | Cl | Br | Br | H | t-Bu | H |
| Cl | Br | F | H | Me | Me | Cl | Br | Br | H | Me | Me |
| Br | Br | F | H | Me | H | Br | Br | Br | H | Me | H |
| Br | Br | F | H | Et | H | Br | Br | Br | H | Et | H |
| Br | Br | F | H | i-Pr | H | Br | Br | Br | H | i-Pr | H |
| Br | Br | F | H | t-Bu | H | Br | Br | Br | H | t-Bu | H |
| Br | Br | F | H | Me | Me | Br | Br | Br | H | Me | Me |
| Cl | $OCH_2CF_3$ | F | H | Me | H | Cl | $OCH_2CF_3$ | Br | H | Me | H |
| Cl | $OCH_2CF_3$ | F | H | Et | H | Cl | $OCH_2CF_3$ | Br | H | Et | H |

TABLE 7-continued

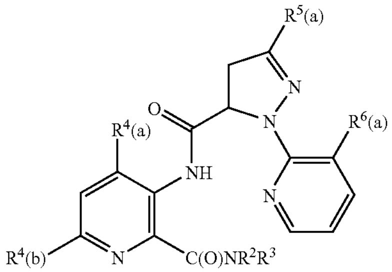

| $R^6$(a) | $R^5$(a) | $R^4$(a) | $R^4$(b) | $R^3$ | $R^2$ | $R^6$(a) | $R^5$(a) | $R^4$(a) | $R^4$(b) | $R^3$ | $R^2$ |
|---|---|---|---|---|---|---|---|---|---|---|---|
| Cl | $OCH_2CF_3$ | F | H | i-Pr | H | Cl | $OCH_2CF_3$ | Br | H | i-Pr | H |
| Cl | $OCH_2CF_3$ | F | H | t-Bu | H | Cl | $OCH_2CF_3$ | Br | H | t-Bu | H |
| Cl | $OCH_2CF_3$ | F | H | Me | Me | Cl | $OCH_2CF_3$ | Br | H | Me | Me |
| Br | $OCH_2CF_3$ | F | H | Me | H | Br | $OCH_2CF_3$ | Br | H | Me | H |
| Br | $OCH_2CF_3$ | F | H | Et | H | Br | $OCH_2CF_3$ | Br | H | Et | H |
| Br | $OCH_2CF_3$ | F | H | i-Pr | H | Br | $OCH_2CF_3$ | Br | H | i-Pr | H |
| Br | $OCH_2CF_3$ | F | H | t-Bu | H | Br | $OCH_2CF_3$ | Br | H | t-Bu | H |
| Br | $OCH_2CF_3$ | F | H | Me | Me | Br | $OCH_2CF_3$ | Br | H | Me | Me |
| Cl | $CF_3$ | F | F | Me | H | Cl | $CF_3$ | Br | F | Me | H |
| Cl | $CF_3$ | F | F | Et | H | Cl | $CF_3$ | Br | F | Et | H |
| Cl | $CF_3$ | F | F | i-Pr | H | Cl | $CF_3$ | Br | F | i-Pr | H |
| Cl | $CF_3$ | F | F | t-Bu | H | Cl | $CF_3$ | Br | F | t-Bu | H |
| Cl | $CF_3$ | F | F | Me | Me | Cl | $CF_3$ | Br | F | Me | Me |
| Br | $CF_3$ | F | F | Me | H | Br | $CF_3$ | Br | F | Me | H |
| Br | $CF_3$ | F | F | Et | H | Br | $CF_3$ | Br | F | Et | H |
| Br | $CF_3$ | F | F | i-Pr | H | Br | $CF_3$ | Br | F | i-Pr | H |
| Br | $CF_3$ | F | F | t-Bu | H | Br | $CF_3$ | Br | F | t-Bu | H |
| Br | $CF_3$ | F | F | Me | Me | Br | $CF_3$ | Br | F | Me | Me |
| Cl | Cl | F | F | Me | H | Cl | Cl | Br | F | Me | H |
| Cl | Cl | F | F | Et | H | Cl | Cl | Br | F | Et | H |
| Cl | Cl | F | F | i-Pr | H | Cl | Cl | Br | F | i-Pr | H |
| Cl | Cl | F | F | t-Bu | H | Cl | Cl | Br | F | t-Bu | H |
| Cl | Cl | F | F | Me | Me | Cl | Cl | Br | F | Me | Me |
| Br | Cl | F | F | Me | H | Br | Cl | Br | F | Me | H |
| Br | Cl | F | F | Et | H | Br | Cl | Br | F | Et | H |
| Br | Cl | F | F | i-Pr | H | Br | Cl | Br | F | i-Pr | H |
| Br | Cl | F | F | t-Bu | H | Br | Cl | Br | F | t-Bu | H |
| Br | Cl | F | F | Me | Me | Br | Cl | Br | F | Me | Me |
| Cl | Br | F | F | Me | H | Cl | Br | Br | F | Me | H |
| Cl | Br | F | F | Et | H | Cl | Br | Br | F | Et | H |
| Cl | Br | F | F | i-Pr | H | Cl | Br | Br | F | i-Pr | H |
| Cl | Br | F | F | t-Bu | H | Cl | Br | Br | F | t-Bu | H |
| Cl | Br | F | F | Me | Me | Cl | Br | Br | F | Me | Me |
| Br | Br | F | F | Me | H | Br | Br | Br | F | Me | H |
| Br | Br | F | F | Et | H | Br | Br | Br | F | Et | H |
| Br | Br | F | F | i-Pr | H | Br | Br | Br | F | i-Pr | H |
| Br | Br | F | F | t-Bu | H | Br | Br | Br | F | t-Bu | H |
| Br | Br | F | F | Me | Me | Br | Br | Br | F | Me | Me |
| Cl | $OCH_2CF_3$ | F | F | Me | H | Cl | $OCH_2CF_3$ | Br | F | Me | H |
| Cl | $OCH_2CF_3$ | F | F | Et | H | Cl | $OCH_2CF_3$ | Br | F | Et | H |
| Cl | $OCH_2CF_3$ | F | F | i-Pr | H | Cl | $OCH_2CF_3$ | Br | F | i-Pr | H |
| Cl | $OCH_2CF_3$ | F | F | t-Bu | H | Cl | $OCH_2CF_3$ | Br | F | t-Bu | H |
| Cl | $OCH_2CF_3$ | F | F | Me | Me | Cl | $OCH_2CF_3$ | Br | F | Me | Me |
| Br | $OCH_2CF_3$ | F | F | Me | H | Br | $OCH_2CF_3$ | Br | F | Me | H |
| Br | $OCH_2CF_3$ | F | F | Et | H | Br | $OCH_2CF_3$ | Br | F | Et | H |
| Br | $OCH_2CF_3$ | F | F | i-Pr | H | Br | $OCH_2CF_3$ | Br | F | i-Pr | H |
| Br | $OCH_2CF_3$ | F | F | t-Bu | H | Br | $OCH_2CF_3$ | Br | F | t-Bu | H |
| Br | $OCH_2CF_3$ | F | F | Me | Me | Br | $OCH_2CF_3$ | Br | F | Me | Me |
| Cl | $CF_3$ | F | Cl | Me | H | Cl | $CF_3$ | Br | Cl | Me | H |
| Cl | $CF_3$ | F | Cl | Et | H | Cl | $CF_3$ | Br | Cl | Et | H |
| Cl | $CF_3$ | F | Cl | i-Pr | H | Cl | $CF_3$ | Br | Cl | i-Pr | H |
| Cl | $CF_3$ | F | Cl | t-Bu | H | Cl | $CF_3$ | Br | Cl | t-Bu | H |
| Cl | $CF_3$ | F | Cl | Me | Me | Cl | $CF_3$ | Br | Cl | Me | Me |
| Br | $CF_3$ | F | Cl | Me | H | Br | $CF_3$ | Br | Cl | Me | H |
| Br | $CF_3$ | F | Cl | Et | H | Br | $CF_3$ | Br | Cl | Et | H |
| Br | $CF_3$ | F | Cl | i-Pr | H | Br | $CF_3$ | Br | Cl | i-Pr | H |
| Br | $CF_3$ | F | Cl | t-Bu | H | Br | $CF_3$ | Br | Cl | t-Bu | H |
| Br | $CF_3$ | F | Cl | Me | Me | Br | $CF_3$ | Br | Cl | Me | Me |
| Cl | Cl | F | Cl | Me | H | Cl | Cl | Br | Cl | Me | H |
| Cl | Cl | F | Cl | Et | H | Cl | Cl | Br | Cl | Et | H |
| Cl | Cl | F | Cl | i-Pr | H | Cl | Cl | Br | Cl | i-Pr | H |
| Cl | Cl | F | Cl | t-Bu | H | Cl | Cl | Br | Cl | t-Bu | H |
| Cl | Cl | F | Cl | Me | Me | Cl | Cl | Br | Cl | Me | Me |

TABLE 7-continued

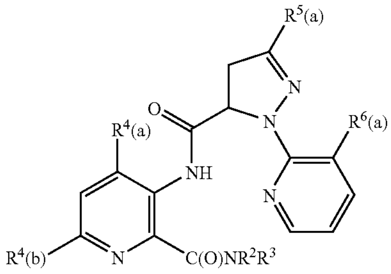

| $R^6$(a) | $R^5$(a) | $R^4$(a) | $R^4$(b) | $R^3$ | $R^2$ | $R^6$(a) | $R^5$(a) | $R^4$(a) | $R^4$(b) | $R^3$ | $R^2$ |
|---|---|---|---|---|---|---|---|---|---|---|---|
| Br | Cl | F | Cl | Me | H | Br | Cl | Br | Cl | Me | H |
| Br | Cl | F | Cl | Et | H | Br | Cl | Br | Cl | Et | H |
| Br | Cl | F | Cl | i-Pr | H | Br | Cl | Br | Cl | i-Pr | H |
| Br | Cl | F | Cl | t-Bu | H | Br | Cl | Br | Cl | t-Bu | H |
| Br | Cl | F | Cl | Me | Me | Br | Cl | Br | Cl | Me | Me |
| Cl | Br | F | Cl | Me | H | Cl | Br | Br | Cl | Me | H |
| Cl | Br | F | Cl | Et | H | Cl | Br | Br | Cl | Et | H |
| Cl | Br | F | Cl | i-Pr | H | Cl | Br | Br | Cl | i-Pr | H |
| Cl | Br | F | Cl | t-Bu | H | Cl | Br | Br | Cl | t-Bu | H |
| Cl | Br | F | Cl | Me | Me | Cl | Br | Br | Cl | Me | Me |
| Br | Br | F | Cl | Me | H | Br | Br | Br | Cl | Me | H |
| Br | Br | F | Cl | Et | H | Br | Br | Br | Cl | Et | H |
| Br | Br | F | Cl | i-Pr | H | Br | Br | Br | Cl | i-Pr | H |
| Br | Br | F | Cl | t-Bu | H | Br | Br | Br | Cl | t-Bu | H |
| Br | Br | F | Cl | Me | Me | Br | Br | Br | Cl | Me | Me |
| Cl | $OCH_2CF_3$ | F | Cl | Me | H | Cl | $OCH_2CF_3$ | Br | Cl | Me | H |
| Cl | $OCH_2CF_3$ | F | Cl | Et | H | Cl | $OCH_2CF_3$ | Br | Cl | Et | H |
| Cl | $OCH_2CF_3$ | F | Cl | i-Pr | H | Cl | $OCH_2CF_3$ | Br | Cl | i-Pr | H |
| Cl | $OCH_2CF_3$ | F | Cl | t-Bu | H | Cl | $OCH_2CF_3$ | Br | Cl | t-Bu | H |
| Cl | $OCH_2CF_3$ | F | Cl | Me | Me | Cl | $OCH_2CF_3$ | Br | Cl | Me | Me |
| Br | $OCH_2CF_3$ | F | Cl | Me | H | Br | $OCH_2CF_3$ | Br | Cl | Me | H |
| Br | $OCH_2CF_3$ | F | Cl | Et | H | Br | $OCH_2CF_3$ | Br | Cl | Et | H |
| Br | $OCH_2CF_3$ | F | Cl | i-Pr | H | Br | $OCH_2CF_3$ | Br | Cl | i-Pr | H |
| Br | $OCH_2CF_3$ | F | Cl | t-Bu | H | Br | $OCH_2CF_3$ | Br | Cl | t-Bu | H |
| Br | $OCH_2CF_3$ | F | Cl | Me | Me | Br | $OCH_2CF_3$ | Br | Cl | Me | Me |
| Cl | $CF_3$ | F | Br | Me | H | Cl | $CF_3$ | Br | Br | Me | H |
| Cl | $CF_3$ | F | Br | Et | H | Cl | $CF_3$ | Br | Br | Et | H |
| Cl | $CF_3$ | F | Br | i-Pr | H | Cl | $CF_3$ | Br | Br | i-Pr | H |
| Cl | $CF_3$ | F | Br | t-Bu | H | Cl | $CF_3$ | Br | Br | t-Bu | H |
| Cl | $CF_3$ | F | Br | Me | Me | Cl | $CF_3$ | Br | Br | Me | Me |
| Br | $CF_3$ | F | Br | Me | H | Br | $CF_3$ | Br | Br | Me | H |
| Br | $CF_3$ | F | Br | Et | H | Br | $CF_3$ | Br | Br | Et | H |
| Br | $CF_3$ | F | Br | i-Pr | H | Br | $CF_3$ | Br | Br | i-Pr | H |
| Br | $CF_3$ | F | Br | t-Bu | H | Br | $CF_3$ | Br | Br | t-Bu | H |
| Br | $CF_3$ | F | Br | Me | Me | Br | $CF_3$ | Br | Br | Me | Me |
| Cl | Cl | F | Br | Me | H | Cl | Cl | Br | Br | Me | H |
| Cl | Cl | F | Br | Et | H | Cl | Cl | Br | Br | Et | H |
| Cl | Cl | F | Br | i-Pr | H | Cl | Cl | Br | Br | i-Pr | H |
| Cl | Cl | F | Br | t-Bu | H | Cl | Cl | Br | Br | t-Bu | H |
| Cl | Cl | F | Br | Me | Me | Cl | Cl | Br | Br | Me | Me |
| Br | Cl | F | Br | Me | H | Br | Cl | Br | Br | Me | H |
| Br | Cl | F | Br | Et | H | Br | Cl | Br | Br | Et | H |
| Br | Cl | F | Br | i-Pr | H | Br | Cl | Br | Br | i-Pr | H |
| Br | Cl | F | Br | t-Bu | H | Br | Cl | Br | Br | t-Bu | H |
| Br | Cl | F | Br | Me | Me | Br | Cl | Br | Br | Me | Me |
| Cl | Br | F | Br | Me | H | Cl | Br | Br | Br | Me | H |
| Cl | Br | F | Br | Et | H | Cl | Br | Br | Br | Et | H |
| Cl | Br | F | Br | i-Pr | H | Cl | Br | Br | Br | i-Pr | H |
| Cl | Br | F | Br | t-Bu | H | Cl | Br | Br | Br | t-Bu | H |
| Cl | Br | F | Br | Me | Me | Cl | Br | Br | Br | Me | Me |
| Br | Br | F | Br | Me | H | Br | Br | Br | Br | Me | H |
| Br | Br | F | Br | Et | H | Br | Br | Br | Br | Et | H |
| Br | Br | F | Br | i-Pr | H | Br | Br | Br | Br | i-Pr | H |
| Br | Br | F | Br | t-Bu | H | Br | Br | Br | Br | t-Bu | H |
| Br | Br | F | Br | Me | Me | Br | Br | Br | Br | Me | Me |
| Cl | $OCH_2CF_3$ | F | Br | Me | H | Cl | $OCH_2CF_3$ | Br | Br | Me | H |
| Cl | $OCH_2CF_3$ | F | Br | Et | H | Cl | $OCH_2CF_3$ | Br | Br | Et | H |
| Cl | $OCH_2CF_3$ | F | Br | i-Pr | H | Cl | $OCH_2CF_3$ | Br | Br | i-Pr | H |
| Cl | $OCH_2CF_3$ | F | Br | t-Bu | H | Cl | $OCH_2CF_3$ | Br | Br | t-Bu | H |
| Cl | $OCH_2CF_3$ | F | Br | Me | Me | Cl | $OCH_2CF_3$ | Br | Br | Me | Me |
| Br | $OCH_2CF_3$ | F | Br | Me | H | Br | $OCH_2CF_3$ | Br | Br | Me | H |
| Br | $OCH_2CF_3$ | F | Br | Et | H | Br | $OCH_2CF_3$ | Br | Br | Et | H |
| Br | $OCH_2CF_3$ | F | Br | i-Pr | H | Br | $OCH_2CF_3$ | Br | Br | i-Pr | H |

TABLE 7-continued

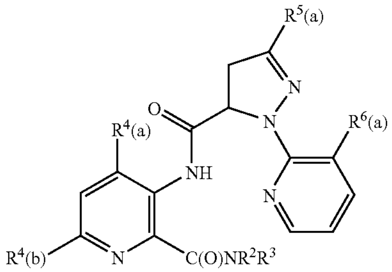

| $R^6$(a) | $R^5$(a) | $R^4$(a) | $R^4$(b) | $R^3$ | $R^2$ | $R^6$(a) | $R^5$(a) | $R^4$(a) | $R^4$(b) | $R^3$ | $R^2$ |
|---|---|---|---|---|---|---|---|---|---|---|---|
| Br | $OCH_2CF_3$ | F | Br | t-Bu | H | Br | $OCH_2CF_3$ | Br | Br | t-Bu | H |
| Br | $OCH_2CF_3$ | F | Br | Me | Me | Br | $OCH_2CF_3$ | Br | Br | Me | Me |
| Cl | $CF_3$ | F | I | Me | H | Cl | $CF_3$ | Br | I | Me | H |
| Cl | $CF_3$ | F | I | Et | H | Cl | $CF_3$ | Br | I | Et | H |
| Cl | $CF_3$ | F | I | i-Pr | H | Cl | $CF_3$ | Br | I | i-Pr | H |
| Cl | $CF_3$ | F | I | t-Bu | H | Cl | $CF_3$ | Br | I | t-Bu | H |
| Cl | $CF_3$ | F | I | Me | Me | Cl | $CF_3$ | Br | I | Me | Me |
| Br | $CF_3$ | F | I | Me | H | Br | $CF_3$ | Br | I | Me | H |
| Br | $CF_3$ | F | I | Et | H | Br | $CF_3$ | Br | I | Et | H |
| Br | $CF_3$ | F | I | i-Pr | H | Br | $CF_3$ | Br | I | i-Pr | H |
| Br | $CF_3$ | F | I | t-Bu | H | Br | $CF_3$ | Br | I | t-Bu | H |
| Br | $CF_3$ | F | I | Me | Me | Br | $CF_3$ | Br | I | Me | Me |
| Cl | Cl | F | I | Me | H | Cl | Cl | Br | I | Me | H |
| Cl | Cl | F | I | Et | H | Cl | Cl | Br | I | Et | H |
| Cl | Cl | F | I | i-Pr | H | Cl | Cl | Br | I | i-Pr | H |
| Cl | Cl | F | I | t-Bu | H | Cl | Cl | Br | I | t-Bu | H |
| Cl | Cl | F | I | Me | Me | Cl | Cl | Br | I | Me | Me |
| Br | Cl | F | I | Me | H | Br | Cl | Br | I | Me | H |
| Br | Cl | F | I | Et | H | Br | Cl | Br | I | Et | H |
| Br | Cl | F | I | i-Pr | H | Br | Cl | Br | I | i-Pr | H |
| Br | Cl | F | I | t-Bu | H | Br | Cl | Br | I | t-Bu | H |
| Br | Cl | F | I | Me | Me | Br | Cl | Br | I | Me | Me |
| Cl | Br | F | I | Me | H | Cl | Br | Br | I | Me | H |
| Cl | Br | F | I | Et | H | Cl | Br | Br | I | Et | H |
| Cl | Br | F | I | i-Pr | H | Cl | Br | Br | I | i-Pr | H |
| Cl | Br | F | I | t-Bu | H | Cl | Br | Br | 1 | t-Bu | H |
| Cl | Br | F | I | Me | Me | Cl | Br | Br | I | Me | Me |
| Br | Br | F | I | Me | H | Br | Br | Br | I | Me | H |
| Br | Br | F | I | Et | H | Br | Br | Br | I | Et | H |
| Br | Br | F | I | i-Pr | H | Br | Br | Br | I | i-Pr | H |
| Br | Br | F | I | t-Bu | H | Br | Br | Br | I | t-Bu | H |
| Br | Br | F | I | Me | Me | Br | Br | Br | I | Me | Me |
| Cl | $OCH_2CF_3$ | F | I | Me | H | Cl | $OCH_2CF_3$ | Br | I | Me | H |
| Cl | $OCH_2CF_3$ | F | I | Et | H | Cl | $OCH_2CF_3$ | Br | I | Et | H |
| Cl | $OCH_2CF_3$ | F | I | i-Pr | H | Cl | $OCH_2CF_3$ | Br | I | i-Pr | H |
| Cl | $OCH_2CF_3$ | F | I | t-Bu | H | Cl | $OCH_2CF_3$ | Br | I | t-Bu | H |
| Cl | $OCH_2CF_3$ | F | I | Me | Me | Cl | $OCH_2CF_3$ | Br | I | Me | Me |
| Br | $OCH_2CF_3$ | F | I | Me | H | Br | $OCH_2CF_3$ | Br | I | Me | H |
| Br | $OCH_2CF_3$ | F | I | Et | H | Br | $OCH_2CF_3$ | Br | I | Et | H |
| Br | $OCH_2CF_3$ | F | I | i-Pr | H | Br | $OCH_2CF_3$ | Br | I | i-Pr | H |
| Br | $OCH_2CF_3$ | F | I | t-Bu | H | Br | $OCH_2CF_3$ | Br | I | t-Bu | H |
| Br | $OCH_2CF_3$ | F | I | Me | Me | Br | $OCH_2CF_3$ | Br | I | Me | Me |
| Cl | $CF_3$ | F | $CF_3$ | Me | H | Cl | $CF_3$ | Br | $CF_3$ | Me | H |
| Cl | $CF_3$ | F | $CF_3$ | Et | H | Cl | $CF_3$ | Br | $CF_3$ | Et | H |
| Cl | $CF_3$ | F | $CF_3$ | i-Pr | H | Cl | $CF_3$ | Br | $CF_3$ | i-Pr | H |
| Cl | $CF_3$ | F | $CF_3$ | t-Bu | H | Cl | $CF_3$ | Br | $CF_3$ | t-Bu | H |
| Cl | $CF_3$ | F | $CF_3$ | Me | Me | Cl | $CF_3$ | Br | $CF_3$ | Me | Me |
| Br | $CF_3$ | F | $CF_3$ | Me | H | Br | $CF_3$ | Br | $CF_3$ | Me | H |
| Br | $CF_3$ | F | $CF_3$ | Et | H | Br | $CF_3$ | Br | $CF_3$ | Et | H |
| Br | $CF_3$ | F | $CF_3$ | i-Pr | H | Br | $CF_3$ | Br | $CF_3$ | i-Pr | H |
| Br | $CF_3$ | F | $CF_3$ | t-Bu | H | Br | $CF_3$ | Br | $CF_3$ | t-Bu | H |
| Br | $CF_3$ | F | $CF_3$ | Me | Me | Br | $CF_3$ | Br | $CF_3$ | Me | Me |
| Cl | Cl | F | $CF_3$ | Me | H | Cl | Cl | Br | $CF_3$ | Me | H |
| Cl | Cl | F | $CF_3$ | Et | H | Cl | Cl | Br | $CF_3$ | Et | H |
| Cl | Cl | F | $CF_3$ | i-Pr | H | Cl | Cl | Br | $CF_3$ | i-Pr | H |
| Cl | Cl | F | $CF_3$ | t-Bu | H | Cl | Cl | Br | $CF_3$ | t-Bu | H |
| Cl | Cl | F | $CF_3$ | Me | Me | Cl | Cl | Br | $CF_3$ | Me | Me |
| Br | Cl | F | $CF_3$ | Me | H | Br | Cl | Br | $CF_3$ | Me | H |
| Br | Cl | F | $CF_3$ | Et | H | Br | Cl | Br | $CF_3$ | Et | H |
| Br | Cl | F | $CF_3$ | i-Pr | H | Br | Cl | Br | $CF_3$ | i-Pr | H |
| Br | Cl | F | $CF_3$ | t-Bu | H | Br | Cl | Br | $CF_3$ | t-Bu | H |
| Br | Cl | F | $CF_3$ | Me | Me | Br | Cl | Br | $CF_3$ | Me | Me |
| Cl | Br | F | $CF_3$ | Me | H | Cl | Br | Br | $CF_3$ | Me | H |

TABLE 7-continued

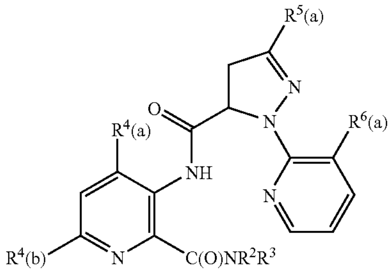

| $R^6$(a) | $R^5$(a) | $R^4$(a) | $R^4$(b) | $R^3$ | $R^2$ | $R^6$(a) | $R^5$(a) | $R^4$(a) | $R^4$(b) | $R^3$ | $R^2$ |
|---|---|---|---|---|---|---|---|---|---|---|---|
| Cl | Br | F | $CF_3$ | Et | H | Cl | Br | Br | $CF_3$ | Et | H |
| Cl | Br | F | $CF_3$ | i-Pr | H | Cl | Br | Br | $CF_3$ | i-Pr | H |
| Cl | Br | F | $CF_3$ | t-Bu | H | Cl | Br | Br | $CF_3$ | t-Bu | H |
| Cl | Br | F | $CF_3$ | Me | Me | Cl | Br | Br | $CF_3$ | Me | Me |
| Br | Br | F | $CF_3$ | Me | H | Br | Br | Br | $CF_3$ | Me | H |
| Br | Br | F | $CF_3$ | Et | H | Br | Br | Br | $CF_3$ | Et | H |
| Br | Br | F | $CF_3$ | i-Pr | H | Br | Br | Br | $CF_3$ | i-Pr | H |
| Br | Br | F | $CF_3$ | t-Bu | H | Br | Br | Br | $CF_3$ | t-Bu | H |
| Br | Br | F | $CF_3$ | Me | Me | Br | Br | Br | $CF_3$ | Me | Me |
| Cl | $OCH_2CF_3$ | F | $CF_3$ | Me | H | Cl | $OCH_2CF_3$ | Br | $CF_3$ | Me | H |
| Cl | $OCH_2CF_3$ | F | $CF_3$ | Et | H | Cl | $OCH_2CF_3$ | Br | $CF_3$ | Et | H |
| Cl | $OCH_2CF_3$ | F | $CF_3$ | i-Pr | H | Cl | $OCH_2CF_3$ | Br | $CF_3$ | i-Pr | H |
| Cl | $OCH_2CF_3$ | F | $CF_3$ | t-Bu | H | Cl | $OCH_2CF_3$ | Br | $CF_3$ | t-Bu | H |
| Cl | $OCH_2CF_3$ | F | $CF_3$ | Me | Me | Cl | $OCH_2CF_3$ | Br | $CF_3$ | Me | Me |
| Br | $OCH_2CF_3$ | F | $CF_3$ | Me | H | Br | $OCH_2CF_3$ | Br | $CF_3$ | Me | H |
| Br | $OCH_2CF_3$ | F | $CF_3$ | Et | H | Br | $OCH_2CF_3$ | Br | $CF_3$ | Et | H |
| Br | $OCH_2CF_3$ | F | $CF_3$ | i-Pr | H | Br | $OCH_2CF_3$ | Br | $CF_3$ | i-Pr | H |
| Br | $OCH_2CF_3$ | F | $CF_3$ | t-Bu | H | Br | $OCH_2CF_3$ | Br | $CF_3$ | t-Bu | H |
| Br | $OCH_2CF_3$ | F | $CF_3$ | Me | Me | Br | $OCH_2CF_3$ | Br | $CF_3$ | Me | Me |

TABLE 8

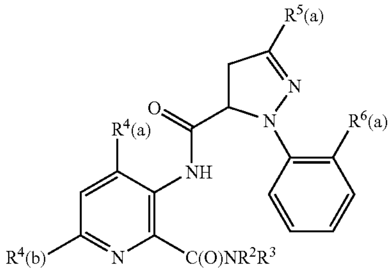

| $R^6$(a) | $R^5$(a) | $R^4$(a) | $R^4$(b) | $R^3$ | $R^2$ | $R^6$(a) | $R^5$(a) | $R^4$(a) | $R^4$(b) | $R^3$ | $R^2$ |
|---|---|---|---|---|---|---|---|---|---|---|---|
| Cl | $CF_3$ | $CH_3$ | H | Me | H | Cl | $CF_3$ | Cl | H | Me | H |
| Cl | $CF_3$ | $CH_3$ | H | Et | H | Cl | $CF_3$ | Cl | H | Et | H |
| Cl | $CF_3$ | $CH_3$ | H | i-Pr | H | Cl | $CF_3$ | Cl | H | i-Pr | H |
| Cl | $CF_3$ | $CH_3$ | H | t-Bu | H | Cl | $CF_3$ | Cl | H | t-Bu | H |
| Cl | $CF_3$ | $CH_3$ | H | Me | Me | Cl | $CF_3$ | Cl | H | Me | Me |
| Br | $CF_3$ | $CH_3$ | H | Me | H | Br | $CF_3$ | Cl | H | Me | H |
| Br | $CF_3$ | $CH_3$ | H | Et | H | Br | $CF_3$ | Cl | H | Et | H |
| Br | $CF_3$ | $CH_3$ | H | i-Pr | H | Br | $CF_3$ | Cl | H | i-Pr | H |
| Br | $CF_3$ | $CH_3$ | H | t-Bu | H | Br | $CF_3$ | Cl | H | t-Bu | H |
| Br | $CF_3$ | $CH_3$ | H | Me | Me | Br | $CF_3$ | Cl | H | Me | Me |
| Cl | Cl | $CH_3$ | H | Me | H | Cl | Cl | Cl | H | Me | H |
| Cl | Cl | $CH_3$ | H | Et | H | Cl | Cl | Cl | H | Et | H |
| Cl | Cl | $CH_3$ | H | i-Pr | H | Cl | Cl | Cl | H | i-Pr | H |
| Cl | Cl | $CH_3$ | H | t-Bu | H | Cl | Cl | Cl | H | t-Bu | H |
| Cl | Cl | $CH_3$ | H | Me | Me | Cl | Cl | Cl | H | Me | Me |
| Br | Cl | $CH_3$ | H | Me | H | Br | Cl | Cl | H | Me | H |
| Br | Cl | $CH_3$ | H | Et | H | Br | Cl | Cl | H | Et | H |
| Br | Cl | $CH_3$ | H | i-Pr | H | Br | Cl | Cl | H | i-Pr | H |
| Br | Cl | $CH_3$ | H | t-Bu | H | Br | Cl | Cl | H | t-Bu | H |
| Br | Cl | $CH_3$ | H | Me | Me | Br | Cl | Cl | H | Me | Me |
| Cl | Br | $CH_3$ | H | Me | H | Cl | Br | Cl | H | Me | H |
| Cl | Br | $CH_3$ | H | Et | H | Cl | Br | Cl | H | Et | H |
| Cl | Br | $CH_3$ | H | i-Pr | H | Cl | Br | Cl | H | i-Pr | H |

TABLE 8-continued

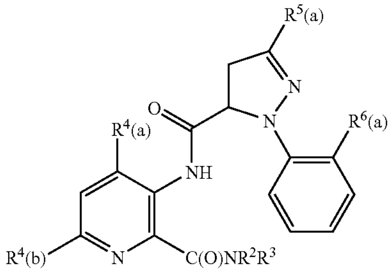

| $R^6$(a) | $R^5$(a) | $R^4$(a) | $R^4$(b) | $R^3$ | $R^2$ | $R^6$(a) | $R^5$(a) | $R^4$(a) | $R^4$(b) | $R^3$ | $R^2$ |
|---|---|---|---|---|---|---|---|---|---|---|---|
| Cl | Br | $CH_3$ | H | t-Bu | H | Cl | Br | Cl | H | t-Bu | H |
| Cl | Br | $CH_3$ | H | Me | Me | Cl | Br | Cl | H | Me | Me |
| Br | Br | $CH_3$ | H | Me | H | Br | Br | Cl | H | Me | H |
| Br | Br | $CH_3$ | H | Et | H | Br | Br | Cl | H | Et | H |
| Br | Br | $CH_3$ | H | i-Pr | H | Br | Br | Cl | H | i-Pr | H |
| Br | Br | $CH_3$ | H | t-Bu | H | Br | Br | Cl | H | t-Bu | H |
| Br | Br | $CH_3$ | H | Me | Me | Br | Br | Cl | H | Me | Me |
| Cl | $OCH_2CF_3$ | $CH_3$ | H | Me | H | Cl | $OCH_2CF_3$ | Cl | H | Me | H |
| Cl | $OCH_2CF_3$ | $CH_3$ | H | Et | H | Cl | $OCH_2CF_3$ | Cl | H | Et | H |
| Cl | $OCH_2CF_3$ | $CH_3$ | H | i-Pr | H | Cl | $OCH_2CF_3$ | Cl | H | i-Pr | H |
| Cl | $OCH_2CF_3$ | $CH_3$ | H | t-Bu | H | Cl | $OCH_2CF_3$ | Cl | H | t-Bu | H |
| Cl | $OCH_2CF_3$ | $CH_3$ | H | Me | Me | Cl | $OCH_2CF_3$ | Cl | H | Me | Me |
| Br | $OCH_2CF_3$ | $CH_3$ | H | Me | H | Br | $OCH_2CF_3$ | Cl | H | Me | H |
| Br | $OCH_2CF_3$ | $CH_3$ | H | Et | H | Br | $OCH_2CF_3$ | Cl | H | Et | H |
| Br | $OCH_2CF_3$ | $CH_3$ | H | i-Pr | H | Br | $OCH_2CF_3$ | Cl | H | i-Pr | H |
| Br | $OCH_2CF_3$ | $CH_3$ | H | t-Bu | H | Br | $OCH_2CF_3$ | Cl | H | t-Bu | H |
| Br | $OCH_2CF_3$ | $CH_3$ | H | Me | Me | Br | $OCH_2CF_3$ | Cl | H | Me | Me |
| Cl | $CF_3$ | $CH_3$ | F | Me | H | Cl | $CF_3$ | Cl | F | Me | H |
| Cl | $CF_3$ | $CH_3$ | F | Et | H | Cl | $CF_3$ | Cl | F | Et | H |
| Cl | $CF_3$ | $CH_3$ | F | i-Pr | H | Cl | $CF_3$ | Cl | F | i-Pr | H |
| Cl | $CF_3$ | $CH_3$ | F | t-Bu | H | Cl | $CF_3$ | Cl | F | t-Bu | H |
| Cl | $CF_3$ | $CH_3$ | F | Me | Me | Cl | $CF_3$ | Cl | F | Me | Me |
| Br | $CF_3$ | $CH_3$ | F | Me | H | Br | $CF_3$ | Cl | F | Me | H |
| Br | $CF_3$ | $CH_3$ | F | Et | H | Br | $CF_3$ | Cl | F | Et | H |
| Br | $CF_3$ | $CH_3$ | F | i-Pr | H | Br | $CF_3$ | Cl | F | i-Pr | H |
| Br | $CF_3$ | $CH_3$ | F | t-Bu | H | Br | $CF_3$ | Cl | F | t-Bu | H |
| Br | $CF_3$ | $CH_3$ | F | Me | Me | Br | $CF_3$ | Cl | F | Me | Me |
| Cl | Cl | $CH_3$ | F | Me | H | Cl | Cl | Cl | F | Me | H |
| Cl | Cl | $CH_3$ | F | Et | H | Cl | Cl | Cl | F | Et | H |
| Cl | Cl | $CH_3$ | F | i-Pr | H | Cl | Cl | Cl | F | i-Pr | H |
| Cl | Cl | $CH_3$ | F | t-Bu | H | Cl | Cl | Cl | F | t-Bu | H |
| Cl | Cl | $CH_3$ | F | Me | Me | Cl | Cl | Cl | F | Me | Me |
| Br | Cl | $CH_3$ | F | Me | H | Br | Cl | Cl | F | Me | H |
| Br | Cl | $CH_3$ | F | Et | H | Br | Cl | Cl | F | Et | H |
| Br | Cl | $CH_3$ | F | i-Pr | H | Br | Cl | Cl | F | i-Pr | H |
| Br | Cl | $CH_3$ | F | t-Bu | H | Br | Cl | Cl | F | t-Bu | H |
| Br | Cl | $CH_3$ | F | Me | Me | Br | Cl | Cl | F | Me | Me |
| Cl | Br | $CH_3$ | F | Me | H | Cl | Br | Cl | F | Me | H |
| Cl | Br | $CH_3$ | F | Et | H | Cl | Br | Cl | F | Ft | H |
| Cl | Br | $CH_3$ | F | i-Pr | H | Cl | Br | Cl | F | i-Pr | H |
| Cl | Br | $CH_3$ | F | t-Bu | H | Cl | Br | Cl | F | t-Bu | H |
| Cl | Br | $CH_3$ | F | Me | Me | Cl | Br | Cl | F | Me | Me |
| Br | Br | $CH_3$ | F | Me | H | Br | Br | Cl | F | Me | H |
| Br | Br | $CH_3$ | F | Et | H | Br | Br | Cl | F | Et | H |
| Br | Br | $CH_3$ | F | i-Pr | H | Br | Br | Cl | F | i-Pr | H |
| Br | Br | $CH_3$ | F | t-Bu | H | Br | Br | Cl | F | t-Bu | H |
| Br | Br | $CH_3$ | F | Me | Me | Br | Br | Cl | F | Me | Me |
| Cl | $OCH_2CF_3$ | $CH_3$ | F | Me | H | Cl | $OCH_2CF_3$ | Cl | F | Me | H |
| Cl | $OCH_2CF_3$ | $CH_3$ | F | Et | H | Cl | $OCH_2CF_3$ | Cl | F | Et | H |
| Cl | $OCH_2CF_3$ | $CH_3$ | F | i-Pr | H | Cl | $OCH_2CF_3$ | Cl | F | i-Pr | H |
| Cl | $OCH_2CF_3$ | $CH_3$ | F | t-Bu | H | Cl | $OCH_2CF_3$ | Cl | F | t-Bu | H |
| Cl | $OCH_2CF_3$ | $CH_3$ | F | Me | Me | Cl | $OCH_2CF_3$ | Cl | F | Me | Me |
| Br | $OCH_2CF_3$ | $CH_3$ | F | Me | H | Br | $OCH_2CF_3$ | Cl | F | Me | H |
| Br | $OCH_2CF_3$ | $CH_3$ | F | Et | H | Br | $OCH_2CF_3$ | Cl | F | Et | H |
| Br | $OCH_2CF_3$ | $CH_3$ | F | i-Pr | H | Br | $OCH_2CF_3$ | Cl | F | i-Pr | H |
| Br | $OCH_2CF_3$ | $CH_3$ | F | t-Bu | H | Br | $OCH_2CF_3$ | Cl | F | t-Bu | H |
| Br | $OCH_2CF_3$ | $CH_3$ | F | Me | Me | Br | $OCH_2CF_3$ | Cl | F | Me | Me |
| Cl | $CF_3$ | $CH_3$ | Cl | Me | H | Cl | $CF_3$ | Cl | Cl | Me | H |
| Cl | $CF_3$ | $CH_3$ | Cl | Et | H | Cl | $CF_3$ | Cl | Cl | Et | H |
| Cl | $CF_3$ | $CH_3$ | Cl | i-Pr | H | Cl | $CF_3$ | Cl | Cl | i-Pr | H |
| Cl | $CF_3$ | $CH_3$ | Cl | t-Bu | H | Cl | $CF_3$ | Cl | Cl | t-Bu | H |
| Cl | $CF_3$ | $CH_3$ | Cl | Me | Me | Cl | $CF_3$ | Cl | Cl | Me | Me |
| Br | $CF_3$ | $CH_3$ | Cl | Me | H | Br | $CF_3$ | Cl | Cl | Me | H |

TABLE 8-continued

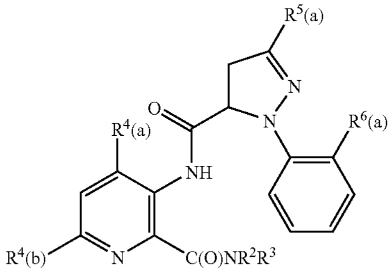

| $R^6$(a) | $R^5$(a) | $R^4$(a) | $R^4$(b) | $R^3$ | $R^2$ | $R^6$(a) | $R^5$(a) | $R^4$(a) | $R^4$(b) | $R^3$ | $R^2$ |
|---|---|---|---|---|---|---|---|---|---|---|---|
| Br | $CF_3$ | $CH_3$ | Cl | Et | H | Br | $CF_3$ | Cl | Cl | Et | H |
| Br | $CF_3$ | $CH_3$ | Cl | i-Pr | H | Br | $CF_3$ | Cl | Cl | i-Pr | H |
| Br | $CF_3$ | $CH_3$ | Cl | t-Bu | H | Br | $CF_3$ | Cl | Cl | t-Bu | H |
| Br | $CF_3$ | $CH_3$ | Cl | Me | Me | Br | $CF_3$ | Cl | Cl | Me | Me |
| Cl | Cl | $CH_3$ | Cl | Me | H | Cl | Cl | Cl | Cl | Me | H |
| Cl | Cl | $CH_3$ | Cl | Et | H | Cl | Cl | Cl | Cl | Et | H |
| Cl | Cl | $CH_3$ | Cl | i-Pr | H | Cl | Cl | Cl | Cl | i-Pr | H |
| Cl | Cl | $CH_3$ | Cl | t-Bu | H | Cl | Cl | Cl | Cl | t-Bu | H |
| Cl | Cl | $CH_3$ | Cl | Me | Me | Cl | Cl | Cl | Cl | Me | Me |
| Br | Cl | $CH_3$ | Cl | Me | H | Br | Cl | Cl | Cl | Me | H |
| Br | Cl | $CH_3$ | Cl | Et | H | Br | Cl | Cl | Cl | Et | H |
| Br | Cl | $CH_3$ | Cl | i-Pr | H | Br | Cl | Cl | Cl | i-Pr | H |
| Br | Cl | $CH_3$ | Cl | t-Bu | H | Br | Cl | Cl | Cl | t-Bu | H |
| Br | Cl | $CH_3$ | Cl | Me | Me | Br | Cl | Cl | Cl | Me | Me |
| Cl | Br | $CH_3$ | Cl | Me | H | Cl | Br | Cl | Cl | Me | H |
| Cl | Br | $CH_3$ | Cl | Et | H | Cl | Br | Cl | Cl | Et | H |
| Cl | Br | $CH_3$ | Cl | i-Pr | H | Cl | Br | Cl | Cl | i-Pr | H |
| Cl | Br | $CH_3$ | Cl | t-Bu | H | Cl | Br | Cl | Cl | t-Bu | H |
| Cl | Br | $CH_3$ | Cl | Me | Me | Cl | Br | Cl | Cl | Me | Me |
| Br | Br | $CH_3$ | Cl | Me | H | Br | Br | Cl | Cl | Me | H |
| Br | Br | $CH_3$ | Cl | Et | H | Br | Br | Cl | Cl | Et | H |
| Br | Br | $CH_3$ | Cl | i-Pr | H | Br | Br | Cl | Cl | i-Pr | H |
| Br | Br | $CH_3$ | Cl | t-Bu | H | Br | Br | Cl | Cl | t-Bu | H |
| Br | Br | $CH_3$ | Cl | Me | Me | Br | Br | Cl | Cl | Me | Me |
| Cl | $OCH_2CF_3$ | $CH_3$ | Cl | Me | H | Cl | $OCH_2CF_3$ | Cl | Cl | Me | H |
| Cl | $OCH_2CF_3$ | $CH_3$ | Cl | Et | H | Cl | $OCH_2CF_3$ | Cl | Cl | Et | H |
| Cl | $OCH_2CF_3$ | $CH_3$ | Cl | i-Pr | H | Cl | $OCH_2CF_3$ | Cl | Cl | i-Pr | H |
| Cl | $OCH_2CF_3$ | $CH_3$ | Cl | t-Bu | H | Cl | $OCH_2CF_3$ | Cl | Cl | t-Bu | H |
| Cl | $OCH_2CF_3$ | $CH_3$ | Cl | Me | Me | Cl | $OCH_2CF_3$ | Cl | Cl | Me | Me |
| Br | $OCH_2CF_3$ | $CH_3$ | Cl | Me | H | Br | $OCH_2CF_3$ | Cl | Cl | Me | H |
| Br | $OCH_2CF_3$ | $CH_3$ | Cl | Et | H | Br | $OCH_2CF_3$ | Cl | Cl | Et | H |
| Br | $OCH_2CF_3$ | $CH_3$ | Cl | i-Pr | H | Br | $OCH_2CF_3$ | Cl | Cl | i-Pr | H |
| Br | $OCH_2CF_3$ | $CH_3$ | Cl | t-Bu | H | Br | $OCH_2CF_3$ | Cl | Cl | t-Bu | H |
| Br | $OCH_2CF_3$ | $CH_3$ | Cl | Me | Me | Br | $OCH_2CF_3$ | Cl | Cl | Me | Me |
| Cl | $CF_3$ | $CH_3$ | Br | Me | H | Cl | $CF_3$ | Cl | Br | Me | H |
| Cl | $CF_3$ | $CH_3$ | Br | Et | H | Cl | $CF_3$ | Cl | Br | Et | H |
| Cl | $CF_3$ | $CH_3$ | Br | i-Pr | H | Cl | $CF_3$ | Cl | Br | i-Pr | H |
| Cl | $CF_3$ | $CH_3$ | Br | t-Bu | H | Cl | $CF_3$ | Cl | Br | t-Bu | H |
| Cl | $CF_3$ | $CH_3$ | Br | Me | Me | Cl | $CF_3$ | Cl | Br | Me | Me |
| Br | $CF_3$ | $CH_3$ | Br | Me | H | Br | $CF_3$ | Cl | Br | Me | H |
| Br | $CF_3$ | $CH_3$ | Br | Et | H | Br | $CF_3$ | Cl | Br | Et | H |
| Br | $CF_3$ | $CH_3$ | Br | i-Pr | H | Br | $CF_3$ | Cl | Br | i-Pr | H |
| Br | $CF_3$ | $CH_3$ | Br | t-Bu | H | Br | $CF_3$ | Cl | Br | t-Bu | H |
| Br | $CF_3$ | $CH_3$ | Br | Me | Me | Br | $CF_3$ | Cl | Br | Me | Me |
| Cl | Cl | $CH_3$ | Br | Me | H | Cl | Cl | Cl | Br | Me | H |
| Cl | Cl | $CH_3$ | Br | Et | H | Cl | Cl | Cl | Br | Et | H |
| Cl | Cl | $CH_3$ | Br | i-Pr | H | Cl | Cl | Cl | Br | i-Pr | H |
| Cl | Cl | $CH_3$ | Br | t-Bu | H | Cl | Cl | Cl | Br | t-Bu | H |
| Cl | Cl | $CH_3$ | Br | Me | Me | Cl | Cl | Cl | Br | Me | Me |
| Br | Cl | $CH_3$ | Br | Me | H | Br | Cl | Cl | Br | Me | H |
| Br | Cl | $CH_3$ | Br | Et | H | Br | Cl | Cl | Br | Et | H |
| Br | Cl | $CH_3$ | Br | i-Pr | H | Br | Cl | Cl | Br | i-Pr | H |
| Br | Cl | $CH_3$ | Br | t-Bu | H | Br | Cl | Cl | Br | t-Bu | H |
| Br | Cl | $CH_3$ | Br | Me | Me | Br | Cl | Cl | Br | Me | Me |
| Cl | Br | $CH_3$ | Br | Me | H | Cl | Br | Cl | Br | Me | H |
| Cl | Br | $CH_3$ | Br | Et | H | Cl | Br | Cl | Br | Et | H |
| Cl | Br | $CH_3$ | Br | i-Pr | H | Cl | Br | Cl | Br | i-Pr | H |
| Cl | Br | $CH_3$ | Br | t-Bu | H | Cl | Br | Cl | Br | t-Bu | H |
| Cl | Br | $CH_3$ | Br | Me | Me | Cl | Br | Cl | Br | Me | Me |
| Br | Br | $CH_3$ | Br | Me | H | Br | Br | Cl | Br | Me | H |
| Br | Br | $CH_3$ | Br | Et | H | Br | Br | Cl | Br | Et | H |
| Br | Br | $CH_3$ | Br | i-Pr | H | Br | Br | Cl | Br | i-Pr | H |
| Br | Br | $CH_3$ | Br | t-Bu | H | Br | Br | Cl | Br | t-Bu | H |

TABLE 8-continued

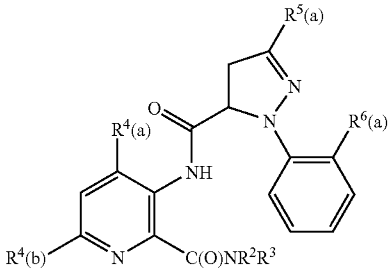

| $R^6$(a) | $R^5$(a) | $R^4$(a) | $R^4$(b) | $R^3$ | $R^2$ | $R^6$(a) | $R^5$(a) | $R^4$(a) | $R^4$(b) | $R^3$ | $R^2$ |
|---|---|---|---|---|---|---|---|---|---|---|---|
| Br | Br | $CH_3$ | Br | Me | Me | Br | Br | Cl | Br | Me | Me |
| Cl | $OCH_2CF_3$ | $CH_3$ | Br | Me | H | Cl | $OCH_2CF_3$ | Cl | Br | Me | H |
| Cl | $OCH_2CF_3$ | $CH_3$ | Br | Et | H | Cl | $OCH_2CF_3$ | Cl | Br | Et | H |
| Cl | $OCH_2CF_3$ | $CH_3$ | Br | i-Pr | H | Cl | $OCH_2CF_3$ | Cl | Br | i-Pr | H |
| Cl | $OCH_2CF_3$ | $CH_3$ | Br | t-Bu | H | Cl | $OCH_2CF_3$ | Cl | Br | t-Bu | H |
| Cl | $OCH_2CF_3$ | $CH_3$ | Br | Me | Me | Cl | $OCH_2CF_3$ | Cl | Br | Me | Me |
| Br | $OCH_2CF_3$ | $CH_3$ | Br | Me | H | Br | $OCH_2CF_3$ | Cl | Br | Me | H |
| Br | $OCH_2CF_3$ | $CH_3$ | Br | Et | H | Br | $OCH_2CF_3$ | Cl | Br | Et | H |
| Br | $OCH_2CF_3$ | $CH_3$ | Br | i-Pr | H | Br | $OCH_2CF_3$ | Cl | Br | i-Pr | H |
| Br | $OCH_2CF_3$ | $CH_3$ | Br | t-Bu | H | Br | $OCH_2CF_3$ | Cl | Br | t-Bu | H |
| Br | $OCH_2CF_3$ | $CH_3$ | Br | Me | Me | Br | $OCH_2CF_3$ | Cl | Br | Me | Me |
| Cl | $CF_3$ | $CH_3$ | I | Me | H | Cl | $CF_3$ | Cl | I | Me | H |
| Cl | $CF_3$ | $CH_3$ | I | Et | H | Cl | $CF_3$ | Cl | I | Et | H |
| Cl | $CF_3$ | $CH_3$ | I | i-Pr | H | Cl | $CF_3$ | Cl | I | i-Pr | H |
| Cl | $CF_3$ | $CH_3$ | I | t-Bu | H | Cl | $CF_3$ | Cl | I | t-Bu | H |
| Cl | $CF_3$ | $CH_3$ | I | Me | Me | Cl | $CF_3$ | Cl | I | Me | Me |
| Br | $CF_3$ | $CH_3$ | I | Me | H | Br | $CF_3$ | Cl | I | Me | H |
| Br | $CF_3$ | $CH_3$ | I | Et | H | Br | $CF_3$ | Cl | I | Et | H |
| Br | $CF_3$ | $CH_3$ | I | i-Pr | H | Br | $CF_3$ | Cl | I | i-Pr | H |
| Br | $CF_3$ | $CH_3$ | I | t-Bu | H | Br | $CF_3$ | Cl | I | t-Bu | H |
| Br | $CF_3$ | $CH_3$ | I | Me | Me | Br | $CF_3$ | Cl | I | Me | Me |
| Cl | Cl | $CH_3$ | I | Me | H | Cl | Cl | Cl | I | Me | H |
| Cl | Cl | $CH_3$ | I | Et | H | Cl | Cl | Cl | I | Et | H |
| Cl | Cl | $CH_3$ | I | i-Pr | H | Cl | Cl | Cl | I | i-Pr | H |
| Cl | Cl | $CH_3$ | I | t-Bu | H | Cl | Cl | Cl | I | t-Bu | H |
| Cl | Cl | $CH_3$ | I | Me | Me | Cl | Cl | Cl | I | Me | Me |
| Br | Cl | $CH_3$ | I | Me | H | Br | Cl | Cl | I | Me | H |
| Br | Cl | $CH_3$ | I | Et | H | Br | Cl | Cl | I | Et | H |
| Br | Cl | $CH_3$ | I | i-Pr | H | Br | Cl | Cl | I | i-Pr | H |
| Br | Cl | $CH_3$ | I | t-Bu | H | Br | Cl | Cl | I | t-Bu | H |
| Br | Cl | $CH_3$ | I | Me | Me | Br | Cl | Cl | I | Me | Me |
| Cl | Br | $CH_3$ | I | Me | H | Cl | Br | Cl | I | Me | H |
| Cl | Br | $CH_3$ | I | Et | H | Cl | Br | Cl | I | Et | H |
| Cl | Br | $CH_3$ | I | i-Pr | H | Cl | Br | Cl | I | i-Pr | H |
| Cl | Br | $CH_3$ | I | t-Bu | H | Cl | Br | Cl | I | t-Bu | H |
| Cl | Br | $CH_3$ | I | Me | Me | Cl | Br | Cl | I | Me | Me |
| Br | Br | $CH_3$ | I | Me | H | Br | Br | Cl | I | Me | H |
| Br | Br | $CH_3$ | I | Et | H | Br | Br | Cl | I | Et | H |
| Br | Br | $CH_3$ | I | i-Pr | H | Br | Br | Cl | I | i-Pr | H |
| Br | Br | $CH_3$ | I | t-Bu | H | Br | Br | Cl | I | t-Bu | H |
| Br | Br | $CH_3$ | I | Me | Me | Br | Br | Cl | I | Me | Me |
| Cl | $OCH_2CF_3$ | $CH_3$ | I | Me | H | Cl | $OCH_2CF_3$ | Cl | I | Me | H |
| Cl | $OCH_2CF_3$ | $CH_3$ | I | Et | H | Cl | $OCH_2CF_3$ | Cl | I | Et | H |
| Cl | $OCH_2CF_3$ | $CH_3$ | I | i-Pr | H | Cl | $OCH_2CF_3$ | Cl | I | i-Pr | H |
| Cl | $OCH_2CF_3$ | $CH_3$ | I | t-Bu | H | Cl | $OCH_2CF_3$ | Cl | I | t-Bu | H |
| Cl | $OCH_2CF_3$ | $CH_3$ | I | Me | Me | Cl | $OCH_2CF_3$ | Cl | I | Me | Me |
| Br | $OCH_2CF_3$ | $CH_3$ | I | Me | H | Br | $OCH_2CF_3$ | Cl | I | Me | H |
| Br | $OCH_2CF_3$ | $CH_3$ | I | Et | H | Br | $OCH_2CF_3$ | Cl | I | Et | H |
| Br | $OCH_2CF_3$ | $CH_3$ | I | i-Pr | H | Br | $OCH_2CF_3$ | Cl | I | i-Pr | H |
| Br | $OCH_2CF_3$ | $CH_3$ | I | t-Bu | H | Br | $OCH_2CF_3$ | Cl | I | t-Bu | H |
| Br | $OCH_2CF_3$ | $CH_3$ | I | Me | Me | Br | $OCH_2CF_3$ | Cl | I | Me | Me |
| Cl | $CF_3$ | $CH_3$ | $CF_3$ | Me | H | Cl | $CF_3$ | Cl | $CF_3$ | Me | H |
| Cl | $CF_3$ | $CH_3$ | $CF_3$ | Et | H | Cl | $CF_3$ | Cl | $CF_3$ | Et | H |
| Cl | $CF_3$ | $CH_3$ | $CF_3$ | i-Pr | H | Cl | $CF_3$ | Cl | $CF_3$ | i-Pr | H |
| Cl | $CF_3$ | $CH_3$ | $CF_3$ | t-Bu | H | Cl | $CF_3$ | Cl | $CF_3$ | t-Bu | H |
| Cl | $CF_3$ | $CH_3$ | $CF_3$ | Me | Me | Cl | $CF_3$ | Cl | $CF_3$ | Me | Me |
| Br | $CF_3$ | $CH_3$ | $CF_3$ | Me | H | Br | $CF_3$ | Cl | $CF_3$ | Me | H |
| Br | $CF_3$ | $CH_3$ | $CF_3$ | Et | H | Br | $CF_3$ | Cl | $CF_3$ | Et | H |
| Br | $CF_3$ | $CH_3$ | $CF_3$ | i-Pr | H | Br | $CF_3$ | Cl | $CF_3$ | i-Pr | H |
| Br | $CF_3$ | $CH_3$ | $CF_3$ | t-Bu | H | Br | $CF_3$ | Cl | $CF_3$ | t-Bu | H |
| Br | $CF_3$ | $CH_3$ | $CF_3$ | Me | Me | Br | $CF_3$ | Cl | $CF_3$ | Me | Me |
| Cl | Cl | $CH_3$ | $CF_3$ | Me | H | Cl | Cl | Cl | $CF_3$ | Me | H |
| Cl | Cl | $CH_3$ | $CF_3$ | Et | H | Cl | Cl | Cl | $CF_3$ | Et | H |

TABLE 8-continued

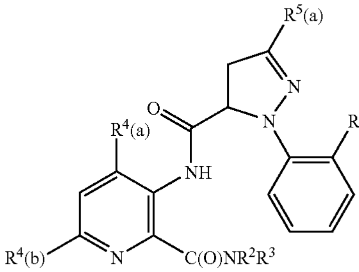

| $R^6$(a) | $R^5$(a) | $R^4$(a) | $R^4$(b) | $R^3$ | $R^2$ | $R^6$(a) | $R^5$(a) | $R^4$(a) | $R^4$(b) | $R^3$ | $R^2$ |
|---|---|---|---|---|---|---|---|---|---|---|---|
| Cl | Cl | $CH_3$ | $CF_3$ | i-Pr | H | Cl | Cl | Cl | $CF_3$ | i-Pr | H |
| Cl | Cl | $CH_3$ | $CF_3$ | t-Bu | H | Cl | Cl | Cl | $CF_3$ | t-Bu | H |
| Cl | Cl | $CH_3$ | $CF_3$ | Me | Me | Cl | Cl | Cl | $CF_3$ | Me | Me |
| Br | Cl | $CH_3$ | $CF_3$ | Me | H | Br | Cl | Cl | $CF_3$ | Me | H |
| Br | Cl | $CH_3$ | $CF_3$ | Et | H | Br | Cl | Cl | $CF_3$ | Et | H |
| Br | Cl | $CH_3$ | $CF_3$ | i-Pr | H | Br | Cl | Cl | $CF_3$ | i-Pr | H |
| Br | Cl | $CH_3$ | $CF_3$ | t-Bu | H | Br | Cl | Cl | $CF_3$ | t-Bu | H |
| Br | Cl | $CH_3$ | $CF_3$ | Me | Me | Br | Cl | Cl | $CF_3$ | Me | Me |
| Cl | Br | $CH_3$ | $CF_3$ | Me | H | Cl | Br | Cl | $CF_3$ | Me | H |
| Cl | Br | $CH_3$ | $CF_3$ | Et | H | Cl | Br | Cl | $CF_3$ | Et | H |
| Cl | Br | $CH_3$ | $CF_3$ | i-Pr | H | Cl | Br | Cl | $CF_3$ | i-Pr | H |
| Cl | Br | $CH_3$ | $CF_3$ | t-Bu | H | Cl | Br | Cl | $CF_3$ | t-Bu | H |
| Cl | Br | $CH_3$ | $CF_3$ | Me | Me | Cl | Br | Cl | $CF_3$ | Me | Me |
| Br | Br | $CH_3$ | $CF_3$ | Me | H | Br | Br | Cl | $CF_3$ | Me | H |
| Br | Br | $CH_3$ | $CF_3$ | Et | H | Br | Br | Cl | $CF_3$ | Et | H |
| Br | Br | $CH_3$ | $CF_3$ | i-Pr | H | Br | Br | Cl | $CF_3$ | i-Pr | H |
| Br | Br | $CH_3$ | $CF_3$ | t-Bu | H | Br | Br | Cl | $CF_3$ | t-Bu | H |
| Br | Br | $CH_3$ | $CF_3$ | Me | Me | Br | Br | Cl | $CF_3$ | Me | Me |
| Cl | $OCH_2CF_3$ | $CH_3$ | $CF_3$ | Me | H | Cl | $OCH_2CF_3$ | Cl | $CF_3$ | Me | H |
| Cl | $OCH_2CF_3$ | $CH_3$ | $CF_3$ | Et | H | Cl | $OCH_2CF_3$ | Cl | $CF_3$ | Et | H |
| Cl | $OCH_2CF_3$ | $CH_3$ | $CF_3$ | i-Pr | H | Cl | $OCH_2CF_3$ | Cl | $CF_3$ | i-Pr | H |
| Cl | $OCH_2CF_3$ | $CH_3$ | $CF_3$ | t-Bu | H | Cl | $OCH_2CF_3$ | Cl | $CF_3$ | t-Bu | H |
| Cl | $OCH_2CF_3$ | $CH_3$ | $CF_3$ | Me | Me | Cl | $OCH_2CF_3$ | Cl | $CF_3$ | Me | Me |
| Br | $OCH_2CF_3$ | $CH_3$ | $CF_3$ | Me | H | Br | $OCH_2CF_3$ | Cl | $CF_3$ | Me | H |
| Br | $OCH_2CF_3$ | $CH_3$ | $CF_3$ | Et | H | Br | $OCH_2CF_3$ | Cl | $CF_3$ | Et | H |
| Br | $OCH_2CF_3$ | $CH_3$ | $CF_3$ | i-Pr | H | Br | $OCH_2CF_3$ | Cl | $CF_3$ | i-Pr | H |
| Br | $OCH_2CF_3$ | $CH_3$ | $CF_3$ | t-Bu | H | Br | $OCH_2CF_3$ | Cl | $CF_3$ | t-Bu | H |
| Br | $OCH_2CF_3$ | $CH_3$ | $CF_3$ | Me | Me | Br | $OCH_2CF_3$ | Cl | $CF_3$ | Me | Me |
| Cl | Cl | $CH_3$ | Cl | n-Pr | H | Cl | Cl | Cl | Cl | n-Pr | H |
| Cl | Cl | $CH_3$ | Cl | n-Bu | H | Cl | Cl | Cl | Cl | n-Bu | H |
| Cl | Cl | $CH_3$ | Cl | s-Bu | H | Cl | Cl | Cl | Cl | s-Bu | H |
| Cl | Cl | $CH_3$ | Cl | i-Bu | H | Cl | Cl | Cl | Cl | i-Bu | H |
| Cl | Cl | $CH_3$ | Cl | Et | Me | Cl | Cl | Cl | Cl | Et | Et |
| Cl | $CF_3$ | F | H | Me | H | Cl | $CF_3$ | Br | H | Me | H |
| Cl | $CF_3$ | F | H | Et | H | Cl | $CF_3$ | Br | H | Et | H |
| Cl | $CF_3$ | F | H | i-Pr | H | Cl | $CF_3$ | Br | H | i-Pr | H |
| Cl | $CF_3$ | F | H | t-Bu | H | Cl | $CF_3$ | Br | H | t-Bu | H |
| Cl | $CF_3$ | F | H | Me | Me | Cl | $CF_3$ | Br | H | Me | Me |
| Br | $CF_3$ | F | H | Me | H | Br | $CF_3$ | Br | H | Me | H |
| Br | $CF_3$ | F | H | Et | H | Br | $CF_3$ | Br | H | Et | H |
| Br | $CF_3$ | F | H | i-Pr | H | Br | $CF_3$ | Br | H | i-Pr | H |
| Br | $CF_3$ | F | H | t-Bu | H | Br | $CF_3$ | Br | H | t-Bu | H |
| Br | $CF_3$ | F | H | Me | Me | Br | $CF_3$ | Br | H | Me | Me |
| Cl | Cl | F | H | Me | H | Cl | Cl | Br | H | Me | H |
| Cl | Cl | F | H | Et | H | Cl | Cl | Br | H | Et | H |
| Cl | Cl | F | H | i-Pr | H | Cl | Cl | Br | H | i-Pr | H |
| Cl | Cl | F | H | t-Bu | H | Cl | Cl | Br | H | t-Bu | H |
| Cl | Cl | F | H | Me | Me | Cl | Cl | Br | H | Me | Me |
| Br | Cl | F | H | Me | H | Br | Cl | Br | H | Me | H |
| Br | Cl | F | H | Et | H | Br | Cl | Br | H | Et | H |
| Br | Cl | F | H | i-Pr | H | Br | Cl | Br | H | i-Pr | H |
| Br | Cl | F | H | t-Bu | H | Br | Cl | Br | H | t-Bu | H |
| Br | Cl | F | H | Me | Me | Br | Cl | Br | H | Me | Me |
| Cl | Br | F | H | Me | H | Cl | Br | Br | H | Me | H |
| Cl | Br | F | H | Et | H | Cl | Br | Br | H | Et | H |
| Cl | Br | F | H | i-Pr | H | Cl | Br | Br | H | i-Pr | H |
| Cl | Br | F | H | t-Bu | H | Cl | Br | Br | H | t-Bu | H |
| Cl | Br | F | H | Me | Me | Cl | Br | Br | H | Me | Me |
| Br | Br | F | H | Me | H | Br | Br | Br | H | Me | H |
| Br | Br | F | H | Et | H | Br | Br | Br | H | Et | H |
| Br | Br | F | H | i-Pr | H | Br | Br | Br | H | i-Pr | H |
| Br | Br | F | H | t-Bu | H | Br | Br | Br | H | t-Bu | H |
| Br | Br | F | H | Me | Me | Br | Br | Br | H | Me | Me |

TABLE 8-continued

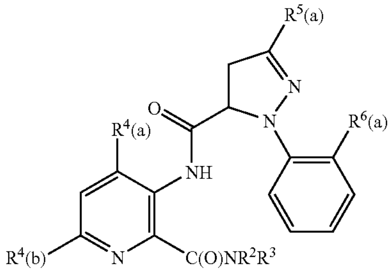

| $R^6$(a) | $R^5$(a) | $R^4$(a) | $R^4$(b) | $R^3$ | $R^2$ | $R^6$(a) | $R^5$(a) | $R^4$(a) | $R^4$(b) | $R^3$ | $R^2$ |
|---|---|---|---|---|---|---|---|---|---|---|---|
| Cl | $OCH_2CF_3$ | F | H | Me | H | Cl | $OCH_2CF_3$ | Br | H | Me | H |
| Cl | $OCH_2CF_3$ | F | H | Et | H | Cl | $OCH_2CF_3$ | Br | H | Et | H |
| Cl | $OCH_2CF_3$ | F | H | i-Pr | H | Cl | $OCH_2CF_3$ | Br | H | i-Pr | H |
| Cl | $OCH_2CF_3$ | F | H | t-Bu | H | Cl | $OCH_2CF_3$ | Br | H | t-Bu | H |
| Cl | $OCH_2CF_3$ | F | H | Me | Me | Cl | $OCH_2CF_3$ | Br | H | Me | Me |
| Br | $OCH_2CF_3$ | F | H | Me | H | Br | $OCH_2CF_3$ | Br | H | Me | H |
| Br | $OCH_2CF_3$ | F | H | Et | H | Br | $OCH_2CF_3$ | Br | H | Et | H |
| Br | $OCH_2CF_3$ | F | H | i-Pr | H | Br | $OCH_2CF_3$ | Br | H | i-Pr | H |
| Br | $OCH_2CF_3$ | F | H | t-Bu | H | Br | $OCH_2CF_3$ | Br | H | t-Bu | H |
| Br | $OCH_2CF_3$ | F | H | Me | Me | Br | $OCH_2CF_3$ | Br | H | Me | Me |
| Cl | $CF_3$ | F | F | Me | H | Cl | $CF_3$ | Br | F | Me | H |
| Cl | $CF_3$ | F | F | Et | H | Cl | $CF_3$ | Br | F | Et | H |
| Cl | $CF_3$ | F | F | i-Pr | H | Cl | $CF_3$ | Br | F | i-Pr | H |
| Cl | $CF_3$ | F | F | t-Bu | H | Cl | $CF_3$ | Br | F | t-Bu | H |
| Cl | $CF_3$ | F | F | Me | Me | Cl | $CF_3$ | Br | F | Me | Me |
| Br | $CF_3$ | F | F | Me | H | Br | $CF_3$ | Br | F | Me | H |
| Br | $CF_3$ | F | F | Et | H | Br | $CF_3$ | Br | F | Et | H |
| Br | $CF_3$ | F | F | i-Pr | H | Br | $CF_3$ | Br | F | i-Pr | H |
| Br | $CF_3$ | F | F | t-Bu | H | Br | $CF_3$ | Br | F | t-Bu | H |
| Br | $CF_3$ | F | F | Me | Me | Br | $CF_3$ | Br | F | Me | Me |
| Cl | Cl | F | F | Me | H | Cl | Cl | Br | F | Me | H |
| Cl | Cl | F | F | Et | H | Cl | Cl | Br | F | Et | H |
| Cl | Cl | F | F | i-Pr | H | Cl | Cl | Br | F | i-Pr | H |
| Cl | Cl | F | F | t-Bu | H | Cl | Cl | Br | F | t-Bu | H |
| Cl | Cl | F | F | Me | Me | Cl | Cl | Br | F | Me | Me |
| Br | Cl | F | F | Me | H | Br | Cl | Br | F | Me | H |
| Br | Cl | F | F | Et | H | Br | Cl | Br | F | Et | H |
| Br | Cl | F | F | i-Pr | H | Br | Cl | Br | F | i-Pr | H |
| Br | Cl | F | F | t-Bu | H | Br | Cl | Br | F | t-Bu | H |
| Br | Cl | F | F | Me | Me | Br | Cl | Br | F | Me | Me |
| Cl | Br | F | F | Me | H | Cl | Br | Br | F | Me | H |
| Cl | Br | F | F | Et | H | Cl | Br | Br | F | Et | H |
| Cl | Br | F | F | i-Pr | H | Cl | Br | Br | F | i-Pr | H |
| Cl | Br | F | F | t-Bu | H | Cl | Br | Br | F | t-Bu | H |
| Cl | Br | F | F | Me | Me | Cl | Br | Br | F | Me | Me |
| Br | Br | F | F | Me | H | Br | Br | Br | F | Me | H |
| Br | Br | F | F | Et | H | Br | Br | Br | F | Et | H |
| Br | Br | F | F | i-Pr | H | Br | Br | Br | F | i-Pr | H |
| Br | Br | F | F | t-Bu | H | Br | Br | Br | F | t-Bu | H |
| Br | Br | F | F | Me | Me | Br | Br | Br | F | Me | Me |
| Cl | $OCH_2CF_3$ | F | F | Me | H | Cl | $OCH_2CF_3$ | Br | F | Me | H |
| Cl | $OCH_2CF_3$ | F | F | Et | H | Cl | $OCH_2CF_3$ | Br | F | Et | H |
| Cl | $OCH_2CF_3$ | F | F | i-Pr | H | Cl | $OCH_2CF_3$ | Br | F | i-Pr | H |
| Cl | $OCH_2CF_3$ | F | F | t-Bu | H | Cl | $OCH_2CF_3$ | Br | F | t-Bu | H |
| Cl | $OCH_2CF_3$ | F | F | Me | Me | Cl | $OCH_2CF_3$ | Br | F | Me | Me |
| Br | $OCH_2CF_3$ | F | F | Me | H | Br | $OCH_2CF_3$ | Br | F | Me | H |
| Br | $OCH_2CF_3$ | F | F | Et | H | Br | $OCH_2CF_3$ | Br | F | Et | H |
| Br | $OCH_2CF_3$ | F | F | i-Pr | H | Br | $OCH_2CF_3$ | Br | F | i-Pr | H |
| Br | $OCH_2CF_3$ | F | F | t-Bu | H | Br | $OCH_2CF_3$ | Br | F | t-Bu | H |
| Br | $OCH_2CF_3$ | F | F | Me | Me | Br | $OCH_2CF_3$ | Br | F | Me | Me |
| Cl | $CF_3$ | F | Cl | Me | H | Cl | $CF_3$ | Br | Cl | Me | H |
| Cl | $CF_3$ | F | Cl | Et | H | Cl | $CF_3$ | Br | Cl | Et | H |
| Cl | $CF_3$ | F | Cl | i-Pr | H | Cl | $CF_3$ | Br | Cl | i-Pr | H |
| Cl | $CF_3$ | F | Cl | t-Bu | H | Cl | $CF_3$ | Br | Cl | t-Bu | H |
| Cl | $CF_3$ | F | Cl | Me | Me | Cl | $CF_3$ | Br | Cl | Me | Me |
| Br | $CF_3$ | F | Cl | Me | H | Br | $CF_3$ | Br | Cl | Me | H |
| Br | $CF_3$ | F | Cl | Et | H | Br | $CF_3$ | Br | Cl | Et | H |
| Br | $CF_3$ | F | Cl | i-Pr | H | Br | $CF_3$ | Br | Cl | i-Pr | H |
| Br | $CF_3$ | F | Cl | t-Bu | H | Br | $CF_3$ | Br | Cl | t-Bu | H |
| Br | $CF_3$ | F | Cl | Me | Me | Br | $CF_3$ | Br | Cl | Me | Me |
| Cl | Cl | F | Cl | Me | H | Cl | Cl | Br | Cl | Me | H |
| Cl | Cl | F | Cl | Et | H | Cl | Cl | Br | Cl | Et | H |
| Cl | Cl | F | Cl | i-Pr | H | Cl | Cl | Br | Cl | i-Pr | H |

TABLE 8-continued

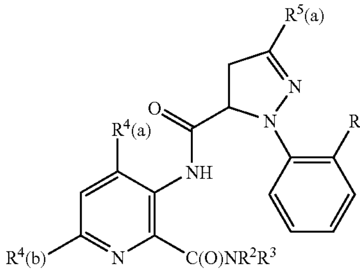

| $R^6$(a) | $R^5$(a) | $R^4$(a) | $R^4$(b) | $R^3$ | $R^2$ | $R^6$(a) | $R^5$(a) | $R^4$(a) | $R^4$(b) | $R^3$ | $R^2$ |
|---|---|---|---|---|---|---|---|---|---|---|---|
| Cl | Cl | F | Cl | t-Bu | H | Cl | Cl | Br | Cl | t-Bu | H |
| Cl | Cl | F | Cl | Me | Me | Cl | Cl | Br | Cl | Me | Me |
| Br | Cl | F | Cl | Me | H | Br | Cl | Br | Cl | Me | H |
| Br | Cl | F | Cl | Et | H | Br | Cl | Br | Cl | Et | H |
| Br | Cl | F | Cl | i-Pr | H | Br | Cl | Br | Cl | i-Pr | H |
| Br | Cl | F | Cl | t-Bu | H | Br | Cl | Br | Cl | t-Bu | H |
| Br | Cl | F | Cl | Me | Me | Br | Cl | Br | Cl | Me | Me |
| Cl | Br | F | Cl | Me | H | Cl | Br | Br | Cl | Me | H |
| Cl | Br | F | Cl | Et | H | Cl | Br | Br | Cl | Et | H |
| Cl | Br | F | Cl | i-Pr | H | Cl | Br | Br | Cl | i-Pr | H |
| Cl | Br | F | Cl | t-Bu | H | Cl | Br | Br | Cl | t-Bu | H |
| Cl | Br | F | Cl | Me | Me | Cl | Br | Br | Cl | Me | Me |
| Br | Br | F | Cl | Me | H | Br | Br | Br | Cl | Me | H |
| Br | Br | F | Cl | Et | H | Br | Br | Br | Cl | Et | H |
| Br | Br | F | Cl | i-Pr | H | Br | Br | Br | Cl | i-Pr | H |
| Br | Br | F | Cl | t-Bu | H | Br | Br | Br | Cl | t-Bu | H |
| Br | Br | F | Cl | Me | Me | Br | Br | Br | Cl | Me | Me |
| Cl | $OCH_2CF_3$ | F | Cl | Me | H | Cl | $OCH_2CF_3$ | Br | Cl | Me | H |
| Cl | $OCH_2CF_3$ | F | Cl | Et | H | Cl | $OCH_2CF_3$ | Br | Cl | Et | H |
| Cl | $OCH_2CF_3$ | F | Cl | i-Pr | H | Cl | $OCH_2CF_3$ | Br | Cl | i-Pr | H |
| Cl | $OCH_2CF_3$ | F | Cl | t-Bu | H | Cl | $OCH_2CF_3$ | Br | Cl | t-Bu | H |
| Cl | $OCH_2CF_3$ | F | Cl | Me | Me | Cl | $OCH_2CF_3$ | Br | Cl | Me | Me |
| Br | $OCH_2CF_3$ | F | Cl | Me | H | Br | $OCH_2CF_3$ | Br | Cl | Me | H |
| Br | $OCH_2CF_3$ | F | Cl | Et | H | Br | $OCH_2CF_3$ | Br | Cl | Et | H |
| Br | $OCH_2CF_3$ | F | Cl | i-Pr | H | Br | $OCH_2CF_3$ | Br | Cl | i-Pr | H |
| Br | $OCH_2CF_3$ | F | Cl | t-Bu | H | Br | $OCH_2CF_3$ | Br | Cl | t-Bu | H |
| Br | $OCH_2CF_3$ | F | Cl | Me | Me | Br | $OCH_2CF_3$ | Br | Cl | Me | Me |
| Cl | $CF_3$ | F | Br | Me | H | Cl | $CF_3$ | Br | Br | Me | H |
| Cl | $CF_3$ | F | Br | Et | H | Cl | $CF_3$ | Br | Br | Et | H |
| Cl | $CF_3$ | F | Br | i-Pr | H | Cl | $CF_3$ | Br | Br | i-Pr | H |
| Cl | $CF_3$ | F | Br | t-Bu | H | Cl | $CF_3$ | Br | Br | t-Bu | H |
| Cl | $CF_3$ | F | Br | Me | Me | Cl | $CF_3$ | Br | Br | Me | Me |
| Br | $CF_3$ | F | Br | Me | H | Br | $CF_3$ | Br | Br | Me | H |
| Br | $CF_3$ | F | Br | Et | H | Br | $CF_3$ | Br | Br | Et | H |
| Br | $CF_3$ | F | Br | i-Pr | H | Br | $CF_3$ | Br | Br | i-Pr | H |
| Br | $CF_3$ | F | Br | t-Bu | H | Br | $CF_3$ | Br | Br | t-Bu | H |
| Br | $CF_3$ | F | Br | Me | Me | Br | $CF_3$ | Br | Br | Me | Me |
| Cl | Cl | F | Br | Me | H | Cl | Cl | Br | Br | Me | H |
| Cl | Cl | F | Br | Et | H | Cl | Cl | Br | Br | Et | H |
| Cl | Cl | F | Br | i-Pr | H | Cl | Cl | Br | Br | i-Pr | H |
| Cl | Cl | F | Br | t-Bu | H | Cl | Cl | Br | Br | t-Bu | H |
| Cl | Cl | F | Br | Me | Me | Cl | Cl | Br | Br | Me | Me |
| Br | Cl | F | Br | Me | H | Br | Cl | Br | Br | Me | H |
| Br | Cl | F | Br | Et | H | Br | Cl | Br | Br | Et | H |
| Br | Cl | F | Br | i-Pr | H | Br | Cl | Br | Br | i-Pr | H |
| Br | Cl | F | Br | t-Bu | H | Br | Cl | Br | Br | t-Bu | H |
| Br | Cl | F | Br | Me | Me | Br | Cl | Br | Br | Me | Me |
| Cl | Br | F | Br | Me | H | Cl | Br | Br | Br | Me | H |
| Cl | Br | F | Br | Et | H | Cl | Br | Br | Br | Et | H |
| Cl | Br | F | Br | i-Pr | H | Cl | Br | Br | Br | i-Pr | H |
| Cl | Br | F | Br | t-Bu | H | Cl | Br | Br | Br | t-Bu | H |
| Cl | Br | F | Br | Me | Me | Cl | Br | Br | Br | Me | Me |
| Br | Br | F | Br | Me | H | Br | Br | Br | Br | Me | H |
| Br | Br | F | Br | Et | H | Br | Br | Br | Br | Et | H |
| Br | Br | F | Br | i-Pr | H | Br | Br | Br | Br | i-Pr | H |
| Br | Br | F | Br | t-Bu | H | Br | Br | Br | Br | t-Bu | H |
| Br | Br | F | Br | Me | Me | Br | Br | Br | Br | Me | Me |
| Cl | $OCH_2CF_3$ | F | Br | Me | H | Cl | $OCH_2CF_3$ | Br | Br | Me | H |
| Cl | $OCH_2CF_3$ | F | Br | Et | H | Cl | $OCH_2CF_3$ | Br | Br | Et | H |
| Cl | $OCH_2CF_3$ | F | Br | i-Pr | H | Cl | $OCH_2CF_3$ | Br | Br | i-Pr | H |
| Cl | $OCH_2CF_3$ | F | Br | t-Bu | H | Cl | $OCH_2CF_3$ | Br | Br | t-Bu | H |
| Cl | $OCH_2CF_3$ | F | Br | Me | Me | Cl | $OCH_2CF_3$ | Br | Br | Me | Me |
| Br | $OCH_2CF_3$ | F | Br | Me | H | Br | $OCH_2CF_3$ | Br | Br | Me | H |

TABLE 8-continued

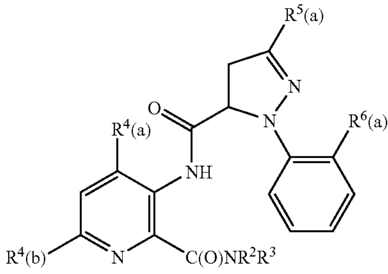

| $R^6$(a) | $R^5$(a) | $R^4$(a) | $R^4$(b) | $R^3$ | $R^2$ | $R^6$(a) | $R^5$(a) | $R^4$(a) | $R^4$(b) | $R^3$ | $R^2$ |
|---|---|---|---|---|---|---|---|---|---|---|---|
| Br | $OCH_2CF_3$ | F | Br | Et | H | Br | $OCH_2CF_3$ | Br | Br | Et | H |
| Br | $OCH_2CF_3$ | F | Br | i-Pr | H | Br | $OCH_2CF_3$ | Br | Br | i-Pr | H |
| Br | $OCH_2CF_3$ | F | Br | t-Bu | H | Br | $OCH_2CF_3$ | Br | Br | t-Bu | H |
| Br | $OCH_2CF_3$ | F | Br | Me | Me | Br | $OCH_2CF_3$ | Br | Br | Me | Me |
| Cl | $CF_3$ | F | I | Me | H | Cl | $CF_3$ | Br | I | Me | H |
| Cl | $CF_3$ | F | I | Et | H | Cl | $CF_3$ | Br | I | Et | H |
| Cl | $CF_3$ | F | I | i-Pr | H | Cl | $CF_3$ | Br | I | i-Pr | H |
| Cl | $CF_3$ | F | I | t-Bu | H | Cl | $CF_3$ | Br | I | t-Bu | H |
| Cl | $CF_3$ | F | I | Me | Me | Cl | $CF_3$ | Br | I | Me | Me |
| Br | $CF_3$ | F | I | Me | H | Br | $CF_3$ | Br | I | Me | H |
| Br | $CF_3$ | F | I | Et | H | Br | $CF_3$ | Br | I | Et | H |
| Br | $CF_3$ | F | I | i-Pr | H | Br | $CF_3$ | Br | I | i-Pr | H |
| Br | $CF_3$ | F | I | t-Bu | H | Br | $CF_3$ | Br | I | t-Bu | H |
| Br | $CF_3$ | F | I | Me | Me | Br | $CF_3$ | Br | I | Me | Me |
| Cl | Cl | F | I | Me | H | Cl | Cl | Br | I | Me | H |
| Cl | Cl | F | I | Et | H | Cl | Cl | Br | I | Et | H |
| Cl | Cl | F | I | i-Pr | H | Cl | Cl | Br | I | i-Pr | H |
| Cl | Cl | F | I | t-Bu | H | Cl | Cl | Br | I | t-Bu | H |
| Cl | Cl | F | I | Me | Me | Cl | Cl | Br | I | Me | Me |
| Br | Cl | F | I | Me | H | Br | Cl | Br | I | Me | H |
| Br | Cl | F | I | Et | H | Br | Cl | Br | I | Et | H |
| Br | Cl | F | I | i-Pr | H | Br | Cl | Br | I | i-Pr | H |
| Br | Cl | F | I | t-Bu | H | Br | Cl | Br | I | t-Bu | H |
| Br | Cl | F | I | Me | Me | Br | Cl | Br | I | Me | Me |
| Cl | Br | F | I | Me | H | Cl | Br | Br | I | Me | H |
| Cl | Br | F | I | Et | H | Cl | Br | Br | I | Et | H |
| Cl | Br | F | I | i-Pr | H | Cl | Br | Br | I | i-Pr | H |
| Cl | Br | F | I | t-Bu | H | Cl | Br | Br | 1 | t-Bu | H |
| Cl | Br | F | I | Me | Me | Cl | Br | Br | I | Me | Me |
| Br | Br | F | I | Me | H | Br | Br | Br | I | Me | H |
| Br | Br | F | I | Et | H | Br | Br | Br | I | Et | H |
| Br | Br | F | I | i-Pr | H | Br | Br | Br | I | i-Pr | H |
| Br | Br | F | I | t-Bu | H | Br | Br | Br | I | t-Bu | H |
| Br | Br | F | I | Me | Me | Br | Br | Br | I | Me | Me |
| Cl | $OCH_2CF_3$ | F | I | Me | H | Cl | $OCH_2CF_3$ | Br | I | Me | H |
| Cl | $OCH_2CF_3$ | F | I | Et | H | Cl | $OCH_2CF_3$ | Br | I | Et | H |
| Cl | $OCH_2CF_3$ | F | I | i-Pr | H | Cl | $OCH_2CF_3$ | Br | I | i-Pr | H |
| Cl | $OCH_2CF_3$ | F | I | t-Bu | H | Cl | $OCH_2CF_3$ | Br | I | t-Bu | H |
| Cl | $OCH_2CF_3$ | F | I | Me | Me | Cl | $OCH_2CF_3$ | Br | I | Me | Me |
| Br | $OCH_2CF_3$ | F | I | Me | H | Br | $OCH_2CF_3$ | Br | I | Me | H |
| Br | $OCH_2CF_3$ | F | I | Et | H | Br | $OCH_2CF_3$ | Br | I | Et | H |
| Br | $OCH_2CF_3$ | F | I | i-Pr | H | Br | $OCH_2CF_3$ | Br | I | i-Pr | H |
| Br | $OCH_2CF_3$ | F | I | t-Bu | H | Br | $OCH_2CF_3$ | Br | I | t-Bu | H |
| Br | $OCH_2CF_3$ | F | I | Me | Me | Br | $OCH_2CF_3$ | Br | I | Me | Me |
| Cl | $CF_3$ | F | $CF_3$ | Me | H | Cl | $CF_3$ | Br | $CF_3$ | Me | H |
| Cl | $CF_3$ | F | $CF_3$ | Et | H | Cl | $CF_3$ | Br | $CF_3$ | Et | H |
| Cl | $CF_3$ | F | $CF_3$ | i-Pr | H | Cl | $CF_3$ | Br | $CF_3$ | i-Pr | H |
| Cl | $CF_3$ | F | $CF_3$ | t-Bu | H | Cl | $CF_3$ | Br | $CF_3$ | t-Bu | H |
| Cl | $CF_3$ | F | $CF_3$ | Me | Me | Cl | $CF_3$ | Br | $CF_3$ | Me | Me |
| Br | $CF_3$ | F | $CF_3$ | Me | H | Br | $CF_3$ | Br | $CF_3$ | Me | H |
| Br | $CF_3$ | F | $CF_3$ | Et | H | Br | $CF_3$ | Br | $CF_3$ | Et | H |
| Br | $CF_3$ | F | $CF_3$ | i-Pr | H | Br | $CF_3$ | Br | $CF_3$ | i-Pr | H |
| Br | $CF_3$ | F | $CF_3$ | t-Bu | H | Br | $CF_3$ | Br | $CF_3$ | t-Bu | H |
| Br | $CF_3$ | F | $CF_3$ | Me | Me | Br | $CF_3$ | Br | $CF_3$ | Me | Me |
| Cl | Cl | F | $CF_3$ | Me | H | Cl | Cl | Br | $CF_3$ | Me | H |
| Cl | Cl | F | $CF_3$ | Et | H | Cl | Cl | Br | $CF_3$ | Et | H |
| Cl | Cl | F | $CF_3$ | i-Pr | H | Cl | Cl | Br | $CF_3$ | i-Pr | H |
| Cl | Cl | F | $CF_3$ | t-Bu | H | Cl | Cl | Br | $CF_3$ | t-Bu | H |
| Cl | Cl | F | $CF_3$ | Me | Me | Cl | Cl | Br | $CF_3$ | Me | Me |
| Br | Cl | F | $CF_3$ | Me | H | Br | Cl | Br | $CF_3$ | Me | H |
| Br | Cl | F | $CF_3$ | Et | H | Br | Cl | Br | $CF_3$ | Et | H |
| Br | Cl | F | $CF_3$ | i-Pr | H | Br | Cl | Br | $CF_3$ | i-Pr | H |
| Br | Cl | F | $CF_3$ | t-Bu | H | Br | Cl | Br | $CF_3$ | t-Bu | H |

TABLE 8-continued

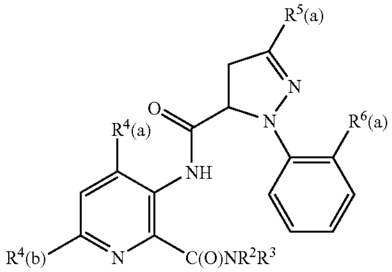

| $R^6$(a) | $R^5$(a) | $R^4$(a) | $R^4$(b) | $R^3$ | $R^2$ | $R^6$(a) | $R^5$(a) | $R^4$(a) | $R^4$(b) | $R^3$ | $R^2$ |
|---|---|---|---|---|---|---|---|---|---|---|---|
| Br | Cl | F | $CF_3$ | Me | Me | Br | Cl | Br | $CF_3$ | Me | Me |
| Cl | Br | F | $CF_3$ | Me | H | Cl | Br | Br | $CF_3$ | Me | H |
| Cl | Br | F | $CF_3$ | Et | H | Cl | Br | Br | $CF_3$ | Et | H |
| Cl | Br | F | $CF_3$ | i-Pr | H | Cl | Br | Br | $CF_3$ | i-Pr | H |
| Cl | Br | F | $CF_3$ | t-Bu | H | Cl | Br | Br | $CF_3$ | t-Bu | H |
| Cl | Br | F | $CF_3$ | Me | Me | Cl | Br | Br | $CF_3$ | Me | Me |
| Br | Br | F | $CF_3$ | Me | H | Br | Br | Br | $CF_3$ | Me | H |
| Br | Br | F | $CF_3$ | Et | H | Br | Br | Br | $CF_3$ | Et | H |
| Br | Br | F | $CF_3$ | i-Pr | H | Br | Br | Br | $CF_3$ | i-Pr | H |
| Br | Br | F | $CF_3$ | t-Bu | H | Br | Br | Br | $CF_3$ | t-Bu | H |
| Br | Br | F | $CF_3$ | Me | Me | Br | Br | Br | $CF_3$ | Me | Me |
| Cl | $OCH_2CF_3$ | F | $CF_3$ | Me | H | Cl | $OCH_2CF_3$ | Br | $CF_3$ | Me | H |
| Cl | $OCH_2CF_3$ | F | $CF_3$ | Et | H | Cl | $OCH_2CF_3$ | Br | $CF_3$ | Et | H |
| Cl | $OCH_2CF_3$ | F | $CF_3$ | i-Pr | H | Cl | $OCH_2CF_3$ | Br | $CF_3$ | i-Pr | H |
| Cl | $OCH_2CF_3$ | F | $CF_3$ | t-Bu | H | Cl | $OCH_2CF_3$ | Br | $CF_3$ | t-Bu | H |
| Cl | $OCH_2CF_3$ | F | $CF_3$ | Me | Me | Cl | $OCH_2CF_3$ | Br | $CF_3$ | Me | Me |
| Br | $OCH_2CF_3$ | F | $CF_3$ | Me | H | Br | $OCH_2CF_3$ | Br | $CF_3$ | Me | H |
| Br | $OCH_2CF_3$ | F | $CF_3$ | Et | H | Br | $OCH_2CF_3$ | Br | $CF_3$ | Et | H |
| Br | $OCH_2CF_3$ | F | $CF_3$ | i-Pr | H | Br | $OCH_2CF_3$ | Br | $CF_3$ | i-Pr | H |
| Br | $OCH_2CF_3$ | F | $CF_3$ | t-Bu | H | Br | $OCH_2CF_3$ | Br | $CF_3$ | t-Bu | H |
| Br | $OCH_2CF_3$ | F | $CF_3$ | Me | Me | Br | $OCH_2CF_3$ | Br | $CF_3$ | Me | Me |

TABLE 9

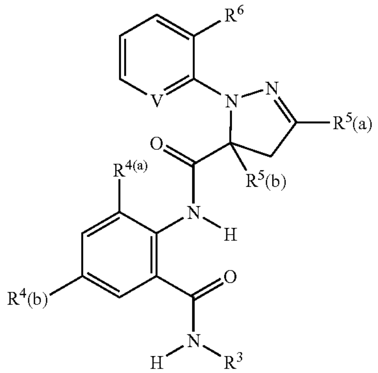

| $R^6$ | $R^{5(a)}$ | $R^{5(b)}$ | $R^{4(a)}$ | $R^{(b)}$ | $R^3$ | V | $R^6$ | $R^{5(a)}$ | $R^{5(b)}$ | $R^{4(a)}$ | $R^{(b)}$ | $R^3$ | V |
|---|---|---|---|---|---|---|---|---|---|---|---|---|---|
| Me | $CF_3$ | H | Me | H | i-Pr | CCl | Me | $CF_3$ | H | Me | H | $CH_2C{\equiv}CH$ | CH |
| Cl | $CF_3$ | H | Me | H | i-Pr | CCl | Cl | $CF_3$ | H | Me | H | $CH_2C{\equiv}CH$ | CH |
| F | $CF_3$ | H | Me | H | i-Pr | CF | F | $CF_3$ | H | Me | H | $CH_2C{\equiv}CH$ | CH |
| Me | $CF_3$ | H | Me | H | t-Bu | CCl | Me | $CF_3$ | H | Me | H | $CH_2C{\equiv}CH$ | CCl |
| Cl | $CF_3$ | H | Me | H | t-Bu | CCl | Cl | $CF_3$ | H | Me | H | $CH_2C{\equiv}CH$ | CCl |
| F | $CF_3$ | H | Me | H | t-Bu | CF | F | $CF_3$ | H | Me | H | $CH_2C{\equiv}CH$ | CF |
| Me | $CF_3$ | H | Me | H | Me | CCl | Me | $CF_3$ | H | Me | H | $CH_2C{\equiv}CH$ | N |
| Cl | $CF_3$ | H | Me | H | Me | CCl | Cl | $CF_3$ | H | Me | H | $CH_2C{\equiv}CH$ | N |
| F | $CF_3$ | H | Me | H | Me | CF | F | $CF_3$ | H | Me | H | $CH_2C{\equiv}CH$ | N |
| Me | $CF_3$ | H | Me | H | Et | CCl | Me | $CO_2Me$ | H | Me | H | i-Pr | CH |
| Cl | $CF_3$ | H | Me | H | Et | CCl | Cl | $CO_2Me$ | H | Me | H | i-Pr | CH |
| F | $CF_3$ | H | Me | H | Et | CF | F | $CO_2Me$ | H | Me | H | i-Pr | CH |
| Me | Br | H | Me | H | i-Pr | CCl | Me | $CO_2Me$ | H | Me | H | i-Pr | CCl |
| Cl | Br | H | Me | H | i-Pr | CCl | Cl | $CO_2Me$ | H | Me | H | i-Pr | CCl |
| F | Br | H | Me | H | i-Pr | CF | F | $CO_2Me$ | H | Me | H | i-Pr | CF |
| Me | $CF_3$ | H | Cl | H | t-Bu | CCl | Me | $CO_2Me$ | H | Me | H | i-Pr | N |

TABLE 9-continued

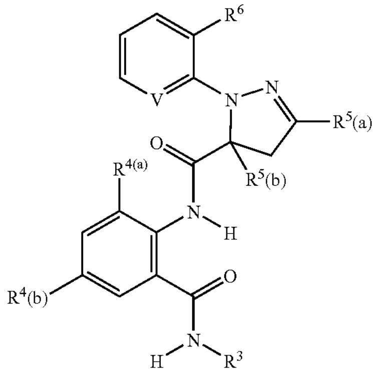

| $R^6$ | $R^{5(a)}$ | $R^{5(b)}$ | $R^{4(a)}$ | $R^{(b)}$ | $R^3$ | V | $R^6$ | $R^{5(a)}$ | $R^{5(b)}$ | $R^{4(a)}$ | $R^{(b)}$ | $R^3$ | V |
|---|---|---|---|---|---|---|---|---|---|---|---|---|---|
| Cl | $CF_3$ | H | Cl | H | t-Bu | CCl | Cl | $CO_2Me$ | H | Me | H | i-Pr | N |
| F | $CF_3$ | H | Cl | H | t-Bu | CF | F | $CO_2Me$ | H | Me | H | i-Pr | N |
| Me | $CF_3$ | H | Cl | H | i-Pr | CCl | Me | $CF_3$ | H | Cl | H | $CH_2C{\equiv}CH$ | CH |
| Cl | $CF_3$ | H | Cl | H | i-Pr | CCl | Cl | $CF_3$ | H | Cl | H | $CH_2C{\equiv}CH$ | CH |
| F | $CF_3$ | H | Cl | H | i-Pr | CF | F | $CF_3$ | H | Cl | H | $CH_2C{\equiv}CH$ | CH |
| Me | $CF_3$ | H | Me | Br | i-Pr | CCl | Me | $CF_3$ | H | Cl | H | $CH_2C{\equiv}CH$ | CCl |
| Cl | $CF_3$ | H | Me | Br | i-Pr | CCl | Cl | $CF_3$ | H | Cl | H | $CH_2C{\equiv}CH$ | CCl |
| F | $CF_3$ | H | Me | Br | i-Pr | CF | F | $CF_3$ | H | Cl | H | $CH_2C{\equiv}CH$ | CF |
| Me | $CF_3$ | Me | Me | H | i-Pr | CCl | Me | $CF_3$ | H | Cl | H | $CH_2C{\equiv}CH$ | N |
| Cl | $CF_3$ | Me | Me | H | i-Pr | CCl | Cl | $CF_3$ | H | Cl | H | $CH_2C{\equiv}CH$ | N |
| F | $CF_3$ | Me | Me | H | i-Pr | CF | F | $CF_3$ | H | Cl | H | $CH_2C{\equiv}CH$ | N |
| Me | $CF_3$ | Me | Me | H | i-Pr | CH | Me | $CF_3$ | Me | Me | H | i-Pr | N |
| Cl | $CF_3$ | Me | Me | H | i-Pr | CH | Cl | $CF_3$ | Me | Me | H | i-Pr | N |
| F | $CF_3$ | Me | Me | H | i-Pr | CH | F | $CF_3$ | Me | Me | H | i-Pr | N |

TABLE 10

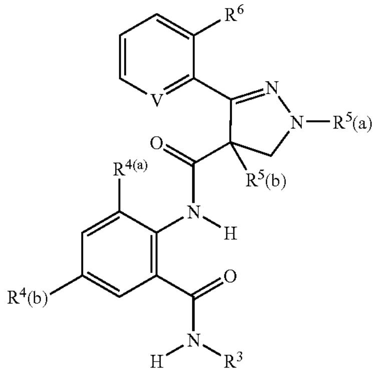

| $R^6$ | $R^{5(a)}$ | $R^{5(b)}$ | $R^{4(a)}$ | $R^{(b)}$ | $R^3$ | V | $R^6$ | $R^{5(a)}$ | $R^{5(b)}$ | $R^{4(a)}$ | $R^{(b)}$ | $R^3$ | V |
|---|---|---|---|---|---|---|---|---|---|---|---|---|---|
| Me | $CF_3$ | H | Me | H | i-Pr | CH | Me | $CF_3$ | H | Me | H | $CH_2C{\equiv}CH$ | CH |
| Cl | $CF_3$ | H | Me | H | i-Pr | CH | Cl | $CF_3$ | H | Me | H | $CH_2C{\equiv}CH$ | CH |
| F | $CF_3$ | H | Me | H | i-Pr | CH | F | $CF_3$ | H | Me | H | $CH_2C{\equiv}CH$ | CH |
| Me | $CF_3$ | H | Me | H | i-Pr | CCl | Me | $CF_3$ | H | Me | H | $CH_2C{\equiv}CH$ | CCl |
| Cl | $CF_3$ | H | Me | H | i-Pr | CCl | Cl | $CF_3$ | H | Me | H | $CH_2C{\equiv}CH$ | CCl |
| F | $CF_3$ | H | Me | H | i-Pr | CF | F | $CF_3$ | H | Me | H | $CH_2C{\equiv}CH$ | CF |
| Me | $CF_3$ | H | Me | H | i-Pr | N | Me | $CF_3$ | H | Me | H | $CH_2C{\equiv}CH$ | N |
| Cl | $CF_3$ | H | Me | H | i-Pr | N | Cl | $CF_3$ | H | Me | H | $CH_2C{\equiv}CH$ | N |
| F | $CF_3$ | H | Me | H | i-Pr | N | F | $CF_3$ | H | Me | H | $CH_2C{\equiv}CH$ | N |
| Me | $CF_3$ | H | Me | H | t-Bu | CH | Me | $CF_3$ | H | Me | Br | i-Pr | CH |
| Cl | $CF_3$ | H | Me | H | t-Bu | CH | Cl | $CF_3$ | H | Me | Br | i-Pr | CH |
| F | $CF_3$ | H | Me | H | t-Bu | CH | F | $CF_3$ | H | Me | Br | i-Pr | CH |
| Me | $CF_3$ | H | Me | H | t-Bu | CCl | Me | $CF_3$ | H | Me | Br | i-Pr | CCl |
| Cl | $CF_3$ | H | Me | H | t-Bu | CCl | Cl | $CF_3$ | H | Me | Br | i-Pr | CCl |
| F | $CF_3$ | H | Me | H | t-Bu | CF | F | $CF_3$ | H | Me | Br | i-Pr | CF |

TABLE 10-continued

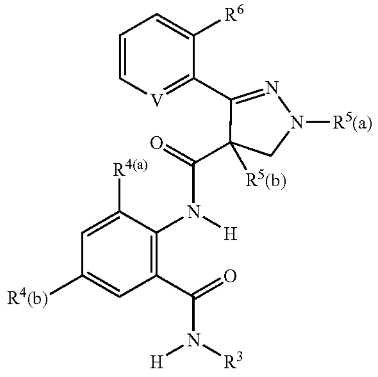

| $R^6$ | $R^{5(a)}$ | $R^{5(b)}$ | $R^{4(a)}$ | $R^{(b)}$ | $R^3$ | V | $R^6$ | $R^{5(a)}$ | $R^{5(b)}$ | $R^{4(a)}$ | $R^{(b)}$ | $R^3$ | V |
|---|---|---|---|---|---|---|---|---|---|---|---|---|---|
| Me | $CF_3$ | H | Me | H | t-Bu | N | Me | $CF_3$ | H | Me | Br | i-Pr | N |
| Cl | $CF_3$ | H | Me | H | t-Bu | N | Cl | $CF_3$ | H | Me | Br | i-Pr | N |
| F | $CF_3$ | H | Me | H | t-Bu | N | F | $CF_3$ | H | Me | Br | i-Pr | N |
| Me | $CF_3$ | H | Me | H | Me | CH | Me | $CF_3$ | Me | Me | H | i-Pr | CH |
| Cl | $CF_3$ | H | Me | H | Me | CH | Cl | $CF_3$ | Me | Me | H | i-Pr | CH |
| F | $CF_3$ | H | Me | H | Me | CH | F | $CF_3$ | Me | Me | H | i-Pr | CH |
| Me | $CF_3$ | H | Me | H | Me | CCl | Me | $CF_3$ | Me | Me | H | i-Pr | CCl |
| Cl | $CF_3$ | H | Me | H | Me | CCl | Cl | $CF_3$ | Me | Me | H | i-Pr | CCl |
| F | $CF_3$ | H | Me | H | Me | CF | F | $CF_3$ | Me | Me | H | i-Pr | CF |
| Me | $CF_3$ | H | Me | H | Me | N | Me | $CF_3$ | Me | Me | H | i-Pr | N |
| Cl | $CF_3$ | H | Me | H | Me | N | Cl | $CF_3$ | Me | Me | H | i-Pr | N |
| F | $CF_3$ | H | Me | H | Me | N | F | $CF_3$ | Me | Me | H | i-Pr | N |
| Me | $CF_3$ | H | Me | H | Et | CH | Me | $CO_2Me$ | H | Me | H | i-Pr | CH |
| Cl | $CF_3$ | H | Me | H | Et | CH | Cl | $CO_2Me$ | H | Me | H | i-Pr | CH |
| F | $CF_3$ | H | Me | H | Et | CH | F | $CO_2Me$ | H | Me | H | i-Pr | CH |
| Me | $CF_3$ | H | Me | H | Et | CCl | Me | $CO_2Me$ | H | Me | H | i-Pr | CCl |
| Cl | $CF_3$ | H | Me | H | Et | CCl | Cl | $CO_2Me$ | H | Me | H | i-Pr | CCl |
| F | $CF_3$ | H | Me | H | Et | CF | F | $CO_2Me$ | H | Me | H | i-Pr | CF |
| Me | $CF_3$ | H | Me | H | Et | N | Me | $CO_2Me$ | H | Me | H | i-Pr | N |
| Cl | $CF_3$ | H | Me | H | Et | N | Cl | $CO_2Me$ | H | Me | H | i-Pr | N |
| F | $CF_3$ | H | Me | H | Et | N | F | $CO_2Me$ | H | Me | H | i-Pr | N |
| Me | Br | H | Me | H | i-Pr | CH | Me | $CF_3$ | H | Cl | H | i-Pr | CH |
| Cl | Br | H | Me | H | i-Pr | CH | Cl | $CF_3$ | H | Cl | H | i-Pr | CH |
| F | Br | H | Me | H | i-Pr | CH | F | $CF_3$ | H | Cl | H | i-Pr | CH |
| Me | Br | H | Me | H | i-Pr | CCl | Me | $CF_3$ | H | Cl | H | i-Pr | CCl |
| Cl | Br | H | Me | H | i-Pr | CCl | Cl | $CF_3$ | H | Cl | H | i-Pr | CCl |
| F | Br | H | Me | H | i-Pr | CF | F | $CF_3$ | H | Cl | H | i-Pr | CF |
| Me | Br | H | Me | H | i-Pr | N | Me | $CF_3$ | H | Cl | H | i-Pr | N |
| Cl | Br | H | Me | H | i-Pr | N | Cl | $CF_3$ | H | Cl | H | i-Pr | N |
| F | Br | H | Me | H | i-Pr | N | F | $CF_3$ | H | Cl | H | i-Pr | N |
| Me | $CF_3$ | H | Cl | H | t-Bu | CH | Me | $CF_3$ | H | Cl | H | $CH_2C{\equiv}CH$ | CH |
| Cl | $CF_3$ | H | Cl | H | t-Bu | CH | Cl | $CF_3$ | H | Cl | H | $CH_2C{\equiv}CH$ | CH |
| F | $CF_3$ | H | Cl | H | t-Bu | CH | F | $CF_3$ | H | Cl | H | $CH_2C{\equiv}CH$ | CH |
| Me | $CF_3$ | H | Cl | H | t-Bu | CCl | Me | $CF_3$ | H | Cl | H | $CH_2C{\equiv}CH$ | CCl |
| Cl | $CF_3$ | H | Cl | H | t-Bu | CCl | Cl | $CF_3$ | H | Cl | H | $CH_2C{\equiv}CH$ | CCl |
| F | $CF_3$ | H | Cl | H | t-Bu | CF | F | $CF_3$ | H | Cl | H | $CH_2C{\equiv}CH$ | CF |
| Me | $CF_3$ | H | Cl | H | t-Bu | N | Me | $CF_3$ | H | Cl | H | $CH_2C{\equiv}CH$ | N |
| Cl | $CF_3$ | H | Cl | H | t-Bu | N | Cl | $CF_3$ | H | Cl | H | $CH_2C{\equiv}CH$ | N |
| F | $CF_3$ | H | Cl | H | t-Bu | N | F | $CF_3$ | H | Cl | H | $CH_2C{\equiv}CH$ | N |

TABLE 11

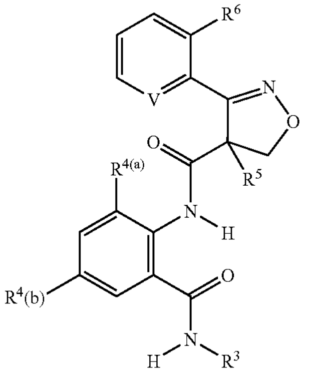

| $R^6$ | $R^{5(a)}$ | $R^{5(b)}$ | $R^{4(a)}$ | $R^{(b)}$ | $R^3$ | V | $R^6$ | $R^{5(a)}$ | $R^{5(b)}$ | $R^{4(a)}$ | $R^{(b)}$ | $R^3$ | V |
|---|---|---|---|---|---|---|---|---|---|---|---|---|---|
| Me | $CF_3$ | H | Me | H | i-Pr | CH | Me | $CF_3$ | H | Me | H | $CH_2{\equiv}CH$ | CH |
| Cl | $CF_3$ | H | Me | H | i-Pr | CH | Cl | $CF_3$ | H | Me | H | $CH_2{\equiv}CH$ | CH |
| F | $CF_3$ | H | Me | H | i-Pr | CH | F | $CF_3$ | H | Me | H | $CH_2{\equiv}CH$ | CH |
| Me | $CF_3$ | H | Me | H | i-Pr | CCl | Me | $CF_3$ | H | Me | H | $CH_2{\equiv}CH$ | CCl |
| Cl | $CF_3$ | H | Me | H | i-Pr | CCl | Cl | $CF_3$ | H | Me | H | $CH_2{\equiv}CH$ | CCl |
| F | $CF_3$ | H | Me | H | i-Pr | CF | F | $CF_3$ | H | Me | H | $CH_2{\equiv}CH$ | CF |
| Me | $CF_3$ | H | Me | H | i-Pr | N | Me | $CF_3$ | H | Me | H | $CH_2{\equiv}CH$ | N |
| Cl | $CF_3$ | H | Me | H | i-Pr | N | Cl | $CF_3$ | H | Me | H | $CH_2{\equiv}CH$ | N |
| F | $CF_3$ | H | Me | H | i-Pr | N | F | $CF_3$ | H | Me | H | $CH_2{\equiv}CH$ | N |
| Me | $CF_3$ | H | Me | H | t-Bu | CH | Me | $CF_3$ | H | Me | Br | i-Pr | CH |
| Cl | $CF_3$ | H | Me | H | t-Bu | CH | Cl | $CF_3$ | H | Me | Br | i-Pr | CH |
| F | $CF_3$ | H | Me | H | t-Bu | CH | F | $CF_3$ | H | Me | Br | i-Pr | CH |
| Me | $CF_3$ | H | Me | H | t-Bu | CCl | Me | $CF_3$ | H | Me | Br | i-Pr | CCl |
| Cl | $CF_3$ | H | Me | H | t-Bu | CCl | Cl | $CF_3$ | H | Me | Br | i-Pr | CCl |
| F | $CF_3$ | H | Me | H | t-Bu | CF | F | $CF_3$ | H | Me | Br | i-Pr | CF |
| Me | $CF_3$ | H | Me | H | t-Bu | N | Me | $CF_3$ | H | Me | Br | i-Pr | N |
| Cl | $CF_3$ | H | Me | H | t-Bu | N | Cl | $CF_3$ | H | Me | Br | i-Pr | N |
| F | $CF_3$ | H | Me | H | t-Bu | N | F | $CF_3$ | H | Me | Br | i-Pr | N |
| Me | $CF_3$ | H | Me | H | Me | CH | Me | $CF_3$ | Me | Me | H | i-Pr | CH |
| Cl | $CF_3$ | H | Me | H | Me | CH | Cl | $CF_3$ | Me | Me | H | i-Pr | CH |
| F | $CF_3$ | H | Me | H | Me | CH | F | $CF_3$ | Me | Me | H | i-Pr | CH |
| Me | $CF_3$ | H | Me | H | Me | CCl | Me | $CF_3$ | Me | Me | H | i-Pr | CCl |
| Cl | $CF_3$ | H | Me | H | Me | CCl | Cl | $CF_3$ | Me | Me | H | i-Pr | CCl |
| F | $CF_3$ | H | Me | H | Me | CF | F | $CF_3$ | Me | Me | H | i-Pr | CF |
| Me | $CF_3$ | H | Me | H | Me | N | Me | $CF_3$ | Me | Me | H | i-Pr | N |
| Cl | $CF_3$ | H | Me | H | Me | N | Cl | $CF_3$ | Me | Me | H | i-Pr | N |
| F | $CF_3$ | H | Me | H | Me | N | F | $CF_3$ | Me | Me | H | i-Pr | N |
| Me | $CF_3$ | H | Me | H | Et | CH | Me | $CO_2Me$ | H | Me | H | i-Pr | CH |
| Cl | $CF_3$ | H | Me | H | Et | CH | Cl | $CO_2Me$ | H | Me | H | i-Pr | CH |
| F | $CF_3$ | H | Me | H | Et | CH | F | $CO_2Me$ | H | Me | H | i-Pr | CH |
| Me | $CF_3$ | H | Me | H | Et | CCl | Me | $CO_2Me$ | H | Me | H | i-Pr | CCl |
| Cl | $CF_3$ | H | Me | H | Et | CCl | Cl | $CO_2Me$ | H | Me | H | i-Pr | CCl |
| F | $CF_3$ | H | Me | H | Et | CF | F | $CO_2Me$ | H | Me | H | i-Pr | CF |
| Me | $CF_3$ | H | Me | H | Et | N | Me | $CO_2Me$ | H | Me | H | i-Pr | N |
| Cl | $CF_3$ | H | Me | H | Et | N | Cl | $CO_2Me$ | H | Me | H | i-Pr | N |
| F | $CF_3$ | H | Me | H | Et | N | F | $CO_2Me$ | H | Me | H | i-Pr | N |
| Me | Br | H | Me | H | i-Pr | CH | Me | $CF_3$ | H | Cl | H | i-Pr | CH |
| Cl | Br | H | Me | H | i-Pr | CH | Cl | $CF_3$ | H | Cl | H | i-Pr | CH |
| F | Br | H | Me | H | i-Pr | CH | F | $CF_3$ | H | Cl | H | i-Pr | CH |
| Me | Br | H | Me | H | i-Pr | CCl | Me | $CF_3$ | H | Cl | H | i-Pr | CCl |
| Cl | Br | H | Me | H | i-Pr | CCl | Cl | $CF_3$ | H | Cl | H | i-Pr | CCl |
| F | Br | H | Me | H | i-Pr | CF | F | $CF_3$ | H | Cl | H | i-Pr | CF |
| Me | Br | H | Me | H | i-Pr | N | Me | $CF_3$ | H | Cl | H | i-Pr | N |
| Cl | Br | H | Me | H | i-Pr | N | Cl | $CF_3$ | H | Cl | H | i-Pr | N |
| F | Br | H | Me | H | i-Pr | N | F | $CF_3$ | H | Cl | H | i-Pr | N |
| Me | $CF_3$ | H | Cl | H | t-Bu | CH | Me | $CF_3$ | H | Cl | H | $CH_2{\equiv}CH$ | CH |
| Cl | $CF_3$ | H | Cl | H | t-Bu | CH | Cl | $CF_3$ | H | Cl | H | $CH_2{\equiv}CH$ | CH |
| F | $CF_3$ | H | Cl | H | t-Bu | CH | F | $CF_3$ | H | Cl | H | $CH_2{\equiv}CH$ | CH |
| Me | $CF_3$ | H | Cl | H | t-Bu | CCl | Me | $CF_3$ | H | Cl | H | $CH_2{\equiv}CH$ | CCl |
| Cl | $CF_3$ | H | Cl | H | t-Bu | CCl | Cl | $CF_3$ | H | Cl | H | $CH_2{\equiv}CH$ | CCl |
| F | $CF_3$ | H | Cl | H | t-Bu | CF | F | $CF_3$ | H | Cl | H | $CH_2{\equiv}CH$ | CF |
| Me | $CF_3$ | H | Cl | H | t-Bu | N | Me | $CF_3$ | H | Cl | H | $CH_2{\equiv}CH$ | N |
| Cl | $CF_3$ | H | Cl | H | t-Bu | N | Cl | $CF_3$ | H | Cl | H | $CH_2{\equiv}CH$ | N |
| F | $CF_3$ | H | Cl | H | t-Bu | N | F | $CF_3$ | H | Cl | H | $CH_2{\equiv}CH$ | N |

TABLE 12

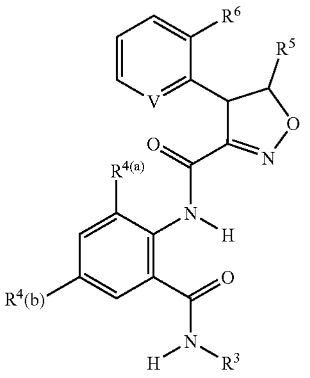

| $R^6$ | $R^{5(a)}$ | $R^{5(b)}$ | $R^{4(a)}$ | $R^{(b)}$ | $R^3$ | V | $R^6$ | $R^{5(a)}$ | $R^{5(b)}$ | $R^{4(a)}$ | $R^{(b)}$ | $R^3$ | V |
|---|---|---|---|---|---|---|---|---|---|---|---|---|---|
| Me | $CF_3$ | H | Me | H | i-Pr | CH | Me | $CF_3$ | H | Me | H | $CH_2C{\equiv}CH$ | CH |
| Cl | $CF_3$ | H | Me | H | i-Pr | CH | Cl | $CF_3$ | H | Me | H | $CH_2C{\equiv}CH$ | CH |
| F | $CF_3$ | H | Me | H | i-Pr | CH | F | $CF_3$ | H | Me | H | $CH_2C{\equiv}CH$ | CH |
| Me | $CF_3$ | H | Me | H | i-Pr | CCl | Me | $CF_3$ | H | Me | H | $CH_2C{\equiv}CH$ | CCl |
| Cl | $CF_3$ | H | Me | H | i-Pr | CCl | Cl | $CF_3$ | H | Me | H | $CH_2C{\equiv}CH$ | CCl |
| F | $CF_3$ | H | Me | H | i-Pr | CF | F | $CF_3$ | H | Me | H | $CH_2C{\equiv}CH$ | CF |
| Me | $CF_3$ | H | Me | H | i-Pr | N | Me | $CF_3$ | H | Me | H | $CH_2C{\equiv}CH$ | N |
| Cl | $CF_3$ | H | Me | H | i-Pr | N | Cl | $CF_3$ | H | Me | H | $CH_2C{\equiv}CH$ | N |
| F | $CF_3$ | H | Me | H | i-Pr | N | F | $CF_3$ | H | Me | H | $CH_2C{\equiv}CH$ | N |
| Me | $CF_3$ | H | Me | H | t-Bu | CH | Me | $CF_3$ | H | Me | Br | i-Pr | CH |
| Cl | $CF_3$ | H | Me | H | t-Bu | CH | Cl | $CF_3$ | H | Me | Br | i-Pr | CH |
| F | $CF_3$ | H | Me | H | t-Bu | CH | F | $CF_3$ | H | Me | Br | i-Pr | CH |
| Me | $CF_3$ | H | Me | H | t-Bu | CCl | Me | $CF_3$ | H | Me | Br | i-Pr | CCl |
| Cl | $CF_3$ | H | Me | H | t-Bu | CCl | Cl | $CF_3$ | H | Me | Br | i-Pr | CCl |
| F | $CF_3$ | H | Me | H | t-Bu | CF | F | $CF_3$ | H | Me | Br | i-Pr | CF |
| Me | $CF_3$ | H | Me | H | t-Bu | N | Me | $CF_3$ | H | Me | Br | i-Pr | N |
| Cl | $CF_3$ | H | Me | H | t-Bu | N | Cl | $CF_3$ | H | Me | Br | i-Pr | N |
| F | $CF_3$ | H | Me | H | t-Bu | N | F | $CF_3$ | H | Me | Br | i-Pr | N |
| Me | $CF_3$ | H | Me | H | Me | CH | Me | $CF_3$ | Me | Me | H | i-Pr | CH |
| Cl | $CF_3$ | H | Me | H | Me | CH | Cl | $CF_3$ | Me | Me | H | i-Pr | CH |
| F | $CF_3$ | H | Me | H | Me | CH | F | $CF_3$ | Me | Me | H | i-Pr | CH |
| Me | $CF_3$ | H | Me | H | Me | CCl | Me | $CF_3$ | Me | Me | H | i-Pr | CCl |
| Cl | $CF_3$ | H | Me | H | Me | CCl | Cl | $CF_3$ | Me | Me | H | i-Pr | CCl |
| F | $CF_3$ | H | Me | H | Me | CF | F | $CF_3$ | Me | Me | H | i-Pr | CF |
| Me | $CF_3$ | H | Me | H | Me | N | Me | $CF_3$ | Me | Me | H | i-Pr | N |
| Cl | $CF_3$ | H | Me | H | Me | N | Cl | $CF_3$ | Me | Me | H | i-Pr | N |
| F | $CF_3$ | H | Me | H | Me | N | F | $CF_3$ | Me | Me | H | i-Pr | N |
| Me | $CF_3$ | H | Me | H | Et | CH | Me | $CO_2Me$ | H | Me | H | i-Pr | CH |
| Cl | $CF_3$ | H | Me | H | Et | CH | Cl | $CO_2Me$ | H | Me | H | i-Pr | CH |
| F | $CF_3$ | H | Me | H | Et | CH | F | $CO_2Me$ | H | Me | H | i-Pr | CH |
| Me | $CF_3$ | H | Me | H | Et | CCl | Me | $CO_2Me$ | H | Me | H | i-Pr | CCl |
| Cl | $CF_3$ | H | Me | H | Et | CCl | Cl | $CO_2Me$ | H | Me | H | i-Pr | CCl |
| F | $CF_3$ | H | Me | H | Et | CF | F | $CO_2Me$ | H | Me | H | i-Pr | CF |
| Me | $CF_3$ | H | Me | H | Et | N | Me | $CO_2Me$ | H | Me | H | i-Pr | N |
| Cl | $CF_3$ | H | Me | H | Et | N | Cl | $CO_2Me$ | H | Me | H | i-Pr | N |
| F | $CF_3$ | H | Me | H | Et | N | F | $CO_2Me$ | H | Me | H | i-Pr | N |
| Me | Br | H | Me | H | i-Pr | CH | Me | $CF_3$ | H | Cl | H | i-Pr | CH |
| Cl | Br | H | Me | H | i-Pr | CH | Cl | $CF_3$ | H | Cl | H | i-Pr | CH |
| F | Br | H | Me | H | i-Pr | CH | F | $CF_3$ | H | Cl | H | i-Pr | CH |
| Me | Br | H | Me | H | i-Pr | CCl | Me | $CF_3$ | H | Cl | H | i-Pr | CCl |
| Cl | Br | H | Me | H | i-Pr | CCl | Cl | $CF_3$ | H | Cl | H | i-Pr | CCl |
| F | Br | H | Me | H | i-Pr | CF | F | $CF_3$ | H | Cl | H | i-Pr | CF |
| Me | Br | H | Me | H | i-Pr | N | Me | $CF_3$ | H | Cl | H | i-Pr | N |
| Cl | Br | H | Me | H | i-Pr | N | Cl | $CF_3$ | H | Cl | H | i-Pr | N |
| F | Br | H | Me | H | i-Pr | N | F | $CF_3$ | H | Cl | H | i-Pr | N |
| Me | $CF_3$ | H | Cl | H | t-Bu | CH | Me | $CF_3$ | H | Cl | H | $CH_2C{\equiv}CH$ | CH |
| Cl | $CF_3$ | H | Cl | H | t-Bu | CH | Cl | $CF_3$ | H | Cl | H | $CH_2C{\equiv}CH$ | CH |
| F | $CF_3$ | H | Cl | H | t-Bu | CH | F | $CF_3$ | H | Cl | H | $CH_2C{\equiv}CH$ | CH |
| Me | $CF_3$ | H | Cl | H | t-Bu | CCl | Me | $CF_3$ | H | Cl | H | $CH_2C{\equiv}CH$ | CCl |
| Cl | $CF_3$ | H | Cl | H | t-Bu | CCl | Cl | $CF_3$ | H | Cl | H | $CH_2C{\equiv}CH$ | CCl |
| F | $CF_3$ | H | Cl | H | t-Bu | CF | F | $CF_3$ | H | Cl | H | $CH_2C{\equiv}CH$ | CF |
| Me | $CF_3$ | H | Cl | H | t-Bu | N | Me | $CF_3$ | H | Cl | H | $CH_2C{\equiv}CH$ | N |
| Cl | $CF_3$ | H | Cl | H | t-Bu | N | Cl | $CF_3$ | H | Cl | H | $CH_2C{\equiv}CH$ | N |
| F | $CF_3$ | H | Cl | H | t-Bu | N | F | $CF_3$ | H | Cl | H | $CH_2C{\equiv}CH$ | N |

TABLE 13

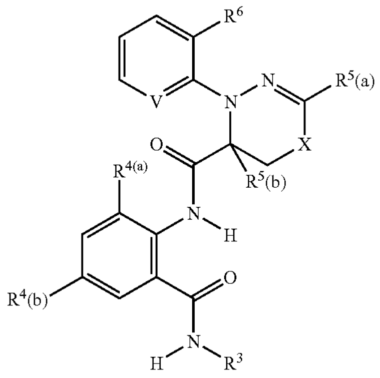

| $R^6$ | $R^{5(a)}$ | $R^{5(b)}$ | $R^{4(a)}$ | $R^{(b)}$ | $R^3$ | V | $R^6$ | $R^{5(a)}$ | $R^{5(b)}$ | $R^{4(a)}$ | $R^{(b)}$ | $R^3$ | V |
|---|---|---|---|---|---|---|---|---|---|---|---|---|---|
| | | | | | | | X is O | | | | | | |
| Me | $CF_3$ | H | Me | H | i-Pr | CH | Me | $CF_3$ | H | Me | H | $CH_2C{\equiv}CH$ | CH |
| Cl | $CF_3$ | H | Me | H | i-Pr | CH | Cl | $CF_3$ | H | Me | H | $CH_2C{\equiv}CH$ | CH |
| F | $CF_3$ | H | Me | H | i-Pr | CH | F | $CF_3$ | H | Me | H | $CH_2C{\equiv}CH$ | CH |
| Me | $CF_3$ | H | Me | H | i-Pr | CCl | Me | $CF_3$ | H | Me | H | $CH_2C{\equiv}CH$ | CCl |
| Cl | $CF_3$ | H | Me | H | i-Pr | CCl | Cl | $CF_3$ | H | Me | H | $CH_2C{\equiv}CH$ | CCl |
| F | $CF_3$ | H | Me | H | i-Pr | CF | F | $CF_3$ | H | Me | H | $CH_2C{\equiv}CH$ | CF |
| Me | $CF_3$ | H | Me | H | i-Pr | N | Me | $CF_3$ | H | Me | H | $CH_2C{\equiv}CH$ | N |
| Cl | $CF_3$ | H | Me | H | i-Pr | N | Cl | $CF_3$ | H | Me | H | $CH_2C{\equiv}CH$ | N |
| F | $CF_3$ | H | Me | H | i-Pr | N | F | $CF_3$ | H | Me | H | $CH_2C{\equiv}CH$ | N |
| Me | $CF_3$ | H | Me | H | t-Bu | CH | Me | $CF_3$ | H | Me | Br | i-Pr | CH |
| Cl | $CF_3$ | H | Me | H | t-Bu | CH | Cl | $CF_3$ | H | Me | Br | i-Pr | CH |
| F | $CF_3$ | H | Me | H | t-Bu | CH | F | $CF_3$ | H | Me | Br | i-Pr | CH |
| Me | $CF_3$ | H | Me | H | t-Bu | CCl | Me | $CF_3$ | H | Me | Br | i-Pr | CCl |
| Cl | $CF_3$ | H | Me | H | t-Bu | CCl | Cl | $CF_3$ | H | Me | Br | i-Pr | CCl |
| F | $CF_3$ | H | Me | H | t-Bu | CF | F | $CF_3$ | H | Me | Br | i-Pr | CF |
| Me | $CF_3$ | H | Me | H | t-Bu | N | Me | $CF_3$ | H | Me | Br | i-Pr | N |
| Cl | $CF_3$ | H | Me | H | t-Bu | N | Cl | $CF_3$ | H | Me | Br | i-Pr | N |
| F | $CF_3$ | H | Me | H | t-Bu | N | F | $CF_3$ | H | Me | Br | i-Pr | N |
| Me | $CF_3$ | H | Me | H | Me | CH | Me | $CF_3$ | Me | Me | H | i-Pr | CH |
| Cl | $CF_3$ | H | Me | H | Me | CH | Cl | $CF_3$ | Me | Me | H | i-Pr | CH |
| F | $CF_3$ | H | Me | H | Me | CH | F | $CF_3$ | Me | Me | H | i-Pr | CH |
| Me | $CF_3$ | H | Me | H | Me | CCl | Me | $CF_3$ | Me | Me | H | i-Pr | CCl |
| Cl | $CF_3$ | H | Me | H | Me | CCl | Cl | $CF_3$ | Me | Me | H | i-Pr | CCl |
| F | $CF_3$ | H | Me | H | Me | CF | F | $CF_3$ | Me | Me | H | i-Pr | CF |
| Me | $CF_3$ | H | Me | H | Me | N | Me | $CF_3$ | Me | Me | H | i-Pr | N |
| Cl | $CF_3$ | H | Me | H | Me | N | Cl | $CF_3$ | Me | Me | H | i-Pr | N |
| F | $CF_3$ | H | Me | H | Me | N | F | $CF_3$ | Me | Me | H | i-Pr | N |
| Me | $CF_3$ | H | Me | H | Et | CH | Me | $CO_2Me$ | H | Me | H | i-Pr | CH |
| Cl | $CF_3$ | H | Me | H | Et | CH | Cl | $CO_2Me$ | H | Me | H | i-Pr | CH |
| F | $CF_3$ | H | Me | H | Et | CH | F | $CO_2Me$ | H | Me | H | i-Pr | CH |
| Me | $CF_3$ | H | Me | H | Et | CCl | Me | $CO_2Me$ | H | Me | H | i-Pr | CCl |
| Cl | $CF_3$ | H | Me | H | Et | CCl | Cl | $CO_2Me$ | H | Me | H | i-Pr | CCl |
| F | $CF_3$ | H | Me | H | Et | CF | F | $CO_2Me$ | H | Me | H | i-Pr | CF |
| Me | $CF_3$ | H | Me | H | Et | N | Me | $CO_2Me$ | H | Me | H | i-Pr | N |
| Cl | $CF_3$ | H | Me | H | Et | N | Cl | $CO_2Me$ | H | Me | H | i-Pr | N |
| F | $CF_3$ | H | Me | H | Et | N | F | $CO_2Me$ | H | Me | H | i-Pr | N |
| Me | Br | H | Me | H | i-Pr | CH | Me | $CF_3$ | H | Cl | H | i-Pr | CH |
| Cl | Br | H | Me | H | i-Pr | CH | Cl | $CF_3$ | H | Cl | H | i-Pr | CH |
| F | Br | H | Me | H | i-Pr | CH | F | $CF_3$ | H | Cl | H | i-Pr | CH |
| Me | Br | H | Me | H | i-Pr | CCl | Me | $CF_3$ | H | Cl | H | i-Pr | CCl |
| Cl | Br | H | Me | H | i-Pr | CCl | Cl | $CF_3$ | H | Cl | H | i-Pr | CCl |
| F | Br | H | Me | H | i-Pr | CF | F | $CF_3$ | H | Cl | H | i-Pr | CF |
| Me | Br | H | Me | H | i-Pr | N | Me | $CF_3$ | H | Cl | H | i-Pr | N |
| Cl | Br | H | Me | H | i-Pr | N | Cl | $CF_3$ | H | Cl | H | i-Pr | N |
| F | Br | H | Me | H | i-Pr | N | F | $CF_3$ | H | Cl | H | i-Pr | N |
| Me | $CF_3$ | H | Cl | H | t-Bu | CH | Me | $CF_3$ | H | Cl | H | $CH_2C{\equiv}CH$ | CH |
| Cl | $CF_3$ | H | Cl | H | t-Bu | CH | Cl | $CF_3$ | H | Cl | H | $CH_2C{\equiv}CH$ | CH |
| F | $CF_3$ | H | Cl | H | t-Bu | CH | F | $CF_3$ | H | Cl | H | $CH_2C{\equiv}CH$ | CH |
| Me | $CF_3$ | H | Cl | H | t-Bu | CCl | Me | $CF_3$ | H | Cl | H | $CH_2C{\equiv}CH$ | CCl |
| Cl | $CF_3$ | H | Cl | H | t-Bu | CCl | Cl | $CF_3$ | H | Cl | H | $CH_2C{\equiv}CH$ | CCl |
| F | $CF_3$ | H | Cl | H | t-Bu | CF | F | $CF_3$ | H | Cl | H | $CH_2C{\equiv}CH$ | CF |
| Me | $CF_3$ | H | Cl | H | t-Bu | N | Me | $CF_3$ | H | Cl | H | $CH_2C{\equiv}CH$ | N |
| Cl | $CF_3$ | H | Cl | H | t-Bu | N | Cl | $CF_3$ | H | Cl | H | $CH_2C{\equiv}CH$ | N |
| F | $CF_3$ | H | Cl | H | t-Bu | N | F | $CF_3$ | H | Cl | H | $CH_2C{\equiv}CH$ | N |

TABLE 13-continued

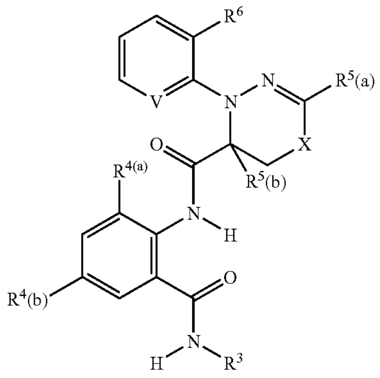

| $R^6$ | $R^{5(a)}$ | $R^{5(b)}$ | $R^{4(a)}$ | $R^{(b)}$ | $R^3$ | V | $R^6$ | $R^{5(a)}$ | $R^{5(b)}$ | $R^{4(a)}$ | $R^{(b)}$ | $R^3$ | V |
|---|---|---|---|---|---|---|---|---|---|---|---|---|---|
| | | | | | | X is S | | | | | | | |
| Me | $CF_3$ | H | Me | H | i-Pr | CH | Me | $CF_3$ | H | Me | H | $CH_2C{\equiv}CH$ | CH |
| Cl | $CF_3$ | H | Me | H | i-Pr | CH | Cl | $CF_3$ | H | Me | H | $CH_2C{\equiv}CH$ | CH |
| F | $CF_3$ | H | Me | H | i-Pr | CH | F | $CF_3$ | H | Me | H | $CH_2C{\equiv}CH$ | CH |
| Me | $CF_3$ | H | Me | H | i-Pr | CCl | Me | $CF_3$ | H | Me | H | $CH_2C{\equiv}CH$ | CCl |
| Cl | $CF_3$ | H | Me | H | i-Pr | CCl | Cl | $CF_3$ | H | Me | H | $CH_2C{\equiv}CH$ | CCl |
| F | $CF_3$ | H | Me | H | i-Pr | CF | F | $CF_3$ | H | Me | H | $CH_2C{\equiv}CH$ | CF |
| Me | $CF_3$ | H | Me | H | i-Pr | N | Me | $CF_3$ | H | Me | H | $CH_2C{\equiv}CH$ | N |
| Cl | $CF_3$ | H | Me | H | i-Pr | N | Cl | $CF_3$ | H | Me | H | $CH_2C{\equiv}CH$ | N |
| F | $CF_3$ | H | Me | H | i-Pr | N | F | $CF_3$ | H | Me | H | $CH_2C{\equiv}CH$ | N |
| Me | $CF_3$ | H | Me | H | t-Bu | CH | Me | $CF_3$ | H | Me | Br | i-Pr | CH |
| Cl | $CF_3$ | H | Me | H | t-Bu | CH | Cl | $CF_3$ | H | Me | Br | i-Pr | CH |
| F | $CF_3$ | H | Me | H | t-Bu | CH | F | $CF_3$ | H | Me | Br | i-Pr | CH |
| Me | $CF_3$ | H | Me | H | t-Bu | CCl | Me | $CF_3$ | H | Me | Br | i-Pr | CCl |
| Cl | $CF_3$ | H | Me | H | t-Bu | CCl | Cl | $CF_3$ | H | Me | Br | i-Pr | CCl |
| F | $CF_3$ | H | Me | H | t-Bu | CF | F | $CF_3$ | H | Me | Br | i-Pr | CF |
| Me | $CF_3$ | H | Me | H | t-Bu | N | Me | $CF_3$ | H | Me | Br | i-Pr | N |
| Cl | $CF_3$ | H | Me | H | t-Bu | N | Cl | $CF_3$ | H | Me | Br | i-Pr | N |
| F | $CF_3$ | H | Me | H | t-Bu | N | F | $CF_3$ | H | Me | Br | i-Pr | N |
| Me | $CF_3$ | H | Me | H | Me | CH | Me | $CF_3$ | Me | Me | H | i-Pr | CH |
| Cl | $CF_3$ | H | Me | H | Me | CH | Cl | $CF_3$ | Me | Me | H | i-Pr | CH |
| F | $CF_3$ | H | Me | H | Me | CH | F | $CF_3$ | Me | Me | H | i-Pr | CH |
| Me | $CF_3$ | H | Me | H | Me | CCl | Me | $CF_3$ | Me | Me | H | i-Pr | CCl |
| Cl | $CF_3$ | H | Me | H | Me | CCl | Cl | $CF_3$ | Me | Me | H | i-Pr | CCl |
| F | $CF_3$ | H | Me | H | Me | CF | F | $CF_3$ | Me | Me | H | i-Pr | CF |
| Me | $CF_3$ | H | Me | H | Me | N | Me | $CF_3$ | Me | Me | H | i-Pr | N |
| Cl | $CF_3$ | H | Me | H | Me | N | Cl | $CF_3$ | Me | Me | H | i-Pr | N |
| F | $CF_3$ | H | Me | H | Me | N | F | $CF_3$ | Me | Me | H | i-Pr | N |
| Me | $CF_3$ | H | Me | H | Et | CH | Me | $CO_2Me$ | H | Me | H | i-Pr | CH |
| Cl | $CF_3$ | H | Me | H | Et | CH | Cl | $CO_2Me$ | H | Me | H | i-Pr | CH |
| F | $CF_3$ | H | Me | H | Et | CH | F | $CO_2Me$ | H | Me | H | i-Pr | CH |
| Me | $CF_3$ | H | Me | H | Et | CCl | Me | $CO_2Me$ | H | Me | H | i-Pr | CCl |
| Cl | $CF_3$ | H | Me | H | Et | CCl | Cl | $CO_2Me$ | H | Me | H | i-Pr | CCl |
| F | $CF_3$ | H | Me | H | Et | CF | F | $CO_2Me$ | H | Me | H | i-Pr | CF |
| Me | $CF_3$ | H | Me | H | Et | N | Me | $CO_2Me$ | H | Me | H | i-Pr | N |
| Cl | $CF_3$ | H | Me | H | Et | N | Cl | $CO_2Me$ | H | Me | H | i-Pr | N |
| F | $CF_3$ | H | Me | H | Et | N | F | $CO_2Me$ | H | Me | H | i-Pr | N |
| Me | Br | H | Me | H | i-Pr | CH | Me | $CF_3$ | H | Cl | H | i-Pr | CH |
| Cl | Br | H | Me | H | i-Pr | CH | Cl | $CF_3$ | H | Cl | H | i-Pr | CH |
| F | Br | H | Me | H | i-Pr | CH | F | $CF_3$ | H | Cl | H | i-Pr | CH |
| Me | Br | H | Me | H | i-Pr | CCl | Me | $CF_3$ | H | Cl | H | i-Pr | CCl |
| Cl | Br | H | Me | H | i-Pr | CCl | Cl | $CF_3$ | H | Cl | H | i-Pr | CCl |
| F | Br | H | Me | H | i-Pr | CF | F | $CF_3$ | H | Cl | H | i-Pr | CF |
| Me | Br | H | Me | H | i-Pr | N | Me | $CF_3$ | H | Cl | H | i-Pr | N |
| Cl | Br | H | Me | H | i-Pr | N | Cl | $CF_3$ | H | Cl | H | i-Pr | N |
| F | Br | H | Me | H | i-Pr | N | F | $CF_3$ | H | Cl | H | i-Pr | N |
| Me | $CF_3$ | H | Cl | H | t-Bu | CH | Me | $CF_3$ | H | Cl | H | $CH_2C{\equiv}CH$ | CH |
| Cl | $CF_3$ | H | Cl | H | t-Bu | CH | Cl | $CF_3$ | H | Cl | H | $CH_2C{\equiv}CH$ | CH |
| F | $CF_3$ | H | Cl | H | t-Bu | CH | F | $CF_3$ | H | Cl | H | $CH_2C{\equiv}CH$ | CH |
| Me | $CF_3$ | H | Cl | H | t-Bu | CCl | Me | $CF_3$ | H | Cl | H | $CH_2C{\equiv}CH$ | CCl |
| Cl | $CF_3$ | H | Cl | H | t-Bu | CCl | Cl | $CF_3$ | H | Cl | H | $CH_2C{\equiv}CH$ | CCl |
| F | $CF_3$ | H | Cl | H | t-Bu | CF | F | $CF_3$ | H | Cl | H | $CH_2C{\equiv}CH$ | CF |
| Me | $CF_3$ | H | Cl | H | t-Bu | N | Me | $CF_3$ | H | Cl | H | $CH_2C{\equiv}CH$ | N |
| Cl | $CF_3$ | H | Cl | H | t-Bu | N | Cl | $CF_3$ | H | Cl | H | $CH_2C{\equiv}CH$ | N |
| F | $CF_3$ | H | Cl | H | t-Bu | N | F | $CF_3$ | H | Cl | H | $CH_2C{\equiv}CH$ | N |

Formulation/Utility

Compounds of this invention will generally be used as a formulation or composition with an agriculturally suitable carrier comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges that add up to 100 percent by weight.

| | Weight Percent | | |
|---|---|---|---|
| | Active Ingredient | Diluent | Surfactant |
| Water-Dispersible and Water-soluble Granules, Tablets and Powders. | 5–90 | 0–94 | 1–15 |
| Suspensions, Emulsions, Solutions (including Emulsifiable Concentrates) | 5–50 | 40–95 | 0–15 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carriers*, 2nd Ed., Dorland Books, Caldwell, N.J. Typical liquid diluents are described in Marsden, *Solvents Guide*, 2nd Ed., Interscience, New York, 1950. *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy4-methyl-2-pentanone, and alcohols such as methanol, cyclohexanol, decanol and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering*, Dec. 4, 1967, pp 147–48, *Perry's Chemical Engineer's Handbook*, 4th Ed., McGraw-Hill, New York, 1963, pages 8–57 and following, and PCT Publication WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods, "The Formulator's Toolbox—Product Forms for Modem Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120–133. See also U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control as a Science*, John Wiley and Sons, Inc., New York, 1961, pp 81–96; and Hance et al., *Weed Control Handbook*, 8th Ed., Blackwell Scientific Publications, Oxford, 1989.

In the following Examples, all percentages are by weight and all formulations are prepared in conventional ways. Compound numbers refer to compounds in Index Table A.

EXAMPLE A

Wettable Powder

| | |
|---|---|
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

EXAMPLE B

Granule

| | |
|---|---|
| Compound 1 | 10.0% |
| attapulgite granules (low volatile matter, 0.71/0.30 mm; U.S.S. No. 25–50 sieves) | 90.0%. |

EXAMPLE C

Extruded Pellet

| | |
|---|---|
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

EXAMPLE D

Emulsifiable Concentrate

| | |
|---|---|
| Compound 1 | 20.0% |
| blend of oil soluble sulfonates and polyoxyethylene ethers | 10.0% |
| isophorone | 70.0%. |

EXAMPLE E

Granule

| | |
|---|---|
| Compound 1 | 0.5% |
| cellulose | 2.5% |
| lactose | 4.0% |
| cornmeal | 93.0%. |

Compounds of this invention are characterized by favorable metabolic and/or soil residual patterns and exhibit activity controlling a spectrum of agronomic and nonagronomic invertebrate pests. (In the context of this disclosure "invertebrate pest control" means inhibition of invertebrate pest development (including mortality) that causes significant reduction in feeding or other injury or damage caused by the pest; related expressions are defined analogously.) As referred to in this disclosure, the term "invertebrate pest" includes arthropods, gastropods and nematodes of economic importance as pests. The term "arthropod" includes insects, mites, spiders, scorpions, centipedes, millipedes, pill bugs and symphylans. The term "gastropod" includes snails, slugs and other Stylommatophora. The term "nematode" includes all of the helminths, such as: roundworms, heartworms, and phytophagous nematodes (Nematoda), flukes (Tematoda), Acanthocephala, and tapeworms (Cestoda). Those skilled in the art will recognize that not all compounds are equally effective against all pests. Compounds of this invention display activity against economically important agronomic and nonagronomic pests. The term "agronomic" refers to the production of field crops such as for food and fiber and includes the growth of cereal crops (e.g., wheat, oats, barley, rye, rice, maize), soybeans, vegetable crops (e.g., lettuce, cabbage, tomatoes, beans), potatoes, sweet potatoes, grapes, cotton, and tree fruits (e.g., pome fruits, stone fruits and citrus fruits). The term "nonagronomic" refers to other horticultural (e.g., forest, greenhouse, nursery or ornamental plants not grown in a field), public (human) and animal health, domestic and commercial structure, household, and stored product applications or pests. For reason of invertebrate pest control spectrum and economic importance, protection (from damage or injury caused by invertebrate pests) of agronomic crops of cotton, maize, soybeans, rice, vegetable crops, potato, sweet potato, grapes and tree fruit by controlling invertebrate pests are preferred embodiments of the invention. Agronomic or nonagronomic pests include larvae of the order Lepidoptera, such as armyworms, cutworms, loopers, and heliothines in the family Noctuidae (e.g., fall armyworm (*Spodoptera fugiperda* J. E. Smith), beet armyworm (*Spodoptera exigua* Hübner), black cutworm (*Agrotis ipsilon* Hufnagel), cabbage looper (*Trichoplusia ni* Hübner), tobacco budworm (*Heliothis virescens* Fabricius)); borers, casebearers, webworms, coneworms, cabbageworms and skeletonizers from the family Pyralidae (e.g., European corn borer (*Ostrinia nubilalis* Hübner), navel orangeworm (*Amyelois transitella* Walker), corn root webworm (*Crambus caliginosellus* Clemens), sod webworm (*Herpetogramma licarsisalis* Walker)); leafrollers, budworms, seed worms, and fruit worms in the family Tortricidae (e.g., codling moth (*Cydia pomonella* Linnaeus), grape berry moth (*Endopiza viteana* Clemens), oriental fruit moth (*Grapholita molesta* Busck)); and many other economically important lepidoptera (e.g., diamondback moth (*Plutella xylostella* Linnaeus), pink bollworm (*Pectinophora gossypiella* Saunders), gypsy moth (*Lymantria dispar* Linnaeus)); nymphs and adults of the order Blattodea including cockroaches from the families Blattellidae and Blattidae (e.g., oriental cockroach (*Blatta orientalis Linnaeus*), Asian cockroach (*Blatella asahinai* Mizukubo), German cockroach (*Blattella germanica* Linnaeus), brownbanded cockroach (*Supella longipalpa* Fabricius), American cockroach (*Periplaneta americana* Linnaeus), brown cockroach (*Periplaneta brunnea* Burmeister), Madeira cockroach (*Leucophaea maderae* Fabricius)); foliar feeding larvae and adults of the order Coleoptera including weevils from the families Anthribidae, Bruchidae, and Curculionidae (e.g., boll weevil (*Anthonomus grandis* Boheman), rice water weevil (*Lissorhoptrus oryzophilus* Kuschel), granary weevil (*Sitophilus granarius* Linnaeus), rice weevil (*Sitophilus oryzae* Linnaeus)); flea beetles, cucumber beetles, rootworms, leaf beetles, potato beetles, and leafminers in the family Chrysomelidae (e.g., Colorado potato beetle (*Leptinotarsa decemlineata* Say), western corn rootworm (*Diabrotica virgifera virgifera* LeConte)); chafers and other beetles from the family Scaribaeidae (e.g., Japanese beetle (*Popillia japonica* Newman) and European chafer (*Rhizotrogus majalis* Razoumowsky)); carpet beetles froim the family Dermestidae; wireworms from the family Elateridae; bark beetles from the family Scolytidae and flour beetles from the family Tenebrionidae. In addition agronoomic and nonagronomic pests include: adults and larvae of the order Dermaptera including earwigs from the family Forficulidae (e.g., European earwig (*Forficula auricularia* Linnaeus), black earwig (*Chelisoches morio* Fabricius)); adults and nymphs of the orders Hemiptera and Homoptera such as, plant bugs from the family Miridae, cicadas from the family Cicadidae, leafhoppers (e.g. *Empoasca* spp.) from the family Cicadellidae, planthoppers from the families Fulgoroidae and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Coccidae, Diaspididae and Margarodidae, lace bugs from the family Tingidae, stink bugs from the family Pentatomidae, cinch bugs (e.g., *Blissus* spp.) and other seed bugs from the family Lygaeidae, spittlebugs from the family Cercopidae squash bugs from the family Coreidae, and red bugs and cotton stainers from the family Pyrrhocoridae. Also included are adults and larvae of the order Acari (mites) such as spider mites and red mites in the family Tetranychidae (e.g., European red mite (*Panonychus ulmi* Koch), two spotted spider mite (*Tetranychus urticae* Koch), McDaniel mite (*Tetranychus mcdanieli* McGregor)), flat mites in the family Tenuipalpidae (e.g., citrus flat mite (*Brevipalpus lewisi* McGregor)), rust and bud mitesin the family Eriophyidae and other foliar feeding mites and mites important in human and animal health, i.e. dust mites in the family Epidermoptidae, follicle mites in the family Demodicidae, grain mites in the family Glycyphagidae, ticks in the order Ixodidae (e.g., deer tick (*Ixodes scapularis* Say), Australian paralysis tick (*Ixodes holocyclus* Neumann), American dog tick (*Dermacentor variabilis* Say), lone star tick (*Amblyomma americanum* Linnaeus) and scab and itch mites in the families Psoroptidae, Pyemotidae, and Sarcoptidae; adults and immatures of the order Orthoptera including grasshoppers, locusts and crickets (e.g., migratory grasshoppers (e.g., *Melanoplus sanguinipes* Fabricius, *M. differentialis* Thomas), American grasshoppers (e.g., *Schistocerca americana* Drury), desert locust (*Schistocerca gregaria* Forskal), migratory locust (*Locusta migratoria* Linnaeus), house cricket (*Acheta domesticus* Linnaeus), mole crickets (*Gryllotalpa* spp.)); adults and immatures of the order Diptera including leafininers, midges, fruit flies (Tephritidae), frit flies (e.g., *Oscinella frit* Linnaeus), soil maggots, house flies (e.g., *Musca domestica* Linnaeus), lesser house flies (e.g., *Fannia canicularis* Linnaeus, *F. femoralis* Stein), stable flies (e.g., *Stomoxys calcitrans* Linnaeus), face flies, horn flies, blow flies (e.g., *Chrysomya* spp., *Phormia* spp.), and other muscoid fly pests, horse flies (e.g., *Tabanus* spp.), bot flies (e.g., *Gastrophilus* spp., *Oestrus* spp.), cattle grubs (e.g., *Hypoderma* spp.), deer flies (e.g., *Chrysops* spp.), keds (e.g., *Melophagus ovinus* Linnaeus) and other Brachycera, mosquitoes (e.g., *Aedes* spp., *Anopheles* spp., *Culex* spp.), black flies (e.g., *Prosimulium* spp., *Simulium* spp.), biting midges, sand flies, sciarids, and other Nematocera; adults and immatures of the order Thysanoptera including onion thrips (*Thrips tabaci* Lindeman) and other foliar feeding thrips; insect pests of the order Hymenoptera including ants (e.g., red carpenter ant (*Camponotus ferrugineus* Fabricius), black carpenter ant (*Camponotus pennsylvanicus* De Geer), Pharaoh ant (*Monomorium pharaonis* Linnaeus), little fire ant (*Wasmannia auropunctata* Roger), fire ant (*Solenopsis geminata* Fabricius), red imported fire ant (*Solenopsis invicta* Buren), Argentine ant (*Iridomyrmex humilis* Mayr), crazy ant (*Paratrechina longicornis* Latreille), pavement ant (*Tetramorium caespitum* Linnaeus), cornfield ant (*Lasius alienus* Förster), odorous house ant (*Tapinoma sessile* Say)), bees (including carpenter bees), hornets, yellow jackets and wasps; insect pests of the order Isoptera including the eastern subterranean termite (*Reticulitermes flavipes* Kollar), western subterranean termite (*Reticulitermes hesperus* Banks), Formosan subterranean termite (*Coptotermes formosanus* Shiraki), West Indian drywood termite (*Incisitermes immigrans* Snyder) and other termites of economic importance; insect pests of the order Thysanura such as silverfish (*Lepisma saccharina* Linnaeus) and firebrat (*Thermobia domestica* Packard); insect pests of the order Mallophaga and including the head louse (*Pediculus humanus capitis* De Geer), body louse (*Pediculus humanus humanus* Linnaeus), chicken body louse (*Menacanthus stramineus* Nitszch), dog biting louse (*Trichodectes canis* De Geer), fluff louse (*Goniocotes gallinae* De Geer), sheep body louse (*Bovicola ovis* Schrank), short-nosed cattle louse (*Haematopinus eurysternus* Nitzsch), long-nosed cattle louse (*Linognathus vituli* Linnaeus) and other sucking and chewing parasitic lice that attack man and animals; insect pests of the order Siphonoptera including the oriental rat flea (*Xenopsylla cheopis* Rothschild), cat flea (*Ctenocephalides felis* Bouche), dog flea (*Ctenocephalides canis* Curtis), hen flea (*Ceratophyllus gallinae* Schrank), sticktight flea (*Echidnophaga gallinacea* Westwood), human flea (*Pulex irritans* Linnaeus) and other fleas afflicting mammals and birds. Additional arthropod pests covered include: spiders in the order Araneae such as the brown recluse spider (*Loxosceles reclusa* Gertsch & Mulaik) and the black widow spider (*Latrodectus mactans* Fabricius), and centipedes in the order Scutigeromorpha such as the house centipede (*Scutigera coleoptrata* Linnaeus). Compounds of the present invention also have activity on members of the Classes Nematoda, Cestoda, Trematoda, and Acanthocephala including economically important members of the orders Strongylida, Ascaridida, Oxyurida, Rhabditida, Spirurida, and Enoplida such as but not limited to economically important agricultural pests (i.e. root knot nematodes in the genus *Meloidogyne,* lesion nematodes in the genus *Pratylenchus,* stubby root nematodes in the genus *Trichodorus,* etc.) and animal and human health pests (i.e. all economically important flukes, tapeworms, and roundworms, such as *Strongylus vulgaris* in horses, *Toxocara canis* in dogs, *Haemonchus contortus* in sheep, *Dirofilaria immitis* Leidy in dogs, *Anoplocephala perfoliata* in horses, *Fasciola hepatica* Linnaeus in ruminants, etc.).

Compounds of the invention show particularly high activity against pests in the order Lepidoptera (e.g., *Alabama argillacea* Hübner (cotton leaf worm), *Archips argyrospila* Walker (fruit tree leaf roller), *A. rosana* Linnaeus (European leaf roller) and other *Archips* species, *Chilo suppressalis* Walker (rice stem borer), *Cnaphalocrosis medinalis* Guenee (rice leaf roller), *Crambus caliginosellus* Clemens (corn root webworm), *Crambus teterrellus* Zincken (bluegrass webworm), *Cydia pomonella* Linnaeus (codling moth), *Earias insulana* Boisduval (spiny bollworm), *Earias vittella* Fabricius (spotted bollworm), *Helicoverpa armigera* Hübner (American bollworm), *Helicoverpa zea* Boddie (corn earworm), *Heliothis virescens* Fabricius (tobacco budworm), *Herpetogramma licarsisalis* Walker (sod webworm), *Lobesia botrana* Denis & Schiffermüller (grape berry moth), *Pectinophora gossypiella* Saunders (ink bollworm), *Phyllocnistis citrella* Stainton (citrus leafminer), *Pieris brassicae* Linnaeus (large white butterfly), *Pieris rapae* Linnaeus (small white butterfly), *Plutella xylostella* Linnaeus (diamondback moth), *Spodoptera exigua* Hübner (beet armyworm), *Spodoptera litura* Fabricius (tobacco cutworm, cluster caterpillar), *Spodoptera frugiperda* J. E. Smith (fall armyworm), *Trichoplusia ni* Hübner (cabbage looper) and *Tuta absoluta* Meyrick (tomato leafminer)). Compounds of the invention also have commercially significant activity on members from the order Homoptera including: *Acyrthisiphon pisum* Harris (pea aphid), *Aphis craccivora* Koch (cowpea aphid), *Aphis fabae* Scopoli (black bean aphid), *Aphis gossypii* Glover (cotton aphid, melon aphid), *Aphis pomi* De Geer (apple aphid), *Aphis spiraecola* Patch (spirea aphid), *Aulacorthum solani* Kaltenbach (foxglove aphid), *Chaetosiphon fragaefolii* Cockerell (strawberry aphid), *Diuraphis noxia* Kurdjumov/Mordvilko (Russian wheat aphid), *Dysaphis plantaginea* Paaserini (rosy apple aphid), *Eriosoma lanigerum* Hausmann (woolly apple aphid), *Hyalopterus pruni* Geoffroy (mealy plum aphid), *Lipaphis erysimi* Kaltenbach (turnip aphid), *Metopolophium dirrhodum* Walker (cereal aphid), *Macrosipum euphorbiae* Thomas (potato aphid), *Myzus persicae* Sulzer (peach-potato aphid, green peach aphid), *Nasonovia ribisnigri* Mosley (lettuce aphid), *Pemphigus* spp. (root aphids and gall aphids), *Rhopalosiphum maidis* Fitch (corn leaf aphid), *Rhopalosiphum padi* Linnaeus (bird cherry-oat aphid), *Schizaphis graminum* Rondani (greenbug), *Sitobion avenae* Fabricius (English grain aphid), *Therioaphis maculata* Buckton (spotted alfalfa aphid), *Toxoptera aurantii* Boyer de Fonscolombe (black citrus aphid), and *Toxoptera citricida* Kirkaldy (brown citrus aphid); *Adelges* spp. (adelgids); *Phylloxera devastatrix* Pergande (pecan *phylloxera*); *Bemisia tabaci* Gennadius (tobacco whitefly, sweetpotato whitefly), *Bemisia argentifolii* Bellows & Perring (silverleaf whitefly), *Dialeurodes citri* Ashmead (citrus whitefly) and *Trialeurodes vaporariorum* Westwood (greenhouse whitefly); *Empoasca fabae* Harris (potato leafhopper), *Laodelphax striatellus* Fallen (smaller brown planthopper), *Macrolestes quadrilineatus* Forbes (aster leafhopper), *Nephotettix cinticeps* Uhler (green leafhopper), *Nephotettix nigropictus* Stål (rice leafhopper), *Nilaparvata lugens* Stål (brown planthopper), *Peregrinus maidis* Ashmead (corn planthopper), *Sogatella furcifera* Horvath (white-backed planthopper), *Sogatodes orizicola* Muir (rice delphacid), *Typhlocyba pomaria* McAtee white apple leafhopper, *Erythroneoura* spp. (grape leafioppers); *Magicidada septendecim* Linnaeus (periodical cicada); *Icerya purchasi* Maskell (cottony cushion scale), *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear *psylla*), *Trioza diospyri* Ashmead (persimmon *psylla*). These compounds also have activity on members from the order Hemiptera including: *Acrosternum hilare* Say (green stink bug), *Anasa tristis* De Geer (squash bug), *Blissus leucopterus leucopterus* Say (chinch bug), *Corythuca gossypii* Fabricius (cotton lace bug), *Cyrtopeltis modesta* Distant (tomato bug), *Dysdercus suturellus* Herrich-Schäffer (cotton stainer), *Euchistus servus* Say (brown stink bug), *Euchistus variolarius* Palisot de Beauvois (one-spotted stink bug), *Graptosthetus* spp. (complex of seed bugs), *Leptoglossus corculus* Say (leaf-footed pine seed bug), *Lygus lineolaris* Palisot de Beauvois (tarnished plant bug), *Nezara viridula* Linnaeus (southern green stink bug), *Oebalus pugnax* Fabricius (rice stink bug), *Oncopeltus fasciatus* Dallas (large milkweed bug), *Pseudatomoscelis seriatus* Reuter (cotton fleahopper). Other insect orders controlled by compounds of the invention include Thysanoptera (e.g., *Frankliniella occidentalis* Pergande (western flower thrip), *Scirthothrips citri* Moulton (citrus thrip), *Sericothrips variabilis* Beach (soybean thrip), and *Thrips tabaci* Lindeman (onion thrip); and the order Coleoptera (e.g., *Leptinotarsa decemlineata* Say (Colorado potato beetle), *Epilachna varivestis* Mulsant (Mexican bean beetle) and wireworms of the genera *Agriotes, Athous* or *Limonius*).

Compounds of this invention can also be mixed with one or more other biologically active compounds or agents including insecticides, fungicides, nematocides, bactericides, acaricides, growth regulators such as rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agricultural utility. Thus compositions of the present invention can further comprise a biologically effective amount of at least one additional biologically active compound or agent. Examples of such biologically active compounds or agents with which compounds of this invention can be formulated are: insecticides such as abamectin, acephate, acetamiprid, avermectin, azadirachtin, azinphos-methyl, bifenthrin, binfenazate, buprofezin, carbofuran, chlorfenapyr, chlorfluazuron, chlorpyrifos, chlorpyrifos-methyl, chromafenozide, clothianidin, cyfluthrin, beta-cyfluthrin, cyhalothrin, lambda-cyhalothrin, cypermethrin, cyromazine, deltamethrin, diafenthiuron, diazinon, diflubenzuron, dimethoate, diofenolan, emamectin, endosulfan, esfenvalerate, ethiprole, fenothicarb, fenoxycarb, fenpropathrin, fenproximate, fenvalerate, fipronil, flonicamid, flucythrinate, tau-fluvalinate, flufenoxuron, fonophos, halofenozide, hexaflumuron, imidacloprid, indoxacarb, isofenphos, lufenuron, malathion, metaldehyde, methamidophos, methidathion, methomyl, methoprene, methoxychlor, monocrotophos, methoxyfenozide, nithiazin, novaluron, oxamyl, parathion, parathion-methyl, permetrm, phorate, phosalone, phosmet, phosphamidon, pirimicarb, profenofos, pymetrozine, pyridalyl, pyriproxyfen, rotenone, spinosad, sulprofos, tebufenozide, teflubenzuron, tefluthrin, terbufos, tetrachlorvinphos, thiacloprid, thiamethoxam, thiodicarb, thiosultap-sodium, tralomethrin, trichlorfon and triflumuron; fungicides such as acibenzolar, azoxystrobin, benomyl, blasticidin-S, Bordeaux mixture (tribasic copper sulfate), bromuconazole, carpropamid, captafol, captan, carbendazim, chloroneb, chlorothalonil, copper oxychloride, copper salts, cyflufenamid, cymoxanil, cyproconazole, cyprodinil, (S)-3,5-dichloro-N-(3-chloro-1-ethyl-1-methyl-2-oxopropyl)-4-methylbenzamide (RH 7281), diclocymet (S-2900), diclomezine, dicloran, difenoconazole, (S)-3,5-dihydro-5-methyl-2-(methylthio)-5-phenyl-3-(phenylamino)-4H-imidazol-4-one (RP 407213), dimethomorph, dimoxystrobin, diniconazole, diniconazole-M, dodine, edifenphos, epoxiconazole, famoxadone, fenamidone, fenarimol, fenbuconazole, fencaramid (SZX0722), fenpiclonil, fenpropidin, fenpropimorph, fentin acetate, fentin hydroxide, fluazinam, fludioxonil, flumetover (RPA 403397), fluquinconazole, flusilazole, flutolanil, flutriafol, folpet, fosetyl-aluminum, furalaxyl, furametapyr (S-82658), hexaconazole, ipconazole, iprobenfos, iprodione, isoprothiolane, kasugamycin, kresoxim-methyl, mancozeb, maneb, mefenoxam, mepronil, metalaxyl, metconazole, metomino-strobin/fenominostrobin (SSF-126), myclobutanil, neo-asozin (ferric methanearsonate), oxadixyl, penconazole, pencycuron, probenazole, prochloraz, propamocarb, propiconazole, pyrifenox, pyraclostrobin, pyrimethanil, pyroquilon, quinoxyfen, spiroxamine, sulfur, tebuconazole, tetraconazole, thiabendazole, thifluzamide, thiophanate-methyl, thiram, tiadinil, triadimefon, triadimenol, tricyclazole, trifloxystrobin, triticonazole, validamycin and vinclozolin; nematocides such as aldicarb, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents such as *Bacillus thuringiensis* including ssp. *aizawai* and *kurstaki, Bacillus thuringiensis* delta endotoxin, baculovirus, and entomopathogenic bacteria, virus and fungi. Compounds of this invention and compositions thereof can be applied to plants genetically transformed to express proteins toxic to invertebrate pests (such as *Bacillus thuringiensis* toxin). The effect of exogenously applied invertebrate pest control compounds of this invention may be synergistic with the expressed toxin proteins.

A general reference for these agricultural protectants is *The Pesticide Manual*, 12*th Edition*, C. D. S. Tomlin, Ed., British Crop Protection Council, Farnham, Surrey, U.K., 2000.

Preferred insecticides and acaricides for mixing with compounds of this invention include pyrethroids such as cypermethrin, cyhalothrin, cyfluthrin, beta-cyfluthrin, esfenvalerate, fenvalerate and tralomethrin; carbamates such as fenothicarb, methomyl, oxamyl and thiodicarb; neonicotinoids such as clothianidin, imidacloprid and thiacloprid; neuronal sodium channel blockers such as indoxacarb; insecticidal macrocyclic lactones such as spinosad, abamectin, avermectin and emamectin; γ-aminobutyric acid (GABA) antagonists such as endosulfan, ethiprole and fipronil; insecticidal ureas such as flufenoxuron and triflumuron; juvenile hormone mimics such as diofenolan and pyriproxyfen; pymetrozine; and amitraz. Preferred biological agents for mixing with compounds of this invention include *Bacillus thuringiensis* and *Bacillus thuringiensis* delta endotoxin as well as naturally occurring and genetically modified viral insecticides including members of the family Baculoviridae as well as entomophagous fungi.

Most preferred mixtures include a mixture of a compound of this invention with cyhalothrin; a mixture of a compound of this invention with beta-cyfluthrin; a mixture of a compound of this invention with esfenvalerate; a mixture of a compound of this invention with methomyl; a mixture of a compound of this invention with imidacloprid; a mixture of a compound of this invention with thiacloprid; a mixture of a compound of this invention with indoxacarb; a mixture of a compound of this invention with abamectin; a mixture of a compound of this invention with endosulfan; a mixture of a compound of this invention with ethiprole; a mixture of a compound of this invention with fipronil; a mixture of a compound of this invention with flufenoxuron; a mixture of a compound of this invention with pyriproxyfen; a mixture of a compound of this invention with pymetrozine; a mixture of a compound of this invention with amitraz; a mixture of a compound of this invention with *Bacillus thuringiensis* and a mixture of a compound of this invention with *Bacillus thuringiensis* delta endotoxin.

In certain instances, combinations with other invertebrate pest control compounds or agents having a similar spectrum of control but a different mode of action will be particularly advantageous for resistance management. Thus, compositions of the present invention can further comprise a biologically effective amount of at least one additional invertebrate pest control compound or agent having a similar spectrum of control but a different mode of action. Contacting a plant genetically modified to express a plant protection compound (e.g., protein) or the locus of the plant with a biologically effective amount of a compound of invention can also provide a broader spectrum of plant protection and be advantageous for resistance management.

Invertebrate pests are controlled in agronomic and nonagronomic applications by applying one or more of the compounds of this invention, in an effective amount, to the environment of the pests including the agronomic and/or nonagronomic locus of infestation, to the area to be protected, or directly on the pests to be controlled. Thus, the present invention further comprises a method for the control of an invertebrate pest in agronomic and/or nonagronomic applications, comprising contacting the invertebrate pest or its environment with a biologically effective amount of one or more of the compounds of the invention, or with a composition comprising at least one such compound or a composition comprising at least one such compound and an effective amount of at least one additional biologically active compound or agent. Examples of suitable compositions comprising a compound of the invention and an effective amount of at least one additional biologically active compound or agent include granular compositions wherein the additional biologically active compound or agent is present on the same granule as the compound of the invention or on granules separate from those of the compound of this invention.

A preferred method of contact is by spraying. Alternatively, a granular composition comprising a compound of the invention can be applied to the plant foliage or the soil. Compounds of this invention are also effectively delivered through plant uptake by contacting the plant with a composition comprising a compound of this invention applied as a soil drench of a liquid formulation, a granular formulation to the soil, a nursery box treatment or a dip of transplants. Compounds are also effective by topical application of a composition comprising a compound of this invention to the locus of infestation. Other methods of contact include application of a compound or a composition of the invention by direct and residual sprays, aerial sprays, gels, seed coatings, microencapsulations, systemic uptake, baits, eartags, boluses, foggers, fumigants, aerosols, dusts and many others. The compounds of this invention may also be impregnated into materials for fabricating invertebrate control devices (e.g. insect netting).

The compounds of this invention can be incorporated into baits that are consumed by the invertebrates or within devices such as traps and the like. Granules or baits comprising between 0.01–5% active ingredient, 0.05–10% moisture retaining agent(s) and 40–99% vegetable flour are effective in controlling soil insects at very low application rates, particularly at doses of active ingredient that are lethal by ingestion rather than by direct contact.

The compounds of this invention can be applied in their pure state, but most often application will be of a formulation comprising one or more compounds with suitable carriers, diluents, and surfactants and possibly in combination with a food depending on the contemplated end use. A preferred method of application involves spraying a water dispersion or refined oil solution of the compounds. Combinations with spray oils, spray oil concentrations, spreader stickers, adjuvants, other solvents, and synergists such as piperonyl butoxide often enhance compound efficacy.

The rate of application required for effective control (i.e. "biologically effective amount") will depend on such factors as the species of invertebrate to be controlled, the pest's life cycle, life stage, its size, location, time of year, host crop or animal, feeding behavior, mating behavior, ambient moisture, temperature, and the like. Under normal circumstances, application rates of about 0.01 to 2 kg of active ingredient per hectare are sufficient to control pests in agronomic ecosystems, but as little as 0.0001 kg/hectare may be sufficient or as much as 8 kg/hectare may be required. For nonagronomic applications, effective use rates will range from about 1.0 to 50 mg/square meter but as little as 0.1 mg/square meter may be sufficient or as much as 150 mg/square meter may be required. One skilled in the art can easily determine the biologically effective amount necessary for the desired level of invertebrate pest control.

The following TESTS demonstrate the control efficacy of compounds of this invention on specific pests. "Control efficacy" represents inhibition of arthropod development (including mortality) that causes significantly reduced feeding. The pest control protection afforded by the compounds is not limited, however, to these species. See Index Tables A–C for compound descriptions. The following abbreviations are used in the Index Tables which follow: t is tertiary, i is iso, Me is methyl, Et is ethyl, Pr is propyl, i-Pr is isopropyl, Bu is butyl The abbreviation "Ex." stands for "Example" and is followed by a number indicating in which example the compound is prepared.

INDEX TABLE A

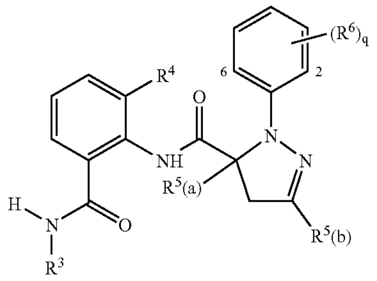

| Compound | $R^3$ | $R^4$ | $R^5$(a) | $R^5$(b) | $(R^6)_q$ | $^1$H NMR |
|---|---|---|---|---|---|---|
| 1 (Ex. 1) | i-Pr | Me | H | $CF_3$ | 2-Cl | * |
| 2 (Ex. 2) | i-Pr | Me | H | $CO_2Me$ | 2-Cl | * |
| 3 | i-Pr | Me | H | $CO_2Me$ | 2-Me | * |
| 4 | i-Pr | Me | H | $CF_3$ | 2-Me | * |
| 5 | i-Pr | Me | H | $CF_3$ | 2-F | * |
| 6 | t-Bu | Me | H | $CF_3$ | 2-Me | * |
| 7 | i-Pr | Me | Me | $CF_3$ | 2-Cl | * |
| 8 | i-Pr | Me | H | $CF_3$ | 2,6-$F_2$ | * |

*See Index Table C for $H^1$ NMR data

INDEX TABLE B

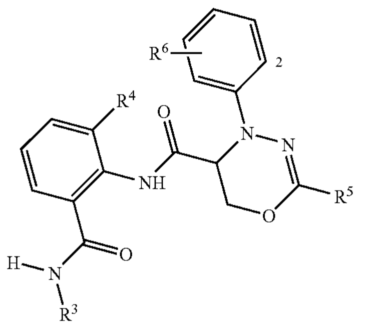

| Compound | $R^3$ | $R^4$ | $R^5$ | $R^6$ | $^1$H NMR |
|---|---|---|---|---|---|
| B1 (Ex. 3) | i-Pr | Me | $CF_3$ | 2-Cl | * |

*See Index Table C for $H^1$ NMR data

INDEX TABLE C

| Compd. No. | $^1$H NMR Data ($CDCl_3$ solution unless indicated otherwise)[a] |
|---|---|
| 1 | 9.4(bs, 1H), 7.6-7.5(d, 1H), 7.4-7.1(m, 6H), 5.8(bd, 1H), 5.4(dd, 1H), 4.3-4.1(m, 1H), 3.6-3.4(m, 2H), 1.84(s, 3H), 1.3-1.2(m, 6H). |
| 2 | 9.4-9.3(bs, 1H), 7.6(d, 1H), 7.4-7.3(d, 1H), 7.3-7.0(m, 5H), 5.8(d, 1H), 5.5(dd, 1H), 4.2-4.1(m, 1H), 3.89(s, 3H), 3.7-3.4(m, 2H), 1.81(s, 3H), 1.3-1.2(m, 6H). |
| 3 | two isomers: 9.5 + 9.3-9.2(2 × bs, 1H), 7.3-7.0(m, 7H), 5.8(bm, 1H), 5.1-5.0(m, 1H), 4.1-4.0(m, 1H), 3.87(s, 3H), 3.7-3.5(m, 1H), 3.5-3.3(m, 1H), 2.5(2 × s, 3H), 2.0-1.9 + 1.87(2 × s, 3H), 1.3-1.1(m, 6H). |

-continued

INDEX TABLE C

| Compd. No. | $^1$H NMR Data ($CDCl_3$ solution unless indicated otherwise)[a] |
|---|---|
| 4 | (DMSO-$d_6$) 9.81(s, 1H), 8.1-8.0(m, 1H), 7.3-6.9(m, 7H), 5.3(m, 1H), 4.0-3.9(m, 1H), 3.6(m, 1H), 1.79(s, 3H), 1.1(m, 6H). |
| 5 | (DMSO-$d_6$) 9.85(s, 1H), 8.1-8.0(d, 1H), 7.4-6.9(m, 7H), 5.5-5.4(m, 1H), 4.0-3.9(m, 1H), 3.7(m, 1H), 3.5-3.3(m, 1H), 2.07(s, 3H), 1.11(d, 3H), 1.06(d, 3H). |
| 6 | (DMSO-$d_6$) 9.3-9.2(s, 1H), 7.4-7.0(m, 7H), 5.8(d, 1H), 5.1-5.0(m, 1H), 3.6-3.3(m, 2H), 1.88(s, 3H), 1.40(s, 9H). |
| 7 | 10.0-9.9(s, 1H), 7.5-7.1(m, 7H), 5.9(d, 1H), 4.2-4.1(m, 1H), 3.7(d, 1H), 3.3-3.2(d, 1H), 2.27(s, 3H), 1.50(s, 3H), 1.3-1.2(m, 6H). |
| 8 | 9.3(s, 1H), 7.3-7.2(m, 3H), 7.0(m, 3H), 5.8(d, 1H), 5.0-4.9(dd, 1H), 4.1(m, 1H), 3.7-3.4(Abd, 2H), 2.10(s, 3H), 1.3-1.1(m, 6H). |
| B1 | 9.6(s, 1H), 7.6-7.1(m, 7H), 5.9-5.8(d, 1H), 5.0-4.9(dd, 1H), 4.8-4.7(m, 1H), 4.3(dd, 1H), 4.2-4.1(m, 1H), 2.10(s, 3H), 1.3-1.2(m, 6H). |

[a] $^1$H NMR data are in ppm downfield from tetramethylsilane. Couplings are designated by(s)-singlet, (d)-doublet, (t)-triplet, (q)-quartet, (m)-multiplet, (dd)-doublet of doublets, (dt)-doublet of triplets, (br s)-broad singlet.

BIOLOGICAL EXAMPLES OF THE INVENTION

Test A

For evaluating control of diamondback moth (*Plutella xylostella*) the test unit consisted of a small open container with a 12–14-day-old radish plant inside. This was pre-infested with 10–15 neonate larvae on a piece of insect diet by use of a core sampler to remove a plug from a sheet of hardened insect diet having many larvae growing on it and transfer the plug containing larvae and diet to the test unit. The larvae moved onto the test plant as the diet plug dried out.

Test compounds were formulated using a solution containing 10% acetone, 90% water and 300 ppm X-77® Spreader Lo-Foam Formula non-ionic surfactant containing alkylarypolyoxyethylene, free fatty acids, glycols and isopropanol (Loveland Industries, Inc.), unless otherwise indicated. The formulated compounds were applied in 1 mL of liquid through a SUJ2 atomizer nozzle with ⅛ JJ custom body (Spraying Systems Co.) positioned 1.27 cm (0.5 inches) above the top of each test unit. All experimental compounds in these tests were sprayed at 250 ppm (or lower) and replicated three times. After spraying of the formulated test compound, each test unit was allowed to dry for 1 hour and then a black, screened cap was placed on top. The test units were held for 6 days in a growth chamber at 25° C. and 70% relative humidity. Plant feeding damage was then visually assessed based on foliage consumed.

Of the compounds tested the following provided excellent levels of plant protection (ratings of 0–1, 10% or less feeding damage): 1*, 3, 4*, 5*, 6*, 7*, 8**.

Test B

For evaluating control of fall armyworm (*Spodoptera frugiperda*) the test unit consisted of a small open container with a 4–5-day-old corn (maize) plant inside. This was pre-infested (using a core sampler) with 10–15 1-day-old larvae on a piece of insect diet.

Test compounds were formulated and sprayed at 250 ppm (or lower) as described for Test A. The applications were replicated three times. After spraying, the test units were maintained in a growth chamber and then visually rated as described for Test A.

Of the compounds tested, the following provided excellent levels of plant protection (10% or less feeding damage): 1*, 4**, 5*.

Test C

For evaluating control of tobacco budworm (*Heliothis virescens*) the test unit consisted of a small open container with a 6–7 day old cotton plant inside. This was pre-infested (using a core sampler) with 8 2-day-old larvae on a piece of insect diet.

Test compounds were formulated and sprayed at 250 ppm (or lower) as described for Test A. The applications were replicated three times. After spraying, the test units were maintained in a growth chamber and then visually rated as described for Test A.

Of the compounds tested, the following provided very good to excellent levels of plant protection (20% or less feeding damage): 1*, 4**, 5*, 6*.

Test D

For evaluating control of beet armyworm (*Spodoptera exigua*) the test unit consisted of a small open container with a 4–5-day-old corn plant inside. This was pre-infested (using a core sampler) with 10–15 1-day-old larvae on a piece of insect diet.

Test compounds were formulated and sprayed at 250 ppm (or lower) as described for Test A. The applications were replicated three times. After spraying, the test units were maintained in a growth chamber and then visually rated as described for Test A.

Of the compounds tested, the following provided very good to excellent levels of plant protection (20% or less feeding damage): 1*, 4*, 5*, 6*.

* Tested at 50 ppm. ** Tested at 10 ppm.

What is claimed is:

1. A compound of Formula Ia, an N-oxide or suitable salt thereof

Ia

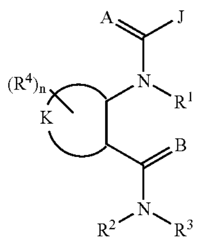

wherein

A and B are independently O or S;

J is

J-1

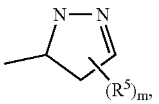

-continued

J-2

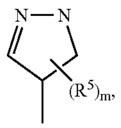

J-5

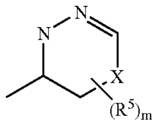

J-17

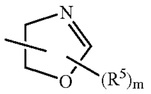

J-19

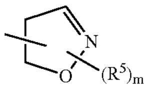

J-22

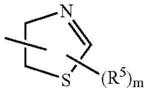

K is taken together with the two linking atoms to form a phenyl ring optionally substituted with from 1 to 4 $R^4$;

X is O or S;

$R^1$ is H;

$R^2$ is H or $C_1$–$C_6$ alkyl;

$R^3$ is H; G; $C_1$–$C_6$ alkyl, $C_2$–$C_6$ alkenyl, $C_2$–$C_6$ alkynyl, $C_3$–$C_6$ cycloalkyl, each optionally substituted with one or more substituents independently selected from the group consisting of halogen, G, CN, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_2$–$C_6$ alkoxycarbonyl, $C_2$–$C_6$ alkylcarbonyl, $C_3$–$C_6$ trialkylsilyl, or a phenyl, phenoxy or 5- or 6-membered heteroaromatic ring, each ring optionally substituted with one to three substituents independently selected from $R^6$; $C_1$–$C_4$ alkylamino; $C_2$–$C_8$ dialkylamino; $C_3$–$C_6$ cycloalkylamino; $C_2$–$C_6$ alkoxycarbonyl or $C_2$–$C_6$ alkylcarbonyl; or G is a 5- or 6-membered nonaromatic carbocyclic or heterocyclic ring, optionally including one or two ring members selected from the group consisting of C(═O), SO or $S(O)_2$ and optionally substituted with from 1 to 4 substituents selected from $R^7$;

each $R^4$ is independently H, $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $C_1$–$C_4$ alkylamino, $C_2$–$C_8$ dialkylamino, $C_3$–$C_6$ cycloalkylamino, or $C_3$–$C_6$ trialkylsilyl; or each $R^4$ is independently phenyl, benzyl or phenoxy, each optionally substituted with from one to three substituents selected from $R^6$;

each $R^5$ is independently H, $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $CO_2H$, $CONH_2$, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $C_1$–$C_4$ alkylamino, $C_2$–$C_8$ dialkylamino, $C_3$–$C_6$ cycloalkylamino, $C_2$–$C_6$ alkylcarbonyl, $C_2$–$C_6$ alkoxycarbonyl, $C_2$–$C_6$ alkylaminocarbonyl, $C_3$–$C_8$ dialkylaminocarbonyl, $C_3$–$C_6$ trialkylsilyl or W;

$(R^5)_2$ when attached to adjacent carbon atoms can be taken together as —$OCF_2O$—, —$CF_2CF_2O$—, or —$OCF_2CF_2O$—;

each W is independently a phenyl, benzyl, benzoyl, phenoxy, 5- or 6-membered heteroaromatic ring or an aromatic 8-, 9- or 10-membered fused heterobicyclic ring system, each ring optionally substituted with from one to three substituents independently selected from $R^6$;

each $R^6$ is independently $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl;

each $R^7$ is independently $C_1$–$C_2$ alkyl, halogen, CN, $NO_2$ and $C_1$–$C_2$ alkoxy;

m is an integer from 1 to 7; and n is an integer from 1 to 3; provided that when J is J-1, m is 1, and $R^5$ is phenyl substituted with methyl and Cl or substituted with Br, then $R^3$ is other than methyl, ethyl, n-butyl of $CH_2C_6H_5$.

2. The compound of claim 1 wherein n is 1 or 2;

$R^2$ is H or $C_1$–$C_4$ alkyl;

$R^3$ is H; or $C_1$–$C_6$ alkyl, $C_2$–$C_6$ alkenyl, $C_2$–$C_6$ alkynyl or $C_3$–$C_6$ cycloalkyl each optionally substituted with one or more substituents selected from the group consisting of halogen, CN, $C_1$–$C_2$ alkoxy, $C_1$–$C_2$ alkylthio, $C_1$–$C_2$ alkylsulfinyl and $C_1$–$C_2$ alkylsulfonyl;

one of the $R^4$ groups is attached to the K ring at one of the two positions ortho to the two linking atoms, and said $R^4$ is $C_1$–$C_4$ alkyl, $C_1$–$C_4$ haloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl or $C_1$–$C_4$ haloalkylsulfonyl;

each $R^5$ is independently H, $C_1$–$C_4$ alkyl, C1–$C_4$ haloalkyl, halogen, CN, $NO_2$, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl or $C_2$–$C_4$ alkoxycarbonyl; and one $R^5$ is optionally W; and W is a phenyl ring or a 5- or 6-membered heteroaromatic ring, each ring optionally substituted with one to three substituents independently selected from $R^6$.

3. The compound of claim 2 wherein

J is J-36;

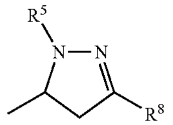

J-36

$R^1$ is H;

$R^2$ is H or $CH_3$;

$R^3$ is H; or $C_1$–$C_4$ alkyl, $C_2$–$C_4$ alkenyl or $C_2$–$C_4$ alkynyl, each optionally substituted with halogen, CN, $OCH_3$, or $S(O)_pCH_3$;

each $R^4$ is independently $CH_3$, $CF_3$, CN or halogen, and one $R^4$ group is attached to the K ring at the atom adjacent to the $NR^1C(=A)J$ moiety;

$R^5$ is H, $C_1$–$C_4$ alkyl, $C_1$–$C_4$ haloalkyl, or W;

W is

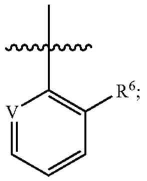

V is N, CH, CF, CCl, CBr or CI;

each $R^6$ and $R^8$ is independently H, $C_1$–$C_4$ alkyl, $C_3$–$C_6$ cycloalkyl, $C_1$–$C_4$ haloalkyl, halogen, CN, $C_1$–$C_4$ alkoxy, or $C_1$–$C_4$ haloalkoxy;

m is 1 or 2; and p is 0, 1 or 2.

4. The compound of claim 3 wherein V is N.

5. The compound of claim 3 wherein V is CH, CF, CCl or CBr.

6. The compound of claim 2 wherein

J is J-37;

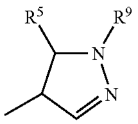

J-37

$R^1$ is H;

$R^2$ is H or $CH_3$;

$R^3$ is H; or $C_1$–$C_4$ alkyl, $C_2$–$C_4$ alkenyl or $C_2$–$C_4$ alkynyl, each optionally substituted with halogen, CN, $OCH_3$, or $S(O)_pCH_3$;

each $R^4$ is independently $CH_3$, $CF_3$, CN or halogen, and one $R^4$ group is attached to the K ring at the atom adjacent to the $NR^1C(=A)J$ moiety;

$R^5$ is H, $C_1$–$C_4$ alkyl, $C_1$–$C_4$ haloalkyl, or W;

W is

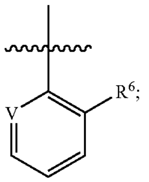

V is N, CH, CF, CCl, CBr or CI;

$R^6$ is independently H, $C_1$–$C_4$ alkyl, $C_3$–$C_6$ cycloalkyl, $C_1$–$C_4$ haloalkyl, halogen, CN,$C_1$–$C_4$ alkoxy, or $C_1$–$C_4$ haloalkoxy;

$R^9$ is H, $C_1$–$C_6$ alkyl, $C_1$–$C_6$ haloalkyl, $C_3$–$C_6$ alkenyl, $C_3$–$C_6$ haloalkenyl, $C_3$–$C_6$ alkynyl or $C_3$–$C_6$ haloalkynyl;

m is 1 or 2; and p is 0, 1 or 2.

7. The compound of claim 1 selected from the group consisting of 1-(2-Chlorophenyl)-4,5-dihydro-N-[2-methyl-6-[[(1-methylethyl)amino]carbonyl]phenyl]-3-(trifluoromethyl)-1H-pyrazole-5-carboxamide, Methyl 1-(2-chlorophenyl)-4,5-dihydro-5-[[[2-methyl-6-[[(1-methylethyl)amino]carbonyl]phenyl]amino]carbonyl]1H-pyrazole-3-carboxylate, Methyl 4,5-dihydro-5-[[[2-methyl-6-[[(1-methylethyl)amino]carbonyl]phenyl]amino]carbonyl]-1-(2-methylphenyl)-1H-pyrazole-3-carboxylate, 4,5-Dihydro-N-[2-methyl-6-[[(1-methylethyl)amino]carbonyl]phenyl]-1-(2-methylphenyl)-3-(trifluormethyl)-1H-pyrazole-5-carboxamide, 1-(2-Fluorophenyl)-4,5-dihydro-N-[2-methyl-6-[[(1-methylethyl)amino]carbonyl]phenyl]-3-(trifluoromethyl)-1H-pyrazole-5-carboxamide, N-[2-[[(1,1-Dimethylethyl)amino]carbonyl]-6-methylphenyl]-4,5-dihydro-1-(2-methylphenyl) -3-(trifluoromethyl)-1H-pyrazole-5-carboxamide, and 1-(2,6-Difluorophenyl)-4,5-dihydro-N-[2-methyl-6-[[1-methylethyl)amino]carbonyl]phenyl]-3-(trifluoromethyl)-1H-pyrazole-5-carboxamide.

8. A method for controlling an invertebrate pest comprising contacting the invertebrate pest or its environment with a biologically effective amount of a compound of claim 1.

9. The method of claim 8 further comprising a biologically effective amount of at least one additional compound or agent for controlling an invertebrate pest.

10. A composition for controlling an invertebrate pest comprising a biologically effective amount of a compound of claim 1 and at least one additional component selected from the group consisting of surfactants, solid diluents and liquid diluents.

11. The composition of claim 10 further comprising an effective amount of at least one additional biologically active compound or agent.

* * * * *